(12) United States Patent
Bourzat et al.

(10) Patent No.: US 6,608,084 B1
(45) Date of Patent: Aug. 19, 2003

(54) AZA-BICYCLES WHICH MODULATE THE INHIBITION OF CELL ADHESION

(75) Inventors: Jean-Dominique Bourzat, Vincennes (FR); Alain Commercon, Vitry-sur-Seine (FR); Bruno Jacques Christophe Filoche, Creteil (FR); Neil Victor Harris, West Malling (GB); Clive McCarthy, West Malling (GB)

(73) Assignees: Aventis Pharma Ltd., Kent (GB); Aventis Recherche Developpment, Vitry-sur-Seine (FR)

( * ) Notice: Subject to any disclaimer, the term of this patent is extended or adjusted under 35 U.S.C. 154(b) by 0 days.

(21) Appl. No.: 09/856,106

(22) PCT Filed: Aug. 26, 1999

(86) PCT No.: PCT/GB99/02819
§ 371 (c)(1),
(2), (4) Date: Oct. 17, 2001

(87) PCT Pub. No.: WO00/15612
PCT Pub. Date: Mar. 23, 2000

Related U.S. Application Data
(60) Provisional application No. 60/110,008, filed on Nov. 25, 1998.

(30) Foreign Application Priority Data

Aug. 26, 1998 (GB) .............................. 9819641

(51) Int. Cl.[7] ...................... A61K 31/47; C07D 215/02; A61P 43/00

(52) U.S. Cl. ...................... 514/311; 514/314; 514/443; 546/164; 548/492; 548/493

(58) Field of Search ................................ 514/311, 314, 514/443; 546/164; 548/492, 493

(56) References Cited

U.S. PATENT DOCUMENTS 3,635,706 A * 1/1972 Kampler et al. .............. 96/1.7
5,688,913 A * 11/1997 Arrhenius et al. ......... 530/330

FOREIGN PATENT DOCUMENTS

| EP | 0042298 A | * 12/1981 |
| EP | 0042298 | 9/1984 |
| EP | 0842945 A | * 5/1998 |
| EP | 0842945 | 5/1998 |
| IE | 921488 | * 11/1992 |
| IE | 208136 | 8/1993 |
| WO | WO98/07716 | 2/1998 |
| WO | 98/ 07716 A | * 2/1998 |

OTHER PUBLICATIONS

Kohno, et al, "Synthesis and antirhuematic activity of novel tetrahydro–o–6–quinalinacetic acid derivtives", Bioorg. Med. Chem. Lett. 1997, 7(12), 1519–1524.*

Stejpan, et al "Orally absorable cephalosporin antibiotics. 2. Structure–activity studies of bicyclic glycine derivatives of 7–aminodeacetoxycephalosporanic acid." 1985, Jouranl of Medicianl Chemistry, 28(12) 1896–1903.*

Chang, et al, "The discovery of small molecule carbamates as potent dual a4b1/a4b7 integrin anatagonists", 2002, Bioorganic and Medicianl Chemistry, 12(2), 159–163.*

Singh, et al, "Indentification of potent and novel a4b7 antagonists using in silico screening", 2002, J. Med. Chem., 45, 2988–2993.*

Kukolja, Stjepan, Orally Absorbable Cephalosporin Antibiotics. 2. Structure–Activity Studies Of Bicyclic Glycine Derivatives Of 7–Aminodeacetoxycephalosporanic Acid., Journal of Medicinal Chemistry, 1985, 1896–1903, vol. 28. No. 12.

Yasushi, Kohno, Synthesis And Antirheumatic Activity Of Novel Tetrahydro–6–Quinolineacetic Acid , Derivatives., Chemical Abstracts, Sep. 15, 1997, vol. 127, No. 11.

* cited by examiner

Primary Examiner—Joseph K. McKane
Assistant Examiner—Andrea D. Small
(74) Attorney, Agent, or Firm—Ronald G. Ort

(57) ABSTRACT

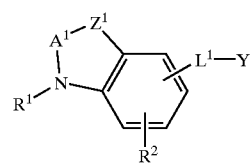

(I)

The invention is directed to physiologically active compounds of formula (I) wherein $R^1$ represents $R^3-Z^3-$, $R^3-L^2-R^4-Z^3-$, $R^3-L^3-Ar^1-L^4-Z^3-$ or $R^3-L^3-Ar^1-L^2-R^4-Z^3-$; $R^2$ represents hydrogen, halogen, lower alkyl or lower alkoxy; $A^1$ represents a straight chain $C_{1-3}$alkylene linkage optionally substituted by one or more groups chosen from alkyl, aryl, arylalkyl, heteroaryl, heteroarylalkyl, imino, oxo, thioxo, or alkyl substituted by $-ZR^6$, $-NY^1Y^2$, $-CO_2R^6$ or $-C(=O)-NY^1Y^2$; $L^1$ represents a direct bond; an alkenylene, alkylene, alkynylene, cycloalkenylene, cycloalkylene, heteroaryldiyl, heterocycloalkylene or arylene linkage each optionally substituted by (a) an acidic functional group, cyano, oxo, $-S(O)_mR^9$, $R^3$, $-C(=O)-R^3$, $-C(=O)-OR^3$, $-N(R^8)-C(=O)R^9$, $-N(R^8)-SO_2-R^9$, $-NY^4Y^5$ or $-[C(=O)-N(R^{10})-C(R^5)(R^{11})]_p-C(=O)-NY^4Y^5$, or by (b) alkyl substituted by an acidic functional group, or $S(O)_mR^9$, $-C(=O)-NY^4Y^5$ or $-NY^4Y^5$; a $-[C(=O)-N(R^{10})-C(R^5)(R^{11})]_p-$ linkage; a $-Z^2-R^{12}-$ linkage; a $-C(=O)-CH_2-C(=O)-$ linkage; a $-R^{12}-Z^2-R^{12}-$ linkage; a $-C(R^4)(R^{13})-[C(=O)-N(R^{10})-C(R^5)(R^{11})]_p-$ linkage; or a $-L^5-L^6-L^7-$ linkage; $Z^1$ is $C(R^7)(R^{7a})$, $C(=O)$ or $CH(OH)$; Y is carboxy or an acid bioisostere; and the corresponding N-oxides, and their prodrugs; and pharmaceutically acceptable salts and solvates of such compounds and their N-oxides and prodrugs. Such compounds have valuable pharmaceutical properties, in particular the ability to regulate the interaction of VCAM-1 and fibronectin with the integrin VLA-4 ($\alpha 4\beta 1$).

38 Claims, No Drawings

AZA-BICYCLES WHICH MODULATE THE INHIBITION OF CELL ADHESION

This application is a 371 of PCT/GB99/02819, filed Aug. 26, 1999, which claims priority from U.S. application Ser. No. 60/110,008, filed Nov. 25, 1998, and GB Application No. 9818641.4, filed Aug. 26, 1998.

This invention is directed to aza-bicycles, their preparation, pharmaceutical compositions containing these compounds, and their pharmaceutical use in the treatment of disease states capable of being modulated by the inhibition of cell adhesion.

Cell adhesion is a process by which cells associate with each other, migrate towards a specific target or localise within the extra-cellular matrix. Many of the cell-cell and cell-extracellular matrix interactions are mediated by protein ligands (e.g. fibronectin, VCAM-1 and vitronectin) and their integrin receptors [e.g. α5β1 (VLA-5), α4β1 (VLA-4) and αVβ3]. Recent studies have shown these interactions to play an important part in many physiological (e.g. embryonic development and wound healing) and pathological conditions (e.g. tumour-cell invasion and metastasis, inflammation, atherosclerosis and autoimmune disease).

A wide variety of proteins serve as ligands for integrin receptors. In general, the proteins recognised by integrins fall into one of three classes: extracellular matrix proteins, plasma proteins and cell surface proteins. Extracellular matrix proteins such as collagen fibronectin, fibrinogen, laminin, thrombospondin and vitronectin bind to a number of integrins. Many of the adhesive proteins also circulate in plasma and bind to activated blood cells. Additional components in plasma that are ligands for integrins include fibrinogen and factor X. Cell bound complement C3bi and several transmembrane proteins, such as Ig-like cell adhesion molecule (ICAM-1,2,3) and vascular cell adhesion molecule (VCAM-1), which are members of the Ig superfamily, also serve as cell-surface ligands for some integrins.

Integrins are heterodimeric cell surface receptors consisting of two subunits called α and β. There are at least fifteen different α-subunits (α1–α9, α-L, α-M, α-X, α-IIb, α-V and α-E) and at least seven different β (β1–β7) subunits. The integrin family can be subdivided into classes based on the β subunits, which can be associated with one or more α-subunits. The most widely distributed integrins belong to the β1 class, also known as the very late antigens (VLA). The second class of integrins are leukocyte specific receptors and consist of one of three α-subunits (α-L, α-M or α-X) complexed with the β2 protein. The cytoadhesins α-IIbβ3 and α-Vβ3, constitute the third class of integrins.

The present invention principally relates to agents which modulate the interaction of the ligand VCAM-1 with its integrin receptor α4β1 (VLA-4), which is expressed on numerous hematopoietic cells and established cell lines, including hematopoietic precursors, peripheral and cytotoxic T lymphocytes, B lymphocytes, monocytes, thymocytes and eosinophils.

The integrin α4β1 mediates both cell-cell and cell-matrix interactions. Cells expressing α4β1 bind to the carboxy-terminal cell binding domain (CS-1) of the extracellular matrix protein fibronectin, to the cytokine-inducible endothelial cell surface protein VCAM-1, and to each other to promote homotypic aggregation. The expression of VCAM-1 by endothelial cells is upregulated by proinflammatory cytokines such as INF-γ, TNF-α, IL-1β and IL-4.

Regulation of α4β1 mediated cell adhesion is important in numerous physiological processes, including T-cell proliferation, B-cell localisation to germinal centres, and adhesion of activated T-cells and eosinophils to endothelial cells. Evidence for the involvement of VLA-4/VCAM-1 interaction in various disease processes such as melanoma cell division in metastasis, T-cell infiltration of synovial membranes in rheumatoid arthritis, autoimmune diabetes, collitis and leukocyte penetration of the blood-brain barrier in experimental autoimmune encephalomyelitis, atherosclerosis, peripheral vascular disease, cardiovascular disease and multiple sclerosis, has been accumulated by investigating the role of the peptide CS-1 (the variable region of fibronectin to which α4β1 binds via the sequence Leu-Asp-Val) and antibodies specific for VLA-4 or VCAM-1 in various in vitro and in vivo experimental models of inflammation. For example, in a Streptococcal cell wall-induced experimental model of arthritis in rats, intravenous administration of CS-1 at the initiation of arthritis suppresses both acute and chronic inflammation (S. M. Wahl et al., J. Clin. Invest., 1994, 94, pages 655–662). In the oxazalone-sensitised model of inflammation (contact hypersensitivity response) in mice, intravenous administration of anti-α4 specific monoclonal antibodies significantly inhibited (50–60% reduction in the ear swelling response) the efferent response (P. L. Chisholm et al. J. Immunol., 1993, 23, pages 682–688). In a sheep model of allergic bronchoconstriction, HP1/2, an anti-α4 monoclonal antibody given intravenously or by aerosol, blocked the late response and the development of airway hyperresponsiveness (W. M. Abraham et al. J. Clin. Invest., 1994, 93 pages 776–787).

We have now found a novel group of aza-bicycles which have valuable pharmaceutical properties, in particular the ability to regulate the interaction of VCAM-1 and fibronectin with the integrin VLA-4 (α4β1).

Thus, in one aspect, the present invention is directed to aza-bicycles of general formula (I):

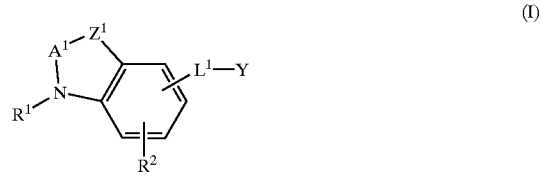

wherein:
R$^1$ represents:
(i) R$^3$—Z$^3$—;
(ii) R$^3$—L$^2$—R$^4$—Z$^3$—;
(iii) R$^3$—L$^3$—Ar$^1$—L$^4$—Z$^3$—; or
(iv) R$^3$—L$^3$—Ar$^1$—L$^2$—R$^4$—Z$^3$;

R$^2$ represents hydrogen, halogen, lower alkyl or lower alkoxy;

R$^3$ represents alkyl, alkenyl, alkynyl, aryl, arylalkyl, arylalkenyl, arylalkynyl, cycloalkyl, cycloalkylalkyl, cycloalkylalkenyl, cycloalkylalkynyl, cycloalkenyl, cycloalkenylalkyl, heteroaryl, heteroarylalkyl, heteroarylalkenyl, heteroarylalkynyl, heterocycloalkyl or heterocycloalkylalkyl;

R$^4$ represents an alkylene chain, an alkenylene chain, or an alkynylene chain;

R$^5$ represents hydrogen or lower alkyl;

R$^6$ represents hydrogen, alkyl, alkenyl, aryl, arylalkyl, cycloalkyl, cycloalkylalkyl, heteroaryl or heteroarylalkyl;

R$^7$ and R$^{7a}$ are each independently hydrogen or lower alkyl;

$R^8$ represents hydrogen, alkyl, aryl, arylalkyl, cycloalkyl, cycloalkylalkyl, heteroaryl, heteroarylalkyl, heterocycloalkyl or heterocycloalkylalkyl;

$R^9$ represents alkyl, aryl, cycloalkyl, heteroaryl or heterocycloalkyl, or alkyl substituted by aryl, an acidic functional group, cycloalkyl, heteroaryl, heterocycloalkyl, —S(O)$_m$R$^3$, —C(=O)—NY$^4$Y$^5$ or —NY$^4$Y$^5$;

$R^{10}$ represents hydrogen, $R^3$ or alkyl substituted with alkoxy, cycloalkyl, hydroxy, mercapto, alkylthio or —NY$^4$Y$^5$;

$R^{11}$ and $R^{13}$ are each independently selected from hydrogen or a group consisting amino acid side chains, an acidic functional group, $R^3$, —C(=O)—R$^3$, or —C(=O)—NY$^4$Y$^5$, or alkyl substituted by an acidic functional group or by $R^3$, —NY$^4$Y$^5$, —NH—C(=O)—R$^3$, —C(=O)—R$^4$—NH$_2$, —C(=O)—Ar$^1$—NH$_2$, —C(=O)—R$^4$—CO$_2$H, or —C(=O)—NY$^4$Y$^5$;

or $R^{10}$ and $R^{11}$ or $R^{10}$ and $R^{12}$ together with the atoms to which they attached form a 3- to 6-membered heterocycloalkyl ring;

$R^{12}$ represents C$_{1-6}$alkylene, optionally substituted by $R^3$;

$R^{14}$ represents alkyl, aryl, arylalkyl, cycloalkyl, cycloalkylalkyl, heteroaryl, heteroarylalkyl, heterocycloalkyl or heterocycloalkylalkyl;

$A^1$ represents a straight chain C$_{1-3}$alkylene linkage optionally substituted by one or more groups chosen from alkyl, aryl, arylalkyl, heteroaryl, heteroarylalkyl, imino, oxo, thioxo, or alkyl substituted by —ZR$^6$, —NY$^1$Y$^2$, —CO$_2$R$^6$ or —C(=O)—NY$^1$Y$^2$;

$Ar^1$ represents arylene or heteroaryldiyl;

$L^1$ represents:
(i) a direct bond;
(ii) an alkenylene, alkylene, alkynylene, cycloalkenylene, cycloalkylene, heteroaryldiyl, heterocycloalkylene or arylene linkage each optionally substituted by (a) an acidic functional group, cyano, oxo, —S(O)$_m$R$^9$, R$^3$, —C(=O)—R$^3$, —C(=O)—OR$^3$, —N(R$^8$)—C(=O)—R$^9$, —N(R$^8$)—C(=O)—OR$^9$, —N(R$^8$)—SO$_2$—R$^9$, —NY$^4$Y$^5$ or —[C(=O)—N(R$^{10}$)—C(R$^5$)(R$^{11}$)]$_p$—C(=O)—NY$^4$Y$^5$, or by (b) alkyl substituted by an acidic functional group, or by S(O)$_m$R$^9$, —C(=O)—NY$^4$Y$^5$ or —NY$^4$Y$^5$;
(iii) a —[C(=O)—N(R$^{10}$)—C(R$^5$)(R$^{11}$)]$_p$— linkage;
(iv) a —Z$^2$—R$^{12}$— linkage;
(v) a —C(=O)—CH$_2$—C(=O)— linkage;
(vi) a —R$^{12}$—Z$^2$—R$^{12}$— linkage;
(vii) a —C(R$^4$)(R$^{13}$)—[C(=O)—N(R$^{10}$)—C(R$^5$)(R$^{11}$)]$_p$— linkage; or
(viii) a —L$^5$—L$^6$—L$^7$— linkage;

$L^2$ represents a —NR$^5$—C(=Z)—NR$^5$—, —C(=Z)—NR$^5$—, —C(=O)—, —C(=Z)—O—, —NR$^5$—C(=Z)—, —Z—, —S(O)$_m$—, —NR$^5$—, —SO$_2$—NR$^5$—, —NR$^5$—SO$_2$—, —NR$^5$—C(=O)—O—, —O—C(=O)—, or —O—C(=O)—NR$^5$— linkage;

$L^3$ represents a heteroaryldiyl, —NR$^5$—C(=Z)—NR$^5$—, —C(=Z)—NR$^5$—, —C(=Z)—O—, —NR$^5$—C(=Z)—, —Z—, —S(O)$_m$—, —NR$^5$—, —SO$_2$—NR$^5$—, —NR$^5$—SO$_2$—, —NR$^5$—C(=O)—O—, —O—C(=O)—, or —O—C(=O)—NR$^5$— linkage;

$L^4$ represents a direct bond, an alkylene, alkenylene or alkynylene chain;

$L^5$ and $L^7$ each independently represent a direct bond or an alkylene chain;

$L^6$ represents a cycloalkylene or heterocycloalkylene linkage;

$Y^1$ and $Y^2$ are independently hydrogen, alkenyl, alkyl, aryl, arylalkyl, cycloalkyl, heteroaryl or heteroarylalkyl; or the group —NY$^1$Y$^2$ may form a cyclic amine;

$Y^4$ and $Y^5$ are independently hydrogen, alkenyl, alkyl, alkynyl, aryl, cycloalkenyl, cycloalkyl, heteroaryl, heterocycloalkyl, or alkyl substituted by alkoxy, aryl, cyano, cycloalkyl, heteroaryl, heterocycloalkyl, hydroxy, oxo, —NY$^1$Y$^2$, or one or more —CO$_2$R$^8$ or —C(=O)—NY$^1$Y$^2$ groups; or the group —NY$^4$Y$^5$ may form a 5- to 7-membered cyclic amine which (i) may be optionally substituted with one or more substituents selected from alkoxy, carboxamido, carboxy, hydroxy, oxo (or a 5-, 6- or 7-membered cyclic acetal derivative thereof), R$^{10}$; (ii) may also contain a further heteroatom selected from O, S, SO$_2$, or NY$^6$; and (iii) may also be fused to additional aryl, heteroaryl, heterocycloalkyl or cycloalkyl rings to form a bicyclic or tricyclic ring system;

$Y^6$ represents hydrogen, alkyl, aryl, arylalkyl, —C(=O)—R$^{14}$, —C(=O)—OR$^{14}$ or —SO$_2$R$^{14}$;

Z is an oxygen or sulphur atom;

$Z^1$ is C(R$^7$)(R$^{7a}$), C(=O) or CH(OH);

$Z^2$ is O, S(O)$_n$, NR$^5$, SONR$^5$, C(=O)NR$^5$ or C(=O);

$Z^3$ is a direct bond, C(=O), OC(=O), NR$^5$C(=O), or SO$_2$;

m is an integer 1 or 2;

n is zero or an integer 1 or 2;

p is zero or an integer 1 to 4; and

Y is carboxy (or an acid bioisostere);

and the corresponding N-oxides, and their prodrugs; and pharmaceutically acceptable salts and solvates (e.g. hydrates) of such compounds and their N-oxides and prodrugs, but excluding compounds where an oxygen, nitrogen or sulphur atom is attached directly to a carbon carbon multiple bond of an alkenylene, alkynylene or cycloalkenylene residue.

In the present specification, the term "compounds of the invention", and equivalent expressions, are meant to embrace compounds of general formula (I) as hereinbefore described, which expression includes the prodrugs, protected derivatives of compounds of formula (I) containing one or more acidic functional groups and/or amino-acid side chains, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986, 21, p283 "Bioisosterism In Drug Design"; Yun, Hwahak Sekye, 1993, 33, p576–579 "Application Of Bioisosterism To New Drug Design"; Zhao, Huaxue Tongbao, 1995, p34–38 "Bioisosteric Replacement And Development Of Lead Compounds In Drug Design";

Graham, Theochem, 1995, 343, p105–109 "Theoretical Studies Applied To Drug Design:ab initio Electronic Distributions In Bioisosteres"). Examples of suitable acid bioisosteres include: —C(=O)—NHOH, —C(=O)—CH$_2$OH, —C(=O)—CH$_2$SH, —C(=O)—NH—CN, sulpho, phosphono, alkylsulphonylcarbamoyl, tetrazolyl, arylsulphonylcarbamoyl, heteroarylsulphonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acidic functional group" means a group with an acidic hydrogen within it. The "protected derivatives" are those where the acidic hydrogen atom has been replaced with a suitable protecting group. For suitable protecting groups see T. W. Greene and P. G. M. Wuts in "Protective Groups in Organic Chemistry" John Wiley and Sons, 1991. Exemplary acidic functional groups include carboxyl (and acid bioisosteres), hydroxy, mercapto and imidazole. Exemplary protected derivatives include esters of carboxy groups (i.e. —CO$_2$R$^{14}$), ethers of hydroxy groups (i.e. —OR$^{14}$), thioethers of mercapto groups (i.e. —SR$^{14}$), and N-benzyl derivatives of imidazoles.

"Acyl" means an H—CO— or alkyl-CO— group in which the alkyl group is as described herein.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkenylene" means an aliphatic bivalent radical derived from a straight or branched alkenyl group, in which the alkenyl group is as described herein. Exemplary alkenylene radicals include vinylene and propylene.

"Alkoxy" means an alkyl-O— group in which the alkyl group is as described herein. Exemplary alkoxy groups include methoxy, ethoxy, n-propoxy, i-propoxy, n-butoxy and heptoxy.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched having about 1 to about 15 carbon atoms in the chain optionally substituted by alkoxy or by one or more halogen atoms. Particular alkyl groups have from 1 to about 6 carbon atoms. "Lower alkyl" as a group or part of a lower alkoxy, lower alkylthio, lower alkylsulphinyl or lower alkylsulphonyl group means unless otherwise specified, an aliphatic hydrocarbon group which may be straight or branched having about 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and dodecyl.

"Alkylene" means an aliphatic bivalent radical derived from a straight or branched C$_{1-6}$alkyl group, in which the alkyl group is as described herein. Exemplary alkylene radicals include methylene, ethylene and trimethylene.

"Alkylenedioxy" means an —O-alkyl-O— group in which the alkyl group is as defined above. Exemplary alkylenedioxy groups include methylenedioxy and ethylenedioxy.

"Alkylsulphinyl" means an alkyl-SO— group in which the alkyl group is as previously described. Preferred alkylsulphinyl groups are those in which the alkyl group is C$_{1-4}$alkyl.

"Alkylsulphonyl" means an alkyl-SO$_2$— group in which the alkyl group is as previously described. Preferred alkylsulphonyl groups are those in which the alkyl group is C$_{1-4}$alkyl.

"Alkylsulphonylcarbamoyl" means an alkyl-SO$_2$—NH—C(=O)— group in which the alkyl group is as previously described. Preferred alkylsulphonylcarbamoyl groups are those in which the alkyl group is C$_{1-4}$alkyl.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Exemplary alkynyl groups include ethynyl, propynyl, n-butynyl, i-butynyl, 3-methylbut-2-ynyl, and n-pentynyl.

"Alkynylene" means an aliphatic bivalent radical derived from a C$_{2-6}$alkynyl group. Exemplary alkynylene radicals include ethynylene and propynylene.

"Amino acid side chains" means the substituent found on the carbon between the amino and carboxy groups in α-amino acids. For examples of "protected derivatives" of amino acid side chains, see T. W. Greene and P. G. M. Wuts in "Protective Groups in Organic Chemistry" John Wiley and Sons, 1991.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Aryl groups may be substituted with one or more aryl group substituents which may be the same or different, where "aryl group substituent" includes, for example, acyl, acylamino, alkoxy, alkoxycarbonyl, alkylenedioxy, alkylsulphinyl, alkylsulphonyl, alkylthio, aroyl, aroylamino, aryl, arylalkyloxy, arylalkyloxycarbonyl, arylalkylthio, aryloxy, aryloxycarbonyl, arylsulphinyl, arylsulphonyl, arylthio, carboxy, cyano, halo, heteroaroyl, heteroaryl, heteroarylalkyloxy, heteroaroylamino, heteroaryloxy, hydroxy, nitro, trifluoromethyl, Y$^1$Y$^2$N—, Y$^1$Y$^2$NCO—, Y$^1$Y$^2$NSO$_2$—, Y$^1$Y$^2$N—C$_{2-6}$alkylene-Z$^4$— {where Z$^4$ is O, NR$^6$ or S(O)$_n$}, alkylC(=O)—Y$^1$N—, alkylSO$_2$—Y$^1$N— or alkyl optionally substituted with aryl, heteroaryl, hydroxy, or Y$^1$Y$^2$N—.

"Arylalkenyl" means an aryl-alkenyl-group in which the aryl and alkenyl are as previously described. Preferred arylalkenyls contain a lower alkenyl moiety. Exemplary arylalkenyl groups include styryl and phenylallyl.

"Arylalkyl" means an aryl-alkyl-group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O—CO— group in which the arylalkyl groups is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Arylalkynyl" means an aryl-alkynyl-group in which the aryl and alkynyl are as previously described. Exemplary arylalkynyl groups include phenylethynyl and 3-phenylbut-2-ynyl.

"Arylene" means an optionally substituted bivalent radical derived from an aryl group. Exemplary arylene groups include optionally substituted phenylene, naphthylene and indanylene. When $Ar^1$ is arylene this may particularly represent an optionally substituted phenylene. Suitable substituents include one or more "aryl group substituents" as defined above, particularly halogen, methyl or methoxy.

"Aryloxy" means an aryl-O— group in which the aryl group is as previously described. Exemplary aryloxy groups include optionally substituted phenoxy and naphthoxy.

"Aryloxycarbonyl" means an aryl-O—C(=O)— group in which the aryl group is as previously described. Exemplary aryloxycarbonyl groups include phenoxycarbonyl and naphthoxycarbonyl.

"Arylsulphinyl" means an aryl-SO— group in which the aryl group is as previously described.

"Arylsulphonyl" means an aryl-$SO_2$— group in which the aryl group is as previously described.

"Arylsulphonylcarbamoyl" means an aryl-$SO_2$—NH—C(=O)— group in which the aryl group is as previously described.

"Arylthio" means an aryl-S— group in which the aryl group is as previously described. Exemplary arylthio groups include phenylthio and naphthylthio.

"Azaheteroaryl" means an aromatic carbocyclic moiety of about 5 to about 10 ring members in which one of the ring members is nitrogen and the other ring members are chosen from carbon, oxygen, sulphur, or nitrogen. Examples of azaheteroaryl groups include pyridyl, pyrimidinyl, quinolinyl, isoquinolinyl, quinazolinyl, imidazolyl, and benzimidazolyl.

"Azaheteroaryldiyl" means an optionally substituted bivalent radical derived from a heteroaryl group.

"Cyclic amine" means a 3 to 8 membered monocyclic cycloalkyl ring system where one of the ring carbon atoms is replaced by nitrogen and which (i) may optionally contain an additional heteroatom selected from O, S or $NY^3$ (where $Y^3$ is hydrogen, alkyl, arylalkyl, and aryl) and (ii) may be fused to additional aryl or heteroaryl ring to form a bicyclic ring system. Exemplary cyclic amines include pyrrolidine, piperidine, morpholine, piperazine, indoline and pyrindoline.

"Cycloalkenyl" means a non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl or cycloheptenyl.

"Cycloalkenylalkyl" means a cycloalkenyl-alkyl-group in which the cycloalkenyl and alkyl moieties are as previously described. Exemplary cycloalkenylalkyl groups include cyclopentenylmethyl, cyclohexenylmethyl or cycloheptenylmethyl.

"Cycloalkenylene" means a bivalent radical derived from an unsaturated monocyclic hydrocarbon of about 3 to about 10 carbon atoms by removing a hydrogen atom from each of two different carbon atoms of the ring. Exemplary cycloalkenylene radicals include cyclopentenylene and cyclohexenylene.

"Cycloalkyl" means a saturated monocyclic or bicyclic ring system of about 3 to about 10 carbon atoms optionally substituted by oxo. Exemplary monocyclic cycloalkyl rings include $C_{3-8}$cycloalkyl rings such as cyclopropyl, cyclopentyl, cyclohexyl and cycloheptyl.

"Cycloalkylalkenyl" means a cycloalkyl-alkenyl-group in which the cycloalkyl and alkenyl moieties are as previously described. Exemplary monocyclic cycloalkylalkenyl groups include cyclopentylvinylene and cyclohexylvinylene.

"Cycloalkylalkyl" means a cycloalkyl-alkyl-group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Cycloalkylalkynyl" means a cycloalkyl-alkynyl-group in which the cycloalkyl and alkynyl moieties are as previously described. Exemplary monocyclic cycloalkylalkynyl groups include cyclopropylethynyl, cyclopentylethynyl and cyclohexylethynyl.

"Cycloalkylene" means a bivalent radical derived from a saturated monocyclic hydrocarbon of about 3 to about 10 carbon atoms by removing a hydrogen atom from each of two different carbon atoms of the ring. Exemplary cycloalkenylene radicals include cyclopentylene and cyclohexylene.

"Halo" or "halogen" means fluoro, chloro, bromo, or iodo. Preferred are fluoro or chloro.

"Heteroaroyl" means a heteroaryl-C(=O)— group in which the heteroaryl group is as described herein. Exemplary groups include pyridylcarbonyl.

"Heteroaroylamino" means a heteroaroyl-NH— group in which the heteroaryl moiety are as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulphur (examples of such groups include benzimidazolyl, benzthiazolyl, furyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above); (ii) an optionally substituted partially saturated multicyclic heterocarbocyclic moiety in which a heteroaryl and a cycloalkyl or cycloalkenyl group are fused together to form a cyclic structure (examples of such groups include pyrindanyl groups). Optional substituents include one or more "aryl group substituents" as defined above. When $R^1$ or $L^1$ contains an optionally substituted heteroaryl group this may particularly represent an optionally substituted "azaheteroaryl" group.

"Heteroarylalkenyl" means a heteroaryl-alkenyl-group in which the heteroaryl and alkenyl moieties are as previously described. Preferred heteroarylalkenyl groups contain a lower alkenyl moiety. Exemplary heteroarylalkenyl groups include pyridylethenyl and pyridylallyl.

"Heteroarylalkyl" means a heteroaryl-alkyl-group in which the heteroaryl and alkyl moieties are as previously described. Preferred heteroarylalkyl groups contain a $C_{1-4}$alkyl moiety. Exemplary heteroarylalkyl groups include pyridylmethyl.

"Heteroarylalkyloxy" means an heteroarylalkyl-O— group in which the heteroarylalkyl group is as previously described. Exemplary heteroaryloxy groups include optionally substituted pyridylmethoxy.

"Heteroarylalkynyl" means a heteroaryl-alkynyl-group in which the heteroaryl and alkynyl moieties are as previously described. Exemplary heteroarylalkenyl groups include pyridylethynyl and 3-pyridylbut-2-ynyl.

"Heteroaryldiyl" means a bivalent radical derived from an aromatic monocyclic or multicyclic organic moiety of about 5 to about 10 ring members in which one or more of the ring members is/are element(s) other than carbon, for example nitrogen, oxygen or sulphur, and optionally substituted by one or more "aryl group substituents" as defined above. When $Ar^1$ is an optionally substituted heteroaryldiyl group this may particularly represent an optionally substituted "azaheteroaryldiyl" group.

"Heteroaryloxy" means an heteroaryl-O— group in which the heteroaryl group is as previously described. Exemplary heteroaryloxy groups include optionally substituted pyridyloxy.

"Heteroarylsulphonylcarbamoyl" means a heteroaryl-$SO_2$—NH—C(=O)— group in which the heteroaryl group is as previously described.

"Heterocycloalkyl" means: (i) a cycloalkyl group of about 3 to 7 ring members which contains one or more heteroatoms selected from O, S or $NY^3$ and which may optionally be substituted by oxo; (ii) an optionally substituted partially saturated multicyclic heterocarbocyclic moiety in which an aryl (or heteroaryl ring) and a heterocycloalkyl group are fused together to form a cyclic structure (examples of such groups include chromanyl, dihydrobenzofuranyl, indolinyl and pyrindolinyl groups).

"Heterocycloalkylalkyl" means a heterocycloalkyl-alkyl-group in which the heterocycloalkyl and alkyl moieties are as previously described.

"Heterocycloalkylene" means a bivalent radical derived from a saturated monocyclic hydrocarbon of about 5 to about 7 atoms, which contains one or more heteroatoms selected from O, S or $NY^3$ and is optionally substituted by oxo, by removing a hydrogen atom from each of two different carbon atoms of the ring, or when $NY^3$ is NH by removing a hydrogen atom from one carbon atom of the ring and a hydrogen atom from the NH, or when the ring contains two $NY^3$ heteroatoms and $NY^3$ is NH by removing a hydrogen atom from both nitrogen atoms. When $L^1$ is a heterocycloalkylene group this may particularly represent a bivalent radical derived pyrrolidine, especially 3,4-pyrrolidinediyl.

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule. Alternatively an ester of a compound of formula (I) containing a carboxy group may be convertible by hydrolysis in vivo to the parent molecule.

Suitable esters of compounds of formula (I) containing a hydroxy group, are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulphamates and quinates.

Suitable esters of compounds of formula (I) containing a carboxy group, are for example those described by F. J. Leinweber, Drug Metab. Res., 1987, 18, page 379.

Suitable esters of compounds of formula (I) containing both a carboxy group and a hydroxy group within the moiety —$L^1$—Y, include lactones, formed by loss of water between said carboxy and hydroxy groups. Examples of lactones include caprolactones and butyrolactones.

An especially useful class of esters of compounds of formula (I) containing a hydroxy group, may be formed from acid moieties selected from those described by Bundgaard et. al., J. Med. Chem., 1989, 32, page 2503–2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Where the compound of the invention contains a carboxy group, or a sufficiently acidic bioisostere, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, tetramethylammonium hydroxide, and the like.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

$R^1$ may particularly represent a group $R^3$—$Z^3$— in which $Z^3$ is as defined above, especially C(=O), and $R^3$ is as defined above, especially (i) optionally substituted aryl, such as optionally substituted phenyl [preferred optional substituents include aryloxy, cyano, halo (e.g. chloro or fluoro), lower alkoxy (e.g. methoxy), lower alkyl (e.g. methyl), nitro and perfluoroloweralkyl (e.g. trifluoromethyl)], (ii) optionally substituted heteroaryl, such as isoquinolinyl, isoxazolyl, pyrazolopyrimidinyl, pyridyl, pyrimidinyl, quinolinyl, thiazolyl and triazolyl, each optionally substituted by one or more aryl group substituents as described hereinbefore [preferred optional substituents include alkyl-C(=O)—, aryl, cyano, halo, (e.g. chloro or fluoro), lower alkoxy (e.g. methoxy), lower alkyl (e.g. methyl), lower alkylsulphonyl, lower alkylthio, nitro and perfluoroloweralkyl (e.g. trifluoromethyl)] or (iii) optionally substituted arylalkyl in which the aryl group is optionally substituted by one, or preferably two aryl group substituents (preferred optional substituents include halo, hydroxy and methoxy). $R^1$ may particularly represent a group $R^3$—C(=O)— in which $R^3$ is a substituted aryl selected from 2-chlorophenyl, 5-chloro-2-cyanophenyl, 2-chloro-6-methylphenyl, 2,6-dichlorophenyl, 2,6-difluorophenyl, 4-fluoro-2-trifluoromethyl, 2-methyl-4-nitrophenyl, 2-methyl-5-nitrophenyl, 2-nitrophenyl, 3-nitrophenyl, 2-phenoxyphenyl or an optionally substituted heteroaryl selected from quinolin-4-yl, isoquinolin-2-yl, 2,4-pyridin-3-yl, 2,6-dimethyl-4-trifluoromethylpyridin-3-yl, 4-trifluoromethylpyridin3-yl, 2-phenyl-4-methyl-1,2,3-triazol-5-yl, 3,5-dimethylisoxazol-4-yl, 2,7-dimethylpyrazolo-[1,5-a]pyrimidin-6-yl, 2-isopropyl-4-methylthiazol-5-yl, 4-trifluoromethylpyrimidin-5-yl, 4-hydroxybenzyl, 3-chloro-4-hydroxybenzyl, 3-fluoro-4-hydroxybenzyl, and 4-hydroxy-3-methoxybenzyl.

$R^1$ may also particularly represent a group $R^3$—$L^3$—$Ar^1$—$L^4$—$Z^3$— in which $Z^3$ is as defined above, especially C(=O); $L^4$ represents a straight or branched $C_{1-6}$alkylene chain, more particularly a straight $C_{1-4}$alkylene chain such as methylene or ethylene, preferably methylene; $Ar^1$ is an optionally substituted phenylene, such as optionally substituted m- or p-phenylene, preferably optionally substituted p-phenylene, more preferably a 3-substituted p-phenylene, in which the substituent is ortho to the $R^3$—$L^3$— group, (preferred optional substituents include halo, $C_{1-4}$alkyl, $C_{1-4}$alkoxy, $C_{1-4}$alkylthio, $C_{1-4}$alkylsulphinyl and $C_{1-4}$alkylsulphonyl, especially chloro, methyl, methoxy, methylthio, methylsulphinyl and methylsulphonyl), or $Ar^1$ is an optionally substituted heteroaryldiyl, such as optionally substituted azaheteroaryidiyl, (e.g. optionally substituted pyridinediyl, preferably a p-pyridinediyl), where the optional substituents include $C_{1-4}$alkyl and $C_{1-4}$alkoxy, especially methyl and methoxy, more preferably a pyridine-2,5-diyl, in which the $R^3$—$L^3$— group is adjacent to the pyridyl nitrogen atom, and which is substituted in the 4- or 6-position with a methyl or methoxy group; $L^3$ represents a —NH—C(=O)—NH— linkage; and $R^3$ is as defined above, particularly an optionally substituted aryl group (such as optionally substituted phenyl) or an optionally substituted heteroaryl (such as optionally substituted pyridyl), and is preferably 2- or 3-methyl(or methoxy) phenyl, more preferably 2-methylphenyl, or 3-methyl-2-pyridyl.

$R^1$ may also particularly represent a group $R^3$—$L^3$—$Ar^1$—$L^4$—$Z^3$— in which: $Z^3$ is as defined above, especially C(=O); $L^4$ represents a straight or branched $C_{1-6}$alkylene chain, more particularly a straight $C_{1-4}$alkylene chain such as methylene or ethylene, preferably methylene; $Ar^1$ is an 8 to 10 membered bicyclic system

in which (i) ring

is a 5 or 6 membered optionally substituted heterocycle, preferably a 5 membered heteroaryl ring, (ii) ring

is a 5 or 6 membered optionally substituted heterocycle or an optionally substituted benzene ring, preferably a benzene ring, (iii) each ring is optionally substituted by one or more "aryl group substituents" as defined above, (iv) the two rings are joined together by a carbon-carbon linkage or a carbon-nitrogen linkage, and

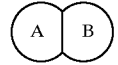

is preferably optionally substituted benzoxazolyl or optionally substituted benzimidazolyl, each [more particularly ring

]

optionally substituted by one or more "aryl group substituents" as defined above [examples of particular aryl group substituents include lower alkyl (e.g. methyl), lower alkoxy (e.g. methoxy), amino, halogen, hydroxy, lower alkylthio, lower alkylsulphinyl, lower alkylsulphonyl, nitro or trifluoromethyl]; $L^3$ represents $NR^5$, especially NH; and $R^3$ is as defined above, particularly optionally substituted aryl, such as a 2-substituted phenyl, [examples of particular aryl group substituents include lower alkyl (e.g. methyl), lower alkoxy (e.g. methoxy), halo (e.g. fluoro or chloro) and $Y^1Y^2N-$ (e.g. dimethylamino)], and is preferably 2-methylphenyl.

$R^1$ may also particularly represent a group $R^3-L^3-Ar^1-L^4-Z^3-$ in which: $Z^3$ is as defined above, especially $C(=O)$; $L^4$ represents a straight or branched $C_{1-6}$alkylene chain, more particularly a straight $C_{1-4}$alkylene chain such as methylene or ethylene, preferably methylene; $Ar^1$ is an optionally substituted phenylene, such as optionally substituted m- or p-phenylene, preferably optionally substituted p-phenylene more preferably a 3-substituted p-phenylene, in which the substituent is ortho to the $R^3-L^3-$ group, (preferred optional substituents include chloro, $C_{1-4}$alkyl, $C_{1-4}$alkoxy, $C_{1-4}$alkylthio, $C_{1-4}$alkylsulphinyl and $C_{1-4}$alkylsulphonyl, especially chloro, methyl, methoxy, methylthio, methylsulphinyl and methylsulphonyl), or $Ar^1$ is an optionally substituted heteroaryldiyl, such as optionally substituted azaheteroaryidiyl, (e.g. optionally substituted pyridinediyl, preferably a p-pyridinediyl), where the optional substituents include $C_{1-4}$alkyl and $C_{1-4}$alkoxy, especially methyl and methoxy, more preferably a pyridine-2,5-diyl, in which the $R^3-L^3-$ group is adjacent to the pyridyl nitrogen atom, and which is substituted in the 4- or 6-position with a methyl or methoxy group; $L^3$ represents $-C(=O)-NH-$ and $R^3$ is heterocycloalkyl, more particularly a bicyclic amine containing 9–10 atoms, especially indolinyl.

$R^2$ may particularly represent hydrogen.

$R^2$ may also particularly represent lower alkyl, (e.g. methyl).

$R^2$ may also particularly represent lower alkoxy (e.g. methoxy).

$A^1$ may particularly represent an unsubstituted straight chain $C_{1-3}$alkylene linkage, i.e. methylene, ethylene and trimethylene, especially methylene or ethylene.

$Z^1$ may particularly represent $C(R^7)(R^{7a})$, especially where $R^7$ and $R^{7a}$ are both hydrogen.

$L^1$ may particularly represent an optionally substituted alkylene linkage, especially optionally substituted ethylene or propylene, preferably optionally substituted ethylene. Preferred optional substituents include lower alkyl, aryl, heteroaryl, $-N(R^8)-C(=O)-R^9$, $-N(R^8)-C(=O)-OR^9$, $-N(R^8)-SO_2-R^9$, $-NY^4Y^5$ and $-[C(=O)-N(R^{10})-C(R^5)(R^{11})]_p-C(=O)-NY^4Y^5$ or alkyl substituted by carboxy (or an acid bioisostere), $-ZH$, $-ZR^3$, $-C(=O)-NY^4Y^5$ or $-NY^4Y^5$.

In one preferred embodiment $L^1$ is a group

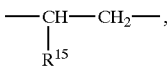

where $R^5$ is hydrogen or lower alkyl (e.g. methyl) and $R^{15}$ represents hydrogen or lower alkyl, or where $R^5$ is hydrogen and $R^{15}$ represents aryl, heteroaryl, $-N(R^8)-C(=O)-R^9$, $-N(R^8)-C(=O)-OR^9$, $-N(R^8)-SO_2-R^9$, $-NY^4Y^5$ or $-[C(=O)-N(R^{10})-C(R^5)(R^{11})]_p-C(=O)-NY^4Y^5$, or alkyl substituted by carboxy (or an acid bioisostere), $-ZH$, $-ZR^3$, $-C(=O)-NY^4Y^5$ or $-NY^4Y^5$], and is more preferably a group

particularly

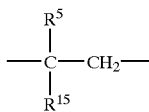

[where $R^{15}$ represents hydrogen, lower alkyl, aryl, heteroaryl, $-N(R^8)-C(=O)-R^9$, $-N(R^8)-C(=O)-OR^9$, $-N(R^8)-SO_2-R^9$ or $-NY^4Y^5$ or alkyl substituted by carboxy, $-OH$, $-OR^3$ or $-C(=O)-NY^4Y^5$]. In another preferred embodiment $L^1$ is a group

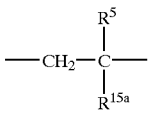

[where $R^5$ is hydrogen or lower alkyl (e.g. methyl) and $R^{15a}$ represents lower alkyl, or where $R^5$ is hydrogen and $R^{15a}$ represents aryl, heteroaryl, $-N(R^8)-C(=O)-R^9$, $-N(R^8)-C(=O)-OR^9$, $-N(R^8)-SO_2-R^9$, $-NY^4Y^5$ or $-[C(=O)-N(R^{10})-C(R^5)(R^{11})]_p-C(=O)-NY^4Y^5$, or alkyl substituted by carboxy (or an acid bioisostere), $-ZH$, $-ZR^3$, $-C(=O)-NY^4Y^5$ or $-NY^4Y^5$], and is more preferably a group

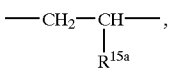

particularly

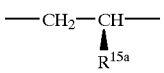

[where $R^{15a}$ represents $-N(R^8)-C(=O)-R^9$, or $-N(R^8)-SO_2-R^9$].

$L^1$ may also particularly represent an unsubstituted alkenylene linkage, especially vinylene.

$L^1$ may also particularly represent a $-Z^2-R^{12}-$ linkage, such as $-O-CH_2-$, $-S(O)_n-CH_2-$, $-S(O)_n-CH_2-CH_2-$, or especially $-NH-CH_2-$.

$L^1$ may also particularly represent a $-L^5-L^6-L^7-$ linkage, in which (i) $L^5$ and $L^7$ are both a direct bond and $L^6$ is optionally substituted heterocycloalkylene, such as pyrrolidindiyl, especially 3,4-pyrrolidindiyl, or cycloalkylene, such as cyclopentyl, (ii) $L^5$ is alkylene, such as methylene, $L^6$ is cycloalkylene, such as cyclopentyl, and $L^7$ is a direct bond, or (iii) $L^5$ is a direct bond, $L^6$ is cycloalkylene, such as cyclopentyl, and $L^7$ is alkylene, such as methylene.

Y may particularly represent carboxy.

It is to be understood that this invention covers all appropriate combinations of the particular and preferred groupings referred to herein.

A particular group of compounds of the invention are compounds of formula (Ix):

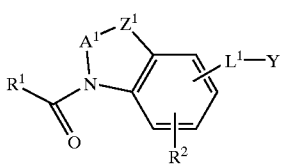

(Ix)

wherein:
$R^1$ represents a group selected from:
(i) $R^3$—
(ii) $R^3$—$L^2$—$R^4$—
(iii) $R^3$—$L^3Ar^1$—$L^4$—
(iv) $R^3$—$L^3$—$Ar^1$—$L^2$—$R^4$—

[where:
$R^3$ is alkyl, alkenyl, alkynyl, aryl, arylalkyl, arylalkenyl, arylalkynyl, cycloalkyl, cycloalkylalkyl, cycloalkylalkenyl, cycloalkylalkynyl, cycloalkenyl, cycloalkenylalkyl, heteroaryl, heteroarylalkyl, heteroarylalkenyl, heteroarylalkynyl, heterocycloalkyl or heterocycloalkylalkyl;

$L^2$ represents a —$NR^5$—$C(=Z)$—$NR^5$—, —$C(=Z)$—$NR^5$—, —$C(=O)$—, —$C(=Z)$—O—, —$NR^5$—C(=Z)—, —Z—, —SO—, —$SO_2$—, —$NR^5$—, —$SO_2$—$NR^5$—, —$NR^5$—$SO_2$—, —$NR^5$—C(=O)—O—, —O—C(=O)—, or —O—C(=O)—$NR^5$— linkage;

$L^3$ represents a heteroaryldiyl, heterocycloalkylene, —$NR^5$—C(=Z)—$NR^5$—, —C(=Z)—$NR^5$—, —C(=Z)—O—, —$NR^5$—C(=Z)—, —Z—, —SO—, —$SO_2$—, —$NR^5$—, —$S_2$—$NR^5$—, —$NR^5$—$SO_2$—, $NR^5$—C(=O)—O—, —O—C(=O)—, or —O—C(=O)—$NR^5$— linkage;

$L^4$ is a direct bond, an alkylene, alkenylene or alkynylene chain, or a —$L^5$—$NR^5$— linkage;
$L^5$ is a direct bond or an alkylene chain;
$R^4$ is an alkylene chain, an alkenylene chain, or an alkynylene chain;
$R^5$ is hydrogen or lower alkyl;
$Ar^1$ is phenylene or heteroaryldiyl; and
Z represents an oxygen or sulphur atom;
but excluding compounds where an oxygen, nitrogen or sulphur atom is attached directly to a carbon carbon multiple bond of an alkenylene or alkynylene residue];

$R^2$ represents hydrogen, halogen, lower alkyl or lower alkoxy;

$A^1$ represents a straight chain $C_{1-3}$alkylene linkage optionally substituted by one or more groups chosen from alkyl, aryl, arylalkyl, heteroaryl, heteroarylalkyl, imino, oxo, thioxo, or alkyl substituted by —$ZR^6$, —$NY^1Y^2$, —$CO_2R^6$ or —C(=O)—$NY^1Y^2$ [where: $R^6$ is hydrogen, alkyl, aryl, arylalkyl, cycloalkyl, cycloalkylalkyl, heteroaryl or heteroarylalkyl; and $Y^1$ and $Y^2$ are independently hydrogen, alkenyl, alkyl, aryl, arylalkyl, cycloalkyl, heteroaryl or heteroarylalkyl; or the group —$NY^1Y^2$ may form a heterocycloalkyl group];

$Z^1$ represents $C(R^7)(R^{7a})$ or C(=O) {where $R^7$ and $R^{7a}$ are each independently hydrogen or lower alkyl};

$L^1$ represents:
(i) a direct bond;
(ii) an alkenylene, alkylene, alkynylene, cycloalkenylene, cycloalkylene, heteroaryldiyl, heterocycloalkylene or arylene linkage each optionally substituted by (a) an acidic functional group (or corresponding protected derivative), $R^3$, —C(=O)—$R^3$, —N($R^8$)—C(=O)—$R^9$, —N($R^8$)—C(=O)—$OR^9$, —N($R^8$)—$SO_2$—$R^9$, —[C(=O)—N($R^{10}$)—C($R^5$)($R^{11}$)]$_p$—C(=O)—$NY^4Y^5$ or —$NY^4Y^5$, or by (b) alkyl substituted by an acidic functional group (or corresponding protected derivative), or by —C(=O)—$NY^4Y^5$ or —$NY^4Y^5$;

(iii) a —[C(=O)—N($R^{10}$)—C($R^5$)($R^{11}$)]$_p$— linkage;
(iv) a —$Z^2$—$R^{12}$— linkage;
(v) a —C(=O)—$CH_2$—C(=O)— linkage;
(vi) a —$R^{12}$—$Z^2$—$R^{12}$— linkage; or
(vii) a —C($R^4$)($R^{13}$)—[C(=O)—N($R^{10}$)—C($R^5$)($R^{11}$)]$_p$— linkage;

{in which
$R^8$ is hydrogen, alkyl, aryl, arylalkyl, cycloalkyl, cycloalkylalkyl, heteroaryl, heteroarylalkyl, heterocycloalkyl or heterocycloalkylalkyl;

$R^9$ is alkyl, aryl, cycloalkyl, heteroaryl or heterocycloalkyl, or alkyl substituted by aryl, an acidic functional group (or corresponding protected derivative), cycloalkyl, heteroaryl, heterocycloalkyl, —ZH, —$ZR^3$, —C(=O)—$NY^4Y^5$ or —$NY^4Y^5$;

$R^{10}$ is hydrogen, $R^3$ or alkyl substituted with alkoxy, cycloalkyl, hydroxy, mercapto, alkylthio or —$NY^4Y^5$;

$R^{11}$ and $R^{13}$ are each independently selected from hydrogen or a group consisting amino acid side chains and corresponding protected derivatives, an acidic functional group (or corresponding protected derivative), $R^3$, —C(=O)—$R^3$, or —C(=O)—$NY^4Y^5$, or alkyl substituted by an acidic functional group (or corresponding protected derivative) or by $R^3$, —$NY^4Y^5$, —NH—C(=O)—$R^3$, —C(=O)—$R^4$—$NH_2$, —C(=O)—$Ar^1$—$NH_2$, —C(=O)—$R^4$—$CO_2H$, or —C(=O)—$NY^4Y^5$;

or $R^{10}$ and $R^{11}$ or $R^{10}$ and $R^{12}$ together with the atoms to which they attached form a 3- to 6-membered heterocycloalkyl ring;

$R^{12}$ is $C_{1-6}$alkylene, optionally substituted by $R^3$;

$Y^4$ and $Y^5$ are independently hydrogen, alkenyl, alkyl, alkynyl, aryl, cycloalkenyl, cycloalkyl, heteroaryl, heterocycloalkyl, or alkyl substituted by alkoxy, aryl, cyano, cycloalkyl, heteroaryl, heterocycloalkyl, hydroxy, oxo, —$NY^1Y^2$, or one or more —$CO_2R^7$ or —C(=O)—$NY^1Y^2$ groups; or the group —$NY^4Y^5$ may form a 5- to 7-membered cyclic amine which (i) may be optionally substituted with one or more substituents selected from alkoxy, carboxamido, carboxy, hydroxy, oxo (or a 5-, 6- or 7-membered cyclic acetal derivative thereof), $R^{10}$; (ii) may also contain a further heteroatom selected from O, S, $SO_2$, or $NY^6$ [where $Y^6$ is hydrogen, alkyl, aryl, arylalkyl, —C(=O)—$R^{14}$, —C(=O)—$OR^{14}$ or —$SO_2R^{14}$ (in which $R^{14}$ is alkyl, aryl, arylalkyl, cycloalkyl, cycloalkylalkyl, heteroaryl, heteroarylalkyl, heterocycloalkyl or heterocycloalkylalkyl)]; and (iii) may also be fused to additional aryl, heteroaryl, heterocycloalkyl or cycloalkyl rings to form a bicyclic or tricyclic ring system;

$Z^2$ is O, S(O)$_n$, $NR^5$, $SONR^5$, C(=O)$NR^5$ or C(=O); and
p is zero or an integer 1 to 4}; and
Y is carboxy (or an acid bioisostere) or —C(=O)—$NY^4Y^5$];

and the corresponding N-oxides, and their prodrugs; and pharmaceutically acceptable salts and solvates (e.g. hydrates) of such compounds and their N-oxides and prodrugs.

Another particular group of compounds of the invention are compounds of formula (Ia):

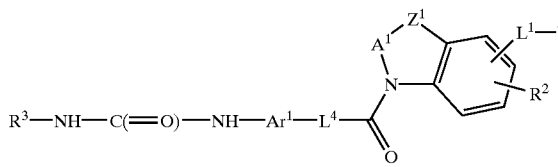
(Ia)

in which $R^2$, $R^3$, $A^1$, $Ar^1$, $L^1$, $L^4$, Y and $Z^1$ are as hereinbefore defined, and the corresponding N-oxides, and their prodrugs; and pharmaceutically acceptable salts and solvates (e.g. hydrates) of such compounds and their N-oxides and prodrugs.

Compounds of formula (Ia) in which $R^3$ represents an optionally substituted aryl group, particularly an optionally substituted phenyl group, such as a 2-substituted phenyl, especially 2-methylphenyl, are preferred.

Compounds of formula (Ia) in which $R^3$ represents an optionally substituted heteroaryl group, particularly an optionally substituted pyridyl, such as optionally substituted 2-pyridyl, especially 3-methyl-2-pyridyl, are also preferred.

Compounds of formula (Ia) in which $Ar^1$ represents an optionally substituted phenylene, especially optionally substituted m- or p-phenylene, more especially optionally substituted p-phenylene, are preferred. Compounds of formula (Ia) in which $Ar^1$ represents 3-substituted p-phenylene, in which the substituent is ortho to the $R^3$—NH—C(=O)—NH— group, are particularly preferred. Preferred optional substituents include halo, $C_{1-4}$alkyl, $C_{1-4}$alkoxy, $C_{1-4}$alkylthio, $C_{1-4}$alkylsulphinyl and $C_{1-4}$alkylsulphonyl, especially chloro, methyl, methoxy, methylthio, methylsulphinyl and methylsulphonyl.

Compounds of formula (Ia) in which $Ar^1$ is an optionally substituted heteroaryldiyl, such as optionally substituted pyridinediyl, particularly a p-pyridinediyl, more particularly a pyridine-2,5-diyl, in which the $R^3$—NH—C(=O)—NH— group is adjacent to the pyridyl nitrogen atom, and which is substituted in the 4- or 6-position, are also preferred. Preferred optional substituents include $C_{1-4}$alkyl and $C_{1-4}$alkoxy, especially methyl and methoxy.

Compounds of formula (Ia) in which $L^4$ represents a straight or branched $C_{1-6}$alkylene chain, more particularly a straight $C_{1-4}$alkylene chain such as methylene or ethylene, especially methylene, are preferred.

Compounds of formula (Ia) in which $A^1$ represents methylene are preferred.

Compounds of formula (Ia) in which $A^1$ represents ethylene are also preferred.

Compounds of formula (Ia) in which $Z^1$ represents $CH_2$ are preferred.

Compounds of formula (Ia) in which $R^2$ represents hydrogen are preferred.

Compounds of formula (Ia) in which $L^1$ represents an optionally substituted alkylene linkage, particularly optionally substituted ethylene or optionally substituted propylene, especially ethylene optionally substituted with lower alkyl, aryl, heteroaryl, —N($R^8$)—C(=O)—$R^9$, N($R^8$)—C(=O)—OR$^9$, —N($R^8$)—SO$_2$—$R^9$, —NY$^4$Y$^5$ or —[C(=O)—N($R^{10}$)—C($R^5$)($R^{11}$)]$_p$—C(=O)—NY$^4$Y$^5$, or alkyl substituted by carboxy (or an acid bioisostere), —ZH, —ZR$^3$, —C(=O)—NY$^4$Y$^5$ or —NY$^4$Y$^5$, are preferred. In one preferred embodiment $L^1$ is a group

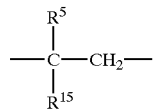

[where $R^5$ is hydrogen or lower alkyl (e.g. methyl) and $R^{15}$ represents hydrogen or lower alkyl, or where $R^5$ is hydrogen and $R^{15}$ represents aryl, heteroaryl, —N($R^8$)—C(=O)—$R^9$, —N($R^8$)—C(=O)—OR$^9$, —N($R^8$)—SO$_2$—$R^9$, —NY$^4$Y$^5$ or —[C(=O)—N($R^{10}$)—C($R^5$)($R^{11}$)]$_p$—C(=O)—NY$^4$Y$^5$, or alkyl substituted by carboxy (or an acid bioisostere), —ZH, —ZR$^3$, —C(=O)—NY$^4$Y$^5$ or —NY$^4$Y$^5$], and is more preferably a group

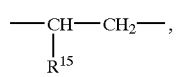

particularly

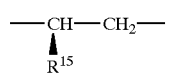

[where $R^{15}$ represents hydrogen, lower alkyl, aryl, heteroaryl, —N($R^8$)—C(=O)—$R^9$, —N($R^8$)—C(=O)—OR$^9$, —N($R^8$)—SO$_2$—$R^9$ or —NY$^4$Y$^5$ or alkyl substituted by carboxy, —OH, —OR$^3$ or —C(=O)—NY$^4$Y$^5$]. In another preferred embodiment $L^1$ is a group

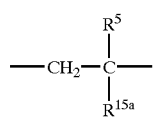

[where $R^5$ is hydrogen or lower alkyl (e.g. methyl) and $R^{15a}$ represents lower alkyl, or where $R^5$ is hydrogen and $R^{15a}$ represents aryl, heteroaryl, —N($R^8$)—C(=O)—$R^9$, —N($R^8$)—C(=O)—OR$^9$, —N($R^8$)—SO$_2$—$R^9$, —NY$^4$Y$^5$ or —[C(=O)—N($R^{10}$)—C($R^5$)($R^{11}$)]$_p$—C(=O)—NY$^4$Y$^5$, or alkyl substituted by carboxy (or an acid bioisostere), —ZH, —ZR$^3$, —C(=O)—NY$^4$Y$^5$ or —NY$^4$Y$^5$], and is more preferably a group

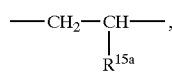

particularly

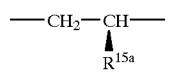

[where $R^{15a}$ represents —N($R^8$)—C(=O)—$R^9$, or —N($R^8$)—SO$_2$—$R^9$].

Compounds of formula (Ia) in which Y represents carboxy are preferred.

A preferred group of compounds of the invention are compounds of formula (Ia) in which: $R^2$ is hydrogen; $R^3$ is a 2-substituted phenyl [especially 2-methyl(or methoxy) phenyl]; $A^1$ is methylene or ethylene; $Ar^1$ is optionally substituted m- or p-phenylene (especially 3-chloro-p-phenylene, 3-methyl-p-phenylene, 3-methoxy-p-phenylene, 3-methylthio-p-phenylene, 3-methylsulphinyl-p-phenylene and 3-methylsulphonyl-p-phenylene) or optionally substituted p-pyridinediyl [especially 4(or 6)-methyl(or methoxy)-p-pyridine-2,5-diyl]; L¹ is a

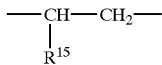

group particularly a

group, where R¹⁵ represents hydrogen, lower alkyl, aryl, heteroaryl, —N(R⁸)—C(=O)—R⁹, —N(R⁸)—C(=O)—OR⁹, —N(R⁸)—SO₂—R⁹ or —NY⁴Y⁵, or alkyl substituted by carboxy (or an acid bioisostere), —OH, —OR³, —C(=O)—NY⁴Y⁵; L⁴ represents a straight or branched C₁₋₆alkylene chain, especially methylene; Y represents carboxy; and Z¹ represents CH₂; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Ia) in which: R² is hydrogen; R³ is a 2-substituted phenyl [especially 2-methyl(or methoxy) phenyl]; A¹ is methylene or ethylene; Ar¹ is optionally substituted m or p-phenylene (especially 3-chloro-p-phenylene, 3-methyl-p-phenylene, 3-methoxy-p-phenylene, 3-methylthio-p-phenylene, 3-methylsulphinyl-p-phenylene and 3-methylsulphonyl-p-phenylene) or optionally substituted p-pridinediyl [especially 4(or 6)-methyl(or methoxy)-p-pyridine-2,5-diyl]; L¹ is a

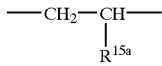

group, particularly

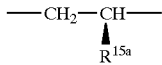

[where R¹⁵ᵃ represents —N(R⁸)—C(=O)—R⁹, or —N(R⁸)—SO₂—R⁹]; L⁴ represents a straight or branched C₁₋₆alkylene chain, especially methylene; Y represents carboxy; and Z¹ represents CH₂; and the corresponding N-oxides, and their prodrugs; and pharmaceutically acceptable salts and solvates (e.g. hydrates) of such compounds and their N-oxides and prodrugs.

Another particular group of compounds of the invention are compounds of formula (Ib):

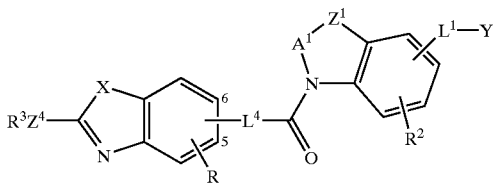

(Ib)

in which R², R³, A¹, L², Y and Z¹ are as hereinbefore defined, X is NR⁵ or O, Z⁴ represents a direct bond, NR⁵, O or S(O)ₙ (where R⁵ and n are as hereinbefore defined), and R is hydrogen or an aryl group substituent, and the corresponding N-oxides, and their prodrugs; and pharmaceutically acceptable salts and solvates (e.g. hydrates) of such compounds and their N-oxides and prodrugs.

Compounds of formula (Ib) in which R³ represents optionally substituted aryl, especially 2-substituted phenyl, are preferred. Preferred optional substituents include lower alkyl (e.g. methyl), lower alkoxy (e.g. methoxy), halo (e.g. fluoro or chloro) and Y¹Y²N— (e.g. dimethylamino). R³ especially represents ortho-tolyl.

Compounds of formula (Ib) in which Z⁴ represents NH are preferred.

Compounds of formula (Ib) in which R represents hydrogen, halo (e.g. chloro), lower alkyl (e.g. methyl or ethyl) or lower alkoxy (e.g. methoxy) are preferred.

Compounds of formula (Ib) in which L⁴ represents a straight or branched C₁₋₆alkylene chain, especially a straight or branched C₁₋₄alkylene chain, more especially methylene, are preferred.

Compounds of formula (Ib) in which A¹ represents methylene are preferred.

Compounds of formula (Ib) in which A¹ represents ethylene are also preferred.

Compounds of formula (Ib) in which Z¹ represents CH₂ are preferred.

Compounds of formula (Ib) in which R² represents hydrogen are preferred.

Compounds of formula (Ib) in which L¹ represents an optionally substituted alkylene linkage, particularly optionally substituted ethylene or optionally substituted propylene, especially ethylene optionally substituted with lower alkyl, aryl, heteroaryl, —N(R⁸)—C(=O)—R⁹, —N(R⁸)—C(=O)—OR⁹, —N(R⁸)—SO₂—R⁹, —NY⁴Y⁵ or —[C(=O)—N(R¹⁰)—C(R⁵)(R¹¹)]ₚ—C(=O)—NY⁴Y⁵, or alkyl substituted by carboxy (or an acid bioisostere), —ZH, —ZR³, —C(=O)—NY⁴Y⁵ or —NY⁴Y⁵, are preferred. In one preferred embodiment L¹ is a group

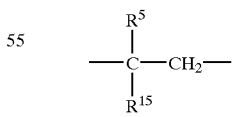

[where R⁵ is hydrogen or lower alkyl (e.g. methyl) and R¹⁵ represents hydrogen or lower alkyl, or where R⁵ is hydrogen and R¹⁵ represents aryl, heteroaryl, —N(R⁸)—C(=O)—R⁹, —N(R⁸)—C(=O)—OR⁹, —N(R⁸)—SO₂—R⁹, —NY⁴Y⁵ or —[C(=O)—N(R¹⁰)—C(R⁵)(R¹¹)]ₚ—C(=O)—NY⁴Y⁵, or alkyl substituted by carboxy (or an acid bioisostere), —ZH, —ZR³, —C(=O)—NY⁴Y⁵ or —NY⁴Y⁵], and is more preferably a group

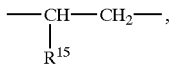

particularly

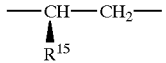

[where $R^{15}$ represents hydrogen, lower alkyl, aryl, heteroaryl, —N($R^8$)—C(=O)—$R^9$, —N($R^8$)—C(=O)—O$R^9$, —N($R^8$)—SO$_2$—$R^9$ or —N$Y^4Y^5$ or alkyl substituted by carboxy, —OH, —O$R^3$ or —C(=O)—N$Y^4Y^5$]. In another preferred embodiment $L^1$ is a group

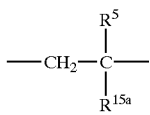

[where $R^5$ is hydrogen or lower alkyl (e.g. methyl) and $R^{15a}$ represents lower alkyl, or where $R^5$ is hydrogen and $R^{15a}$ represents aryl, heteroaryl, —N($R^8$)—C(=O)—$R^9$, —N($R^8$)—C(=O)—O$R^9$, —N($R^8$)—SO$_2$—$R^9$, —N$Y^4Y^5$ or —[C(=O)—N($R^{10}$)—C($R^5$)($R^{11}$)]$_p$—C(=O)—N$Y^4Y^5$, or alkyl substituted by carboxy (or an acid bioisostere), —ZH, —Z$R^3$, —C(=O)—N$Y^4Y^5$ or —N$Y^4Y^5$], and is more preferably a group

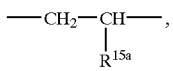

particularly

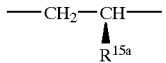

[where $R^{15a}$ represents —N($R^8$)—C(=O)—$R^9$, or —N$R^8$)—SO$_2$—$R^9$].

Compounds of formula (Ib) in which Y represents carboxy are preferred.

The group

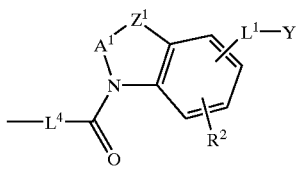

may preferably be attached at the ring 6 position or the ring 5 or 6 position when X is N$R^5$ and $R^5$ is lower alkyl.

A preferred group of compounds of the invention are compounds of formula (Ib) in which: R is hydrogen, chloro, methyl, ethyl or methoxy; $R^2$ is hydrogen; $R^3$ is optionally substituted aryl (especially ortho-tolyl); $A^1$ is methylene or ethylene; $L^1$ is a

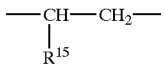

group particularly a

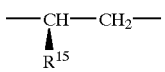

group, where $R^{15}$ represents hydrogen, lower alkyl, aryl, heteroaryl, —N($R^8$)—C(=O)—$R^9$, —N($R^8$)—C(=O)—O$R^9$, —N($R^8$)—SO$_2$—$R^9$ or —N$Y^4Y^5$, or alkyl substituted by carboxy (or an acid bioisostere), —OH, —Z$R^3$, —C(=O)—N$Y^4Y^5$ or —N$Y^4Y^5$; $L^4$ is a straight or branched $C_{1-4}$alkylene chain, especially methylene; X is O; Y is carboxy; $Z^1$ is CH$_2$; $Z^4$ is NH; and the group

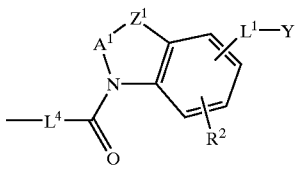

is attached at the ring 6 position; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Ib) in which: R is hydrogen, chloro, methyl, ethyl or methoxy; $R^2$ is hydrogen; $R^3$ is optionally substituted aryl (especially ortho-tolyl); $A^1$ is methylene or ethylene; $L^1$ is a

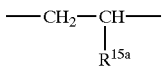

group, particularly

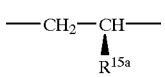

[where $R^{15a}$ represents —N($R^8$)—C(=O)—$R^9$, or —N($R^8$)—SO$_2$—$R^9$]; $L^4$ is a straight or branched $C_{1-4}$alkylene chain, especially methylene; X is O; Y is carboxy; $Z^1$ is CH$_2$; $Z^4$ is NH; and the group

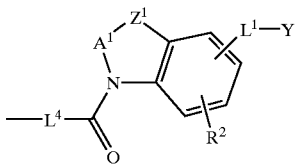

is attached at the ring 6 position; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Ib) in which: $R^2$ is hydrogen; $R^3$ is optionally substituted aryl (especially ortho-tolyl); $A^1$ is methylene or ethylene; $L^1$ is a

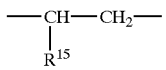

group particularly a

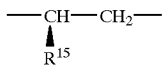

group, where R¹⁵ represents hydrogen, lower alkyl, aryl, heteroaryl, —N(R⁸)—C(=O)—R⁹, —N(R⁸)—C(=O)—OR⁹, —N(R⁸)—SO₂—R⁹ or —NY⁴Y⁵, or alkyl substituted by carboxy (or an acid bioisostere), —OH, —OR³, —C(=O)—NY⁴Y⁵ or —NY⁴Y⁵; L⁴ is a straight or branched $C_{1-4}$alkylene chain, (especially methylene); X is NR⁵ (especially NH); Y is carboxy; Z¹ is CH₂; Z⁴ is NH; and the group

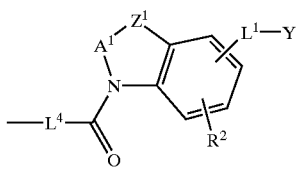

is attached at the ring 5 or 6 position; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Ib) in which: R² is hydrogen; R³ is optionally substituted aryl (especially ortho-tolyl); A¹ is methylene or ethylene; L¹ is a

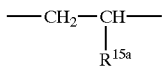

group, particularly

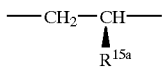

[where R¹⁵ᵃ represents —N(R⁸)—C(=O)—R⁹, or —N(R⁸)—SO₂—R⁹]; L⁴ is a straight or branched $C_{1-4}$alkylene chain, (especially methylene); X is NR⁵ (especially NH); Y is carboxy; Z¹ is CH₂; Z⁴ is NH; and the group

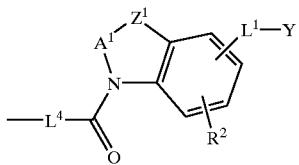

is attached at the ring 5 or 6 position; and the corresponding N-oxides, and their prodrugs; and pharmaceutically acceptable salts and solvates (e.g. hydrates) of such compounds and their N-oxides and prodrugs.

Another particular group of compounds of the invention are compounds of formula (Ic):

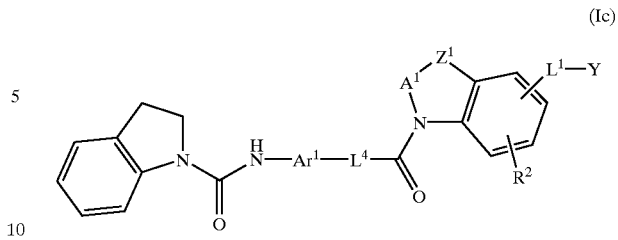

in which Ar¹, L⁴, A¹, R², L¹, Y and Z¹ are as hereinbefore defined, and the corresponding N-oxides, and their prodrugs; and pharmaceutically acceptable salts and solvates (e.g. hydrates) of such compounds and their N-oxides and prodrugs.

Compounds of formula (Ic) in which Ar¹ represents an optionally substituted phenylene, especially optionally substituted m- or p-phenylene, more especially optionally substituted p-phenylene, are preferred. Compounds of formula (Ic) in which Ar¹ represents 3-substituted p-phenylene, in which the substituent is ortho to the

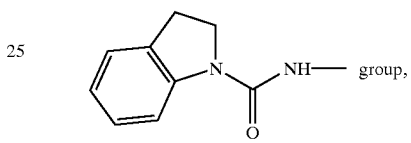

are particularly preferred. Preferred optional substituents include halo, $C_{1-4}$alkyl, $C_{1-4}$alkoxy, $C_{1-4}$alkylthio, $C_{1-4}$alkylsulphinyl and $C_{1-4}$alkylsulphonyl, especially chloro, methyl, methoxy, methylthio, methylsulphinyl and methylsulphonyl.

Compounds of formula (Ic) in which Ar¹ is an optionally substituted heteroaryldiyl, such as optionally substituted pyridinediyl, particularly a p-pyridinediyl, more particularly a pyridine-2,5-diyl, in which the

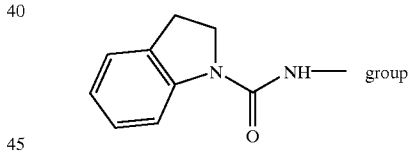

is adjacent to the pyridyl nitrogen atom, and which is substituted in the 4- or 6-position, are also preferred. Preferred optional substituents include $C_{1-4}$alkyl and $C_{1-4}$alkoxy, especially methyl and methoxy.

Compounds of formula (Ic) in which L⁴ represents a straight or branched $C_{1-6}$alkylene chain, especially a straight or branched $C_{1-4}$alkylene chain, more especially methylene, are preferred.

Compounds of formula (Ic) in which A¹ represents methylene are preferred.

Compounds of formula (Ic) in which A¹ represents ethylene are also preferred.

Compounds of formula (Ic) in which Z¹ represents CH₂ are preferred.

Compounds of formula (Ic) in which R² represents hydrogen are preferred.

Compounds of formula (Ic) in which L¹ represents an optionally substituted alkylene linkage, particularly optionally substituted ethylene or optionally substituted propylene, especially ethylene optionally substituted with lower alkyl, aryl, heteroaryl, —N(R⁸)—C(=O)—R⁹, —N(R⁸)—C (=O)—OR⁹, —N(R⁸)—SO₂—R⁹, —NY⁴Y⁵ or —[C(=O)—N(R¹⁰)—C(R⁵)(R¹¹)]ₚ—C(=O)—NY⁴Y⁵, or alkyl substituted by carboxy (or an acid bioisostere), —ZH, —ZR³, —C(=O)—NY⁴Y⁵ or —NY⁴Y⁵, are preferred. In one preferred embodiment L¹ is a group

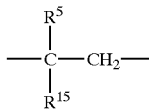

[where R⁵ is hydrogen or lower alkyl (e.g. methyl) and R¹⁵ represents hydrogen or lower alkyl, or where R⁵ is hydrogen and R¹⁵ represents aryl, heteroaryl, —N(R⁸)—C(=O)—R⁹, —N(R⁸)—C(=O)—OR⁹, —N(R⁸)—SO₂—R⁹, —NY⁴Y⁵ or —[C(=O)—N(R¹⁰)—C(R⁵)(R¹¹)]ₚ—C(=O)—NY⁴Y⁵, or alkyl substituted by carboxy (or an acid bioisostere), —ZH, —ZR³, —C(=O)—NY⁴Y⁵ or NY⁴Y⁵], and is more preferably a group

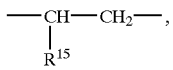

particularly

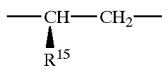

[where R¹⁵ represents hydrogen, lower alkyl, aryl, heteroaryl, —N(R⁸)—C(=O)—R⁹, —N(R⁸)—C(=O)—OR⁹, —N(R⁸)—SO₂—R⁹ or —NY⁴Y⁵ or alkyl substituted by carboxy, —OH, —OR³ or —C(=O)—NY⁴Y⁵]. In another preferred embodiment L¹ is a group

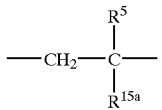

[where R⁵ is hydrogen or lower alkyl (e.g. methyl) and R¹⁵ᵃ represents lower alkyl (e.g. methyl), or where R⁵ is hydrogen and R¹⁵ᵃ represents aryl, heteroaryl, —N(R⁸)—C(=O)—R⁹, —N(R⁸)—C(=O)—OR⁹, —N(R⁸)—SO₂—R⁹, —NY⁴Y⁵ or —[C(=O)—N(R¹⁰)—C(R⁵)(R¹¹)]ₚ—C(=O)—NY⁴Y⁵, or alkyl substituted by carboxy (or an acid bioisostere), —ZH, —ZR³, —C(=O)—NY⁴Y⁵ or —NY⁴Y⁵], and is more preferably a group

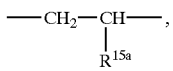

particularly

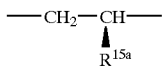

[where R¹⁵ᵃ represents —N(R⁸)—C(=O)—R⁹, or —N(R⁸)—SO₂—R⁹].

Compounds of formula (Ic) in which Y represents carboxy are preferred.

A preferred group of compounds of the invention are compounds of formula (Ic) in which: R² is hydrogen; A¹ is methylene or ethylene; Ar¹ is optionally substituted m- or p-phenylene (especially 3-chloro-p-phenylene, 3-methyl-p-phenylene, 3-methoxy-p-phenylene, 3-methylthio-p-phenylene, 3-methylsulphinyl-p-phenylene and 3-methylsulphonyl-p-phenylene) or optionally substituted p-pyridinediyl [especially or 4(or 6)-methyl(or methoxy)-p-pyridine-2,5-diyl]; L¹ is a

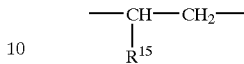

group particularly a

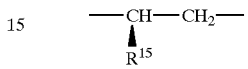

group, where R¹⁵ represents hydrogen, methyl, aryl, heteroaryl, —N(R⁸)—C(=O)—R⁹, —N(R⁸)—C(=O)—OR⁹, —N(R⁸)—SO₂—R⁹ or —NY⁴Y⁵, or alkyl substituted by carboxy, —OH, —OR³ or —C(=O)—NY⁴Y⁵]; L⁴ is a straight or branched C₁₋₄alkylene chain, (especially methylene); Y is carboxy; and Z¹ is CH₂; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Ic) in which: R² is hydrogen; A¹ is methylene or ethylene; Ar¹ is optionally substituted m- or p-phenylene (especially 3-chloro-p-phenylene, 3-methyl-p-phenylene, 3-methoxy-p-phenylene, 3-methylthio-p-phenylene, 3-methylsulphinyl-p-phenylene and 3-methylsulphonyl-p-phenylene) or optionally substituted p-pyridinediyl [especially 4(or 6)-methyl(or methoxy)-p-pyridine-2,5-diyl]; L¹ is a

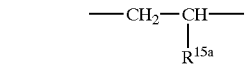

group, particularly

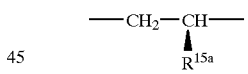

[where R¹⁵ᵃ represents —N(R⁸)—C(=O)—R⁹, or —N(R⁸)—SO₂—R⁹]; L⁴ is a straight or branched C₁₋₄alkylene chain, (especially methylene); Y is carboxy; and Z¹ is CH₂; and the corresponding N-oxides, and their prodrugs; and pharmaceutically acceptable salts and solvates (e.g. hydrates) of such compounds and their N-oxides and prodrugs.

Another particular group of compounds of the invention are compounds of formula (Id):

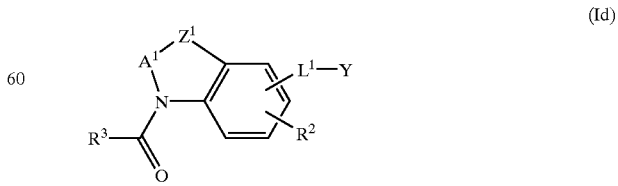

(Id)

in which R³, A¹, R², L¹, Y and Z¹ are as hereinbefore defined, and the corresponding N-oxides, and their prodrugs;

and pharmaceutically acceptable salts and solvates (e.g. hydrates) of such compounds and their N-oxides and prodrugs.

Compounds of formula (Id) in which $R^3$ represents optionally substituted aryl, especially optionally substituted phenyl, are preferred. Preferred optional substituents include aryloxy, cyano, halo (e.g. chloro or fluoro), lower alkoxy (e.g. methoxy), lower alkyl (e.g. methyl), nitro and perfluoroloweralkyl (e.g. trifluoromethyl). $R^3$ especially represents 2-chlorophenyl, 5-chloro-2-cyanophenyl, 2-chloro-6-methylphenyl, 2,6-dichlorophenyl, 2,6-difluorophenyl, 4-fluoro-2-trifluoromethyl, 2-methyl-4-nitrophenyl, 2-methyl-5-nitrophenyl, 2-nitrophenyl, 3-nitrophenyl and 2-phenoxyphenyl.

Compounds of formula (Id) in which $R^3$ represents optionally substituted heteroaryl, especially isoquinolinyl, isoxazolyl, pyrazolopyrimidinyl, pyridyl, pyrimidinyl, quinolinyl, thiazolyl and triazolyl, each optionally substituted by one or more aryl group substituents, are preferred. Preferred optional substituents include alkyl-C(=O)—, aryl, cyano, halo, (e.g. chloro or fluoro), lower alkoxy (e.g. methoxy), lower alkyl (e.g. methyl), lower alkylsulphonyl, lower alkylthio, nitro and perfluoroloweralkyl (e.g. trifluoromethyl). $R^3$ especially represents quinolin-4-yl, isoquinolin-2-yl, 2,4-pyridin-3-yl, 2,6-dimethyl-4-trifluoromethylpyridin-3-yl, 4-trifluoromethylpyridin3-yl, 2-phenyl-4-methyl-1,2,3-triazol-5-yl, 3,5-dimethylisoxazol-4-yl, 2,7-dimethylpyrazolo[1,5-a]pyrimidin-6-yl, 2-isopropyl-4-methylthiazol-5-yl and 4-trifluoromethylpyrimidin-5-yl.

Compounds of formula (Id) in which $R^3$ represents arylalkyl in which the aryl is optionally substituted by one or more aryl group substituents (particular optional substituents include halo, hydroxy and methoxy) are also preferred. $R^3$ especially represents optionally substituted benzyl, particularly 4-hydroxybenzyl, 3-chloro-4-hydroxybenzyl, 3-fluoro-4-hydroxybenzyl and 4-hydroxy-3-methoxybenzyl.

Compounds of formula (Id) in which $A^1$ represents methylene are preferred.

Compounds of formula (Id) in which $A^1$ represents ethylene are also preferred.

Compounds of formula (Id) in which $Z^1$ represents $CH_2$ are preferred.

Compounds of formula (Id) in which $R^2$ represents hydrogen are preferred.

Compounds of formula (Id) in which $L^1$ represents an optionally substituted alkylene linkage, particularly optionally substituted ethylene or optionally substituted propylene, especially ethylene optionally substituted with lower alkyl (e.g. methyl), aryl, heteroaryl, —N($R^8$)—C(=O)—$R^9$, —N($R^8$)—C(=O)—$OR^9$, —N($R^8$)—$SO_2$—$R^9$, —$NY^4Y^5$ or —[C(=O)—N($R^{10}$)—C($R^5$)($R^{11}$)]$_p$—C(=O)—$NY^4Y^5$, or alkyl substituted by carboxy (or an acid bioisostere), —ZH, —$ZR^3$, —C(=O)—$NY^4Y^5$ or —$NY^4Y^5$, are preferred. In one preferred embodiment $L^1$ is a group

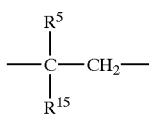

[where $R^5$ is hydrogen or lower alkyl (e.g. methyl) and $R^{15}$ represents hydrogen or lower alkyl, or where $R^5$ is hydrogen and $R^{15}$ represents aryl, heteroaryl, —N($R^8$)—C(=O)—$R^9$, —N($R^8$)—C(=O)—$OR^9$, —N($R^8$)—$SO_2$—$R^9$, —$NY^4Y^5$ or —[C(=O)—N($R^{10}$)—C($R^5$)($R^{11}$)]$_p$—C(=O)—$NY^4Y^5$, or alkyl substituted by carboxy (or an acid bioisostere), —ZH, —$ZR^3$, —C(O)—$NY^4Y^5$ or —$NY^4Y^5$], and is more preferably a group

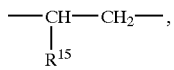

particularly

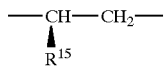

[where $R^{15}$ represents hydrogen, lower alkyl, aryl, heteroaryl, —N($R^8$)—C(=O)—$R^9$, —N($R^8$)—C(=O)—$OR^9$, —N($R^8$)—$SO_2$—$R^9$ or —$NY^4Y^5$ or alkyl substituted by carboxy, —OH, —$OR^3$ or —C(=O)—$NY^4Y^5$]. In another preferred embodiment $L^1$ is a group

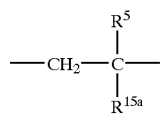

[where $R^5$ is hydrogen or lower alkyl (e.g. methyl) and $R^{15a}$ represents lower alkyl, or where $R^5$ is hydrogen and $R^{15a}$ represents aryl, heteroaryl, —N($R^8$)—C(=O)—$R^9$, —N($R^8$)—C(=O)—$OR^9$, —N($R^8$)—$SO_2$—$R^9$, —$NY^4Y^5$ or —[C(=O)—N($R^{10}$)—C($R^5$)($R^{11}$)]$_p$—C(=O)—$NY^4Y^5$, or alkyl substituted by carboxy (or an acid bioisostere), —ZH, —$ZR^3$, —C(=O)—$NY^4Y^5$ or —$NY^4Y^5$], and is more preferably a group

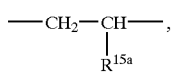

particularly

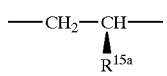

[where $R^{15a}$ represents —N($R^8$)—C(=O)—$R^9$, or —N($R^8$)—$SO_2$—$R^9$].

Compounds of formula (Id) in which Y represents carboxy are preferred.

A preferred group of compounds of the invention are compounds of formula (Id) in which: $R^2$ is hydrogen; $R^3$ is optionally substituted phenyl (especially 2-chlorophenyl, 5-chloro-2-cyanophenyl, 2-chloro-6-methylphenyl, 2,6-dichlorophenyl, 2,6-difluorophenyl, 4-fluoro-2-trifluoromethyl, 2-methyl-4-nitrophenyl, 2-methyl-5-nitrophenyl, 2-nitrophenyl, 3-nitrophenyl and 2-phenoxyphenyl), optionally substituted heteroaryl (especially quinolin4yl, isoquinolin-2-yl, 2,4-pyridin-3-yl, 2,6-dimethyl-4-trifluoromethylpyridin-3-yl, 4-trifluoromethylpyridin3-yl, 2-phenyl-4-methyl-1,2,3-triazol-5-yl, 3,5-dimethylisoxazol-4-yl, 2,7-dimethylpyrazolo-[1,5-a]pyrimidin-6-yl, 2-isopropyl-4-methylthiazol-5-yl and 4-trifluoromethylpyrimidin-5-yl) or optionally substituted benzyl (especially 4-hydroxybenzyl, 3-chloro-4-hydroxybenzyl, 3-fluoro-4-hydroxybenzyl and 4-hydroxy-3-methoxybenzyl); $A^1$ is methylene or ethylene; $L^1$ is a

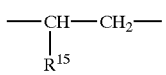

group particularly a

group, where $R^{15}$ represents hydrogen, methyl, aryl, heteroaryl, —N($R^8$)—C(=O)—$R^9$, —N($R^8$)—C(=O)—O$R^9$, —N($R^8$)—SO$_2$—$R^9$ or —N$Y^4Y^5$, or alkyl substituted by carboxy, —OH, —O$R^3$ or —C(=O)—N$Y^4Y^5$]; Y is carboxy; and $Z^1$ is CH$_2$; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Id) in which: $R^2$ is hydrogen; $R^3$ is optionally substituted phenyl (especially 2-chlorophenyl, 5-chloro-2-cyanophenyl, 2-chloro-6-methylphenyl, 2,6-dichlorophenyl, 2,6-difluorophenyl, 4-fluoro-2-trifluoromethyl, 2-methyl-4-nitrophenyl, 2-methyl-5-nitrophenyl, 2-nitrophenyl, 3-nitrophenyl and 2-phenoxyphenyl), optionally substituted heteroaryl (especially quinolin4-yl, isoquinolin-2-yl, 2,4-pyridin-3-yl, 2,6-dimethyl-4-trifluoromethylpyridin-3-yl, 4-trifluoromethylpyridin3-yl, 2-phenyl-4-methyl-1,2,3-triazol-5yl, 3,5-dimethylisoxazol-4-yl, 2,7-dimethylpyrazolo-[1,5-a]pyrimidin-6-yl, 2-isopropyl-4-methylthiazol-5-yl and 4-trifluoromethylpyrimidin-5-yl) or optionally substituted benzyl (especially 4-hydroxybenzyl, 3-chloro-4-hydroxybenzyl, 3-fluoro-4-hydroxybenzyl and 4-hydroxy-3-methoxybenzyl); $A^1$ is methylene or ethylene; $L^1$ is a

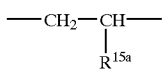

group, particularly

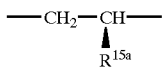

[where $R^{15a}$ represents —N($R^8$)—C(=O)—$R^9$, or —N($R^8$)—SO$_2$—$R^9$]; Y is carboxy; and $Z^1$ is CH$_2$; and the corresponding N-oxides, and their prodrugs; and pharmaceutically acceptable salts and solvates (e.g. hydrates) of such compounds and their N-oxides and prodrugs.

Compounds of formula (Ia), (Ib), (Ic) and (Id) in which $R^{15}$ represents hydrogen are preferred.

Compounds of formula (Ia), (Ib), (Ic) and (Id) in which $R^{15}$ represents lower alkyl (e.g. methyl, ethyl, propyl, butyl) are also preferred.

Compounds of formula (Ia), (Ib), (Ic) and (Id) in which $R^{15}$ represents aryl (e.g. optionally substituted phenyl) are also preferred.

Compounds of formula (Ia), (Ib), (Ic) and (Id) in which $R^{15}$ represents —N($R^8$)—C(=O)—$R^9$, especially where $R^8$ is hydrogen or lower alkyl (e.g. methyl) and $R^9$ is lower alkyl (e.g. methyl), aryl (e.g. optionally substituted phenyl), heteroaryl (e.g. pyridyl, isoxazolyl, triazolyl, pyrimidinyl, thiazolyl, or pyrazolopyrimidinyl each optionally substituted by one or more aryl group substituents), alkyl substituted by alkoxy (e.g. —CH$_2$—O—CH$_2$—CH$_2$—OCH$_3$), alkyl substituted by carboxy (e.g. —CH$_2$—CH$_2$—CO$_2$H and —CH$_2$—CH$_2$—CH$_2$—CO$_2$H) or alkyl substituted by —N$Y^4Y^5$ (e.g. aminomethyl and morpholin-1-ylmethyl), are preferred.

Compounds of formula (Ia), (Ib), (Ic) and (Id) in which $R^{15}$ represents —N($R^8$)—C(=O)—O$R^9$, especially where $R^8$ is hydrogen or lower alkyl (e.g. methyl) and $R^9$ is lower alkyl (e.g. ethyl) or alkyl substituted by aryl (e.g. benzyl), are also preferred.

Compounds of formula(Ia), (Ib), (Ic) and (Id) in which $R^{15}$ represents —N($R^8$)—SO$_2$—$R^9$, especially where $R^8$ is hydrogen or lower alkyl (e.g. methyl) and $R^9$ is lower alkyl (e.g. methyl), aryl [e.g. optionally substituted phenyl or optionally substituted naphthyl (especially dimethylaminonaphth-1-yl)]), heteroaryl (e.g. optionally substituted pyridyl or optionally substituted imidazolyl), are also preferred.

Compounds of formula (Ia), (Ib), (Ic) and (Id) in which $R^{15}$ represents N$Y^4Y^5$, especially where $Y^4$ and $Y^5$ represent hydrogen are also preferred.

Compounds of formula (Ia), (Ib), (Ic) and (Id) in which $R^{15}$ represents —N$Y^4Y^5$, especially where $Y^4$ is hydrogen and $Y^5$ is or lower alkyl (e.g. propyl), or alkyl substituted by aryl (e.g. —CH$_2$-Ph or —CH$_2$—CH$_2$-Ph), are also preferred.

Compounds of formula (Ia), (Ib), (Ic) and (Id) in which $R^{15}$ represents —N$Y^4Y^5$, especially where $Y^4$ and $Y^5$ represent alkyl substituted by aryl (e.g. —CH$_2$-Ph or —CH(CH$_3$)-Ph), are also preferred.

Compounds of formula (Ia), (Ib), (Ic) and (Id) in which $R^1$ represents alkyl substituted by carboxy (or an acid bioisostere), especially lower alkyl substituted by carboxy (e.g. carboxymethyl), are also preferred.

Compounds of formula (Ia), (Ib), (Ic) and (Id) in which $R^{15}$ represents alkyl substituted by —OH, especially lower alkyl substituted by —OH (e.g. hydroxymethyl), are also preferred.

Compounds of formula (Ia), (Ib), (Ic) and (Id) in which $R^{15}$ represents alkyl substituted by —O$R^3$, especially lower alkyl substituted by —O$R^3$ (e.g. methoxymethyl), are also preferred.

Compounds of formula (Ia), (Ib), (Ic) and (Id) in which $R^{15}$ represents alkyl substituted by —C(=O)—N$Y^4Y^5$, especially lower alkyl substituted by —C(=O)—N$Y^4Y^5$ (e.g.

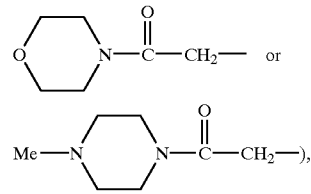

are also preferred.

Particularly preferred compounds of formula (Ia), (Ib), (Ic) and (Id) are those in which $R^{15}$ is

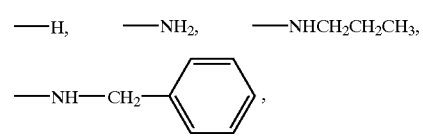

Compounds of formula (Ia), (Ib), (Ic) and (Id) in which $R^{15a}$ represents —N($R^8$)—C(=O)—$R^9$, especially where $R^8$ is hydrogen or lower alkyl (e.g. methyl) and $R^9$ is lower alkyl (e.g. methyl), aryl (e.g. optionally substituted phenyl), heteroaryl (e.g. pyridyl, isoxazolyl, triazolyl, pyrimidinyl, thiazolyl, or pyrazolopyrimidinyl each optionally substituted by one or more aryl group substituents), alkyl substituted by alkoxy (e.g. —CH₂—O—CH₂—CH₂—OCH₃), alkyl substituted by carboxy (e.g. —CH₂—CH₂—CO₂H and —CH₂—CH₂—CH₂—CO₂H) or alkyl substituted by —N$Y^4Y^5$ (e.g. aminomethyl and morpholin-1-ylmethyl), are preferred.

Compounds of formula (Ia), (Ib), (Ic) and (Id) in which $R^{15a}$ represents —N($R^8$)—C(=O)—$R^9$ where $R^9$ is substituted phenyl selected from 2-chlorophenyl, 5-chloro-2-cyanophenyl, 2-chloro-6-methylphenyl, 2,6-dichlorophenyl, 2,6-difluorophenyl, 4-fluoro-2-trifluoromethyl, 2-methyl-4-nitrophenyl, 2-methyl-5-nitrophenyl, 2-nitrophenyl, 3-nitrophenyl or 2-phenoxyphenyl are particularly preferred.

Compounds of formula (Ia), (Ib), (Ic) and (Id) in which $R^{15a}$ represents —N($R^8$)—C(=O)—$R^9$ where $R^9$ is an optionally substituted heteroaryl selected from quinolin-4-yl, isoquinolin-2-yl, 2,4-pyridin-3-yl, 2,6-dimethyl-4-trifluoromethylpyridin-3-yl, 4-trifluoromethylpyridin3-yl, 2-phenyl-4-methyl-1,2,3-triazol-5-yl, 3,5-dimethylisoxazol-4-yl, 2,7-dimethylpyrazolo-[1,5-a]pyrimidin-6-yl, 2-isopropyl-4-methylthiazol-5-yl and 4-trifluoromethylpyrimidin-5-yl are also particularly preferred.

Particular compounds of the invention are selected from the compounds formed by joining the acyl carbon atom (C*) of one of the fragments (A1 to A34) shown in Table 1 to the nitrogen atom (N*) of one of the aza-bicyclic fragments (B1 to B6) shown in Table 2, and joining the carbon atom (C*) of the phenyl ring in one of the aza-bicyclic fragments (B1 to B6) shown in Table 2 to the carbon atom (C*) of one of the acidic fragments (C1 to C59) depicted in Table 3.

TABLE 1
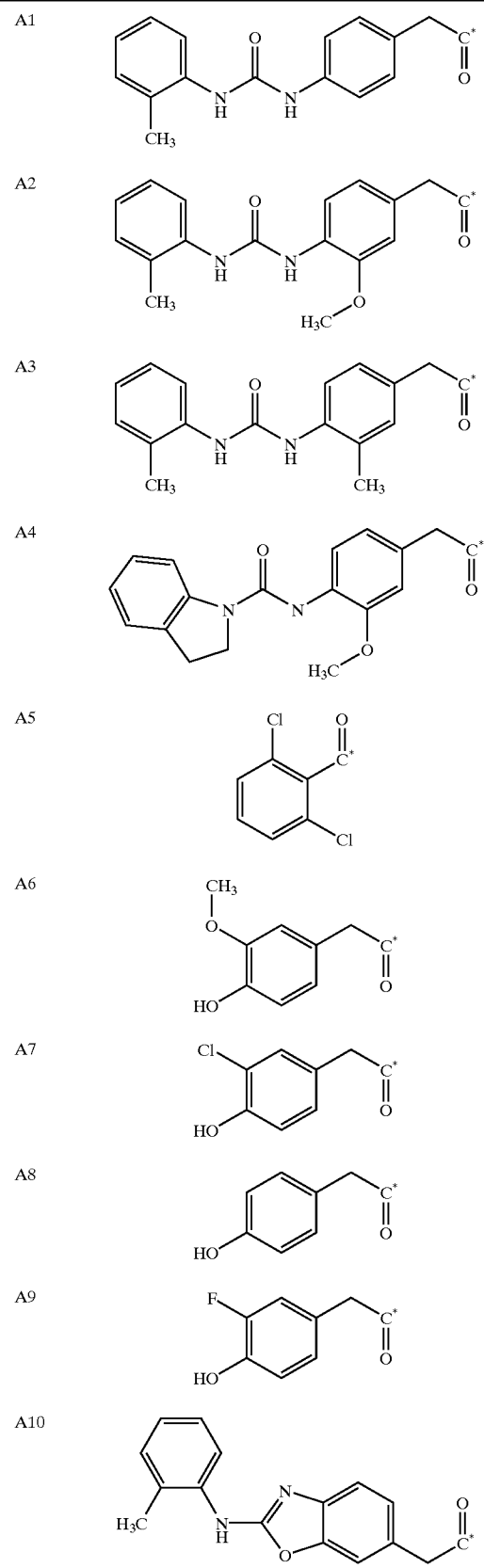
TABLE 1-continued
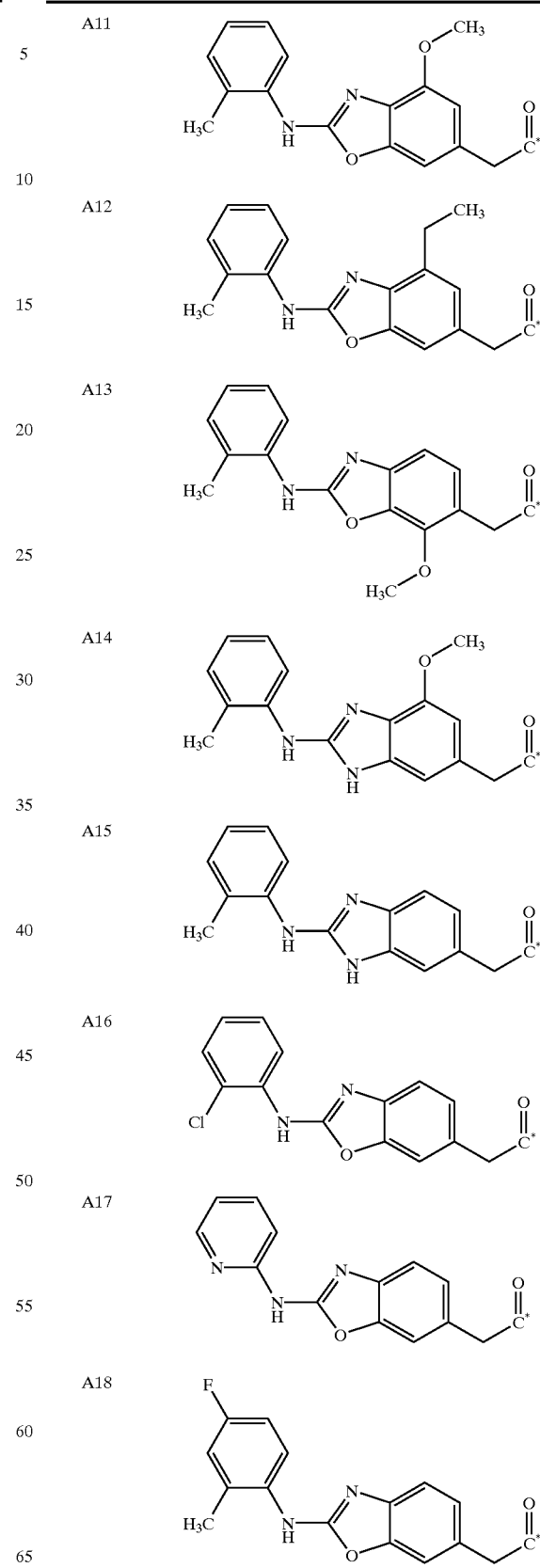

TABLE 1-continued
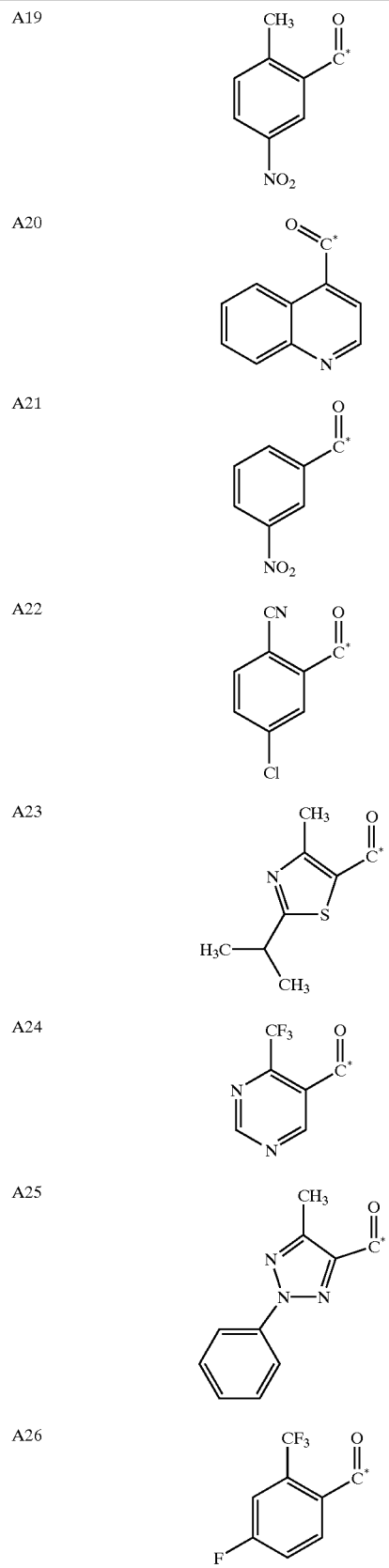
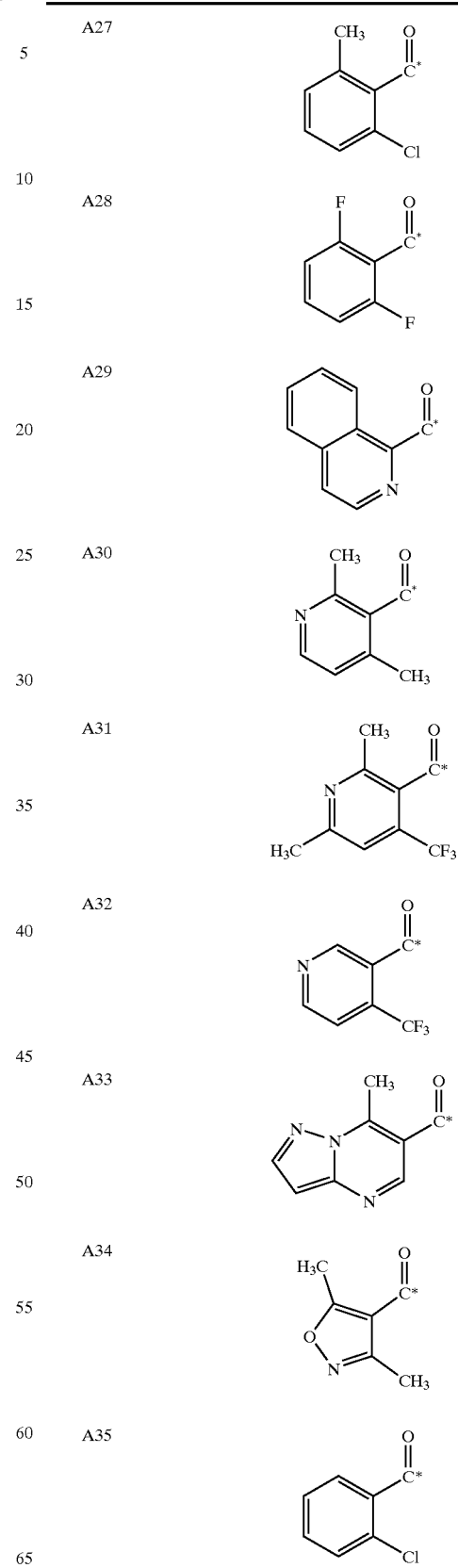

TABLE 2

| | | |
|---|---|---|
| B1 | 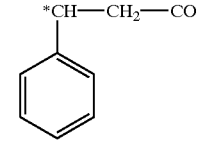 | |
| B2 | 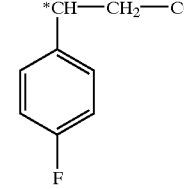 | |
| B3 | 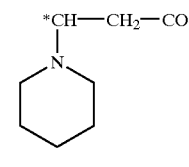 | |
| B4 | 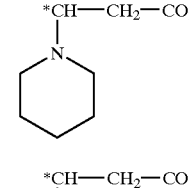 | |
| B5 | 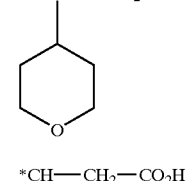 | |
| B6 | 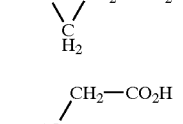 | |

TABLE 3

| | |
|---|---|
| C1 | *CH$_2$—CH$_2$—CO$_2$H |
| C2 | *CH(CH$_3$)—CH$_2$—CO$_2$H |
| C3 | *CH(CH$_2$CH$_3$)—CH$_2$—CO$_2$H |
| C4 | *CH((CH$_2$)$_3$CH$_3$)—CH$_2$—CO$_2$H |
| C5 | *CH(CH(CH$_3$)$_2$)—CH$_2$—CO$_2$H |
| C6 | *CH(CH$_2$CH(CH$_3$)$_2$)—CH$_2$—CO$_2$H |

TABLE 3-continued

| | |
|---|---|
| C7 | 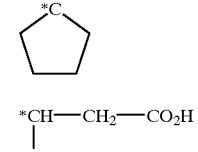 |
| C8 | 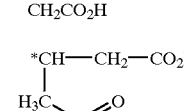 |
| C9 | 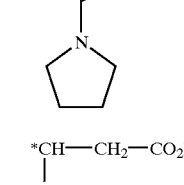 |
| C10 | 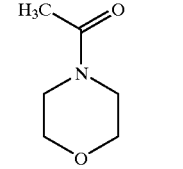 |
| C11 | *CH(—CH$_2$—CO$_2$H)— (tetrahydropyran-4-yl) |
| C12 | *CH(—CH$_2$—CO$_2$H)—CH$_2$ (cyclopropyl) |
| C13 | *C(cyclopentyl)—CH$_2$—CO$_2$H |
| C14 | *CH(—CH$_2$—CO$_2$H)—CH$_2$CO$_2$H |
| C15 | *CH(—CH$_2$—CO$_2$H)—CH(CH$_3$)—C(O)—N(pyrrolidine) |
| C16 | *CH(—CH$_2$—CO$_2$H)—CH(CH$_3$)—C(O)—N(morpholine) |

TABLE 3-continued
| | |
|---|---|
| C17 | 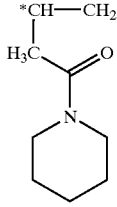 |
| C18 | 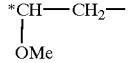 |
| C19 | 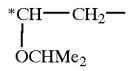 |
| C20 | 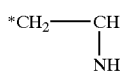 |
| C21 | 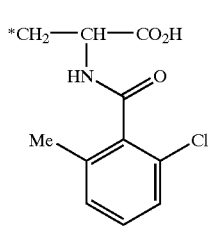 |
| C22 | 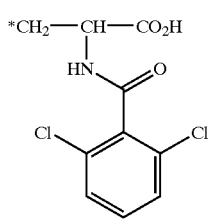 |
| C23 | 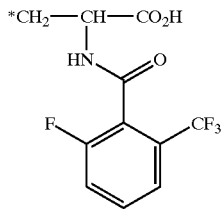 |
| C24 | 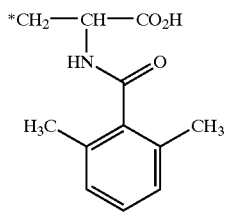 |
| C25 | 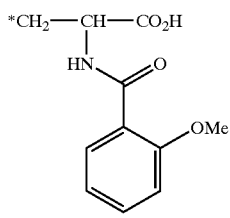 |
| C26 | 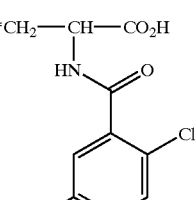 |
| C27 | 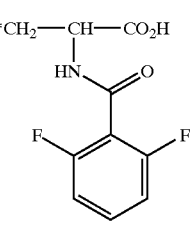 |
| C28 | 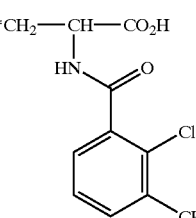 |
| C29 | 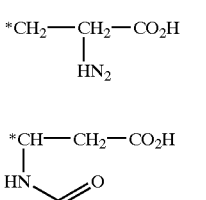 |
| C30 | 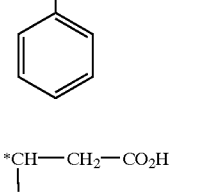 |
| C31 | 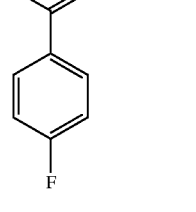 |
| C32 | 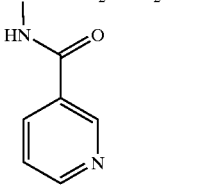 |

TABLE 3-continued

| | | |
|---|---|---|
| C33 | *CH—CH₂—CO₂H, HN-C(=O)-(4-pyridyl) | |
| C34 | *CH—CH₂—CO₂H, HN-C(=O)-(2-thienyl) | |
| C35 | *CH—CH₂—CO₂H, HN-C(=O)-(3-thienyl) | |
| C36 | *CH—CH₂—CO₂H, HN-C(=O)-(5-methylisoxazol-3-yl) | |
| C37 | *CH—CH₂—CO₂H, HN-C(=O)-(tetrahydropyran-4-yl) | |
| C38 | *CH—CH₂—CO₂H, N(Me)-C(=O)-(tetrahydropyran-4-yl) | |
| C39 | *CH—CH₂—CO₂H, N(Me)-C(=O)-(2-thienyl) | |

TABLE 3-continued

| | | |
|---|---|---|
| C40 | *CH—CH₂—CO₂H, N(Me)-C(=O)-phenyl | |
| C41 | δ-valerolactone with *CH | |
| C42 | ε-caprolactone with *CH | |
| C43 | *CH₂—CH—CO₂H, HN-C(=O)-(2-CMe₃-phenyl) | |
| C44 | *CH₂—CH—CO₂H, HN-C(=O)-(2-Me-3-CHMe₂-phenyl) | |
| C45 | *CH₂—CH—CO₂H, HN-C(=O)-(2,4,6-triMe-phenyl) | |
| C46 | *CH₂—CH—CO₂H, HN-C(=O)-(2-Et-6-Me-phenyl) | |

TABLE 3-continued
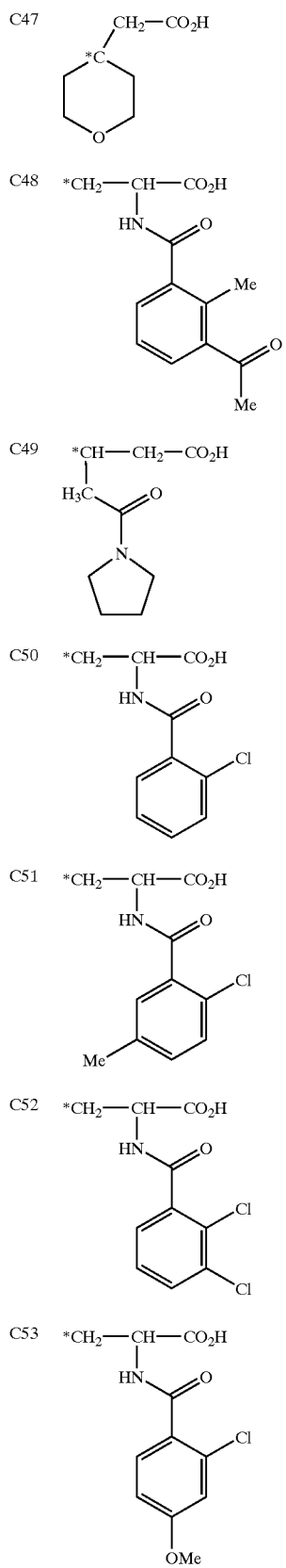
TABLE 3-continued
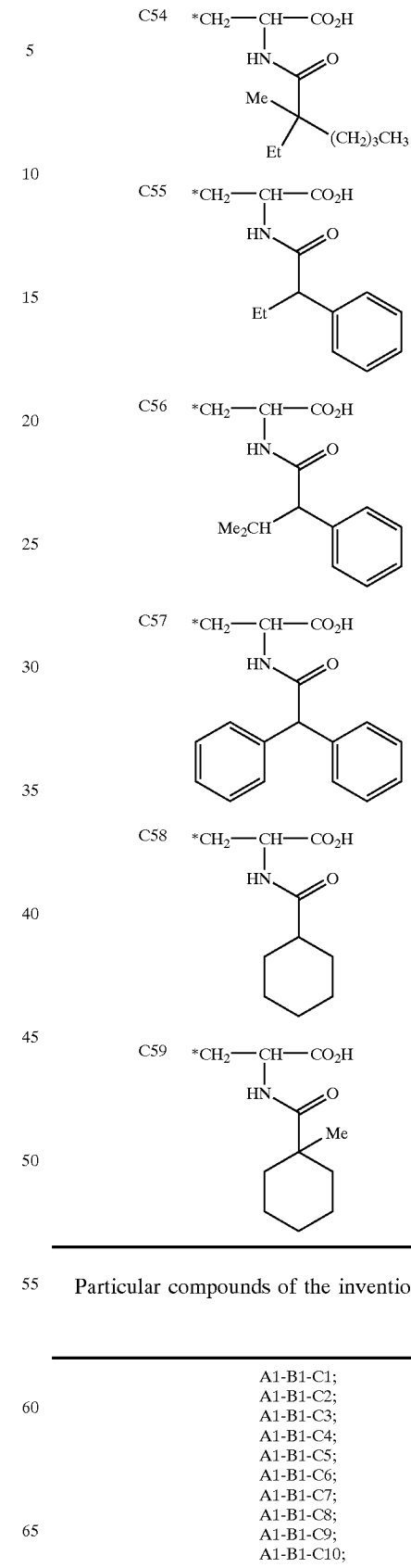
Particular compounds of the invention are:
A1-B1-C1;
A1-B1-C2;
A1-B1-C3;
A1-B1-C4;
A1-B1-C5;
A1-B1-C6;
A1-B1-C7;
A1-B1-C8;
A1-B1-C9;
A1-B1-C10;

-continued

A1-B1-C11;
A1-B1-C12;
A1-B1-C13;
A1-B1-C14;
A1-B1-C15;
A1-B1-C16;
A1-B1-C17;
A1-B1-C18;
A1-B1-C19;
A1-B1-C20;
A1-B1-C21;
A1-B1-C22;
A1-B1-C23;
A1-B1-C24;
A1-B1-C25;
A1-B1-C26;
A1-B1-C27;
A1-B1-C28;
A1-B1-C29;
A1-B1-C30;
A1-B1-C31;
A1-B1-C32;
A1-B1-C33;
A1-B1-C34;
A1-B1-C35;
A1-B1-C36;
A1-B1-C37;
A1-B1-C38;
A1-B1-C39;
A1-B1-C40;
A1-B1-C41;
A1-B1-C42;
A1-B1-C43;
A1-B1-C44;
A1-B1-C45;
A1-B1-C46;
A1-B1-C47;
A1-B1-C48;
A1-B1-C49;
A1-B1-C50;
A1-B1-C51;
A1-B1-C52;
A1-B1-C53;
A1-B1-C54;
A1-B1-C55;
A1-B1-C56;
A1-B1-C57;
A1-B1-C58;
A1-B1-C59;
A2-B1-C1;
A2-B1-C2;
A2-B1-C3;
A2-B1-C4;
A2-B1-C5;
A2-B1-C6;
A2-B1-C7;
A2-B1-C8;
A2-B1-C9;
A2-B1-C10;
A2-B1-C11;
A2-B1-C12;
A2-B1-C13;
A2-B1-C14;
A2-B1-C15;
A2-B1-C16;
A2-B1-C17;
A2-B1-C18;
A2-B1-C19;
A2-B1-C20;
A2-B1-C21;
A2-B1-C22;
A2-B1-C23;
A2-B1-C24;
A2-B1-C25;
A2-B1-C26;
A2-B1-C27;
A2-B1-C28;
A2-B1-C29;
A2-B1-C30;

-continued

A2-B1-C31;
A2-B1-C32;
A2-B1-C33;
A2-B1-C34;
A2-B1-C35;
A2-B1-C36;
A2-B1-C37;
A2-B1-C38;
A2-B1-C39;
A2-B1-C40;
A2-B1-C41;
A2-B1-C42;
A2-B1-C43;
A2-B1-C44;
A2-B1-C45;
A2-B1-C46;
A2-B1-C47;
A2-B1-C48;
A2-B1-C49;
A2-B1-C50;
A2-B1-C51;
A2-B1-C52;
A2-B1-C53;
A2-B1-C54;
A2-B1-C55;
A2-B1-C56;
A2-B1-C57;
A2-B1-C58;
A2-B1-C59;
A3-B1-C1;
A3-B1-C2;
A3-B1-C3;
A3-B1-C4;
A3-B1-C5;
A3-B1-C6;
A3-B1-C7;
A3-B1-C8;
A3-B1-C9;
A3-B1-C10;
A3-B1-C11;
A3-B1-C12;
A3-B1-C13;
A3-B1-C14;
A3-B1-C15;
A3-B1-C16;
A3-B1-C17;
A3-B1-C18;
A3-B1-C19;
A3-B1-C20;
A3-B1-C21;
A3-B1-C22;
A3-B1-C23;
A3-B1-C24;
A3-B1-C25;
A3-B1-C26;
A3-B1-C27;
A3-B1-C28;
A3-B1-C29;
A3-B1-C30;
A3-B1-C31;
A3-B1-C32;
A3-B1-C33;
A3-B1-C34;
A3-B1-C35;
A3-B1-C36;
A3-B1-C37;
A3-B1-C38;
A3-B1-C39;
A3-B1-C40;
A3-B1-C41;
A3-B1-C42;
A3-B1-C43;
A3-B1-C44;
A3-B1-C45;
A3-B1-C46;
A3-B1-C47;
A3-B1-C48;
A3-B1-C49;
A3-B1-C50;

-continued

A3-B1-C51;
A3-B1-C52;
A3-B1-C53;
A3-B1-C54;
A3-B1-C55;
A3-B1-C56;
A3-B1-C57;
A3-B1-C58;
A3-B1-C59;
A4-B1-C1;
A4-B1-C2;
A4-B1-C3;
A4-B1-C4;
A4-B1-C5;
A4-B1-C6;
A4-B1-C7;
A4-B1-C5;
A4-B1-C9;
A4-B1-C10;
A4-B1-C11;
A4-B1-C12;
A4-B1-C13;
A4-B1-C14;
A4-B1-C15;
A4-B1-C16;
A4-B1-C17;
A4-B1-C18;
A4-B1-C19;
A4-B1-C20;
A4-B1-C21,
A4-B1-C22;
A4-B1-C23;
A4-B1-C24;
A4-B1-C25;
A4-B1-C26;
A4-B1-C27;
A4-B1-C28;
A4-B1-C29;
A4-B1-C30;
A4-B1-C31;
A4-B1-C32;
A4-B1-C33;
A4-B1-C34;
A4-B1-C35;
A4-B1-C36;
A4-B1-C37;
A4-B1-C38;
A4-B1-C39;
A4-B1-C40;
A4-B1-C41;
A4-B1-C42;
A4-B1-C43;
A4-B1-C44;
A4-B1-C45;
A4-B1-C46;
A4-B1-C47;
A4-B1-C48;
A4-B1-C49;
A4-B1-C50;
A4-B1-C51;
A4-B1-C52;
A4-B1-C53;
A4-B1-C54;
A4-B1-C55;
A4-B1-C56;
A4-B1-C57;
A4-B1-C58;
A4-B1-C59;
A5-B1-C1;
A5-B1-C2;
A5-B1-C3;
A5-B1-C4;
A5-B1-C5;
A5-B1-C6;
A5-B1-C7;
A5-B1-C8;
A5-B1-C9;
A5-B1-C10;
A5-B1-C11;

-continued

A5-B1-C12;
A5-B1-C13;
A5-B1-C14;
A5-B1-C15;
A5-B1-C16;
A5-B1-C17;
A5-B1-C18;
A5-B1-C19;
A5-B1-C20;
A5-B1-C21;
A5-B1-C22;
A5-B1-C23;
A5-B1-C24;
A5-B1-C25;
A5-B1-C26;
A5-B1-C27;
A5-B1-C28;
A5-B1-C29;
A5-B1-C30;
A5-B1-C31;
A5-B1-C32;
A5-B1-C33;
A5-B1-C34;
A5-B1-C35;
A5-B1-C36;
A5-B1-C37;
A5-B1-C38;
A5-B1-C39;
A5-B1-C40;
A5-B1-C41;
A5-B1-C42;
A5-B1-C43;
A5-B1-C44;
A5-B1-C45;
A5-B1-C46;
A5-B1-C47;
A5-B1-C48;
A5-B1-C49;
A5-B1-C50;
A5-B1-C51;
A5-B1-C52;
A5-B1-C53;
A5-B1-C54;
A5-B1-C55;
A5-B1-C56;
A5-B1-C57;
A5-B1-C58;
A5-B1-C59;
A6-B1-C1;
A6-B1-C2;
A6-B1-C3;
A6-B1-C4;
A6-B1-C5;
A6-B1-C6;
A6-B1-C7;
A6-B1-C8;
A6-B1-C9;
A6-B1-C10;
A6-B1-C11;
A6-B1-C12;
A6-B1-C13;
A6-B1-C14;
A6-B1-C15;
A6-B1-C16;
A6-B1-C17;
A6-B1-C18;
A6-B1-C19;
A6-B1-C20;
A6-B1-C21;
A6-B1-C22;
A6-B1-C23;
A6-B1-C24;
A6-B1-C25;
A6-B1-C26;
A6-B1-C27;
A6-B1-C28;
A6-B1-C29;
A6-B1-C30;
A6-B1-C31;

-continued

A6-B1-C32;
A6-B1-C33;
A6-B1-C34;
A6-B1-C35;
A6-B1-C36;
A6-B1-C37;
A6-B1-C38;
A6-B1-C39;
A6-B1-C40;
A6-B1-C41;
A6-B1-C42;
A6-B1-C43;
A6-B1-C44;
A6-B1-C45;
A6-B1-C46;
A6-B1-C47;
A6-B1-C48;
A6-B1-C49;
A6-B1-C50;
A6-B1-C51;
A6-B1-C52;
A6-B1-C53;
A6-B1-C54;
A6-B1-C55;
A6-B1-C56;
A6-B1-C57;
A6-B1-C58;
A6-B1-C59;
A7-B1-C1;
A7-B1-C2;
A7-B1-C3;
A7-B1-C4;
A7-B1-C5;
A7-B1-C6;
A7-B1-C7;
A7-B1-C8;
A7-B1-C9;
A7-B1-C10;
A7-B1-C11;
A7-B1-C12;
A7-B1-C13;
A7-B1-C14;
A7-B1-C15;
A7-B1-C16;
A7-B1-C17;
A7-B1-C18;
A7-B1-C19;
A7-B1-C20;
A7-B1-C21;
A7-B1-C22;
A7-B1-C23;
A7-B1-C24;
A7-B1-C25;
A7-B1-C26;
A7-B1-C27;
A7-B1-C28;
A7-B1-C29;
A7-B1-C30;
A7-B1-C31;
A7-B1-C32;
A7-B1-C33;
A7-B1-C34;
A7-B1-C35;
A7-B1-C36;
A7-B1-C37;
A7-B1-C38;
A7-B1-C39;
A7-B1-C40;
A7-B1-C41;
A7-B1-C42;
A7-B1-C43;
A7-B1-C44;
A7-B1-C45;
A7-B1-C46;
A7-B1-C47;
A7-B1-C48;
A7-B1-C49;
A7-B1-C50;
A7-B1-C51;

-continued

A7-B1-C52;
A7-B1-C53;
A7-B1-C54;
A7-B1-C55;
A7-B1-C56;
A7-B1-C57;
A7-B1-C58;
A7-B1-C59;
A8-B1-C1;
A8-B1-C2;
A8-B1-C3;
A8-B1-C4;
A8-B1-C5;
A8-B1-C6;
A8-B1-C7;
A8-B1-C8;
A8-B1-C9;
A8-B1-C10;
A8-B1-C11;
A8-B1-C12;
A8-B1-C13;
A8-B1-C14;
A8-B1-C15;
A8-B1-C16;
A8-B1-C17;
A8-B1-C18;
A8-B1-C19;
A8-B1-C20;
A8-B1-C21;
A8-B1-C22;
A8-B1-C23;
A8-B1-C24;
A8-B1-C25;
A8-B1-C26;
A8-B1-C27;
A8-B1-C28;
A8-B1-C29;
A8-B1-C30;
A8-B1-C31;
A8-B1-C32;
A8-B1-C33;
A8-B1-C34;
A8-B1-C35;
A8-B1-C36;
A8-B1-C37;
A8-B1-C38;
A8-B1-C39;
A8-B1-C40;
A8-B1-C41;
A8-B1-C42;
A8-B1-C43;
A8-B1-C44;
A8-B1-C45;
A8-B1-C46;
A8-B1-C47;
A8-B1-C48;
A8-B1-C49;
A8-B1-C50;
A8-B1-C51;
A8-B1-C52;
A8-B1-C53;
A8-B1-C54;
A8-B1-C55;
A8-B1-C56;
A8-B1-C57;
A8-B1-C58;
A8-B1-C59;
A9-B1-C1;
A9-B1-C2;
A9-B1-C3;
A9-B1-C4;
A9-B1-C5;
A9-B1-C6;
A9-B1-C7;
A9-B1-C8;
A9-B1-C9;
A9-B1-C10;
A9-B1-C11;
A9-B1-C12;

-continued

A9-B1-C13;
A9-B1-C14;
A9-B1-C15;
A9-B1-C16;
A9-B1-C17;
A9-B1-C18;
A9-B1-C19;
A9-B1-C20;
A9-B1-C21;
A9-B1-C22;
A9-B1-C23;
A9-B1-C24;
A9-B1-C25;
A9-B1-C26;
A9-B1-C27;
A9-B1-C28;
A9-B1-C29;
A9-B1-C30;
A9-B1-C31;
A9-B1-C32;
A9-B1-C33;
A9-B1-C34;
A9-B1-C35;
A9-B1-C36;
A9-B1-C37;
A9-B1-C38;
A9-B1-C39;
A9-B1-C40;
A9-B1-C41;
A9-B1-C42;
A9-B1-C43;
A9-B1-C44;
A9-B1-C45;
A9-B1-C46;
A9-B1-C47;
A9-B1-C48;
A9-B1-C49;
A9-B1-C50;
A9-B1-C51;
A9-B1-C52;
A9-B1-C53;
A9-B1-C54;
A9-B1-C55;
A9-B1-C56;
A9-B1-C57;
A9-B1-C58;
A9-B1-C59;
A10-B1-C1;
A10-B1-C2;
A10-B1-C3;
A10-B1-C4;
A10-B1-C5;
A10-B1-C6;
A10-B1-C7;
A10-B1-C8;
A10-B1-C9;
A10-B1-C10;
A10-B1-C11;
A10-B1-C12;
A10-B1-C13;
A10-B1-C14;
A10-B1-C15;
A10-B1-C16;
A10-B1-C17;
A10-B1-C18;
A10-B1-C19;
A10-B1-C20;
A10-B1-C21;
A10-B1-C22;
A10-B1-C23;
A10-B1-C24;
A10-B1-C25;
A10-B1-C26;
A10-B1-C27;
A10-B1-C28;
A10-B1-C29;
A10-B1-C30;
A10-B1-C31;
A10-B1-C32;

-continued

A10-B1-C33;
A10-B1-C34;
A10-B1-C35;
A10-B1-C36;
A10-B1-C37;
A10-B1-C38;
A10-B1-C39;
A10-B1-C40;
A10-B1-C41;
A10-B1-C42;
A10-B1-C43;
A10-B1-C44;
A10-B1-C45;
A10-B1-C46;
A10-B1-C47;
A10-B1-C48;
A10-B1-C49;
A10-B1-C50;
A10-B1-C51;
A10-B1-C52;
A10-B1-C53;
A10-B1-C54;
A10-B1-C55;
A10-B1-C56;
A10-B1-C57;
A10-B1-C58;
A10-B1-C59;
A11-B1-C1;
A11-B1-C2;
A11-B1-C3;
A11-B1-C4;
A11-B1-C5;
A11-B1-C6;
A11-B1-C7;
A11-B1-C8;
A11-B1-C9;
A11-B1-C10;
A11-B1-C11;
A11-B1-C12;
A11-B1-C13;
A11-B1-C14;
A11-B1-C15;
A11-B1-C16;
A11-B1-C17;
A11-B1-C18;
A11-B1-C19;
A11-B1-C20;
A11-B1-C21;
A11-B1-C22;
A11-B1-C23;
A11-B1-C24;
A11-B1-C25;
A11-B1-C26;
A11-B1-C27;
A11-B1-C28;
A11-B1-C29;
A11-B1-C30;
A11-B1-C31;
A11-B1-C32;
A11-B1-C33;
A11-B1-C34;
A11-B1-C35;
A11-B1-C36;
A11-B1-C37;
A11-B1-C38;
A11-B1-C39;
A11-B1-C40;
A11-B1-C41;
A11-B1-C42;
A11-B1-C43;
A11-B1-C44;
A11-B1-C45;
A11-B1-C46;
A11-B1-C47;
A11-B1-C48;
A11-B1-C49;
A11-B1-C50;
A11-B1-C51;
A11-B1-C52;

-continued

A11-B1-C53;
A11-B1-C54;
A11-B1-C55;
A11-B1-C56;
A11-B1-C57;
A11-B1-C58;
A11-B1-C59;
A12-B1-C1;
A12-B1-C2;
A12-B1-C3;
A12-B1-C4;
A12-B1-C5;
A12-B1-C6;
A12-B1-C7;
A12-B1-C8;
A12-B1-C9;
A12-B1-C10;
A12-B1-C11;
A12-B1-C12;
A12-B1-C13;
A12-B1-C14;
A12-B1-C15;
A12-B1-C16;
A12-B1-C17;
A12-B1-C18;
A12-B1-C19;
A12-B1-C20;
A12-B1-C21;
A12-B1-C22;
A12-B1-C23;
A12-B1-C24;
A12-B1-C25;
A12-B1-C26;
A12-B1-C27;
A12-B1-C28;
A12-B1-C29;
A12-B1-C30;
A12-B1-C31;
A12-B1-C32;
A12-B1-C33;
A12-B1-C34;
A12-B1-C35;
A12-B1-C36;
A12-B1-C37;
A12-B1-C38;
A12-B1-C39;
A12-B1-C40;
A12-B1-C41;
A12-B1-C42;
A12-B1-C43;
A12-B1-C44;
A12-B1-C45;
A12-B1-C46;
A12-B1-C47;
A12-B1-C48;
A12-B1-C49;
A12-B1-C50;
A12-B1-C51;
A12-B1-C52;
A12-B1-C53;
A12-B1-C54;
A12-B1-C55;
A12-B1-C56;
A12-B1-C57;
A12-B1-C58;
A12-B1-C59;
A13-B1-C1;
A13-B1-C2;
A13-B1-C3;
A13-B1-C4;
A13-B1-C5;
A13-B1-C6;
A13-B1-C7;
A13-B1-C8;
A13-B1-C9;
A13-B1-C10;
A13-B1-C11;
A13-B1-C12;
A13-B1-C13;

-continued

A13-B1-C14;
A13-B1-C15;
A13-B1-C16;
A13-B1-C17;
A13-B1-C18;
A13-B1-C19;
A13-B1-C20;
A13-B1-C21;
A13-B1-C22;
A13-B1-C23;
A13-B1-C24;
A13-B1-C25;
A13-B1-C26;
A13-B1-C27;
A13-B1-C28;
A13-B1-C29;
A13-B1-C30;
A13-B1-C31;
A13-B1-C32;
A13-B1-C33;
A13-B1-C34;
A13-B1-C35;
A13-B1-C36;
A13-B1-C37;
A13-B1-C38;
A13-B1-C39;
A13-B1-C40;
A13-B1-C41;
A13-B1-C42;
A13-B1-C43;
A13-B1-C44;
A13-B1-C45;
A13-B1-C46;
A13-B1-C47;
A13-B1-C48;
A13-B1-C49;
A13-B1-C50;
A13-B1-C51;
A13-B1-C52;
A13-B1-C53;
A13-B1-C54;
A13-B1-C55;
A13-B1-C56;
A13-B1-C57;
A13-B1-C58;
A13-B1-C59;
A14-B1-C1;
A14-B1-C2;
A14-B1-C3;
A14-B1-C4;
A14-B1-C5;
A14-B1-C6;
A14-B1-C7;
A14-B1-C8;
A14-B1-C9;
A14-B1-C10;
A14-B1-C11;
A14-B1-C12;
A14-B1-C13;
A14-B1-C14;
A14-B1-C15;
A14-B1-C16;
A14-B1-C17;
A14-B1-C18;
A14-B1-C19;
A14-B1-C20;
A14-B1-C21;
A14-B1-C22;
A14-B1-C23;
A14-B1-C24;
A14-B1-C25;
A14-B1-C26;
A14-B1-C27;
A14-B1-C28;
A14-B1-C29;
A14-B1-C30;
A14-B1-C31;
A14-B1-C32;
A14-B1-C33;

-continued

A14-B1-C34;
A14-B1-C35;
A14-B1-C36;
A14-B1-C37;
A14-B1-C38;
A14-B1-C39;
A14-B1-C40;
A14-B1-C41;
A14-B1-C42;
A14-B1-C43;
A14-B1-C44;
A14-B1-C45;
A14-B1-C46;
A14-B1-C47;
A14-B1-C48;
A14-B1-C49;
A14-B1-C50;
A14-B1-C51;
A14-B1-C52;
A14-B1-C53;
A14-B1-C54;
A14-B1-C55;
A14-B1-C56;
A14-B1-C57;
A14-B1-C58;
A14-B1-C59;
A15-B1-C1;
A15-B1-C2;
A15-B1-C3;
A15-B1-C4;
A15-B1-C5;
A15-B1-C6;
A15-B1-C7;
A15-B1-C8;
A15-B1-C9;
A15-B1-C10;
A15-B1-C11;
A15-B1-C12;
A15-B1-C13;
A15-B1-C14;
A15-B1-C15;
A15-B1-C16;
A15-B1-C17;
A15-B1-C18;
A15-B1-C19;
A15-B1-C20;
A15-B1-C21;
A15-B1-C22;
A15-B1-C23;
A15-B1-C24;
A15-B1-C25;
A15-B1-C26;
A15-B1-C27;
A15-B1-C28;
A15-B1-C29;
A15-B1-C30;
A15-B1-C31;
A15-B1-C32;
A15-B1-C33;
A15-B1-C34;
A15-B1-C35;
A15-B1-C36;
A15-B1-C37;
A15-B1-C38;
A15-B1-C39;
A15-B1-C40;
A15-B1-C41;
A15-B1-C42;
A15-B1-C43;
A15-B1-C44;
A15-B1-C45;
A15-B1-C46;
A15-B1-C47;
A15-B1-C48;
A15-B1-C49;
A15-B1-C50;
A15-B1-C51;
A15-B1-C52;
A15-B1-C53;

-continued

A15-B1-C54;
A15-B1-C55;
A15-B1-C56;
A15-B1-C57;
A15-B1-C58;
A15-B1-C59;
A16-B1-C1;
A16-B1-C2;
A16-B1-C3;
A16-B1-C4;
A16-B1-C5;
A16-B1-C6;
A16-B1-C7;
A16-B1-C8;
A16-B1-C9;
A16-B1-C10;
A16-B1-C11;
A16-B1-C12;
A16-B1-C13;
A16-B1-C14;
A16-B1-C15;
A16-B1-C16;
A16-B1-C17;
A16-B1-C18;
A16-B1-C19;
A16-B1-C20;
A16-B1-C21;
A16-B1-C22;
A16-B1-C23;
A16-B1-C24;
A16-B1-C25;
A16-B1-C26;
A16-B1-C27;
A16-B1-C28;
A16-B1-C29;
A16-B1-C30;
A16-B1-C31;
A16-B1-C32;
A16-B1-C33;
A16-B1-C34;
A16-B1-C35;
A16-B1-C36;
A16-B1-C37;
A16-B1-C38;
A16-B1-C39;
A16-B1-C40;
A16-B1-C41;
A16-B1-C42;
A16-B1-C43;
A16-B1-C44;
A16-B1-C45;
A16-B1-C46;
A16-B1-C47;
A16-B1-C48;
A16-B1-C49;
A16-B1-C50;
A16-B1-C51;
A16-B1-C52;
A16-B1-C53;
A16-B1-C54;
A16-B1-C55;
A16-B1-C56;
A16-B1-C57;
A16-B1-C58;
A16-B1-C59;
A17-B1-C1;
A17-B1-C2;
A17-B1-C3;
A17-B1-C4;
A17-B1-C5;
A17-B1-C6;
A17-B1-C7;
A17-B1-C8;
A17-B1-C9;
A17-B1-C10;
A17-B1-C11;
A17-B1-C12;
A17-B1-C13;
A17-B1-C14;

A17-B1-C15;
A17-B1-C16;
A17-B1-C17;
A17-B1-C18;
A17-B1-C19;
A17-B1-C20;
A17-B1-C21;
A17-B1-C22;
A17-B1-C23;
A17-B1-C24;
A17-B1-C25;
A17-B1-C26;
A17-B1-C27;
A17-B1-C28;
A17-B1-C29;
A17-B1-C30;
A17-B1-C31;
A17-B1-C32;
A17-B1-C33;
A17-B1-C34;
A17-B1-C35;
A17-B1-C36;
A17-B1-C37;
A17-B1-C38;
A17-B1-C39;
A17-B1-C40;
A17-B1-C41;
A17-B1-C42;
A17-B1-C43;
A17-B1-C44;
A17-B1-C45;
A17-B1-C46;
A17-B1-C47;
A17-B1-C48;
A17-B1-C49;
A17-B1-C50;
A17-B1-C51;
A17-B1-C52;
A17-B1-C53;
A17-B1-C54;
A17-B1-C55;
A17-B1-C56;
A17-B1-C57;
A17-B1-C58;
A17-B1-C59;
A18-B1-C1;
A18-B1-C2;
A18-B1-C3;
A18-B1-C4;
A18-B1-C5;
A18-B1-C6;
A18-B1-C7;
A18-B1-C8;
A18-B1-C9;
A18-B1-C10;
A18-B1-C11;
A18-B1-C12;
A18-B1-C13;
A18-B1-C14;
A18-B1-C15;
A18-B1-C16;
A18-B1-C17;
A18-B1-C18;
A18-B1-C19;
A18-B1-C20;
A18-B1-C21;
A18-B1-C22;
A18-B1-C23;
A18-B1-C24;
A18-B1-C25;
A18-B1-C26;
A18-B1-C27;
A18-B1-C28;
A18-B1-C29;
A18-B1-C30;
A18-B1-C31;
A18-B1-C32;
A18-B1-C33;
A18-B1-C34;
A18-B1-C35;
A18-B1-C36;
A18-B1-C37;
A18-B1-C38;
A18-B1-C39;
A18-B1-C40;
A18-B1-C41;
A18-B1-C42;
A18-B1-C43;
A18-B1-C44;
A18-B1-C45;
A18-B1-C46;
A18-B1-C47;
A18-B1-C48;
A18-B1-C49;
A18-B1-C50;
A18-B1-C51;
A18-B1-C52;
A18-B1-C53;
A18-B1-C54;
A18-B1-C55;
A18-B1-C56;
A18-B1-C57;
A18-B1-C58;
A18-B1-C59;
A19-B1-C1;
A19-B1-C2;
A19-B1-C3;
A19-B1-C4;
A19-B1-C5;
A19-B1-C6;
A19-B1-C7;
A19-B1-C8;
A19-B1-C9;
A19-B1-C10;
A19-B1-C11;
A19-B1-C12;
A19-B1-C13;
A19-B1-C14;
A19-B1-C15;
A19-B1-C16;
A19-B1-C17;
A19-B1-C18;
A19-B1-C19;
A19-B1-C20;
A19-B1-C21;
A19-B1-C22;
A19-B1-C23;
A19-B1-C24;
A19-B1-C25;
A19-B1-C26;
A19-B1-C27;
A19-B1-C28;
A19-B1-C29;
A19-B1-C30;
A19-B1-C31;
A19-B1-C32;
A19-B1-C33;
A19-B1-C34;
A19-B1-C35;
A19-B1-C36;
A19-B1-C37;
A19-B1-C38;
A19-B1-C39;
A19-B1-C40;
A19-B1-C41;
A19-B1-C42;
A19-B1-C43;
A19-B1-C44;
A19-B1-C45;
A19-B1-C46;
A19-B1-C47;
A19-B1-C48;
A19-B1-C49;
A19-B1-C50;
A19-B1-C51;
A19-B1-C52;
A19-B1-C53;
A19-B1-C54;

A19-B1-C55;
A19-B1-C56;
A19-B1-C57;
A19-B1-C58;
A19-B1-C59;
A20-B1-C1;
A20-B1-C2;
A20-B1-C3;
A20-B1-C4;
A20-B1-C5;
A20-B1-C6;
A20-B1-C7;
A20-B1-C8;
A20-B1-C9;
A20-B1-C10;
A20-B1-C11;
A20-B1-C12;
A20-B1-C13;
A20-B1-C14;
A20-B1-C15;
A20-B1-C16;
A20-B1-C17;
A20-B1-C18;
A20-B1-C19;
A20-B1-C20;
A20-B1-C21;
A20-B1-C22;
A20-B1-C23;
A20-B1-C24;
A20-B1-C25;
A20-B1-C26;
A20-B1-C27;
A20-B1-C28;
A20-B1-C29;
A20-B1-C30;
A20-B1-C31;
A20-B1-C32;
A20-B1-C33;
A20-B1-C34;
A20-B1-C35;
A20-B1-C36;
A20-B1-C37;
A20-B1-C38;
A20-B1-C39;
A20-B1-C40;
A20-B1-C41;
A20-B1-C42;
A20-B1-C43;
A20-B1-C44;
A20-B1-C45;
A20-B1-C46;
A20-B1-C47;
A20-B1-C48;
A20-B1-C49;
A20-B1-C50;
A20-B1-C51;
A20-B1-C52;
A20-B1-C53;
A20-B1-C54;
A20-B1-C55;
A20-B1-C56;
A20-B1-C57;
A20-B1-C58;
A20-B1-C59;
A21-B1-C1;
A21-B1-C2;
A21-B1-C3;
A21-B1-C4;
A21-B1-C5;
A21-B1-C6;
A21-B1-C7;
A21-B1-C8;
A21-B1-C9;
A21-B1-C10;
A21-B1-C11;
A21-B1-C12;
A21-B1-C13;
A21-B1-C14;
A21-B1-C15;
A21-B1-C16;
A21-B1-C17;
A21-B1-C18;
A21-B1-C19;
A21-B1-C20;
A21-B1-C21;
A21-B1-C22;
A21-B1-C23;
A21-B1-C24;
A21-B1-C25;
A21-B1-C26;
A21-B1-C27;
A21-B1-C28;
A21-B1-C29;
A21-B1-C30;
A21-B1-C31;
A21-B1-C32;
A21-B1-C33;
A21-B1-C34;
A21-B1-C35;
A21-B1-C36;
A21-B1-C37;
A21-B1-C38;
A21-B1-C39;
A21-B1-C40;
A21-B1-C41;
A21-B1-C42;
A21-B1-C43;
A21-B1-C44;
A21-B1-C45;
A21-B1-C46;
A21-B1-C47;
A21-B1-C48;
A21-B1-C49;
A21-B1-C50;
A21-B1-C51;
A21-B1-C52;
A21-B1-C53;
A21-B1-C54;
A21-B1-C55;
A21-B1-C56;
A21-B1-C57;
A21-B1-C58;
A21-B1-C59;
A22-B1-C1;
A22-B1-C2;
A22-B1-C3;
A22-B1-C4;
A22-B1-C5;
A22-B1-C6;
A22-B1-C7;
A22-B1-C8;
A22-B1-C9;
A22-B1-C10;
A22-B1-C11;
A22-B1-C12;
A22-B1-C13;
A22-B1-C14;
A22-B1-C15;
A22-B1-C16;
A22-B1-C17;
A22-B1-C18;
A22-B1-C19;
A22-B1-C20;
A22-B1-C21;
A22-B1-C22;
A22-B1-C23;
A22-B1-C24;
A22-B1-C25;
A22-B1-C26;
A22-B1-C27;
A22-B1-C28;
A22-B1-C29;
A22-B1-C30;
A22-B1-C31;
A22-B1-C32;
A22-B1-C33;
A22-B1-C34;
A22-B1-C35;

-continued

A22-B1-C36;
A22-B1-C37;
A22-B1-C38;
A22-B1-C39;
A22-B1-C40;
A22-B1-C41;
A22-B1-C42;
A22-B1-C43;
A22-B1-C44;
A22-B1-C45;
A22-B1-C46;
A22-B1-C47;
A22-B1-C48;
A22-B1-C49;
A22-B1-C50;
A22-B1-C51;
A22-B1-C52;
A22-B1-C53;
A22-B1-C54;
A22-B1-C55;
A22-B1-C56;
A22-B1-C57;
A22-B1-C58;
A22-B1-C59;
A23-B1-C1;
A23-B1-C2;
A23-B1-C3;
A23-B1-C4;
A23-B1-C5;
A23-B1-C6;
A23-B1-C7;
A23-B1-C8;
A23-B1-C9;
A23-B1-C10;
A23-B1-C11;
A23-B1-C12;
A23-B1-C13;
A23-B1-C14;
A23-B1-C15;
A23-B1-C16;
A23-B1-C17;
A23-B1-C18;
A23-B1-C19;
A23-B1-C20;
A23-B1-C21;
A23-B1-C22;
A23-B1-C23;
A23-B1-C24;
A23-B1-C25;
A23-B1-C26;
A23-B1-C27;
A23-B1-C28;
A23-B1-C29;
A23-B1-C30;
A23-B1-C31;
A23-B1-C32;
A23-B1-C33;
A23-B1-C34;
A23-B1-C35;
A23-B1-C36;
A23-B1-C37;
A23-B1-C38;
A23-B1-C39;
A23-B1-C40;
A23-B1-C41;
A23-B1-C42;
A23-B1-C43;
A23-B1-C44;
A23-B1-C45;
A23-B1-C46;
A23-B1-C47;
A23-B1-C48;
A23-B1-C49;
A23-B1-C50;
A23-B1-C51;
A23-B1-C52;
A23-B1-C53;
A23-B1-C54;
A23-B1-C55;

-continued

A23-B1-C56;
A23-B1-C57;
A23-B1-C58;
A23-B1-C59;
A24-B1-C1;
A24-B1-C2;
A24-B1-C3;
A24-B1-C4;
A24-B1-C5;
A24-B1-C6;
A24-B1-C7;
A24-B1-C8;
A24-B1-C9;
A24-B1-C10;
A24-B1-C11;
A24-B1-C12;
A24-B1-C13;
A24-B1-C14;
A24-B1-C15;
A24-B1-C16;
A24-B1-C17;
A24-B1-C18;
A24-B1-C19;
A24-B1-C20;
A24-B1-C21;
A24-B1-C22;
A24-B1-C23;
A24-B1-C24;
A24-B1-C25;
A24-B1-C26;
A24-B1-C27;
A24-B1-C28;
A24-B1-C29;
A24-B1-C30;
A24-B1-C31;
A24-B1-C32;
A24-B1-C33;
A24-B1-C34;
A24-B1-C35;
A24-B1-C36;
A24-B1-C37;
A24-B1-C38;
A24-B1-C39;
A24-B1-C40;
A24-B1-C41;
A24-B1-C42;
A24-B1-C43;
A24-B1-C44;
A24-B1-C45;
A24-B1-C46;
A24-B1-C47;
A24-B1-C48;
A24-B1-C49;
A24-B1-C50;
A24-B1-C51;
A24-B1-C52;
A24-B1-C53;
A24-B1-C54;
A24-B1-C55;
A24-B1-C56;
A24-B1-C57;
A24-B1-C58;
A24-B1-C59;
A25-B1-C1;
A25-B1-C2;
A25-B1-C3;
A25-B1-C4;
A25-B1-C5;
A25-B1-C6;
A25-B1-C7;
A25-B1-C8;
A25-B1-C9;
A25-B1-C10;
A25-B1-C11;
A25-B1-C12;
A25-B1-C13;
A25-B1-C14;
A25-B1-C15;
A25-B1-C16;

-continued

A25-B1-C17;
A25-B1-C18;
A25-B1-C19;
A25-B1-C20;
A25-B1-C21;
A25-B1-C22;
A25-B1-C23;
A25-B1-C24;
A25-B1-C25;
A25-B1-C26;
A25-B1-C27;
A25-B1-C28;
A25-B1-C29;
A25-B1-C30;
A25-B1-C31;
A25-B1-C32;
A25-B1-C33;
A25-B1-C34;
A25-B1-C35;
A25-B1-C36;
A25-B1-C37;
A25-B1-C38;
A25-B1-C39;
A25-B1-C40;
A25-B1-C41;
A25-B1-C42;
A25-B1-C43;
A25-B1-C44;
A25-B1-C45;
A25-B1-C46;
A25-B1-C47;
A25-B1-C48;
A25-B1-C49;
A25-B1-C50;
A25-B1-C51;
A25-B1-C52;
A25-B1-C53;
A25-B1-C54;
A25-B1-C55;
A25-B1-C56;
A25-B1-C57;
A25-B1-C58;
A25-B1-C59;
A26-B1-C1;
A26-B1-C2;
A26-B1-C3;
A26-B1-C4;
A26-B1-C5;
A26-B1-C6;
A26-B1-C7;
A26-B1-C8;
A26-B1-C9;
A26-B1-C10;
A26-B1-C11;
A26-B1-C12;
A26-B1-C13;
A26-B1-C14;
A26-B1-C15;
A26-B1-C16;
A26-B1-C17;
A26-B1-C18;
A26-B1-C19;
A26-B1-C20;
A26-B1-C21;
A26-B1-C22;
A26-B1-C23;
A26-B1-C24;
A26-B1-C25;
A26-B1-C26;
A26-B1-C27;
A26-B1-C28;
A26-B1-C29;
A26-B1-C30;
A26-B1-C31;
A26-B1-C32;
A26-B1-C33;
A26-B1-C34;
A26-B1-C35;
A26-B1-C36;

-continued

A26-B1-C37;
A26-B1-C38;
A26-B1-C39;
A26-B1-C40;
A26-B1-C41;
A26-B1-C42;
A26-B1-C43;
A26-B1-C44;
A26-B1-C45;
A26-B1-C46;
A26-B1-C47;
A26-B1-C48;
A26-B1-C49;
A26-B1-C50;
A26-B1-C51;
A26-B1-C52;
A26-B1-C53;
A26-B1-C54;
A26-B1-C55;
A26-B1-C56;
A26-B1-C57;
A26-B1-C58;
A26-B1-C59;
A27-B1-C1;
A27-B1-C2;
A27-B1-C3;
A27-B1-C4;
A27-B1-C5;
A27-B1-C6;
A27-B1-C7;
A27-B1-C8;
A27-B1-C9;
A27-B1-C10;
A27-B1-C11;
A27-B1-C12;
A27-B1-C13;
A27-B1-C14;
A27-B1-C15;
A27-B1-C16;
A27-B1-C17;
A27-B1-C18;
A27-B1-C19;
A27-B1-C20;
A27-B1-C21;
A27-B1-C22;
A27-B1-C23;
A27-B1-C24;
A27-B1-C25;
A27-B1-C26;
A27-B1-C27;
A27-B1-C28;
A27-B1-C29;
A27-B1-C30;
A27-B1-C31;
A27-B1-C32;
A27-B1-C33;
A27-B1-C34;
A27-B1-C35;
A27-B1-C36;
A27-B1-C37;
A27-B1-C38;
A27-B1-C39;
A27-B1-C40;
A27-B1-C41;
A27-B1-C42;
A27-B1-C43;
A27-B1-C44;
A27-B1-C45;
A27-B1-C46;
A27-B1-C47;
A27-B1-C48;
A27-B1-C49;
A27-B1-C50;
A27-B1-C51;
A27-B1-C52;
A27-B1-C53;
A27-B1-C54;
A27-B1-C55;
A27-B1-C56;

-continued

A27-B1-C57;
A27-B1-C58;
A27-B1-C59;
A28-B1-C1;
A28-B1-C2;
A28-B1-C3;
A28-B1-C4;
A28-B1-C5;
A28-B1-C6;
A28-B1-C7;
A28-B1-C8;
A28-B1-C9;
A28-B1-C10;
A28-B1-C11;
A28-B1-C12;
A28-B1-C13;
A28-B1-C14;
A28-B1-C15;
A28-B1-C16;
A28-B1-C17;
A28-B1-C18;
A28-B1-C19;
A28-B1-C20;
A28-B1-C21;
A28-B1-C22;
A28-B1-C23;
A28-B1-C24;
A28-B1-C25;
A28-B1-C26;
A28-B1-C27;
A28-B1-C28;
A28-B1-C29;
A28-B1-C30;
A28-B1-C31;
A28-B1-C32;
A28-B1-C33;
A28-B1-C34;
A28-B1-C35;
A28-B1-C36;
A28-B1-C37;
A28-B1-C38;
A28-B1-C39;
A28-B1-C40;
A28-B1-C41;
A28-B1-C42;
A28-B1-C43;
A28-B1-C44;
A28-B1-C45;
A28-B1-C46;
A28-B1-C47;
A28-B1-C48;
A28-B1-C49;
A28-B1-C50;
A28-B1-C51;
A28-B1-C52;
A28-B1-C53;
A28-B1-C54;
A28-B1-C55;
A28-B1-C56;
A28-B1-C57;
A28-B1-C58;
A28-B1-C59;
A29-B1-C1;
A29-B1-C2;
A29-B1-C3;
A29-B1-C4;
A29-B1-C5;
A29-B1-C6;
A29-B1-C7;
A29-B1-C8;
A29-B1-C9;
A29-B1-C10;
A29-B1-C11;
A29-B1-C12;
A29-B1-C13;
A29-B1-C14;
A29-B1-C15;
A29-B1-C16;
A29-B1-C17;

-continued

A29-B1-C18;
A29-B1-C19;
A29-B1-C20;
A29-B1-C21;
A29-B1-C22;
A29-B1-C23;
A29-B1-C24;
A29-B1-C25;
A29-B1-C26;
A29-B1-C27;
A29-B1-C28;
A29-B1-C29;
A29-B1-C30;
A29-B1-C31;
A29-B1-C32;
A29-B1-C33;
A29-B1-C34;
A29-B1-C35;
A29-B1-C36;
A29-B1-C37;
A29-B1-C38;
A29-B1-C39;
A29-B1-C40;
A29-B1-C41;
A29-B1-C42;
A29-B1-C43;
A29-B1-C44;
A29-B1-C45;
A29-B1-C46;
A29-B1-C47;
A29-B1-C48;
A29-B1-C49;
A29-B1-C50;
A29-B1-C51;
A29-B1-C52;
A29-B1-C53;
A29-B1-C54;
A29-B1-C55;
A29-B1-C56;
A29-B1-C57;
A29-B1-C58;
A29-B1-C59;
A30-B1-C1;
A30-B1-C2;
A30-B1-C3;
A30-B1-C4;
A30-B1-C5;
A30-B1-C6;
A30-B1-C7;
A30-B1-C8;
A30-B1-C9;
A30-B1-C10;
A30-B1-C11;
A30-B1-C12;
A30-B1-C13;
A30-B1-C14;
A30-B1-C15;
A30-B1-C16;
A30-B1-C17;
A30-B1-C18;
A30-B1-C19;
A30-B1-C20;
A30-B1-C21;
A30-B1-C22;
A30-B1-C23;
A30-B1-C24;
A30-B1-C25;
A30-B1-C26;
A30-B1-C27;
A30-B1-C28;
A30-B1-C29;
A30-B1-C30;
A30-B1-C31;
A30-B1-C32;
A30-B1-C33;
A30-B1-C34;
A30-B1-C35;
A30-B1-C36;
A30-B1-C37;

-continued

A30-B1-C38;
A30-B1-C39;
A30-B1-C40;
A30-B1-C41;
A30-B1-C42;
A30-B1-C43;
A30-B1-C44;
A30-B1-C45;
A30-B1-C46;
A30-B1-C47;
A30-B1-C48;
A30-B1-C49;
A30-B1-C50;
A30-B1-C51;
A30-B1-C52;
A30-B1-C53;
A30-B1-C54;
A30-B1-C55;
A30-B1-C56;
A30-B1-C57;
A30-B1-C58;
A30-B1-C59;
A31-B1-C1;
A31-B1-C2;
A31-B1-C3;
A31-B1-C4;
A31-B1-C5;
A31-B1-C6;
A31-B1-C7;
A31-B1-C8;
A31-B1-C9;
A31-B1-C10;
A31-B1-C11;
A31-B1-C12;
A31-B1-C13;
A31-B1-C14;
A31-B1-C15;
A31-B1-C16;
A31-B1-C17;
A31-B1-C18;
A31-B1-C19;
A31-B1-C20;
A31-B1-C21;
A31-B1-C22;
A31-B1-C23;
A31-B1-C24;
A31-B1-C25;
A31-B1-C26;
A31-B1-C27;
A31-B1-C28;
A31-B1-C29;
A31-B1-C30;
A31-B1-C31;
A31-B1-C32;
A31-B1-C33;
A31-B1-C34;
A31-B1-C35;
A31-B1-C36;
A31-B1-C37;
A31-B1-C38;
A31-B1-C39;
A31-B1-C40;
A31-B1-C41;
A31-B1-C42;
A31-B1-C43;
A31-B1-C44;
A31-B1-C45;
A31-B1-C46;
A31-B1-C47;
A31-B1-C48;
A31-B1-C49;
A31-B1-C50;
A31-B1-C51;
A31-B1-C52;
A31-B1-C53;
A31-B1-C54;
A31-B1-C55;
A31-B1-C56;
A31-B1-C57;

-continued

A31-B1-C58;
A31-B1-C59;
A32-B1-C1;
A32-B1-C2;
A32-B1-C3;
A32-B1-C4;
A32-B1-C5;
A32-B1-C6;
A32-B1-C7;
A32-B1-C8;
A32-B1-C9;
A32-B1-C10;
A32-B1-C11;
A32-B1-C12;
A32-B1-C13;
A32-B1-C14;
A32-B1-C15;
A32-B1-C16;
A32-B1-C17;
A32-B1-C18;
A32-B1-C19;
A32-B1-C20;
A32-B1-C21;
A32-B1-C22;
A32-B1-C23;
A32-B1-C24;
A32-B1-C25;
A32-B1-C26;
A32-B1-C27;
A32-B1-C28;
A32-B1-C29;
A32-B1-C30;
A32-B1-C31;
A32-B1-C32;
A32-B1-C33;
A32-B1-C34;
A32-B1-C35;
A32-B1-C36;
A32-B1-C37;
A32-B1-C38;
A32-B1-C39;
A32-B1-C40;
A32-B1-C41;
A32-B1-C42;
A32-B1-C43;
A32-B1-C44;
A32-B1-C45;
A32-B1-C46;
A32-B1-C47;
A32-B1-C48;
A32-B1-C49;
A32-B1-C50;
A32-B1-C51;
A32-B1-C52;
A32-B1-C53;
A32-B1-C54;
A32-B1-C55;
A32-B1-C56;
A32-B1-C57;
A32-B1-C58;
A32-B1-C59;
A33-B1-C1;
A33-B1-C2;
A33-B1-C3;
A33-B1-C4;
A33-B1-C5;
A33-B1-C6;
A33-B1-C7;
A33-B1-C8;
A33-B1-C9;
A33-B1-C10;
A33-B1-C11;
A33-B1-C12;
A33-B1-C13;
A33-B1-C14;
A33-B1-C15;
A33-B1-C16;
A33-B1-C17;
A33-B1-C18;

-continued

A33-B1-C19;
A33-B1-C20;
A33-B1-C21;
A33-B1-C22;
A33-B1-C23;
A33-B1-C24;
A33-B1-C25;
A33-B1-C26;
A33-B1-C27;
A33-B1-C28;
A33-B1-C29;
A33-B1-C30;
A33-B1-C31;
A33-B1-C32;
A33-B1-C33;
A33-B1-C34;
A33-B1-C35;
A33-B1-C36;
A33-B1-C37;
A33-B1-C38;
A33-B1-C39;
A33-B1-C40;
A33-B1-C41;
A33-B1-C42;
A33-B1-C43;
A33-B1-C44;
A33-B1-C45;
A33-B1-C46;
A33-B1-C47;
A33-B1-C48;
A33-B1-C49;
A33-B1-C50;
A33-B1-C51;
A33-B1-C52;
A33-B1-C53;
A33-B1-C54;
A33-B1-C55;
A33-B1-C56;
A33-B1-C57;
A33-B1-C58;
A33-B1-C59;
A34-B1-C1;
A34-B1-C2;
A34-B1-C3;
A34-B1-C4;
A34-B1-C5;
A34-B1-C6;
A34-B1-C7;
A34-B1-C8;
A34-B1-C9;
A34-B1-C10;
A34-B1-C11;
A34-B1-C12;
A34-B1-C13;
A34-B1-C14;
A34-B1-C15;
A34-B1-C16;
A34-B1-C17;
A34-B1-C18;
A34-B1-C19;
A34-B1-C20;
A34-B1-C21;
A34-B1-C22;
A34-B1-C23;
A34-B1-C24;
A34-B1-C25;
A34-B1-C26;
A34-B1-C27;
A34-B1-C28;
A34-B1-C29;
A34-B1-C30;
A34-B1-C31;
A34-B1-C32;
A34-B1-C33;
A34-B1-C34;
A34-B1-C35;
A34-B1-C36;
A34-B1-C37;
A34-B1-C38;

-continued

A34-B1-C39;
A34-B1-C40;
A34-B1-C41;
A34-B1-C42;
A34-B1-C43;
A34-B1-C44;
A34-B1-C45;
A34-B1-C46;
A34-B1-C47;
A34-B1-C48;
A34-B1-C49;
A34-B1-C50;
A34-B1-C51;
A34-B1-C52;
A34-B1-C53;
A34-B1-C54;
A34-B1-C55;
A34-B1-C56;
A34-B1-C57;
A34-B1-C58;
A34-B1-C59;
A35-B1-C1;
A35-B1-C2;
A35-B1-C3;
A35-B1-C4;
A35-B1-C5;
A35-B1-C6;
A35-B1-C7;
A35-B1-C8;
A35-B1-C9;
A35-B1-C10;
A35-B1-C11;
A35-B1-C12;
A35-B1-C13;
A35-B1-C14;
A35-B1-C15;
A35-B1-C16;
A35-B1-C17;
A35-B1-C18;
A35-B1-C19;
A35-B1-C20;
A35-B1-C21;
A35-B1-C22;
A35-B1-C23;
A35-B1-C24;
A35-B1-C25;
A35-B1-C26;
A35-B1-C27;
A35-B1-C28;
A35-B1-C29;
A35-B1-C30;
A35-B1-C31;
A35-B1-C32;
A35-B1-C33;
A35-B1-C34;
A35-B1-C35;
A35-B1-C36;
A35-B1-C37;
A35-B1-C38;
A35-B1-C39;
A35-B1-C40;
A35-B1-C41;
A35-B1-C42;
A35-B1-C43;
A35-B1-C44;
A35-B1-C45;
A35-B1-C46;
A35-B1-C47;
A35-B1-C48;
A35-B1-C49;
A35-B1-C50;
A35-B1-C51;
A35-B1-C52;
A35-B1-C53;
A35-B1-C54;
A35-B1-C55;
A35-B1-C56;
A35-B1-C57;
A35-B1-C58;

-continued

A35-B1-C59;
A1-B2-C1;
A1-B2-C2;
A1-B2-C3;
A1-B2-C4;
A1-B2-C5;
A1-B2-C6;
A1-B2-C7;
A1-B2-C8;
A1-B2-C9;
A1-B2-C10;
A1-B2-C11;
A1-B2-C12;
A1-B2-C13;
A1-B2-C14;
A1-B2-C15;
A1-B2-C16;
A1-B2-C17;
A1-B2-C18;
A1-B2-C19;
A1-B2-C20;
A1-B2-C21;
A1-B2-C22;
A1-B2-C23;
A1-B2-C24;
A1-B2-C25;
A1-B2-C26;
A1-B2-C27;
A1-B2-C28;
A1-B2-C29;
A1-B2-C30;
A1-B2-C31;
A1-B2-C32;
A1-B2-C33;
A1-B2-C34;
A1-B2-C35;
A1-B2-C36;
A1-B2-C37;
A1-B2-C38;
A1-B2-C39;
A1-B2-C40;
A1-B2-C41;
A1-B2-C42;
A1-B2-C43;
A1-B2-C44;
A1-B2-C45;
A1-B2-C46;
A1-B2-C47;
A1-B2-C48;
A1-B2-C49;
A1-B2-C50;
A1-B1-C51;
A1-B2-C52;
A1-B2-C53;
A1-B2-C54;
A1-B1-C55;
A1-B1-C56;
A1-B2-C57;
A1-B2-C58;
A1-B2-C59;
A2-B2-C1;
A2-B2-C2;
A2-B2-C3;
A2-B2-C4;
A2-B2-C5;
A2-B2-C6;
A2-B2-C7;
A2-B2-C8;
A2-B2-C9;
A2-B2-C10;
A2-B2-C11;
A2-B2-C12;
A2-B2-C13;
A2-B2-C14;
A2-B2-C15;
A2-B2-C16;
A2-B2-C17;
A2-B2-C18;
A2-B2-C19;

-continued

A2-B2-C20;
A2-B2-C21;
A2-B2-C22;
A2-B2-C23;
A2-B2-C24;
A2-B2-C25;
A2-B2-C26;
A2-B2-C27;
A2-B2-C28;
A2-B2-C29;
A2-B2-C30;
A2-B2-C31;
A2-B2-C32;
A2-B2-C33;
A2-B2-C34;
A2-B2-C35;
A2-B2-C36;
A2-B2-C37;
A2-B2-C38;
A2-B2-C39;
A2-B2-C40;
A2-B2-C41;
A2-B2-C42;
A2-B2-C43;
A2-B2-C44;
A2-B2-C45;
A2-B2-C46;
A2-B2-C47;
A2-B2-C48;
A2-B2-C49;
A2-B2-C50;
A2-B2-C51;
A2-B2-C52;
A2-B2-C53;
A2-B2-C54;
A2-B2-C55;
A2-B2-C56;
A2-B2-C57;
A2-B2-C58;
A2-B2-C59;
A3-B2-C1;
A3-B2-C2;
A3-B2-C3;
A3-B2-C4;
A3-B2-C5;
A3-B2-C6;
A3-B2-C7;
A3-B2-C8;
A3-B2-C9;
A3-B2-C10;
A3-B2-C11;
A3-B2-C12;
A3-B2-C13;
A3-B2-C14;
A3-B2-C15;
A3-B2-C16;
A3-B2-C17;
A3-B2-C18;
A3-B2-C19;
A3-B2-C20;
A3-B2-C21;
A3-B2-C22;
A3-B2-C23;
A3-B2-C24;
A3-B2-C25;
A3-B2-C26;
A3-B2-C27;
A3-B2-C28;
A3-B2-C29;
A3-B2-C30;
A3-B2-C31;
A3-B2-C32;
A3-B2-C33;
A3-B2-C34;
A3-B2-C35;
A3-B2-C36;
A3-B2-C37;
A3-B2-C38;
A3-B2-C39;

-continued

A3-B2-C40;
A3-B2-C41;
A3-B2-C42;
A3-B2-C43;
A3-B2-C44;
A3-B2-C45;
A3-B2-C46;
A3-B2-C47;
A3-B2-C48;
A3-B2-C49;
A3-B2-C50;
A3-B2-C51;
A3-B2-C52;
A3-B2-C53;
A3-B2-C54;
A3-B2-C55;
A3-B2-C56;
A3-B2-C57;
A3-B2-C58;
A3-B2-C59;
A4-B2-C1;
A4-B2-C2;
A4-B2-C3;
A4-B2-C4;
A4-B2-C5;
A4-B2-C6;
A4-B2-C7;
A4-B2-C5;
A4-B2-C9;
A4-B2-C10;
A4-B2-C11;
A4-B2-C12;
A4-B2-C13;
A4-B2-C14;
A4-B2-C15;
A4-B2-C16;
A4-B2-C17;
A4-B2-C18;
A4-B2-C19;
A4-B2-C20;
A4-B2-C21,
A4-B2-C22;
A4-B2-C23;
A4-B2-C24;
A4-B2-C25;
A4-B2-C26;
A4-B2-C27;
A4-B2-C28;
A4-B2-C29;
A4-B2-C30;
A4-B2-C31;
A4-B2-C32;
A4-B2-C33;
A4-B2-C34;
A4-B2-C35;
A4-B2-C36;
A4-B2-C37;
A4-B2-C38;
A4-B2-C39;
A4-B2-C40;
A4-B2-C41;
A4-B2-C42;
A4-B2-C43;
A4-B2-C44;
A4-B2-C45;
A4-B2-C46;
A4-B2-C47;
A4-B2-C48;
A4-B2-C49;
A4-B2-C50;
A4-B2-C51;
A4-B2-C52;
A4-B2-C53;
A4-B2-C54;
A4-B2-C55;
A4-B2-C56;
A4-B2-C57;
A4-B2-C58;
A4-B2-C59;

-continued

A5-B2-C1;
A5-B2-C2;
A5-B2-C3;
A5-B2-C4;
A5-B2-C5;
A5-B2-C6;
A5-B2-C7;
A5-B2-C8;
A5-B2-C9;
A5-B2-C10;
A5-B2-C11;
A5-B2-C12;
A5-B2-C13;
A5-B2-C14;
A5-B2-C15;
A5-B2-C16;
A5-B2-C17;
A5-B2-C18;
A5-B2-C19;
A5-B2-C20;
A5-B2-C21;
A5-B2-C22;
A5-B2-C23;
A5-B2-C24;
A5-B2-C25;
A5-B2-C26;
A5-B2-C27;
A5-B2-C28;
A5-B2-C29;
A5-B2-C30;
A5-B2-C31;
A5-B2-C32;
A5-B2-C33;
A5-B2-C34;
A5-B2-C35;
A5-B2-C36;
A5-B2-C37;
A5-B2-C38;
A5-B2-C39;
A5-B2-C40;
A5-B2-C41;
A5-B2-C42;
A5-B2-C43;
A5-B2-C44;
A5-B2-C45;
A5-B2-C46;
A5-B2-C47;
A5-B2-C48;
A5-B2-C49;
A5-B2-C50;
A5-B2-C51;
A5-B2-C52;
A5-B2-C53;
A5-B2-C54;
A5-B2-C55;
A5-B2-C56;
A5-B2-C57;
A5-B2-C58;
A5-B2-C59;
A6-B2-C1;
A6-B2-C2;
A6-B2-C3;
A6-B2-C4;
A6-B2-C5;
A6-B2-C6;
A6-B2-C7;
A6-B2-C8;
A6-B2-C9;
A6-B2-C10;
A6-B2-C11;
A6-B2-C12;
A6-B2-C13;
A6-B2-C14;
A6-B2-C15;
A6-B2-C16;
A6-B2-C17;
A6-B2-C18;
A6-B2-C19;
A6-B2-C20;

-continued

A6-B2-C21;
A6-B2-C22;
A6-B2-C23;
A6-B2-C24;
A6-B2-C25;
A6-B2-C26;
A6-B2-C27;
A6-B2-C28;
A6-B2-C29;
A6-B2-C30;
A6-B2-C31;
A6-B2-C32;
A6-B2-C33;
A6-B2-C34;
A6-B2-C35;
A6-B2-C36;
A6-B2-C37;
A6-B2-C38;
A6-B2-C39;
A6-B2-C40;
A6-B2-C41;
A6-B2-C42;
A6-B2-C43;
A6-B2-C44;
A6-B2-C45;
A6-B2-C46;
A6-B2-C47;
A6-B2-C48;
A6-B2-C49;
A6-B2-C50;
A6-B2-C51;
A6-B2-C52;
A6-B2-C53;
A6-B2-C54;
A6-B2-C55;
A6-B2-C56;
A6-B2-C57;
A6-B2-C58;
A6-B2-C59;
A7-B2-C1;
A7-B2-C2;
A7-B2-C3;
A7-B2-C4;
A7-B2-C5;
A7-B2-C6;
A7-B2-C7;
A7-B2-C8;
A7-B2-C9;
A7-B2-C10;
A7-B2-C11;
A7-B2-C12;
A7-B2-C13;
A7-B2-C14;
A7-B2-C15;
A7-B2-C16;
A7-B2-C17;
A7-B2-C18;
A7-B2-C19;
A7-B2-C20;
A7-B2-C21;
A7-B2-C22;
A7-B2-C23;
A7-B2-C24;
A7-B2-C25;
A7-B2-C26;
A7-B2-C27;
A7-B2-C28;
A7-B2-C29;
A7-B2-C30;
A7-B2-C31;
A7-B2-C32;
A7-B2-C33;
A7-B2-C34;
A7-B2-C35;
A7-B2-C36;
A7-B2-C37;
A7-B2-C38;
A7-B2-C39;
A7-B2-C40;
A7-B2-C41;
A7-B2-C42;
A7-B2-C43;
A7-B2-C44;
A7-B2-C45;
A7-B2-C46;
A7-B2-C47;
A7-B2-C48;
A7-B2-C49;
A7-B2-C50;
A7-B2-C51;
A7-B2-C52;
A7-B2-C53;
A7-B2-C54;
A7-B2-C55;
A7-B2-C56;
A7-B2-C57;
A7-B2-C58;
A7-B2-C59;
A8-B2-C1;
A8-B2-C2;
A8-B2-C3;
A8-B2-C4;
A8-B2-C5;
A8-B2-C6;
A8-B2-C7;
A8-B2-C8;
A8-B2-C9;
A8-B2-C10;
A8-B2-C11;
A8-B2-C12;
A8-B2-C13;
A8-B2-C14;
A8-B2-C15;
A8-B2-C16;
A8-B2-C17;
A8-B2-C18;
A8-B2-C19;
A8-B2-C20;
A8-B2-C21;
A8-B2-C22;
A8-B2-C23;
A8-B2-C24;
A8-B2-C25;
A8-B2-C26;
A8-B2-C27;
A8-B2-C28;
A8-B2-C29;
A8-B2-C30;
A8-B2-C31;
A8-B2-C32;
A8-B2-C33;
A8-B2-C34;
A8-B2-C35;
A8-B2-C36;
A8-B2-C37;
A8-B2-C38;
A8-B2-C39;
A8-B2-C40;
A8-B2-C41;
A8-B2-C42;
A8-B2-C43;
A8-B2-C44;
A8-B2-C45;
A8-B2-C46;
A8-B2-C47;
A8-B2-C48;
A8-B2-C49;
A8-B2-C50;
A8-B2-C51;
A8-B2-C52;
A8-B2-C53;
A8-B2-C54;
A8-B2-C55;
A8-B2-C56;
A8-B2-C57;
A8-B2-C58;
A8-B2-C59;
A9-B2-C1;

-continued

A9-B2-C2;
A9-B2-C3;
A9-B2-C4;
A9-B2-C5;
A9-B2-C6;
A9-B2-C7;
A9-B2-C8;
A9-B2-C9;
A9-B2-C10;
A9-B2-C11;
A9-B2-C12;
A9-B2-C13;
A9-B2-C14;
A9-B2-C15;
A9-B2-C16;
A9-B2-C17;
A9-B2-C18;
A9-B2-C19;
A9-B2-C20;
A9-B2-C21;
A9-B2-C22;
A9-B2-C23;
A9-B2-C24;
A9-B2-C25;
A9-B2-C26;
A9-B2-C27;
A9-B2-C28;
A9-B2-C29;
A9-B2-C30;
A9-B2-C31;
A9-B2-C32;
A9-B2-C33;
A9-B2-C34;
A9-B2-C35;
A9-B2-C36;
A9-B2-C37;
A9-B2-C38;
A9-B2-C39;
A9-B2-C40;
A9-B2-C41;
A9-B2-C42;
A9-B2-C43;
A9-B2-C44;
A9-B2-C45;
A9-B2-C46;
A9-B2-C47;
A9-B2-C48;
A9-B2-C49;
A9-B2-C50;
A9-B2-C51;
A9-B2-C52;
A9-B2-C53;
A9-B2-C54;
A9-B2-C55;
A9-B2-C56;
A9-B2-C57;
A9-B2-C58;
A9-B2-C59;
A10-B2-C1;
A10-B2-C2;
A10-B2-C3;
A10-B2-C4;
A10-B2-C5;
A10-B2-C6;
A10-B2-C7;
A10-B2-C8;
A10-B2-C9;
A10-B2-C10;
A10-B2-C11;
A10-B2-C12;
A10-B2-C13;
A10-B2-C14;
A10-B2-C15;
A10-B2-C16;
A10-B2-C17;
A10-B2-C18;
A10-B2-C19;
A10-B2-C20;
A10-B2-C21;

-continued

A10-B2-C22;
A10-B2-C23;
A10-B2-C24;
A10-B2-C25;
A10-B2-C26;
A10-B2-C27;
A10-B2-C28;
A10-B2-C29;
A10-B2-C30;
A10-B2-C31;
A10-B2-C32;
A10-B2-C33;
A10-B2-C34;
A10-B2-C35;
A10-B2-C36;
A10-B2-C37;
A10-B2-C38;
A10-B2-C39;
A10-B2-C40;
A10-B2-C41;
A10-B2-C42;
A10-B2-C43;
A10-B2-C44;
A10-B2-C45;
A10-B2-C46;
A10-B2-C47;
A10-B2-C48;
A10-B2-C49;
A10-B2-C50;
A10-B2-C51;
A10-B2-C52;
A10-B2-C53;
A10-B2-C54;
A10-B2-C55;
A10-B2-C56;
A10-B2-C57;
A10-B2-C58;
A10-B2-C59;
A11-B2-C1;
A11-B2-C2;
A11-B2-C3;
A11-B2-C4;
A11-B2-C5;
A11-B2-C6;
A11-B2-C7;
A11-B2-C8;
A11-B2-C9;
A11-B2-C10;
A11-B2-C11;
A11-B2-C12;
A11-B2-C13;
A11-B2-C14;
A11-B2-C15;
A11-B2-C16;
A11-B2-C17;
A11-B2-C18;
A11-B2-C19;
A11-B2-C20;
A11-B2-C21;
A11-B2-C22;
A11-B2-C23;
A11-B2-C24;
A11-B2-C25;
A11-B2-C26;
A11-B2-C27;
A11-B2-C28;
A11-B2-C29;
A11-B2-C30;
A11-B2-C31;
A11-B2-C32;
A11-B2-C33;
A11-B2-C34;
A11-B2-C35;
A11-B2-C36;
A11-B2-C37;
A11-B2-C38;
A11-B2-C39;
A11-B2-C40;
A11-B2-C41;

-continued

A11-B2-C42;
A11-B2-C43;
A11-B2-C44;
A11-B2-C45;
A11-B2-C46;
A11-B2-C47;
A11-B2-C48;
A11-B2-C49;
A11-B2-C50;
A11-B2-C51;
A11-B2-C52;
A11-B2-C53;
A11-B2-C54;
A11-B2-C55;
A11-B2-C56;
A11-B2-C57;
A11-B2-C58;
A11-B2-C59;
A12-B2-C1;
A12-B2-C2;
A12-B2-C3;
A12-B2-C4;
A12-B2-C5;
A12-B2-C6;
A12-B2-C7;
A12-B2-C8;
A12-B2-C9;
A12-B2-C10;
A12-B2-C11;
A12-B2-C12;
A12-B2-C13;
A12-B2-C14;
A12-B2-C15;
A12-B2-C16;
A12-B2-C17;
A12-B2-C18;
A12-B2-C19;
A12-B2-C20;
A12-B2-C21;
A12-B2-C22;
A12-B2-C23;
A12-B2-C24;
A12-B2-C25;
A12-B2-C26;
A12-B2-C27;
A12-B2-C28;
A12-B2-C29;
A12-B2-C30;
A12-B2-C31;
A12-B2-C32;
A12-B2-C33;
A12-B2-C34;
A12-B2-C35;
A12-B2-C36;
A12-B2-C37;
A12-B2-C38;
A12-B2-C39;
A12-B2-C40;
A12-B2-C41;
A12-B2-C42;
A12-B2-C43;
A12-B2-C44;
A12-B2-C45;
A12-B2-C46;
A12-B2-C47;
A12-B2-C48;
A12-B2-C49;
A12-B2-C50;
A12-B2-C51;
A12-B2-C52;
A12-B2-C53;
A12-B2-C54;
A12-B2-C55;
A12-B2-C56;
A12-B2-C57;
A12-B2-C58;
A12-B2-C59;
A13-B2-C1;
A13-B2-C2;

-continued

A13-B2-C3;
A13-B2-C4;
A13-B2-C5;
A13-B2-C6;
A13-B2-C7;
A13-B2-C8;
A13-B2-C9;
A13-B2-C10;
A13-B2-C11;
A13-B2-C12;
A13-B2-C13;
A13-B2-C14;
A13-B2-C15;
A13-B2-C16;
A13-B2-C17;
A13-B2-C18;
A13-B2-C19;
A13-B2-C20;
A13-B2-C21;
A13-B2-C22;
A13-B2-C23;
A13-B2-C24;
A13-B2-C25;
A13-B2-C26;
A13-B2-C27;
A13-B2-C28;
A13-B2-C29;
A13-B2-C30;
A13-B2-C31;
A13-B2-C32;
A13-B2-C33;
A13-B2-C34;
A13-B2-C35;
A13-B2-C36;
A13-B2-C37;
A13-B2-C38;
A13-B2-C39;
A13-B2-C40;
A13-B2-C41;
A13-B2-C42;
A13-B2-C43;
A13-B2-C44;
A13-B2-C45;
A13-B2-C46;
A13-B2-C47;
A13-B2-C48;
A13-B2-C49;
A13-B2-C50;
A13-B2-C51;
A13-B2-C52;
A13-B2-C53;
A13-B2-C54;
A13-B2-C55;
A13-B2-C56;
A13-B2-C57;
A13-B2-C58;
A13-B2-C59;
A14-B2-C1;
A14-B2-C2;
A14-B2-C3;
A14-B2-C4;
A14-B2-C5;
A14-B2-C6;
A14-B2-C7;
A14-B2-C8;
A14-B2-C9;
A14-B2-C10;
A14-B2-C11;
A14-B2-C12;
A14-B2-C13;
A14-B2-C14;
A14-B2-C15;
A14-B2-C16;
A14-B2-C17;
A14-B2-C18;
A14-B2-C19;
A14-B2-C20;
A14-B2-C21;
A14-B2-C22;

-continued

A14-B2-C23;
A14-B2-C24;
A14-B2-C25;
A14-B2-C26;
A14-B2-C27;
A14-B2-C28;
A14-B2-C29;
A14-B2-C30;
A14-B2-C31;
A14-B2-C32;
A14-B2-C33;
A14-B2-C34;
A14-B2-C35;
A14-B2-C36;
A14-B2-C37;
A14-B2-C38;
A14-B2-C39;
A14-B2-C40;
A14-B2-C41;
A14-B2-C42;
A14-B2-C43;
A14-B2-C44;
A14-B2-C45;
A14-B2-C46;
A14-B2-C47;
A14-B2-C48;
A14-B2-C49;
A14-B2-C50;
A14-B2-C51;
A14-B2-C52;
A14-B2-C53;
A14-B2-C54;
A14-B2-C55;
A14-B2-C56;
A14-B2-C57;
A14-B2-C58;
A14-B2-C59;
A15-B2-C1;
A15-B2-C2;
A15-B2-C3;
A15-B2-C4;
A15-B2-C5;
A15-B2-C6;
A15-B2-C7;
A15-B2-C8;
A15-B2-C9;
A15-B2-C10;
A15-B2-C11;
A15-B2-C12;
A15-B2-C13;
A15-B2-C14;
A15-B2-C15;
A15-B2-C16;
A15-B2-C17;
A15-B2-C18;
A15-B2-C19;
A15-B2-C20;
A15-B2-C21;
A15-B2-C22;
A15-B2-C23;
A15-B2-C24;
A15-B2-C25;
A15-B2-C26;
A15-B2-C27;
A15-B2-C28;
A15-B2-C29;
A15-B2-C30;
A15-B2-C31;
A15-B2-C32;
A15-B2-C33;
A15-B2-C34;
A15-B2-C35;
A15-B2-C36;
A15-B2-C37;
A15-B2-C38;
A15-B2-C39;
A15-B2-C40;
A15-B2-C41;
A15-B2-C42;

-continued

A15-B2-C43;
A15-B2-C44;
A15-B2-C45;
A15-B2-C46;
A15-B2-C47;
A15-B2-C48;
A15-B2-C49;
A15-B2-C50;
A15-B2-C51;
A15-B2-C52;
A15-B2-C53;
A15-B2-C54;
A15-B2-C55;
A15-B2-C56;
A15-B2-C57;
A15-B2-C58;
A15-B2-C59;
A16-B2-C1;
A16-B2-C2;
A16-B2-C3;
A16-B2-C4;
A16-B2-C5;
A16-B2-C6;
A16-B2-C7;
A16-B2-C8;
A16-B2-C9;
A16-B2-C10;
A16-B2-C11;
A16-B2-C12;
A16-B2-C13;
A16-B2-C14;
A16-B2-C15;
A16-B2-C16;
A16-B2-C17;
A16-B2-C18;
A16-B2-C19;
A16-B2-C20;
A16-B2-C21;
A16-B2-C22;
A16-B2-C23;
A16-B2-C24;
A16-B2-C25;
A16-B2-C26;
A16-B2-C27;
A16-B2-C28;
A16-B2-C29;
A16-B2-C30;
A16-B2-C31;
A16-B2-C32;
A16-B2-C33;
A16-B2-C34;
A16-B2-C35;
A16-B2-C36;
A16-B2-C37;
A16-B2-C38;
A16-B2-C39;
A16-B2-C40;
A16-B2-C41;
A16-B2-C42;
A16-B2-C43;
A16-B2-C44;
A16-B2-C45;
A16-B2-C46;
A16-B2-C47;
A16-B2-C48;
A16-B2-C49;
A16-B2-C50;
A16-B2-C51;
A16-B2-C52;
A16-B2-C53;
A16-B2-C54;
A16-B2-C55;
A16-B2-C56;
A16-B2-C57;
A16-B2-C58;
A16-B2-C59;
A17-B2-C1;
A17-B2-C2;
A17-B2-C3;

A17-B2-C4;
A17-B2-C5;
A17-B2-C6;
A17-B2-C7;
A17-B2-C8;
A17-B2-C9;
A17-B2-C10;
A17-B2-C11;
A17-B2-C12;
A17-B2-C13;
A17-B2-C14;
A17-B2-C15;
A17-B2-C16;
A17-B2-C17;
A17-B2-C18;
A17-B2-C19;
A17-B2-C20;
A17-B2-C21;
A17-B2-C22;
A17-B2-C23;
A17-B2-C24;
A17-B2-C25;
A17-B2-C26;
A17-B2-C27;
A17-B2-C28;
A17-B2-C29;
A17-B2-C30;
A17-B2-C31;
A17-B2-C32;
A17-B2-C33;
A17-B2-C34;
A17-B2-C35;
A17-B2-C36;
A17-B2-C37;
A17-B2-C38;
A17-B2-C39;
A17-B2-C40;
A17-B2-C41;
A17-B2-C42;
A17-B2-C43;
A17-B2-C44;
A17-B2-C45;
A17-B2-C46;
A17-B2-C47;
A17-B2-C48;
A17-B2-C49;
A17-B2-C50;
A17-B2-C51;
A17-B2-C52;
A17-B2-C53;
A17-B2-C54;
A17-B2-C55;
A17-B2-C56;
A17-B2-C57;
A17-B2-C58;
A17-B2-C59;
A18-B2-C1;
A18-B2-C2;
A18-B2-C3;
A18-B2-C4;
A18-B2-C5;
A18-B2-C6;
A18-B2-C7;
A18-B2-C8;
A18-B2-C9;
A18-B2-C10;
A18-B2-C11;
A18-B2-C12;
A18-B2-C13;
A18-B2-C14;
A18-B2-C15;
A18-B2-C16;
A18-B2-C17;
A18-B2-C18;
A18-B2-C19;
A18-B2-C20;
A18-B2-C21;
A18-B2-C22;
A18-B2-C23;
A18-B2-C24;
A18-B2-C25;
A18-B2-C26;
A18-B2-C27;
A18-B2-C28;
A18-B2-C29;
A18-B2-C30;
A18-B2-C31;
A18-B2-C32;
A18-B2-C33;
A18-B2-C34;
A18-B2-C35;
A18-B2-C36;
A18-B2-C37;
A18-B2-C38;
A18-B2-C39;
A18-B2-C40;
A18-B2-C41;
A18-B2-C42;
A18-B2-C43;
A18-B2-C44;
A18-B2-C45;
A18-B2-C46;
A18-B2-C47;
A18-B2-C48;
A18-B2-C49;
A18-B2-C50;
A18-B2-C51;
A18-B2-C52;
A18-B2-C53;
A18-B2-C54;
A18-B2-C55;
A18-B2-C56;
A18-B2-C57;
A18-B2-C58;
A18-B2-C59;
A19-B2-C1;
A19-B2-C2;
A19-B2-C3;
A19-B2-C4;
A19-B2-C5;
A19-B2-C6;
A19-B2-C7;
A19-B2-C8;
A19-B2-C9;
A19-B2-C10;
A19-B2-C11;
A19-B2-C12;
A19-B2-C13;
A19-B2-C14;
A19-B2-C15;
A19-B2-C16;
A19-B2-C17;
A19-B2-C18;
A19-B2-C19;
A19-B2-C20;
A19-B2-C21;
A19-B2-C22;
A19-B2-C23;
A19-B2-C24;
A19-B2-C25;
A19-B2-C26;
A19-B2-C27;
A19-B2-C28;
A19-B2-C29;
A19-B2-C30;
A19-B2-C31;
A19-B2-C32;
A19-B2-C33;
A19-B2-C34;
A19-B2-C35;
A19-B2-C36;
A19-B2-C37;
A19-B2-C38;
A19-B2-C39;
A19-B2-C40;
A19-B2-C41;
A19-B2-C42;
A19-B2-C43;

-continued

A19-B2-C44;
A19-B2-C45;
A19-B2-C46;
A19-B2-C47;
A19-B2-C48;
A19-B2-C49;
A19-B2-C50;
A19-B2-C51;
A19-B2-C52;
A19-B2-C53;
A19-B2-C54;
A19-B2-C55;
A19-B2-C56;
A19-B2-C57;
A19-B2-C58;
A19-B2-C59;
A20-B2-C1;
A20-B2-C2;
A20-B2-C3;
A20-B2-C4;
A20-B2-C5;
A20-B2-C6;
A20-B2-C7;
A20-B2-C8;
A20-B2-C9;
A20-B2-C10;
A20-B2-C11;
A20-B2-C12;
A20-B2-C13;
A20-B2-C14;
A20-B2-C15;
A20-B2-C16;
A20-B2-C17;
A20-B2-C18;
A20-B2-C19;
A20-B2-C20;
A20-B2-C21;
A20-B2-C22;
A20-B2-C23;
A20-B2-C24;
A20-B2-C25;
A20-B2-C26;
A20-B2-C27;
A20-B2-C28;
A20-B2-C29;
A20-B2-C30;
A20-B2-C31;
A20-B2-C32;
A20-B2-C33;
A20-B2-C34;
A20-B2-C35;
A20-B2-C36;
A20-B2-C37;
A20-B2-C38;
A20-B2-C39;
A20-B2-C40;
A20-B2-C41;
A20-B2-C42;
A20-B2-C43;
A20-B2-C44;
A20-B2-C45;
A20-B2-C46;
A20-B2-C47;
A20-B2-C48;
A20-B2-C49;
A20-B2-C50;
A20-B2-C51;
A20-B2-C52;
A20-B2-C53;
A20-B2-C54;
A20-B2-C55;
A20-B2-C56;
A20-B2-C57;
A20-B2-C58;
A20-B2-C59;
A21-B2-C1;
A21-B2-C2;
A21-B2-C3;
A21-B2-C4;

-continued

A21-B2-C5;
A21-B2-C6;
A21-B2-C7;
A21-B2-C8;
A21-B2-C9;
A21-B2-C10;
A21-B2-C11;
A21-B2-C12;
A21-B2-C13;
A21-B2-C14;
A21-B2-C15;
A21-B2-C16;
A21-B2-C17;
A21-B2-C18;
A21-B2-C19;
A21-B2-C20;
A21-B2-C21;
A21-B2-C22;
A21-B2-C23;
A21-B2-C24;
A21-B2-C25;
A21-B2-C26;
A21-B2-C27;
A21-B2-C28;
A21-B2-C29;
A21-B2-C30;
A21-B2-C31;
A21-B2-C32;
A21-B2-C33;
A21-B2-C34;
A21-B2-C35;
A21-B2-C36;
A21-B2-C37;
A21-B2-C38;
A21-B2-C39;
A21-B2-C40;
A21-B2-C41;
A21-B2-C42;
A21-B2-C43;
A21-B2-C44;
A21-B2-C45;
A21-B2-C46;
A21-B2-C47;
A21-B2-C48;
A21-B2-C49;
A21-B2-C50;
A21-B2-C51;
A21-B2-C52;
A21-B2-C53;
A21-B2-C54;
A21-B2-C55;
A21-B2-C56;
A21-B2-C57;
A21-B2-C58;
A21-B2-C59;
A22-B2-C1;
A22-B2-C2;
A22-B2-C3;
A22-B2-C4;
A22-B2-C5;
A22-B2-C6;
A22-B2-C7;
A22-B2-C8;
A22-B2-C9;
A22-B2-C10;
A22-B2-C11;
A22-B2-C12;
A22-B2-C13;
A22-B2-C14;
A22-B2-C15;
A22-B2-C16;
A22-B2-C17;
A22-B2-C18;
A22-B2-C19;
A22-B2-C20;
A22-B2-C21;
A22-B2-C22;
A22-B2-C23;
A22-B2-C24;

-continued

A22-B2-C25;
A22-B2-C26;
A22-B2-C27;
A22-B2-C28;
A22-B2-C29;
A22-B2-C30;
A22-B2-C31;
A22-B2-C32;
A22-B2-C33;
A22-B2-C34;
A22-B2-C35;
A22-B2-C36;
A22-B2-C37;
A22-B2-C38;
A22-B2-C39;
A22-B2-C40;
A22-B2-C41;
A22-B2-C42;
A22-B2-C43;
A22-B2-C44;
A22-B2-C45;
A22-B2-C46;
A22-B2-C47;
A22-B2-C48;
A22-B2-C49;
A22-B2-C50;
A22-B2-C51;
A22-B2-C52;
A22-B2-C53;
A22-B2-C54;
A22-B2-C55;
A22-B2-C56;
A22-B2-C57;
A22-B2-C58;
A22-B2-C59;
A23-B2-C1;
A23-B2-C2;
A23-B2-C3;
A23-B2-C4;
A23-B2-C5;
A23-B2-C6;
A23-B2-C7;
A23-B2-C8;
A23-B2-C9;
A23-B2-C10;
A23-B2-C11;
A23-B2-C12;
A23-B2-C13;
A23-B2-C14;
A23-B2-C15;
A23-B2-C16;
A23-B2-C17;
A23-B2-C18;
A23-B2-C19;
A23-B2-C20;
A23-B2-C21;
A23-B2-C22;
A23-B2-C23;
A23-B2-C24;
A23-B2-C25;
A23-B2-C26;
A23-B2-C27;
A23-B2-C28;
A23-B2-C29;
A23-B2-C30;
A23-B2-C31;
A23-B2-C32;
A23-B2-C33;
A23-B2-C34;
A23-B2-C35;
A23-B2-C36;
A23-B2-C37;
A23-B2-C38;
A23-B2-C39;
A23-B2-C40;
A23-B2-C41;
A23-B2-C42;
A23-B2-C43;
A23-B2-C44;

-continued

A23-B2-C45;
A23-B2-C46;
A23-B2-C47;
A23-B2-C48;
A23-B2-C49;
A23-B2-C50;
A23-B2-C51;
A23-B2-C52;
A23-B2-C53;
A23-B2-C54;
A23-B2-C55;
A23-B2-C56;
A23-B2-C57;
A23-B2-C58;
A23-B2-C59;
A24-B2-C1;
A24-B2-C2;
A24-B2-C3;
A24-B2-C4;
A24-B2-C5;
A24-B2-C6;
A24-B2-C7;
A24-B2-C8;
A24-B2-C9;
A24-B2-C10;
A24-B2-C11;
A24-B2-C12;
A24-B2-C13;
A24-B2-C14;
A24-B2-C15;
A24-B2-C16;
A24-B2-C17;
A24-B2-C18;
A24-B2-C19;
A24-B2-C20;
A24-B2-C21;
A24-B2-C22;
A24-B2-C23;
A24-B2-C24;
A24-B2-C25;
A24-B2-C26;
A24-B2-C27;
A24-B2-C28;
A24-B2-C29;
A24-B2-C30;
A24-B2-C31;
A24-B2-C32;
A24-B2-C33;
A24-B2-C34;
A24-B2-C35;
A24-B2-C36;
A24-B2-C37;
A24-B2-C38;
A24-B2-C39;
A24-B2-C40;
A24-B2-C41;
A24-B2-C42;
A24-B2-C43;
A24-B2-C44;
A24-B2-C45;
A24-B2-C46;
A24-B2-C47;
A24-B2-C48;
A24-B2-C49;
A24-B2-C50;
A24-B2-C51;
A24-B2-C52;
A24-B2-C53;
A24-B2-C54;
A24-B2-C55;
A24-B2-C56;
A24-B2-C57;
A24-B2-C58;
A24-B2-C59;
A25-B2-C1;
A25-B2-C2;
A25-B2-C3;
A25-B2-C4;
A25-B2-C5;

-continued

A25-B2-C6;
A25-B2-C7;
A25-B2-C8;
A25-B2-C9;
A25-B2-C10;
A25-B2-C11;
A25-B2-C12;
A25-B2-C13;
A25-B2-C14;
A25-B2-C15;
A25-B2-C16;
A25-B2-C17;
A25-B2-C18;
A25-B2-C19;
A25-B2-C20;
A25-B2-C21;
A25-B2-C22;
A25-B2-C23;
A25-B2-C24;
A25-B2-C25;
A25-B2-C26;
A25-B2-C27;
A25-B2-C28;
A25-B2-C29;
A25-B2-C30;
A25-B2-C31;
A25-B2-C32;
A25-B2-C33;
A25-B2-C34;
A25-B2-C35;
A25-B2-C36;
A25-B2-C37;
A25-B2-C38;
A25-B2-C39;
A25-B2-C40;
A25-B2-C41;
A25-B2-C42;
A25-B2-C43;
A25-B2-C44;
A25-B2-C45;
A25-B2-C46;
A25-B2-C47;
A25-B2-C48;
A25-B2-C49;
A25-B2-C50;
A25-B2-C51;
A25-B2-C52;
A25-B2-C53;
A25-B2-C54;
A25-B2-C55;
A25-B2-C56;
A25-B2-C57;
A25-B2-C58;
A25-B2-C59;
A26-B2-C1;
A26-B2-C2;
A26-B2-C3;
A26-B2-C4;
A26-B2-C5;
A26-B2-C6;
A26-B2-C7;
A26-B2-C8;
A26-B2-C9;
A26-B2-C10;
A26-B2-C11;
A26-B2-C12;
A26-B2-C13;
A26-B2-C14;
A26-B2-C15;
A26-B2-C16;
A26-B2-C17;
A26-B2-C18;
A26-B2-C19;
A26-B2-C20;
A26-B2-C21;
A26-B2-C22;
A26-B2-C23;
A26-B2-C24;
A26-B2-C25;

-continued

A26-B2-C26;
A26-B2-C27;
A26-B2-C28;
A26-B2-C29;
A26-B2-C30;
A26-B2-C31;
A26-B2-C32;
A26-B2-C33;
A26-B2-C34;
A26-B2-C35;
A26-B2-C36;
A26-B2-C37;
A26-B2-C38;
A26-B2-C39;
A26-B2-C40;
A26-B2-C41;
A26-B2-C42;
A26-B2-C43;
A26-B2-C44;
A26-B2-C45;
A26-B2-C46;
A26-B2-C47;
A26-B2-C48;
A26-B2-C49;
A26-B2-C50;
A26-B2-C51;
A26-B2-C52;
A26-B2-C53;
A26-B2-C54;
A26-B2-C55;
A26-B2-C56;
A26-B2-C57;
A26-B2-C58;
A26-B2-C59;
A27-B2-C1;
A27-B2-C2;
A27-B2-C3;
A27-B2-C4;
A27-B2-C5;
A27-B2-C6;
A27-B2-C7;
A27-B2-C8;
A27-B2-C9;
A27-B2-C10;
A27-B2-C11;
A27-B2-C12;
A27-B2-C13;
A27-B2-C14;
A27-B2-C15;
A27-B2-C16;
A27-B2-C17;
A27-B2-C18;
A27-B2-C19;
A27-B2-C20;
A27-B2-C21;
A27-B2-C22;
A27-B2-C23;
A27-B2-C24;
A27-B2-C25;
A27-B2-C26;
A27-B2-C27;
A27-B2-C28;
A27-B2-C29;
A27-B2-C30;
A27-B2-C31;
A27-B2-C32;
A27-B2-C33;
A27-B2-C34;
A27-B2-C35;
A27-B2-C36;
A27-B2-C37;
A27-B2-C38;
A27-B2-C39;
A27-B2-C40;
A27-B2-C41;
A27-B2-C42;
A27-B2-C43;
A27-B2-C44;
A27-B2-C45;

-continued

A27-B2-C46;
A27-B2-C47;
A27-B2-C48;
A27-B2-C49;
A27-B2-C50;
A27-B2-C51;
A27-B2-C52;
A27-B2-C53;
A27-B2-C54;
A27-B2-C55;
A27-B2-C56;
A27-B2-C57;
A27-B2-C58;
A27-B2-C59;
A28-B2-C1;
A28-B2-C2;
A28-B2-C3;
A28-B2-C4;
A28-B2-C5;
A28-B2-C6;
A28-B2-C7;
A28-B2-C8;
A28-B2-C9;
A28-B2-C10;
A28-B2-C11;
A28-B2-C12;
A28-B2-C13;
A28-B2-C14;
A28-B2-C15;
A28-B2-C16;
A28-B2-C17;
A28-B2-C18;
A28-B2-C19;
A28-B2-C20;
A28-B2-C21;
A28-B2-C22;
A28-B2-C23;
A28-B2-C24;
A28-B2-C25;
A28-B2-C26;
A28-B2-C27;
A28-B2-C28;
A28-B2-C29;
A28-B2-C30;
A28-B2-C31;
A28-B2-C32;
A28-B2-C33;
A28-B2-C34;
A28-B2-C35;
A28-B2-C36;
A28-B2-C37;
A28-B2-C38;
A28-B2-C39;
A28-B2-C40;
A28-B2-C41;
A28-B2-C42;
A28-B2-C43;
A28-B2-C44;
A28-B2-C45;
A28-B2-C46;
A28-B2-C47;
A28-B2-C48;
A28-B2-C49;
A28-B2-C50;
A28-B2-C51;
A28-B2-C52;
A28-B2-C53;
A28-B2-C54;
A28-B2-C55;
A28-B2-C56;
A28-B2-C57;
A28-B2-C58;
A28-B2-C59;
A29-B2-C1;
A29-B2-C2;
A29-B2-C3;
A29-B2-C4;
A29-B2-C5;
A29-B2-C6;

-continued

A29-B2-C7;
A29-B2-C8;
A29-B2-C9;
A29-B2-C10;
A29-B2-C11;
A29-B2-C12;
A29-B2-C13;
A29-B2-C14;
A29-B2-C15;
A29-B2-C16;
A29-B2-C17;
A29-B2-C18;
A29-B2-C19;
A29-B2-C20;
A29-B2-C21;
A29-B2-C22;
A29-B2-C23;
A29-B2-C24;
A29-B2-C25;
A29-B2-C26;
A29-B2-C27;
A29-B2-C28;
A29-B2-C29;
A29-B2-C30;
A29-B2-C31;
A29-B2-C32;
A29-B2-C33;
A29-B2-C34;
A29-B2-C35;
A29-B2-C36;
A29-B2-C37;
A29-B2-C38;
A29-B2-C39;
A29-B2-C40;
A29-B2-C41;
A29-B2-C42;
A29-B2-C43;
A29-B2-C44;
A29-B2-C45;
A29-B2-C46;
A29-B2-C47;
A29-B2-C48;
A29-B2-C49;
A29-B2-C50;
A29-B2-C51;
A29-B2-C52;
A29-B2-C53;
A29-B2-C54;
A29-B2-C55;
A29-B2-C56;
A29-B2-C57;
A29-B2-C58;
A29-B2-C59;
A30-B2-C1;
A30-B2-C2;
A30-B2-C3;
A30-B2-C4;
A30-B2-C5;
A30-B2-C6;
A30-B2-C7;
A30-B2-C8;
A30-B2-C9;
A30-B2-C10;
A30-B2-C11;
A30-B2-C12;
A30-B2-C13;
A30-B2-C14;
A30-B2-C15;
A30-B2-C16;
A30-B2-C17;
A30-B2-C18;
A30-B2-C19;
A30-B2-C20;
A30-B2-C21;
A30-B2-C22;
A30-B2-C23;
A30-B2-C24;
A30-B2-C25;
A30-B2-C26;

A30-B2-C27;
A30-B2-C28;
A30-B2-C29;
A30-B2-C30;
A30-B2-C31;
A30-B2-C32;
A30-B2-C33;
A30-B2-C34;
A30-B2-C35;
A30-B2-C36;
A30-B2-C37;
A30-B2-C38;
A30-B2-C39;
A30-B2-C40;
A30-B2-C41;
A30-B2-C42;
A30-B2-C43;
A30-B2-C44;
A30-B2-C45;
A30-B2-C46;
A30-B2-C47;
A30-B2-C48;
A30-B2-C49;
A30-B2-C50;
A30-B2-C51;
A30-B2-C52;
A30-B2-C53;
A30-B2-C54;
A30-B2-C55;
A30-B2-C56;
A30-B2-C57;
A30-B2-C58;
A30-B2-C59;
A31-B2-C1;
A31-B2-C2;
A31-B2-C3;
A31-B2-C4;
A31-B2-C5;
A31-B2-C6;
A31-B2-C7;
A31-B2-C8;
A31-B2-C9;
A31-B2-C10;
A31-B2-C11;
A31-B2-C12;
A31-B2-C13;
A31-B2-C14;
A31-B2-C15;
A31-B2-C16;
A31-B2-C17;
A31-B2-C18;
A31-B2-C19;
A31-B2-C20;
A31-B2-C21;
A31-B2-C22;
A31-B2-C23;
A31-B2-C24;
A31-B2-C25;
A31-B2-C26;
A31-B2-C27;
A31-B2-C28;
A31-B2-C29;
A31-B2-C30;
A31-B2-C31;
A31-B2-C32;
A31-B2-C33;
A31-B2-C34;
A31-B2-C35;
A31-B2-C36;
A31-B2-C37;
A31-B2-C38;
A31-B2-C39;
A31-B2-C40;
A31-B2-C41;
A31-B2-C42;
A31-B2-C43;
A31-B2-C44;
A31-B2-C45;
A31-B2-C46;
A31-B2-C47;
A31-B2-C48;
A31-B2-C49;
A31-B2-C50;
A31-B2-C51;
A31-B2-C52;
A31-B2-C53;
A31-B2-C54;
A31-B2-C55;
A31-B2-C56;
A31-B2-C57;
A31-B2-C58;
A31-B2-C59;
A32-B2-C1;
A32-B2-C2;
A32-B2-C3;
A32-B2-C4;
A32-B2-C5;
A32-B2-C6;
A32-B2-C7;
A32-B2-C8;
A32-B2-C9;
A32-B2-C10;
A32-B2-C11;
A32-B2-C12;
A32-B2-C13;
A32-B2-C14;
A32-B2-C15;
A32-B2-C16;
A32-B2-C17;
A32-B2-C18;
A32-B2-C19;
A32-B2-C20;
A32-B2-C21;
A32-B2-C22;
A32-B2-C23;
A32-B2-C24;
A32-B2-C25;
A32-B2-C26;
A32-B2-C27;
A32-B2-C28;
A32-B2-C29;
A32-B2-C30;
A32-B2-C31;
A32-B2-C32;
A32-B2-C33;
A32-B2-C34;
A32-B2-C35;
A32-B2-C36;
A32-B2-C37;
A32-B2-C38;
A32-B2-C39;
A32-B2-C40;
A32-B2-C41;
A32-B2-C42;
A32-B2-C43;
A32-B2-C44;
A32-B2-C45;
A32-B2-C46;
A32-B2-C47;
A32-B2-C48;
A32-B2-C49;
A32-B2-C50;
A32-B2-C51;
A32-B2-C52;
A32-B2-C53;
A32-B2-C54;
A32-B2-C55;
A32-B2-C56;
A32-B2-C57;
A32-B2-C58;
A32-B2-C59;
A33-B2-C1;
A33-B2-C2;
A33-B2-C3;
A33-B2-C4;
A33-B2-C5;
A33-B2-C6;
A33-B2-C7;

-continued

A33-B2-C8;
A33-B2-C9;
A33-B2-C10;
A33-B2-C11;
A33-B2-C12;
A33-B2-C13;
A33-B2-C14;
A33-B2-C15;
A33-B2-C16;
A33-B2-C17;
A33-B2-C18;
A33-B2-C19;
A33-B2-C20;
A33-B2-C21;
A33-B2-C22;
A33-B2-C23;
A33-B2-C24;
A33-B2-C25;
A33-B2-C26;
A33-B2-C27;
A33-B2-C28;
A33-B2-C29;
A33-B2-C30;
A33-B2-C31;
A33-B2-C32;
A33-B2-C33;
A33-B2-C34;
A33-B2-C35;
A33-B2-C36;
A33-B2-C37;
A33-B2-C38;
A33-B2-C39;
A33-B2-C40;
A33-B2-C41;
A33-B2-C42;
A33-B2-C43;
A33-B2-C44;
A33-B2-C45;
A33-B2-C46;
A33-B2-C47;
A33-B2-C48;
A33-B2-C49;
A33-B2-C50;
A33-B2-C51;
A33-B2-C52;
A33-B2-C53;
A33-B2-C54;
A33-B2-C55;
A33-B2-C56;
A33-B2-C57;
A33-B2-C58;
A33-B2-C59;
A34-B2-C1;
A34-B2-C2;
A34-B2-C3;
A34-B2-C4;
A34-B2-C5;
A34-B2-C6;
A34-B2-C7;
A34-B2-C8;
A34-B2-C9;
A34-B2-C10;
A34-B2-C11;
A34-B2-C12;
A34-B2-C13;
A34-B2-C14;
A34-B2-C15;
A34-B2-C16;
A34-B2-C17;
A34-B2-C18;
A34-B2-C19;
A34-B2-C20;
A34-B2-C21;
A34-B2-C22;
A34-B2-C23;
A34-B2-C24;
A34-B2-C25;
A34-B2-C26;
A34-B2-C27;

-continued

A34-B2-C28;
A34-B2-C29;
A34-B2-C30;
A34-B2-C31;
A34-B2-C32;
A34-B2-C33;
A34-B2-C34;
A34-B2-C35;
A34-B2-C36;
A34-B2-C37;
A34-B2-C38;
A34-B2-C39;
A34-B2-C40;
A34-B2-C41;
A34-B2-C42;
A34-B2-C43;
A34-B2-C44;
A34-B2-C45;
A34-B2-C46;
A34-B2-C47;
A34-B2-C48;
A34-B2-C49;
A34-B2-C50;
A34-B2-C51;
A34-B2-C52;
A34-B2-C53;
A34-B2-C54;
A34-B2-C55;
A34-B2-C56;
A34-B2-C57;
A34-B2-C58;
A34-B2-C59;
A35-B2-C1;
A35-B2-C2;
A35-B2-C3;
A35-B2-C4;
A35-B2-C5;
A35-B2-C6;
A35-B2-C7;
A35-B2-C8;
A35-B2-C9;
A35-B2-C10;
A35-B2-C11;
A35-B2-C12;
A35-B2-C13;
A35-B2-C14;
A35-B2-C15;
A35-B2-C16;
A35-B2-C17;
A35-B2-C18;
A35-B2-C19;
A35-B2-C20;
A35-B2-C21;
A35-B2-C22;
A35-B2-C23;
A35-B2-C24;
A35-B2-C25;
A35-B2-C26;
A35-B2-C27;
A35-B2-C28;
A35-B2-C29;
A35-B2-C30;
A35-B2-C31;
A35-B2-C32;
A35-B2-C33;
A35-B2-C34;
A35-B2-C35;
A35-B2-C36;
A35-B2-C37;
A35-B2-C38;
A35-B2-C39;
A35-B2-C40;
A35-B2-C41;
A35-B2-C42;
A35-B2-C43;
A35-B2-C44;
A35-B2-C45;
A35-B2-C46;
A35-B2-C47;

-continued

A35-B2-C48;
A35-B2-C49;
A35-B2-C50;
A35-B2-C51;
A35-B2-C52;
A35-B2-C53;
A35-B2-C54;
A35-B2-C55;
A35-B2-C56;
A35-B2-C57;
A35-B2-C58;
A35-B2-C59;
A1-B3-C1;
A1-B3-C2;
A1-B3-C3;
A1-B3-C4;
A1-B3-C5;
A1-B3-C6;
A1-B3-C7;
A1-B3-C8;
A1-B3-C9;
A1-B3-C10;
A1-B3-C1i;
A1-B3-C12;
A1-B3-C13;
A1-B3-C14;
A1-B3-C15;
A1-B3-C16;
A1-B3-C17;
A1-B3-C18;
A1-B3-C19;
A1-B3-C20;
A1-B3-C21;
A1-B3-C22;
A1-B3-C23;
A1-B3-C24;
A1-B3-C25;
A1-B3-C26;
A1-B3-C27;
A1-B3-C28;
A1-B3-C29;
A1-B3-C30;
A1-B3-C31;
A1-B3-C32;
A1-B3-C33;
A1-B3-C34;
A1-B3-C35;
A1-B3-C36;
A1-B3-C37;
A1-B3-C38;
A1-B3-C39;
A1-B3-C40;
A1-B3-C41;
A1-B3-C42;
A1-B3-C43;
A1-B3-C44;
A1-B3-C45;
A1-B3-C46;
A1-B3-C47;
A1-B3-C48;
A1-B3-C49;
A1-B3-C50;
A1-B1-C51;
A1-B3-C52;
A1-B3-C53;
A1-B3-C54;
A1-B3-C55;
A1-B3-C56;
A1-B3-C57;
A1-B3-C58;
A1-B3-C59;
A2-B3-C1;
A2-B3-C2;
A2-B3-C3;
A2-B3-C4;
A2-B3-C5;
A2-B3-C6;
A2-B3-C7;
A2-B3-C8;

-continued

A2-B3-C9;
A2-B3-C10;
A2-B3-C11;
A2-B3-C12;
A2-B3-C13;
A2-B3-C14;
A2-B3-C15;
A2-B3-C16;
A2-B3-C17;
A2-B3-C18;
A2-B3-C19;
A2-B3-C20;
A2-B3-C21;
A2-B3-C22;
A2-B3-C23;
A2-B3-C24;
A2-B3-C25;
A2-B3-C26;
A2-B3-C27;
A2-B3-C28;
A2-B3-C29;
A2-B3-C30;
A2-B3-C31;
A2-B3-C32;
A2-B3-C33;
A2-B3-C34;
A2-B3-C35;
A2-B3-C36;
A2-B3-C37;
A2-B3-C38;
A2-B3-C39;
A2-B3-C40;
A2-B3-C41;
A2-B3-C42;
A2-B3-C43;
A2-B3-C44;
A2-B3-C45;
A2-B3-C46;
A2-B3-C47;
A2-B3-C48;
A2-B3-C49;
A2-B3-C50;
A2-B3-C51;
A2-B3-C52;
A2-B3-C53;
A2-B3-C54;
A2-B3-C55;
A2-B3-C56;
A2-B3-C57;
A2-B3-C58;
A2-B3-C59;
A3-B3-C1;
A3-B3-C2;
A3-B3-C3;
A3-B3-C4;
A3-B3-C5;
A3-B3-C6;
A3-B3-C7;
A3-B3-C8;
A3-B3-C9;
A3-B3-C10;
A3-B3-C11;
A3-B3-C12;
A3-B3-C13;
A3-B3-C14;
A3-B3-C15;
A3-B3-C16;
A3-B3-C17;
A3-B3-C18;
A3-B3-C19;
A3-B3-C20;
A3-B3-C21;
A3-B3-C22;
A3-B3-C23;
A3-B3-C24;
A3-B3-C25;
A3-B3-C26;
A3-B3-C27;
A3-B3-C28;

A3-B3-C29;
A3-B3-C30;
A3-B3-C31;
A3-B3-C32;
A3-B3-C33;
A3-B3-C34;
A3-B3-C35;
A3-B3-C36;
A3-B3-C37;
A3-B3-C38;
A3-B3-C39;
A3-B3-C40;
A3-B3-C41;
A3-B3-C42;
A3-B3-C43;
A3-B3-C44;
A3-B3-C45;
A3-B3-C46;
A3-B3-C47;
A3-B3-C48;
A3-B3-C49;
A3-B3-C50;
A3-B3-C51;
A3-B3-C52;
A3-B3-C53;
A3-B3-C54;
A3-B3-C55;
A3-B3-C56;
A3-B3-C57;
A3-B3-C58;
A3-B3-C59;
A4-B3-C1;
A4-B3-C2;
A4-B3-C3;
A4-B3-C4;
A4-B3-C5;
A4-B3-C6;
A4-B3-C7;
A4-B3-C5;
A4-B3-C9;
A4-B3-C10;
A4-B3-C11;
A4-B3-C12;
A4-B3-C13;
A4-B3-C14;
A4-B3-C15;
A4-B3-C16;
A4-B3-C17;
A4-B3-C18;
A4-B3-C19;
A4-B3-C20;
A4-B3-C21,
A4-B3-C22;
A4-B3-C23;
A4-B3-C24;
A4-B3-C25;
A4-B3-C26;
A4-B3-C27;
A4-B3-C28;
A4-B3-C29;
A4-B3-C30;
A4-B3-C31;
A4-B3-C32;
A4-B3-C33;
A4-B3-C34;
A4-B3-C35;
A4-B3-C36;
A4-B3-C37;
A4-B3-C38;
A4-B3-C39;
A4-B3-C40;
A4-B3-C41;
A4-B3-C42;
A4-B3-C43;
A4-B3-C44;
A4-B3-C45;
A4-B3-C46;
A4-B3-C47;
A4-B3-C48;
A4-B3-C49;
A4-B3-C50;
A4-B3-C51;
A4-B3-C52;
A4-B3-C53;
A4-B3-C54;
A4-B3-C55;
A4-B3-C56;
A4-B3-C57;
A4-B3-C58;
A4-B3-C59;
A5-B3-C1;
A5-B3-C2;
A5-B3-C3;
A5-B3-C4;
A5-B3-C5;
A5-B3-C6;
A5-B3-C7;
A5-B3-C8;
A5-B3-C9;
A5-B3-C10;
A5-B3-C11;
A5-B3-C12;
A5-B3-C13;
A5-B3-C14;
A5-B3-C15;
A5-B3-C16;
A5-B3-C17;
A5-B3-C18;
A5-B3-C19;
A5-B3-C20;
A5-B3-C21;
A5-B3-C22;
A5-B3-C23;
A5-B3-C24;
A5-B3-C25;
A5-B3-C26;
A5-B3-C27;
A5-B3-C28;
A5-B3-C29;
A5-B3-C30;
A5-B3-C31;
A5-B3-C32;
A5-B3-C33;
A5-B3-C34;
A5-B3-C35;
A5-B3-C36;
A5-B3-C37;
A5-B3-C38;
A5-B3-C39;
A5-B3-C40;
A5-B3-C41;
A5-B3-C42;
A5-B3-C43;
A5-B3-C44;
A5-B3-C45;
A5-B3-C46;
A5-B3-C47;
A5-B3-C48;
A5-B3-C49;
A5-B3-C50;
A5-B3-C51;
A5-B3-C52;
A5-B3-C53;
A5-B3-C54;
A5-B3-C55;
A5-B3-C56;
A5-B3-C57;
A5-B3-C58;
A5-B3-C59;
A6-B3-C1;
A6-B3-C2;
A6-B3-C3;
A6-B3-C4;
A6-B3-C5;
A6-B3-C6;
A6-B3-C7;
A6-B3-C8;
A6-B3-C9;

-continued

A6-B3-C10;
A6-B3-C11;
A6-B3-C12;
A6-B3-C13;
A6-B3-C14;
A6-B3-C15;
A6-B3-C16;
A6-B3-C17;
A6-B3-C18;
A6-B3-C19;
A6-B3-C20;
A6-B3-C21;
A6-B3-C22;
A6-B3-C23;
A6-B3-C24;
A6-B3-C25;
A6-B3-C26;
A6-B3-C27;
A6-B3-C28;
A6-B3-C29;
A6-B3-C30;
A6-B3-C31;
A6-B3-C32;
A6-B3-C33;
A6-B3-C34;
A6-B3-C35;
A6-B3-C36;
A6-B3-C37;
A6-B3-C38;
A6-B3-C39;
A6-B3-C40;
A6-B3-C41;
A6-B3-C42;
A6-B3-C43;
A6-B3-C44;
A6-B3-C45;
A6-B3-C46;
A6-B3-C47;
A6-B3-C48;
A6-B3-C49;
A6-B3-C50;
A6-B3-C5i;
A6-B3-C52;
A6-B3-C53;
A6-B3-C54;
A6-B3-C55;
A6-B3-C56;
A6-B3-C57;
A6-B3-C58;
A6-B3-C59;
A7-B3-C1;
A7-B3-C2;
A7-B3-C3;
A7-B3-C4;
A7-B3-C5;
A7-B3-C6;
A7-B3-C7;
A7-B3-C8;
A7-B3-C9;
A7-B3-C10;
A7-B3-C11;
A7-B3-C12;
A7-B3-C13;
A7-B3-C14;
A7-B3-C15;
A7-B3-C16;
A7-B3-C17;
A7-B3-C18;
A7-B3-C19;
A7-B3-C20;
A7-B3-C21;
A7-B3-C22;
A7-B3-C23;
A7-B3-C24;
A7-B3-C25;
A7-B3-C26;
A7-B3-C27;
A7-B3-C28;
A7-B3-C29;

-continued

A7-B3-C30;
A7-B3-C31;
A7-B3-C32;
A7-B3-C33;
A7-B3-C34;
A7-B3-C35;
A7-B3-C36;
A7-B3-C37;
A7-B3-C38;
A7-B3-C39;
A7-B3-C40;
A7-B3-C41;
A7-B3-C42;
A7-B3-C43;
A7-B3-C44;
A7-B3-C45;
A7-B3-C46;
A7-B3-C47;
A7-B3-C48;
A7-B3-C49;
A7-B3-C50;
A7-B3-C51;
A7-B3-C52;
A7-B3-C53;
A7-B3-C54;
A7-B3-C55;
A7-B3-C56;
A7-B3-C57;
A7-B3-C58;
A7-B3-C59;
A8-B3-C1;
A8-B3-C2;
A8-B3-C3;
A8-B3-C4;
A8-B3-C5;
A8-B3-C6;
A8-B3-C7;
A8-B3-C8;
A8-B3-C9;
A8-B3-C10;
A8-B3-C11;
A8-B3-C12;
A8-B3-C13;
A8-B3-C14;
A8-B3-C15;
A8-B3-C16;
A8-B3-C17;
A8-B3-C18;
A8-B3-C19;
A8-B3-C20;
A8-B3-C21;
A8-B3-C22;
A8-B3-C23;
A8-B3-C24;
A8-B3-C25;
A8-B3-C26;
A8-B3-C27;
A8-B3-C28;
A8-B3-C29;
A8-B3-C30;
A8-B3-C31;
A8-B3-C32;
A8-B3-C33;
A8-B3-C34;
A8-B3-C35;
A8-B3-C36;
A8-B3-C37;
A8-B3-C38;
A8-B3-C39;
A8-B3-C40;
A8-B3-C41;
A8-B3-C42;
A8-B3-C43;
A8-B3-C44;
A8-B3-C45;
A8-B3-C46;
A8-B3-C47;
A8-B3-C48;
A8-B3-C49;

-continued

A8-B3-C50;
A8-B3-C51;
A8-B3-C52;
A8-B3-C53;
A8-B3-C54;
A8-B3-C55;
A8-B3-C56;
A8-B3-C57;
A8-B3-C58;
A8-B3-C59;
A9-B3-C1;
A9-B3-C2;
A9-B3-C3;
A9-B3-C4;
A9-B3-C5;
A9-B3-C6;
A9-B3-C7;
A9-B3-C8;
A9-B3-C9;
A9-B3-C10;
A9-B3-C11;
A9-B3-C12;
A9-B3-C13;
A9-B3-C14;
A9-B3-C15;
A9-B3-C16;
A9-B3-C17;
A9-B3-C18;
A9-B3-C19;
A9-B3-C20;
A9-B3-C21;
A9-B3-C22;
A9-B3-C23;
A9-B3-C24;
A9-B3-C25;
A9-B3-C26;
A9-B3-C27;
A9-B3-C28;
A9-B3-C29;
A9-B3-C30;
A9-B3-C31;
A9-B3-C32;
A9-B3-C33;
A9-B3-C34;
A9-B3-C35;
A9-B3-C36;
A9-B3-C37;
A9-B3-C38;
A9-B3-C39;
A9-B3-C40;
A9-B3-C41;
A9-B3-C42;
A9-B3-C43;
A9-B3-C44;
A9-B3-C45;
A9-B3-C46;
A9-B3-C47;
A9-B3-C48;
A9-B3-C49;
A9-B3-C50;
A9-B3-C51;
A9-B3-C52;
A9-B3-C53;
A9-B3-C54;
A9-B3-C55;
A9-B3-C56;
A9-B3-C57;
A9-B3-C58;
A9-B3-C59;
A10-B3-C1;
A10-B3-C2;
A10-B3-C3;
A10-B3-C4;
A10-B3-C5;
A10-B3-C6;
A10-B3-C7;
A10-B3-C8;
A10-B3-C9;
A10-B3-C10;
A10-B3-C11;
A10-B3-C12;
A10-B3-C13;
A10-B3-C14;
A10-B3-C15;
A10-B3-C16;
A10-B3-C17;
A10-B3-C18;
A10-B3-C19;
A10-B3-C20;
A10-B3-C21;
A10-B3-C22;
A10-B3-C23;
A10-B3-C24;
A10-B3-C25;
A10-B3-C26;
A10-B3-C27;
A10-B3-C28;
A10-B3-C29;
A10-B3-C30;
A10-B3-C31;
A10-B3-C32;
A10-B3-C33;
A10-B3-C34;
A10-B3-C35;
A10-B3-C36;
A10-B3-C37;
A10-B3-C38;
A10-B3-C39;
A10-B3-C40;
A10-B3-C41;
A10-B3-C42;
A10-B3-C43;
A10-B3-C44;
A10-B3-C45;
A10-B3-C46;
A10-B3-C47;
A10-B3-C48;
A10-B3-C49;
A10-B3-C50;
A10-B3-C51;
A10-B3-C52;
A10-B3-C53;
A10-B3-C54;
A10-B3-C55;
A10-B3-C56;
A10-B3-C57;
A10-B3-C58;
A10-B3-C59;
A11-B3-C1;
A11-B3-C2;
A11-B3-C3;
A11-B3-C4;
A11-B3-C5;
A11-B3-C6;
A11-B3-C7;
A11-B3-C8;
A11-B3-C9;
A11-B3-C10;
A11-B3-C11;
A11-B3-C12;
A11-B3-C13;
A11-B3-C14;
A11-B3-C15;
A11-B3-C16;
A11-B3-C17;
A11-B3-C18;
A11-B3-C19;
A11-B3-C20;
A11-B3-C21;
A11-B3-C22;
A11-B3-C23;
A11-B3-C24;
A11-B3-C25;
A11-B3-C26;
A11-B3-C27;
A11-B3-C28;
A11-B3-C29;
A11-B3-C30;

-continued

A11-B3-C31;
A11-B3-C32;
A11-B3-C33;
A11-B3-C34;
A11-B3-C35;
A11-B3-C36;
A11-B3-C37;
A11-B3-C38;
A11-B3-C39;
A11-B3-C40;
A11-B3-C41;
A11-B3-C42;
A11-B3-C43;
A11-B3-C44;
A11-B3-C45;
A11-B3-C46;
A11-B3-C47;
A11-B3-C48;
A11-B3-C49;
A11-B3-C50;
A11-B3-C51;
A11-B3-C52;
A11-B3-C53;
A11-B3-C54;
A11-B3-C55;
A11-B3-C56;
A11-B3-C57;
A11-B3-C58;
A11-B3-C59;
A12-B3-C1;
A12-B3-C2;
A12-B3-C3;
A12-B3-C4;
A12-B3-C5;
A12-B3-C6;
A12-B3-C7;
A12-B3-C8;
A12-B3-C9;
A12-B3-C10;
A12-B3-C11;
A12-B3-C12;
A12-B3-C13;
A12-B3-C14;
A12-B3-C15;
A12-B3-C16;
A12-B3-C17;
A12-B3-C18;
A12-B3-C19;
A12-B3-C20;
A12-B3-C21;
A12-B3-C22;
A12-B3-C23;
A12-B3-C24;
A12-B3-C25;
A12-B3-C26;
A12-B3-C27;
A12-B3-C28;
A12-B3-C29;
A12-B3-C30;
A12-B3-C31;
A12-B3-C32;
A12-B3-C33;
A12-B3-C34;
A12-B3-C35;
A12-B3-C36;
A12-B3-C37;
A12-B3-C38;
A12-B3-C39;
A12-B3-C40;
A12-B3-C41;
A12-B3-C42;
A12-B3-C43;
A12-B3-C44;
A12-B3-C45;
A12-B3-C46;
A12-B3-C47;
A12-B3-C48;
A12-B3-C49;
A12-B3-C50;

-continued

A12-B3-C51;
A12-B3-C52;
A12-B3-C53;
A12-B3-C54;
A12-B3-C55;
A12-B3-C56;
A12-B3-C57;
A12-B3-C58;
A12-B3-C59;
A13-B3-C1;
A13-B3-C2;
A13-B3-C3;
A13-B3-C4;
A13-B3-C5;
A13-B3-C6;
A13-B3-C7;
A13-B3-C8;
A13-B3-C9;
A13-B3-C10;
A13-B3-C11;
A13-B3-C12;
A13-B3-C13;
A13-B3-C14;
A13-B3-C15;
A13-B3-C16;
A13-B3-C17;
A13-B3-C18;
A13-B3-C19;
A13-B3-C20;
A13-B3-C21;
A13-B3-C22;
A13-B3-C23;
A13-B3-C24;
A13-B3-C25;
A13-B3-C26;
A13-B3-C27;
A13-B3-C28;
A13-B3-C29;
A13-B3-C30;
A13-B3-C31;
A13-B3-C32;
A13-B3-C33;
A13-B3-C34;
A13-B3-C35;
A13-B3-C36;
A13-B3-C37;
A13-B3-C38;
A13-B3-C39;
A13-B3-C40;
A13-B3-C41;
A13-B3-C42;
A13-B3-C43;
A13-B3-C44;
A13-B3-C45;
A13-B3-C46;
A13-B3-C47;
A13-B3-C48;
A13-B3-C49;
A13-B3-C50;
A13-B3-C51;
A13-B3-C52;
A13-B3-C53;
A13-B3-C54;
A13-B3-C55;
A13-B3-C56;
A13-B3-C57;
A13-B3-C58;
A13-B3-C59;
A14-B3-C1;
A14-B3-C2;
A14-B3-C3;
A14-B3-C4;
A14-B3-C5;
A14-B3-C6;
A14-B3-C7;
A14-B3-C8;
A14-B3-C9;
A14-B3-C10;
A14-B3-C11;

A14-B3-C12;
A14-B3-C13;
A14-B3-C14;
A14-B3-C15;
A14-B3-C16;
A14-B3-C17;
A14-B3-C18;
A14-B3-C19;
A14-B3-C20;
A14-B3-C21;
A14-B3-C22;
A14-B3-C23;
A14-B3-C24;
A14-B3-C25;
A14-B3-C26;
A14-B3-C27;
A14-B3-C28;
A14-B3-C29;
A14-B3-C30;
A14-B3-C31;
A14-B3-C32;
A14-B3-C33;
A14-B3-C34;
A14-B3-C35;
A14-B3-C36;
A14-B3-C37;
A14-B3-C38;
A14-B3-C39;
A14-B3-C40;
A14-B3-C41;
A14-B3-C42;
A14-B3-C43;
A14-B3-C44;
A14-B3-C45;
A14-B3-C46;
A14-B3-C47;
A14-B3-C48;
A14-B3-C49;
A14-B3-C50;
A14-B3-C51;
A14-B3-C52;
A14-B3-C53;
A14-B3-C54;
A14-B3-C55;
A14-B3-C56;
A14-B3-C57;
A14-B3-C58;
A14-B3-C59;
A15-B3-C1;
A15-B3-C2;
A15-B3-C3;
A15-B3-C4;
A15-B3-C5;
A15-B3-C6;
A15-B3-C7;
A15-B3-C8;
A15-B3-C9;
A15-B3-C10;
A15-B3-C11;
A15-B3-C12;
A15-B3-C13;
A15-B3-C14;
A15-B3-C15;
A15-B3-C16;
A15-B3-C17;
A15-B3-C18;
A15-B3-C19;
A15-B3-C20;
A15-B3-C21;
A15-B3-C22;
A15-B3-C23;
A15-B3-C24;
A15-B3-C25;
A15-B3-C26;
A15-B3-C27;
A15-B3-C28;
A15-B3-C29;
A15-B3-C30;
A15-B3-C31;
A15-B3-C32;
A15-B3-C33;
A15-B3-C34;
A15-B3-C35;
A15-B3-C36;
A15-B3-C37;
A15-B3-C38;
A15-B3-C39;
A15-B3-C40;
A15-B3-C41;
A15-B3-C42;
A15-B3-C43;
A15-B3-C44;
A15-B3-C45;
A15-B3-C46;
A15-B3-C47;
A15-B3-C48;
A15-B3-C49;
A15-B3-C50;
A15-B3-C51;
A15-B3-C52;
A15-B3-C53;
A15-B3-C54;
A15-B3-C55;
A15-B3-C56;
A15-B3-C57;
A15-B3-C58;
A15-B3-C59;
A16-B3-C1;
A16-B3-C2;
A16-B3-C3;
A16-B3-C4;
A16-B3-C5;
A16-B3-C6;
A16-B3-C7;
A16-B3-C8;
A16-B3-C9;
A16-B3-C10;
A16-B3-C11;
A16-B3-C12;
A16-B3-C13;
A16-B3-C14;
A16-B3-C15;
A16-B3-C16;
A16-B3-C17;
A16-B3-C18;
A16-B3-C19;
A16-B3-C20;
A16-B3-C21;
A16-B3-C22;
A16-B3-C23;
A16-B3-C24;
A16-B3-C25;
A16-B3-C26;
A16-B3-C27;
A16-B3-C28;
A16-B3-C29;
A16-B3-C30;
A16-B3-C31;
A16-B3-C32;
A16-B3-C33;
A16-B3-C34;
A16-B3-C35;
A16-B3-C36;
A16-B3-C37;
A16-B3-C38;
A16-B3-C39;
A16-B3-C40;
A16-B3-C41;
A16-B3-C42;
A16-B3-C43;
A16-B3-C44;
A16-B3-C45;
A16-B3-C46;
A16-B3-C47;
A16-B3-C48;
A16-B3-C49;
A16-B3-C50;
A16-B3-C51;

-continued

A16-B3-C52;
A16-B3-C53;
A16-B3-C54;
A16-B3-C55;
A16-B3-C56;
A16-B3-C57;
A16-B3-C58;
A16-B3-C59;
A17-B3-C1;
A17-B3-C2;
A17-B3-C3;
A17-B3-C4;
A17-B3-C5;
A17-B3-C6;
A17-B3-C7;
A17-B3-C8;
A17-B3-C9;
A17-B3-C10;
A17-B3-C11;
A17-B3-C12;
A17-B3-C13;
A17-B3-C14;
A17-B3-C15;
A17-B3-C16;
A17-B3-C17;
A17-B3-C18;
A17-B3-C19;
A17-B3-C20;
A17-B3-C21;
A17-B3-C22;
A17-B3-C23;
A17-B3-C24;
A17-B3-C25;
A17-B3-C26;
A17-B3-C27;
A17-B3-C28;
A17-B3-C29;
A17-B3-C30;
A17-B3-C31;
A17-B3-C32;
A17-B3-C33;
A17-B3-C34;
A17-B3-C35;
A17-B3-C36;
A17-B3-C37;
A17-B3-C38;
A17-B3-C39;
A17-B3-C40;
A17-B3-C41;
A17-B3-C42;
A17-B3-C43;
A17-B3-C44;
A17-B3-C45;
A17-B3-C46;
A17-B3-C47;
A17-B3-C48;
A17-B3-C49;
A17-B3-C50;
A17-B3-C51;
A17-B3-C52;
A17-B3-C53;
A17-B3-C54;
A17-B3-C55;
A17-B3-C56;
A17-B3-C57;
A17-B3-C58;
A17-B3-C59;
A18-B3-C1;
A18-B3-C2;
A18-B3-C3;
A18-B3-C4;
A18-B3-C5;
A18-B3-C6;
A18-B3-C7;
A18-B3-C8;
A18-B3-C9;
A18-B3-C10;
A18-B3-C11;
A18-B3-C12;

-continued

A18-B3-C13;
A18-B3-C14;
A18-B3-C15;
A18-B3-C16;
A18-B3-C17;
A18-B3-C18;
A18-B3-C19;
A18-B3-C20;
A18-B3-C21;
A18-B3-C22;
A18-B3-C23;
A18-B3-C24;
A18-B3-C25;
A18-B3-C26;
A18-B3-C27;
A18-B3-C28;
A18-B3-C29;
A18-B3-C30;
A18-B3-C31;
A18-B3-C32;
A18-B3-C33;
A18-B3-C34;
A18-B3-C35;
A18-B3-C36;
A18-B3-C37;
A18-B3-C38;
A18-B3-C39;
A18-B3-C40;
A18-B3-C41;
A18-B3-C42;
A18-B3-C43;
A18-B3-C44;
A18-B3-C45;
A18-B3-C46;
A18-B3-C47;
A18-B3-C48;
A18-B3-C49;
A18-B3-C50;
A18-B3-C51;
A18-B3-C52;
A18-B3-C53;
A18-B3-C54;
A18-B3-C55;
A18-B3-C56;
A18-B3-C57;
A18-B3-C58;
A18-B3-C59;
A19-B3-C1;
A19-B3-C2;
A19-B3-C3;
A19-B3-C4;
A19-B3-C5;
A19-B3-C6;
A19-B3-C7;
A19-B3-C8;
A19-B3-C9;
A19-B3-C10;
A19-B3-C11;
A19-B3-C12;
A19-B3-C13;
A19-B3-C14;
A19-B3-C15;
A19-B3-C16;
A19-B3-C17;
A19-B3-C18;
A19-B3-C19;
A19-B3-C20;
A19-B3-C21;
A19-B3-C22;
A19-B3-C23;
A19-B3-C24;
A19-B3-C25;
A19-B3-C26;
A19-B3-C27;
A19-B3-C28;
A19-B3-C29;
A19-B3-C30;
A19-B3-C31;
A19-B3-C32;

A19-B3-C33;
A19-B3-C34;
A19-B3-C35;
A19-B3-C36;
A19-B3-C37;
A19-B3-C38;
A19-B3-C39;
A19-B3-C40;
A19-B3-C41;
A19-B3-C42;
A19-B3-C43;
A19-B3-C44;
A19-B3-C45;
A19-B3-C46;
A19-B3-C47;
A19-B3-C48;
A19-B3-C49;
A19-B3-C50;
A19-B3-C51;
A19-B3-C52;
A19-B3-C53;
A19-B3-C54;
A19-B3-C55;
A19-B3-C56;
A19-B3-C57;
A19-B3-C58;
A19-B3-C59;
A20-B3-C1;
A20-B3-C2;
A20-B3-C3;
A20-B3-C4;
A20-B3-C5;
A20-B3-C6;
A20-B3-C7;
A20-B3-C8;
A20-B3-C9;
A20-B3-C10;
A20-B3-C11;
A20-B3-C12;
A20-B3-C13;
A20-B3-C14;
A20-B3-C15;
A20-B3-C16;
A20-B3-C17;
A20-B3-C18;
A20-B3-C19;
A20-B3-C20;
A20-B3-C21;
A20-B3-C22;
A20-B3-C23;
A20-B3-C24;
A20-B3-C25;
A20-B3-C26;
A20-B3-C27;
A20-B3-C28;
A20-B3-C29;
A20-B3-C30;
A20-B3-C31;
A20-B3-C32;
A20-B3-C33;
A20-B3-C34;
A20-B3-C35;
A20-B3-C36;
A20-B3-C37;
A20-B3-C38;
A20-B3-C39;
A20-B3-C40;
A20-B3-C41;
A20-B3-C42;
A20-B3-C43;
A20-B3-C44;
A20-B3-C45;
A20-B3-C46;
A20-B3-C47;
A20-B3-C48;
A20-B3-C49;
A20-B3-C50;
A20-B3-C51;
A20-B3-C52;
A20-B3-C53;
A20-B3-C54;
A20-B3-C55;
A20-B3-C56;
A20-B3-C57;
A20-B3-C58;
A20-B3-C59;
A21-B3-C1;
A21-B3-C2;
A21-B3-C3;
A21-B3-C4;
A21-B3-C5;
A21-B3-C6;
A21-B3-C7;
A21-B3-C8;
A21-B3-C9;
A21-B3-C10;
A21-B3-C11;
A21-B3-C12;
A21-B3-C13;
A21-B3-C14;
A21-B3-C15;
A21-B3-C16;
A21-B3-C17;
A21-B3-C18;
A21-B3-C19;
A21-B3-C20;
A21-B3-C21;
A21-B3-C22;
A21-B3-C23;
A21-B3-C24;
A21-B3-C25;
A21-B3-C26;
A21-B3-C27;
A21-B3-C28;
A21-B3-C29;
A21-B3-C30;
A21-B3-C31;
A21-B3-C32;
A21-B3-C33;
A21-B3-C34;
A21-B3-C35;
A21-B3-C36;
A21-B3-C37;
A21-B3-C38;
A21-B3-C39;
A21-B3-C40;
A21-B3-C41;
A21-B3-C42;
A21-B3-C43;
A21-B3-C44;
A21-B3-C45;
A21-B3-C46;
A21-B3-C47;
A21-B3-C48;
A21-B3-C49;
A21-B3-C50;
A21-B3-C51;
A21-B3-C52;
A21-B3-C53;
A21-B3-C54;
A21-B3-C55;
A21-B3-C56;
A21-B3-C57;
A21-B3-C58;
A21-B3-C59;
A22-B3-C1;
A22-B3-C2;
A22-B3-C3;
A22-B3-C4;
A22-B3-C5;
A22-B3-C6;
A22-B3-C7;
A22-B3-C8;
A22-B3-C9;
A22-B3-C10;
A22-B3-C11;
A22-B3-C12;
A22-B3-C13;

-continued

A22-B3-C14;
A22-B3-C15;
A22-B3-C16;
A22-B3-C17;
A22-B3-C18;
A22-B3-C19;
A22-B3-C20;
A22-B3-C21;
A22-B3-C22;
A22-B3-C23;
A22-B3-C24;
A22-B3-C25;
A22-B3-C26;
A22-B3-C27;
A22-B3-C28;
A22-B3-C29;
A22-B3-C30;
A22-B3-C31;
A22-B3-C32;
A22-B3-C33;
A22-B3-C34;
A22-B3-C35;
A22-B3-C36;
A22-B3-C37;
A22-B3-C38;
A22-B3-C39;
A22-B3-C40;
A22-B3-C41;
A22-B3-C42;
A22-B3-C43;
A22-B3-C44;
A22-B3-C45;
A22-B3-C46;
A22-B3-C47;
A22-B3-C48;
A22-B3-C49;
A22-B3-C50;
A22-B3-C51;
A22-B3-C52;
A22-B3-C53;
A22-B3-C54;
A22-B3-C55;
A22-B3-C56;
A22-B3-C57;
A22-B3-C58;
A22-B3-C59;
A23-B3-C1;
A23-B3-C2;
A23-B3-C3;
A23-B3-C4;
A23-B3-C5;
A23-B3-C6;
A23-B3-C7;
A23-B3-C8;
A23-B3-C9;
A23-B3-C10;
A23-B3-C11;
A23-B3-C12;
A23-B3-C13;
A23-B3-C14;
A23-B3-C15;
A23-B3-C16;
A23-B3-C17;
A23-B3-C18;
A23-B3-C19;
A23-B3-C20;
A23-B3-C21;
A23-B3-C22;
A23-B3-C23;
A23-B3-C24;
A23-B3-C25;
A23-B3-C26;
A23-B3-C27;
A23-B3-C28;
A23-B3-C29;
A23-B3-C30;
A23-B3-C31;
A23-B3-C32;
A23-B3-C33;

-continued

A23-B3-C34;
A23-B3-C35;
A23-B3-C36;
A23-B3-C37;
A23-B3-C38;
A23-B3-C39;
A23-B3-C40;
A23-B3-C41;
A23-B3-C42;
A23-B3-C43;
A23-B3-C44;
A23-B3-C45;
A23-B3-C46;
A23-B3-C47;
A23-B3-C48;
A23-B3-C49;
A23-B3-C50;
A23-B3-C51;
A23-B3-C52;
A23-B3-C53;
A23-B3-C54;
A23-B3-C55;
A23-B3-C56;
A23-B3-C57;
A23-B3-C58;
A23-B3-C59;
A24-B3-C1;
A24-B3-C2;
A24-B3-C3;
A24-B3-C4;
A24-B3-C5;
A24-B3-C6;
A24-B3-C7;
A24-B3-C8;
A24-B3-C9;
A24-B3-C10;
A24-B3-C11;
A24-B3-C12;
A24-B3-C13;
A24-B3-C14;
A24-B3-C15;
A24-B3-C16;
A24-B3-C17;
A24-B3-C18;
A24-B3-C19;
A24-B3-C20;
A24-B3-C21;
A24-B3-C22;
A24-B3-C23;
A24-B3-C24;
A24-B3-C25;
A24-B3-C26;
A24-B3-C27;
A24-B3-C28;
A24-B3-C29;
A24-B3-C30;
A24-B3-C31;
A24-B3-C32;
A24-B3-C33;
A24-B3-C34;
A24-B3-C35;
A24-B3-C36;
A24-B3-C37;
A24-B3-C38;
A24-B3-C39;
A24-B3-C40;
A24-B3-C41;
A24-B3-C42;
A24-B3-C43;
A24-B3-C44;
A24-B3-C45;
A24-B3-C46;
A24-B3-C47;
A24-B3-C48;
A24-B3-C49;
A24-B3-C50;
A24-B3-C51;
A24-B3-C52;
A24-B3-C53;

A24-B3-C54;
A24-B3-C55;
A24-B3-C56;
A24-B3-C57;
A24-B3-C58;
A24-B3-C59;
A25-B3-C1;
A25-B3-C2;
A25-B3-C3;
A25-B3-C4;
A25-B3-C5;
A25-B3-C6;
A25-B3-C7;
A25-B3-C8;
A25-B3-C9;
A25-B3-C10;
A25-B3-C11;
A25-B3-C12;
A25-B3-C13;
A25-B3-C14;
A25-B3-C15;
A25-B3-C16;
A25-B3-C17;
A25-B3-C18;
A25-B3-C19;
A25-B3-C20;
A25-B3-C21;
A25-B3-C22;
A25-B3-C23;
A25-B3-C24;
A25-B3-C25;
A25-B3-C26;
A25-B3-C27;
A25-B3-C28;
A25-B3-C29;
A25-B3-C30;
A25-B3-C31;
A25-B3-C32;
A25-B3-C33;
A25-B3-C34;
A25-B3-C35;
A25-B3-C36;
A25-B3-C37;
A25-B3-C38;
A25-B3-C39;
A25-B3-C40;
A25-B3-C41;
A25-B3-C42;
A25-B3-C43;
A25-B3-C44;
A25-B3-C45;
A25-B3-C46;
A25-B3-C47;
A25-B3-C48;
A25-B3-C49;
A25-B3-C50;
A25-B3-C51;
A25-B3-C52;
A25-B3-C53;
A25-B3-C54;
A25-B3-C55;
A25-B3-C56;
A25-B3-C57;
A25-B3-C58;
A25-B3-C59;
A26-B3-C1;
A26-B3-C2;
A26-B3-C3;
A26-B3-C4;
A26-B3-C5;
A26-B3-C6;
A26-B3-C7;
A26-B3-C8;
A26-B3-C9;
A26-B3-C10;
A26-B3-C11;
A26-B3-C12;
A26-B3-C13;
A26-B3-C14;
A26-B3-C15;
A26-B3-C16;
A26-B3-C17;
A26-B3-C18;
A26-B3-C19;
A26-B3-C20;
A26-B3-C21;
A26-B3-C22;
A26-B3-C23;
A26-B3-C24;
A26-B3-C25;
A26-B3-C26;
A26-B3-C27;
A26-B3-C28;
A26-B3-C29;
A26-B3-C30;
A26-B3-C31;
A26-B3-C32;
A26-B3-C33;
A26-B3-C34;
A26-B3-C35;
A26-B3-C36;
A26-B3-C37;
A26-B3-C38;
A26-B3-C39;
A26-B3-C40;
A26-B3-C41;
A26-B3-C42;
A26-B3-C43;
A26-B3-C44;
A26-B3-C45;
A26-B3-C46;
A26-B3-C47;
A26-B3-C48;
A26-B3-C49;
A26-B3-C50;
A26-B3-C51;
A26-B3-C52;
A26-B3-C53;
A26-B3-C54;
A26-B3-C55;
A26-B3-C56;
A26-B3-C57;
A26-B3-C58;
A26-B3-C59;
A27-B3-C1;
A27-B3-C2;
A27-B3-C3;
A27-B3-C4;
A27-B3-C5;
A27-B3-C6;
A27-B3-C7;
A27-B3-C8;
A27-B3-C9;
A27-B3-C10;
A27-B3-C11;
A27-B3-C12;
A27-B3-C13;
A27-B3-C14;
A27-B3-C15;
A27-B3-C16;
A27-B3-C17;
A27-B3-C18;
A27-B3-C19;
A27-B3-C20;
A27-B3-C21;
A27-B3-C22;
A27-B3-C23;
A27-B3-C24;
A27-B3-C25;
A27-B3-C26;
A27-B3-C27;
A27-B3-C28;
A27-B3-C29;
A27-B3-C30;
A27-B3-C31;
A27-B3-C32;
A27-B3-C33;
A27-B3-C34;

-continued

A27-B3-C35;
A27-B3-C36;
A27-B3-C37;
A27-B3-C38;
A27-B3-C39;
A27-B3-C40;
A27-B3-C41;
A27-B3-C42;
A27-B3-C43;
A27-B3-C44;
A27-B3-C45;
A27-B3-C46;
A27-B3-C47;
A27-B3-C48;
A27-B3-C49;
A27-B3-C50;
A27-B3-C51;
A27-B3-C52;
A27-B3-C53;
A27-B3-C54;
A27-B3-C55;
A27-B3-C56;
A27-B3-C57;
A27-B3-C58;
A27-B3-C59;
A28-B3-C1;
A28-B3-C2;
A28-B3-C3;
A28-B3-C4;
A28-B3-C5;
A28-B3-C6;
A28-B3-C7;
A28-B3-C8;
A28-B3-C9;
A28-B3-C10;
A28-B3-C11;
A28-B3-C12;
A28-B3-C13;
A28-B3-C14;
A28-B3-C15;
A28-B3-C16;
A28-B3-C17;
A28-B3-C18;
A28-B3-C19;
A28-B3-C20;
A28-B3-C21;
A28-B3-C22;
A28-B3-C23;
A28-B3-C24;
A28-B3-C25;
A28-B3-C26;
A28-B3-C27;
A28-B3-C28;
A28-B3-C29;
A28-B3-C30;
A28-B3-C31;
A28-B3-C32;
A28-B3-C33;
A28-B3-C34;
A28-B3-C35;
A28-B3-C36;
A28-B3-C37;
A28-B3-C38;
A28-B3-C39;
A28-B3-C40;
A28-B3-C41;
A28-B3-C42;
A28-B3-C43;
A28-B3-C44;
A28-B3-C45;
A28-B3-C46;
A28-B3-C47;
A28-B3-C48;
A28-B3-C49;
A28-B3-C50;
A28-B3-C51;
A28-B3-C52;
A28-B3-C53;
A28-B3-C54;

-continued

A28-B3-C55;
A28-B3-C56;
A28-B3-C57;
A28-B3-C58;
A28-B3-C59;
A29-B3-C1;
A29-B3-C2;
A29-B3-C3;
A29-B3-C4;
A29-B3-C5;
A29-B3-C6;
A29-B3-C7;
A29-B3-C8;
A29-B3-C9;
A29-B3-C10;
A29-B3-C11;
A29-B3-C12;
A29-B3-C13;
A29-B3-C14;
A29-B3-C15;
A29-B3-C16;
A29-B3-C17;
A29-B3-C18;
A29-B3-C19;
A29-B3-C20;
A29-B3-C21;
A29-B3-C22;
A29-B3-C23;
A29-B3-C24;
A29-B3-C25;
A29-B3-C26;
A29-B3-C27;
A29-B3-C28;
A29-B3-C29;
A29-B3-C30;
A29-B3-C31;
A29-B3-C32;
A29-B3-C33;
A29-B3-C34;
A29-B3-C35;
A29-B3-C36;
A29-B3-C37;
A29-B3-C38;
A29-B3-C39;
A29-B3-C40;
A29-B3-C41;
A29-B3-C42;
A29-B3-C43;
A29-B3-C44;
A29-B3-C45;
A29-B3-C46;
A29-B3-C47;
A29-B3-C48;
A29-B3-C49;
A29-B3-C50;
A29-B3-C51;
A29-B3-C52;
A29-B3-C53;
A29-B3-C54;
A29-B3-C55;
A29-B3-C56;
A29-B3-C57;
A29-B3-C58;
A29-B3-C59;
A30-B3-C1;
A30-B3-C2;
A30-B3-C3;
A30-B3-C4;
A30-B3-C5;
A30-B3-C6;
A30-B3-C7;
A30-B3-C8;
A30-B3-C9;
A30-B3-C10;
A30-B3-C11;
A30-B3-C12;
A30-B3-C13;
A30-B3-C14;
A30-B3-C15;

A30-B3-C16;
A30-B3-C17;
A30-B3-C18;
A30-B3-C19;
A30-B3-C20;
A30-B3-C21;
A30-B3-C22;
A30-B3-C23;
A30-B3-C24;
A30-B3-C25;
A30-B3-C26;
A30-B3-C27;
A30-B3-C28;
A30-B3-C29;
A30-B3-C30;
A30-B3-C31;
A30-B3-C32;
A30-B3-C33;
A30-B3-C34;
A30-B3-C35;
A30-B3-C36;
A30-B3-C37;
A30-B3-C38;
A30-B3-C39;
A30-B3-C40;
A30-B3-C41;
A30-B3-C42;
A30-B3-C43;
A30-B3-C44;
A30-B3-C45;
A30-B3-C46;
A30-B3-C47;
A30-B3-C48;
A30-B3-C49;
A30-B3-C50;
A30-B3-C51;
A30-B3-C52;
A30-B3-C53;
A30-B3-C54;
A30-B3-C55;
A30-B3-C56;
A30-B3-C57;
A30-B3-C58;
A30-B3-C59;
A31-B3-C1;
A31-B3-C2;
A31-B3-C3;
A31-B3-C4;
A31-B3-C5;
A31-B3-C6;
A31-B3-C7;
A31-B3-C8;
A31-B3-C9;
A31-B3-C10;
A31-B3-C11;
A31-B3-C12;
A31-B3-C13;
A31-B3-C14;
A31-B3-C15;
A31-B3-C16;
A31-B3-C17;
A31-B3-C18;
A31-B3-C19;
A31-B3-C20;
A31-B3-C21;
A31-B3-C22;
A31-B3-C23;
A31-B3-C24;
A31-B3-C25;
A31-B3-C26;
A31-B3-C27;
A31-B3-C28;
A31-B3-C29;
A31-B3-C30;
A31-B3-C31;
A31-B3-C32;
A31-B3-C33;
A31-B3-C34;
A31-B3-C35;
A31-B3-C36;
A31-B3-C37;
A31-B3-C38;
A31-B3-C39;
A31-B3-C40;
A31-B3-C41;
A31-B3-C42;
A31-B3-C43;
A31-B3-C44;
A31-B3-C45;
A31-B3-C46;
A31-B3-C47;
A31-B3-C48;
A31-B3-C49;
A31-B3-C50;
A31-B3-C51;
A31-B3-C52;
A31-B3-C53;
A31-B3-C54;
A31-B3-C55;
A31-B3-C56;
A31-B3-C57;
A31-B3-C58;
A31-B3-C59;
A32-B3-C1;
A32-B3-C2;
A32-B3-C3;
A32-B3-C4;
A32-B3-C5;
A32-B3-C6;
A32-B3-C7;
A32-B3-C8;
A32-B3-C9;
A32-B3-C10;
A32-B3-C11;
A32-B3-C12;
A32-B3-C13;
A32-B3-C14;
A32-B3-C15;
A32-B3-C16;
A32-B3-C17;
A32-B3-C18;
A32-B3-C19;
A32-B3-C20;
A32-B3-C21;
A32-B3-C22;
A32-B3-C23;
A32-B3-C24;
A32-B3-C25;
A32-B3-C26;
A32-B3-C27;
A32-B3-C28;
A32-B3-C29;
A32-B3-C30;
A32-B3-C31;
A32-B3-C32;
A32-B3-C33;
A32-B3-C34;
A32-B3-C35;
A32-B3-C36;
A32-B3-C37;
A32-B3-C38;
A32-B3-C39;
A32-B3-C40;
A32-B3-C41;
A32-B3-C42;
A32-B3-C43;
A32-B3-C44;
A32-B3-C45;
A32-B3-C46;
A32-B3-C47;
A32-B3-C48;
A32-B3-C49;
A32-B3-C50;
A32-B3-C51;
A32-B3-C52;
A32-B3-C53;
A32-B3-C54;
A32-B3-C55;

-continued

A32-B3-C56;
A32-B3-C57;
A32-B3-C58;
A32-B3-C59;
A33-B3-C1;
A33-B3-C2;
A33-B3-C3;
A33-B3-C4;
A33-B3-C5;
A33-B3-C6;
A33-B3-C7;
A33-B3-C8;
A33-B3-C9;
A33-B3-C10;
A33-B3-C11;
A33-B3-C12;
A33-B3-C13;
A33-B3-C14;
A33-B3-C15;
A33-B3-C16;
A33-B3-C17;
A33-B3-C18;
A33-B3-C19;
A33-B3-C20;
A33-B3-C21;
A33-B3-C22;
A33-B3-C23;
A33-B3-C24;
A33-B3-C25;
A33-B3-C26;
A33-B3-C27;
A33-B3-C28;
A33-B3-C29;
A33-B3-C30;
A33-B3-C31;
A33-B3-C32;
A33-B3-C33;
A33-B3-C34;
A33-B3-C35;
A33-B3-C36;
A33-B3-C37;
A33-B3-C38;
A33-B3-C39;
A33-B3-C40;
A33-B3-C41;
A33-B3-C42;
A33-B3-C43;
A33-B3-C44;
A33-B3-C45;
A33-B3-C46;
A33-B3-C47;
A33-B3-C48;
A33-B3-C49;
A33-B3-C50;
A33-B3-C51;
A33-B3-C52;
A33-B3-C53;
A33-B3-C54;
A33-B3-C55;
A33-B3-C56;
A33-B3-C57;
A33-B3-C58;
A33-B3-C59;
A34-B3-C1;
A34-B3-C2;
A34-B3-C3;
A34-B3-C4;
A34-B3-C5;
A34-B3-C6;
A34-B3-C7;
A34-B3-C8;
A34-B3-C9;
A34-B3-C10;
A34-B3-C11;
A34-B3-C12;
A34-B3-C13;
A34-B3-C14;
A34-B3-C15;
A34-B3-C16;

-continued

A34-B3-C17;
A34-B3-C18;
A34-B3-C19;
A34-B3-C20;
A34-B3-C21;
A34-B3-C22;
A34-B3-C23;
A34-B3-C24;
A34-B3-C25;
A34-B3-C26;
A34-B3-C27;
A34-B3-C28;
A34-B3-C29;
A34-B3-C30;
A34-B3-C31;
A34-B3-C32;
A34-B3-C33;
A34-B3-C34;
A34-B3-C35;
A34-B3-C36;
A34-B3-C37;
A34-B3-C38;
A34-B3-C39;
A34-B3-C40;
A34-B3-C41;
A34-B3-C42;
A34-B3-C43;
A34-B3-C44;
A34-B3-C45;
A34-B3-C46;
A34-B3-C47;
A34-B3-C48;
A34-B3-C49;
A34-B3-C50;
A34-B3-C51;
A34-B3-C52;
A34-B3-C53;
A34-B3-C54;
A34-B3-C55;
A34-B3-C56;
A34-B3-C57;
A34-B3-C58;
A34-B3-C59;
A35-B3-C1;
A35-B3-C2;
A35-B3-C3;
A35-B3-C4;
A35-B3-C5;
A35-B3-C6;
A35-B3-C7;
A35-B3-C8;
A35-B3-C9;
A35-B3-C10;
A35-B3-C11;
A35-B3-C12;
A35-B3-C13;
A35-B3-C14;
A35-B3-C15;
A35-B3-C16;
A35-B3-C17;
A35-B3-C18;
A35-B3-C19;
A35-B3-C20;
A35-B3-C21;
A35-B3-C22;
A35-B3-C23;
A35-B3-C24;
A35-B3-C25;
A35-B3-C26;
A35-B3-C27;
A35-B3-C28;
A35-B3-C29;
A35-B3-C30;
A35-B3-C31;
A35-B3-C32;
A35-B3-C33;
A35-B3-C34;
A35-B3-C35;
A35-B3-C36;

-continued

A35-B3-C37;
A35-B3-C38;
A35-B3-C39;
A35-B3-C40;
A35-B3-C41;
A35-B3-C42;
A35-B3-C43;
A35-B3-C44;
A35-B3-C45;
A35-B3-C46;
A35-B3-C47;
A35-B3-C48;
A35-B3-C49;
A35-B3-C50;
A35-B3-C51;
A35-B3-C52;
A35-B3-C53;
A35-B3-C54;
A35-B3-C55;
A35-B3-C56;
A35-B3-C57;
A35-B3-C58;
A35-B3-C59;
A1-B4-C36;
A1-B4-C37;
A1-B4-C38;
A1-B4-C39;
A1-B4-C40;
A1-B4-C41;
A1-B4-C42;
A1-B4-C43;
A1-B4-C44;
A1-B4-C45;
A1-B4-C46;
A1-B4-C47;
A1-B4-C48;
A1-B4-C49;
A1-B4-C50;
A1-B1-C51;
A1-B4-C52;
A1-B4-C53;
A1-B4-C54;
A1-B4-C55;
A1-B4-C56;
A1-B4-C57;
A1-B4-C58;
A1-B4-C59;
A2-B4-C1;
A2-B4-C2;
A2-B4-C3;
A2-B4-C4;
A2-B4-C5;
A2-B4-C6;
A2-B4-C7;
A2-B4-C8;
A2-B4-C9;
A2-B4-C10;
A2-B4-C11;
A2-B4-C12;
A2-B4-C13;
A2-B4-C14;
A2-B4-C15;
A2-B4-C16;
A2-B4-C17;
A2-B4-C18;
A2-B4-C19;
A2-B4-C20;
A2-B4-C21;
A2-B4-C22;
A2-B4-C23;
A2-B4-C24;
A2-B4-C25;
A2-B4-C26;
A2-B4-C27;
A2-B4-C28;
A2-B4-C29;
A2-B4-C30;
A2-B4-C31;
A2-B4-C32;

-continued

A2-B4-C33;
A2-B4-C34;
A2-B4-C35;
A2-B4-C36;
A2-B4-C37;
A2-B4-C38;
A2-B4-C39;
A2-B4-C40;
A2-B4-C41;
A2-B4-C42;
A2-B4-C43;
A2-B4-C44;
A2-B4-C45;
A2-B4-C46;
A2-B4-C47;
A2-B4-C48;
A2-B4-C49;
A2-B4-C50;
A2-B4-C51;
A2-B4-C52;
A2-B4-C53;
A2-B4-C54;
A2-B4-C55;
A2-B4-C56;
A2-B4-C57;
A2-B4-C58;
A2-B4-C59;
A3-B4-C1;
A3-B4-C2;
A3-B4-C3;
A3-B4-C4;
A3-B4-C5;
A3-B4-C6;
A3-B4-C7;
A3-B4-C8;
A3-B4-C9;
A3-B4-C10;
A3-B4-C11;
A3-B4-C12;
A3-B4-C13;
A3-B4-C14;
A3-B4-C15;
A3-B4-C16;
A3-B4-C17;
A3-B4-C18;
A3-B4-C19;
A3-B4-C20;
A3-B4-C21;
A3-B4-C22;
A3-B4-C23;
A3-B4-C24;
A3-B4-C25;
A3-B4-C26;
A3-B4-C27;
A3-B4-C28;
A3-B4-C29;
A3-B4-C30;
A3-B4-C31;
A3-B4-C32;
A3-B4-C33;
A3-B4-C34;
A3-B4-C35;
A3-B4-C36;
A3-B4-C37;
A3-B4-C38;
A3-B4-C39;
A3-B4-C40;
A3-B4-C41;
A3-B4-C42;
A3-B4-C43;
A3-B4-C44;
A3-B4-C45;
A3-B4-C46;
A3-B4-C47;
A3-B4-C48;
A3-B4-C49;
A3-B4-C50;
A3-B4-C51;
A3-B4-C52;

-continued

A3-B4-C53;
A3-B4-C54;
A3-B4-C55;
A3-B4-C56;
A3-B4-C57;
A3-B4-C58;
A3-B4-C59;
A4-B4-C1;
A4-B4-C2;
A4-B4-C3;
A4-B4-C4;
A4-B4-C5;
A4-B4-C6;
A4-B4-C7;
A4-B4-C5;
A4-B4-C9;
A4-B4-C10;
A4-B4-C11;
A4-B4-C12;
A4-B4-C13;
A4-B4-C14;
A4-B4-C15;
A4-B4-C16;
A4-B4-C17;
A4-B4-C18;
A4-B4-C19;
A4-B4-C20;
A4-B4-C21,
A4-B4-C22;
A4-B4-C23;
A4-B4-C24;
A4-B4-C25;
A4-B4-C26;
A4-B4-C27;
A4-B4-C28;
A4-B4-C29;
A4-B4-C30;
A4-B4-C31;
A4-B4-C32;
A4-B4-C33;
A4-B4-C34;
A4-B4-C35;
A4-B4-C36;
A4-B4-C37;
A4-B4-C38;
A4-B4-C39;
A4-B4-C40;
A4-B4-C41;
A4-B4-C42;
A4-B4-C43;
A4-B4-C44;
A4-B4-C45;
A4-B4-C46;
A4-B4-C47;
A4-B4-C48;
A4-B4-C49;
A4-B4-C50;
A4-B4-C51;
A4-B4-C52;
A4-B4-C53;
A4-B4-C54;
A4-B4-C55;
A4-B4-C56;
A4-B4-C57;
A4-B4-C58;
A4-B4-C59;
A5-B4-C1;
A5-B4-C2;
A5-B4-C3;
A5-B4-C4;
A5-B4-C5;
A5-B4-C6;
A5-B4-C7;
A5-B4-C8;
A5-B4-C9;
A5-B4-C10;
A5-B4-C11;
A5-B4-C12;
A5-B4-C13;

-continued

A5-B4-C14;
A5-B4-C15;
A5-B4-C16;
A5-B4-C17;
A5-B4-C18;
A5-B4-C19;
A5-B4-C20;
A5-B4-C21;
A5-B4-C22;
A5-B4-C23;
A5-B4-C24;
A5-B4-C25;
A5-B4-C26;
A5-B4-C27;
A5-B4-C28;
A5-B4-C29;
A5-B4-C30;
A5-B4-C31;
A5-B4-C32;
A5-B4-C33;
A5-B4-C34;
A5-B4-C35;
A5-B4-C36;
A5-B4-C37;
A5-B4-C38;
A5-B4-C39;
A5-B4-C40;
A5-B4-C41;
A5-B4-C42;
A5-B4-C43;
A5-B4-C44;
A5-B4-C45;
A5-B4-C46;
A5-B4-C47;
A5-B4-C48;
A5-B4-C49;
A5-B4-C50;
A5-B4-C51;
A5-B4-C52;
A5-B4-C53;
A5-B4-C54;
A5-B4-C55;
A5-B4-C56;
A5-B4-C57;
A5-B4-C58;
A5-B4-C59;
A6-B4-C1;
A6-B4-C2;
A6-B4-C3;
A6-B4-C4;
A6-B4-C5;
A6-B4-C6;
A6-B4-C7;
A6-B4-C8;
A6-B4-C9;
A6-B4-C10;
A6-B4-C11;
A6-B4-C12;
A6-B4-C13;
A6-B4-C14;
A6-B4-C15;
A6-B4-C16;
A6-B4-C17;
A6-B4-C18;
A6-B4-C19;
A6-B4-C20;
A6-B4-C21;
A6-B4-C22;
A6-B4-C23;
A6-B4-C24;
A6-B4-C25;
A6-B4-C26;
A6-B4-C27;
A6-B4-C28;
A6-B4-C29;
A6-B4-C30;
A6-B4-C31;
A6-B4-C32;
A6-B4-C33;

A6-B4-C34;
A6-B4-C35;
A6-B4-C36;
A6-B4-C37;
A6-B4-C38;
A6-B4-C39;
A6-B4-C40;
A6-B4-C41;
A6-B4-C42;
A6-B4-C43;
A6-B4-C44;
A6-B4-C45;
A6-B4-C46;
A6-B4-C47;
A6-B4-C48;
A6-B4-C49;
A6-B4-C50;
A6-B4-C5i;
A6-B4-C52;
A6-B4-C53;
A6-B4-C54;
A6-B4-C55;
A6-B4-C56;
A6-B4-C57;
A6-B4-C58;
A6-B4-C59;
A7-B4-C1;
A7-B4-C2;
A7-B4-C3;
A7-B4-C4;
A7-B4-C5;
A7-B4-C6;
A7-B4-C7;
A7-B4-C8;
A7-B4-C9;
A7-B4-C10;
A7-B4-C11;
A7-B4-C12;
A7-B4-C13;
A7-B4-C14;
A7-B4-C15;
A7-B4-C16;
A7-B4-C17;
A7-B4-C18;
A7-B4-C19;
A7-B4-C20;
A7-B4-C21;
A7-B4-C22;
A7-B4-C23;
A7-B4-C24;
A7-B4-C25;
A7-B4-C26;
A7-B4-C27;
A7-B4-C28;
A7-B4-C29;
A7-B4-C30;
A7-B4-C31;
A7-B4-C32;
A7-B4-C33;
A7-B4-C34;
A7-B4-C35;
A7-B4-C36;
A7-B4-C37;
A7-B4-C38;
A7-B4-C39;
A7-B4-C40;
A7-B4-C41;
A7-B4-C42;
A7-B4-C43;
A7-B4-C44;
A7-B4-C45;
A7-B4-C46;
A7-B4-C47;
A7-B4-C48;
A7-B4-C49;
A7-B4-C50;
A7-B4-C51;
A7-B4-C52;
A7-B4-C53;
A7-B4-C54;
A7-B4-C55;
A7-B4-C56;
A7-B4-C57;
A7-B4-C58;
A7-B4-C59;
A8-B4-C1;
A8-B4-C2;
A8-B4-C3;
A8-B4-C4;
A8-B4-C5;
A8-B4-C6;
A8-B4-C7;
A8-B4-C8;
A8-B4-C9;
A8-B4-C10;
A8-B4-C11;
A8-B4-C12;
A8-B4-C13;
A8-B4-C14;
A8-B4-C15;
A8-B4-C16;
A8-B4-C17;
A8-B4-C18;
A8-B4-C19;
A8-B4-C20;
A8-B4-C21;
A8-B4-C22;
A8-B4-C23;
A8-B4-C24;
A8-B4-C25;
A8-B4-C26;
A8-B4-C27;
A8-B4-C28;
A8-B4-C29;
A8-B4-C30;
A8-B4-C31;
A8-B4-C32;
A8-B4-C33;
A8-B4-C34;
A8-B4-C35;
A8-B4-C36;
A8-B4-C37;
A8-B4-C38;
A8-B4-C39;
A8-B4-C40;
A8-B4-C41;
A8-B4-C42;
A8-B4-C43;
A8-B4-C44;
A8-B4-C45;
A8-B4-C46;
A8-B4-C47;
A8-B4-C48;
A8-B4-C49;
A8-B4-C50;
A8-B4-C51;
A8-B4-C52;
A8-B4-C53;
A8-B4-C54;
A8-B4-C55;
A8-B4-C56;
A8-B4-C57;
A8-B4-C58;
A8-B4-C59;
A9-B4-C1;
A9-B4-C2;
A9-B4-C3;
A9-B4-C4;
A9-B4-C5;
A9-B4-C6;
A9-B4-C7;
A9-B4-C8;
A9-B4-C9;
A9-B4-C10;
A9-B4-C11;
A9-B4-C12;
A9-B4-C13;
A9-B4-C14;

-continued

A9-B4-C15;
A9-B4-C16;
A9-B4-C17;
A9-B4-C18;
A9-B4-C19;
A9-B4-C20;
A9-B4-C21;
A9-B4-C22;
A9-B4-C23;
A9-B4-C24;
A9-B4-C25;
A9-B4-C26;
A9-B4-C27;
A9-B4-C28;
A9-B4-C29;
A9-B4-C30;
A9-B4-C31;
A9-B4-C32;
A9-B4-C33;
A9-B4-C34;
A9-B4-C35;
A9-B4-C36;
A9-B4-C37;
A9-B4-C38;
A9-B4-C39;
A9-B4-C40;
A9-B4-C41;
A9-B4-C42;
A9-B4-C43;
A9-B4-C44;
A9-B4-C45;
A9-B4-C46;
A9-B4-C47;
A9-B4-C48;
A9-B4-C49;
A9-B4-C50;
A9-B4-C51;
A9-B4-C52;
A9-B4-C53;
A9-B4-C54;
A9-B4-C55;
A9-B4-C56;
A9-B4-C57;
A9-B4-C58;
A9-B4-C59;
A10-B4-C1;
A10-B4-C2;
A10-B4-C3;
A10-B4-C4;
A10-B4-C5;
A10-B4-C6;
A10-B4-C7;
A10-B4-C8;
A10-B4-C9;
A10-B4-C10;
A10-B4-C11;
A10-B4-C12;
A10-B4-C13;
A10-B4-C14;
A10-B4-C15;
A10-B4-C16;
A10-B4-C17;
A10-B4-C18;
A10-B4-C19;
A10-B4-C20;
A10-B4-C21;
A10-B4-C22;
A10-B4-C23;
A10-B4-C24;
A10-B4-C25;
A10-B4-C26;
A10-B4-C27;
A10-B4-C28;
A10-B4-C29;
A10-B4-C30;
A10-B4-C31;
A10-B4-C32;
A10-B4-C33;
A10-B4-C34;

-continued

A10-B4-C35;
A10-B4-C36;
A10-B4-C37;
A10-B4-C38;
A10-B4-C39;
A10-B4-C40;
A10-B4-C41;
A10-B4-C42;
A10-B4-C43;
A10-B4-C44;
A10-B4-C45;
A10-B4-C46;
A10-B4-C47;
A10-B4-C48;
A10-B4-C49;
A10-B4-C50;
A10-B4-C51;
A10-B4-C52;
A10-B4-C53;
A10-B4-C54;
A10-B4-C55;
A10-B4-C56;
A10-B4-C57;
A10-B4-C58;
A10-B4-C59;
A11-B4-C1;
A11-B4-C2;
A11-B4-C3;
A11-B4-C4;
A11-B4-C5;
A11-B4-C6;
A11-B4-C7;
A11-B4-C8;
A11-B4-C9;
A11-B4-C10;
A11-B4-C11;
A11-B4-C12;
A11-B4-C13;
A11-B4-C14;
A11-B4-C15;
A11-B4-C16;
A11-B4-C17;
A11-B4-C18;
A11-B4-C19;
A11-B4-C20;
A11-B4-C21;
A11-B4-C22;
A11-B4-C23;
A11-B4-C24;
A11-B4-C25;
A11-B4-C26;
A11-B4-C27;
A11-B4-C28;
A11-B4-C29;
A11-B4-C30;
A11-B4-C31;
A11-B4-C32;
A11-B4-C33;
A11-B4-C34;
A11-B4-C35;
A11-B4-C36;
A11-B4-C37;
A11-B4-C38;
A11-B4-C39;
A11-B4-C40;
A11-B4-C41;
A11-B4-C42;
A11-B4-C43;
A11-B4-C44;
A11-B4-C45;
A11-B4-C46;
A11-B4-C47;
A11-B4-C48;
A11-B4-C49;
A11-B4-C50;
A11-B4-C51;
A11-B4-C52;
A11-B4-C53;
A11-B4-C54;

A11-B4-C55;
A11-B4-C56;
A11-B4-C57;
A11-B4-C58;
A11-B4-C59;
A12-B4-C1;
A12-B4-C2;
A12-B4-C3;
A12-B4-C4;
A12-B4-C5;
A12-B4-C6;
A12-B4-C7;
A12-B4-C8;
A12-B4-C9;
A12-B4-C10;
A12-B4-C11;
A12-B4-C12;
A12-B4-C13;
A12-B4-C14;
A12-B4-C15;
A12-B4-C16;
A12-B4-C17;
A12-B4-C18;
A12-B4-C19;
A12-B4-C20;
A12-B4-C21;
A12-B4-C22;
A12-B4-C23;
A12-B4-C24;
A12-B4-C25;
A12-B4-C26;
A12-B4-C27;
A12-B4-C28;
A12-B4-C29;
A12-B4-C30;
A12-B4-C31;
A12-B4-C32;
A12-B4-C33;
A12-B4-C34;
A12-B4-C35;
A12-B4-C36;
A12-B4-C37;
A12-B4-C38;
A12-B4-C39;
A12-B4-C40;
A12-B4-C41;
A12-B4-C42;
A12-B4-C43;
A12-B4-C44;
A12-B4-C45;
A12-B4-C46;
A12-B4-C47;
A12-B4-C48;
A12-B4-C49;
A12-B4-C50;
A12-B4-C51;
A12-B4-C52;
A12-B4-C53;
A12-B4-C54;
A12-B4-C55;
A12-B4-C56;
A12-B4-C57;
A12-B4-C58;
A12-B4-C59;
A13-B4-C1;
A13-B4-C2;
A13-B4-C3;
A13-B4-C4;
A13-B4-C5;
A13-B4-C6;
A13-B4-C7;
A13-B4-C8;
A13-B4-C9;
A13-B4-C10;
A13-B4-C11;
A13-B4-C12;
A13-B4-C13;
A13-B4-C14;
A13-B4-C15;
A13-B4-C16;
A13-B4-C17;
A13-B4-C18;
A13-B4-C19;
A13-B4-C20;
A13-B4-C21;
A13-B4-C22;
A13-B4-C23;
A13-B4-C24;
A13-B4-C25;
A13-B4-C26;
A13-B4-C27;
A13-B4-C28;
A13-B4-C29;
A13-B4-C30;
A13-B4-C31;
A13-B4-C32;
A13-B4-C33;
A13-B4-C34;
A13-B4-C35;
A13-B4-C36;
A13-B4-C37;
A13-B4-C38;
A13-B4-C39;
A13-B4-C40;
A13-B4-C41;
A13-B4-C42;
A13-B4-C43;
A13-B4-C44;
A13-B4-C45;
A13-B4-C46;
A13-B4-C47;
A13-B4-C48;
A13-B4-C49;
A13-B4-C50;
A13-B4-C51;
A13-B4-C52;
A13-B4-C53;
A13-B4-C54;
A13-B4-C55;
A13-B4-C56;
A13-B4-C57;
A13-B4-C58;
A13-B4-C59;
A14-B4-C1;
A14-B4-C2;
A14-B4-C3;
A14-B4-C4;
A14-B4-C5;
A14-B4-C6;
A14-B4-C7;
A14-B4-C8;
A14-B4-C9;
A14-B4-C10;
A14-B4-C11;
A14-B4-C12;
A14-B4-C13;
A14-B4-C14;
A14-B4-C15;
A14-B4-C16;
A14-B4-C17;
A14-B4-C18;
A14-B4-C19;
A14-B4-C20;
A14-B4-C21;
A14-B4-C22;
A14-B4-C23;
A14-B4-C24;
A14-B4-C25;
A14-B4-C26;
A14-B4-C27;
A14-B4-C28;
A14-B4-C29;
A14-B4-C30;
A14-B4-C31;
A14-B4-C32;
A14-B4-C33;
A14-B4-C34;
A14-B4-C35;

-continued

A14-B4-C36;
A14-B4-C37;
A14-B4-C38;
A14-B4-C39;
A14-B4-C40;
A14-B4-C41;
A14-B4-C42;
A14-B4-C43;
A14-B4-C44;
A14-B4-C45;
A14-B4-C46;
A14-B4-C47;
A14-B4-C48;
A14-B4-C49;
A14-B4-C50;
A14-B4-C51;
A14-B4-C52;
A14-B4-C53;
A14-B4-C54;
A14-B4-C55;
A14-B4-C56;
A14-B4-C57;
A14-B4-C58;
A14-B4-C59;
A15-B4-C1;
A15-B4-C2;
A15-B4-C3;
A15-B4-C4;
A15-B4-C5;
A15-B4-C6;
A15-B4-C7;
A15-B4-C8;
A15-B4-C9;
A15-B4-C10;
A15-B4-C11;
A15-B4-C12;
A15-B4-C13;
A15-B4-C14;
A15-B4-C15;
A15-B4-C16;
A15-B4-C17;
A15-B4-C18;
A15-B4-C19;
A15-B4-C20;
A15-B4-C21;
A15-B4-C22;
A15-B4-C23;
A15-B4-C24;
A15-B4-C25;
A15-B4-C26;
A15-B4-C27;
A15-B4-C28;
A15-B4-C29;
A15-B4-C30;
A15-B4-C31;
A15-B4-C32;
A15-B4-C33;
A15-B4-C34;
A15-B4-C35;
A15-B4-C36;
A15-B4-C37;
A15-B4-C38;
A15-B4-C39;
A15-B4-C40;
A15-B4-C41;
A15-B4-C42;
A15-B4-C43;
A15-B4-C44;
A15-B4-C45;
A15-B4-C46;
A15-B4-C47;
A15-B4-C48;
A15-B4-C49;
A15-B4-C50;
A15-B4-C51;
A15-B4-C52;
A15-B4-C53;
A15-B4-C54;
A15-B4-C55;

-continued

A15-B4-C56;
A15-B4-C57;
A15-B4-C58;
A15-B4-C59;
A16-B4-C1;
A16-B4-C2;
A16-B4-C3;
A16-B4-C4;
A16-B4-C5;
A16-B4-C6;
A16-B4-C7;
A16-B4-C8;
A16-B4-C9;
A16-B4-C10;
A16-B4-C11;
A16-B4-C12;
A16-B4-C13;
A16-B4-C14;
A16-B4-C15;
A16-B4-C16;
A16-B4-C17;
A16-B4-C18;
A16-B4-C19;
A16-B4-C20;
A16-B4-C21;
A16-B4-C22;
A16-B4-C23;
A16-B4-C24;
A16-B4-C25;
A16-B4-C26;
A16-B4-C27;
A16-B4-C28;
A16-B4-C29;
A16-B4-C30;
A16-B4-C31;
A16-B4-C32;
A16-B4-C33;
A16-B4-C34;
A16-B4-C35;
A16-B4-C36;
A16-B4-C37;
A16-B4-C38;
A16-B4-C39;
A16-B4-C40;
A16-B4-C41;
A16-B4-C42;
A16-B4-C43;
A16-B4-C44;
A16-B4-C45;
A16-B4-C46;
A16-B4-C47;
A16-B4-C48;
A16-B4-C49;
A16-B4-C50;
A16-B4-C51;
A16-B4-C52;
A16-B4-C53;
A16-B4-C54;
A16-B4-C55;
A16-B4-C56;
A16-B4-C57;
A16-B4-C58;
A16-B4-C59;
A17-B4-C1;
A17-B4-C2;
A17-B4-C3;
A17-B4-C4;
A17-B4-C5;
A17-B4-C6;
A17-B4-C7;
A17-B4-C8;
A17-B4-C9;
A17-B4-C10;
A17-B4-C11;
A17-B4-C12;
A17-B4-C13;
A17-B4-C14;
A17-B4-C15;
A17-B4-C16;

A17-B4-C17;
A17-B4-C18;
A17-B4-C19;
A17-B4-C20;
A17-B4-C21;
A17-B4-C22;
A17-B4-C23;
A17-B4-C24;
A17-B4-C25;
A17-B4-C26;
A17-B4-C27;
A17-B4-C28;
A17-B4-C29;
A17-B4-C30;
A17-B4-C31;
A17-B4-C32;
A17-B4-C33;
A17-B4-C34;
A17-B4-C35;
A17-B4-C36;
A17-B4-C37;
A17-B4-C38;
A17-B4-C39;
A17-B4-C40;
A17-B4-C41;
A17-B4-C42;
A17-B4-C43;
A17-B4-C44;
A17-B4-C45;
A17-B4-C46;
A17-B4-C47;
A17-B4-C48;
A17-B4-C49;
A17-B4-C50;
A17-B4-C51;
A17-B4-C52;
A17-B4-C53;
A17-B4-C54;
A17-B4-C55;
A17-B4-C56;
A17-B4-C57;
A17-B4-C58;
A17-B4-C59;
A18-B4-C1;
A18-B4-C2;
A18-B4-C3;
A18-B4-C4;
A18-B4-C5;
A18-B4-C6;
A18-B4-C7;
A18-B4-C8;
A18-B4-C9;
A18-B4-C10;
A18-B4-C11;
A18-B4-C12;
A18-B4-C13;
A18-B4-C14;
A18-B4-C15;
A18-B4-C16;
A18-B4-C17;
A18-B4-C18;
A18-B4-C19;
A18-B4-C20;
A18-B4-C21;
A18-B4-C22;
A18-B4-C23;
A18-B4-C24;
A18-B4-C25;
A18-B4-C26;
A18-B4-C27;
A18-B4-C28;
A18-B4-C29;
A18-B4-C30;
A18-B4-C31;
A18-B4-C32;
A18-B4-C33;
A18-B4-C34;
A18-B4-C35;
A18-B4-C36;
A18-B4-C37;
A18-B4-C38;
A18-B4-C39;
A18-B4-C40;
A18-B4-C41;
A18-B4-C42;
A18-B4-C43;
A18-B4-C44;
A18-B4-C45;
A18-B4-C46;
A18-B4-C47;
A18-B4-C48;
A18-B4-C49;
A18-B4-C50;
A18-B4-C51;
A18-B4-C52;
A18-B4-C53;
A18-B4-C54;
A18-B4-C55;
A18-B4-C56;
A18-B4-C57;
A18-B4-C58;
A18-B4-C59;
A19-B4-C1;
A19-B4-C2;
A19-B4-C3;
A19-B4-C4;
A19-B4-C5;
A19-B4-C6;
A19-B4-C7;
A19-B4-C8;
A19-B4-C9;
A19-B4-C10;
A19-B4-C11;
A19-B4-C12;
A19-B4-C13;
A19-B4-C14;
A19-B4-C15;
A19-B4-C16;
A19-B4-C17;
A19-B4-C18;
A19-B4-C19;
A19-B4-C20;
A19-B4-C21;
A19-B4-C22;
A19-B4-C23;
A19-B4-C24;
A19-B4-C25;
A19-B4-C26;
A19-B4-C27;
A19-B4-C28;
A19-B4-C29;
A19-B4-C30;
A19-B4-C31;
A19-B4-C32;
A19-B4-C33;
A19-B4-C34;
A19-B4-C35;
A19-B4-C36;
A19-B4-C37;
A19-B4-C38;
A19-B4-C39;
A19-B4-C40;
A19-B4-C41;
A19-B4-C42;
A19-B4-C43;
A19-B4-C44;
A19-B4-C45;
A19-B4-C46;
A19-B4-C47;
A19-B4-C48;
A19-B4-C49;
A19-B4-C50;
A19-B4-C51;
A19-B4-C52;
A19-B4-C53;
A19-B4-C54;
A19-B4-C55;
A19-B4-C56;

-continued

A19-B4-C57;
A19-B4-C58;
A19-B4-C59;
A20-B4-C1;
A20-B4-C2;
A20-B4-C3;
A20-B4-C4;
A20-B4-C5;
A20-B4-C6;
A20-B4-C7;
A20-B4-C8;
A20-B4-C9;
A20-B4-C10;
A20-B4-C11;
A20-B4-C12;
A20-B4-C13;
A20-B4-C14;
A20-B4-C15;
A20-B4-C16;
A20-B4-C17;
A20-B4-C18;
A20-B4-C19;
A20-B4-C20;
A20-B4-C21;
A20-B4-C22;
A20-B4-C23;
A20-B4-C24;
A20-B4-C25;
A20-B4-C26;
A20-B4-C27;
A20-B4-C28;
A20-B4-C29;
A20-B4-C30;
A20-B4-C31;
A20-B4-C32;
A20-B4-C33;
A20-B4-C34;
A20-B4-C35;
A20-B4-C36;
A20-B4-C37;
A20-B4-C38;
A20-B4-C39;
A20-B4-C40;
A20-B4-C41;
A20-B4-C42;
A20-B4-C43;
A20-B4-C44;
A20-B4-C45;
A20-B4-C46;
A20-B4-C47;
A20-B4-C48;
A20-B4-C49;
A20-B4-C50;
A20-B4-C51;
A20-B4-C52;
A20-B4-C53;
A20-B4-C54;
A20-B4-C55;
A20-B4-C56;
A20-B4-C57;
A20-B4-C58;
A20-B4-C59;
A21-B4-C1;
A21-B4-C2;
A21-B4-C3;
A21-B4-C4;
A21-B4-C5;
A21-B4-C6;
A21-B4-C7;
A21-B4-C8;
A21-B4-C9;
A21-B4-C10;
A21-B4-C11;
A21-B4-C12;
A21-B4-C13;
A21-B4-C14;
A21-B4-C15;
A21-B4-C16;
A21-B4-C17;

-continued

A21-B4-C18;
A21-B4-C19;
A21-B4-C20;
A21-B4-C21;
A21-B4-C22;
A21-B4-C23;
A21-B4-C24;
A21-B4-C25;
A21-B4-C26;
A21-B4-C27;
A21-B4-C28;
A21-B4-C29;
A21-B4-C30;
A21-B4-C31;
A21-B4-C32;
A21-B4-C33;
A21-B4-C34;
A21-B4-C35;
A21-B4-C36;
A21-B4-C37;
A21-B4-C38;
A21-B4-C39;
A21-B4-C40;
A21-B4-C41;
A21-B4-C42;
A21-B4-C43;
A21-B4-C44;
A21-B4-C45;
A21-B4-C46;
A21-B4-C47;
A21-B4-C48;
A21-B4-C49;
A21-B4-C50;
A21-B4-C51;
A21-B4-C52;
A21-B4-C53;
A21-B4-C54;
A21-B4-C55;
A21-B4-C56;
A21-B4-C57;
A21-B4-C58;
A21-B4-C59;
A22-B4-C1;
A22-B4-C2;
A22-B4-C3;
A22-B4-C4;
A22-B4-C5;
A22-B4-C6;
A22-B4-C7;
A22-B4-C8;
A22-B4-C9;
A22-B4-C10;
A22-B4-C11;
A22-B4-C12;
A22-B4-C13;
A22-B4-C14;
A22-B4-C15;
A22-B4-C16;
A22-B4-C17;
A22-B4-C18;
A22-B4-C19;
A22-B4-C20;
A22-B4-C21;
A22-B4-C22;
A22-B4-C23;
A22-B4-C24;
A22-B4-C25;
A22-B4-C26;
A22-B4-C27;
A22-B4-C28;
A22-B4-C29;
A22-B4-C30;
A22-B4-C31;
A22-B4-C32;
A22-B4-C33;
A22-B4-C34;
A22-B4-C35;
A22-B4-C36;
A22-B4-C37;

-continued

A22-B4-C38;
A22-B4-C39;
A22-B4-C40;
A22-B4-C41;
A22-B4-C42;
A22-B4-C43;
A22-B4-C44;
A22-B4-C45;
A22-B4-C46;
A22-B4-C47;
A22-B4-C48;
A22-B4-C49;
A22-B4-C50;
A22-B4-C51;
A22-B4-C52;
A22-B4-C53;
A22-B4-C54;
A22-B4-C55;
A22-B4-C56;
A22-B4-C57;
A22-B4-C58;
A22-B4-C59;
A23-B4-C1;
A23-B4-C2;
A23-B4-C3;
A23-B4-C4;
A23-B4-C5;
A23-B4-C6;
A23-B4-C7;
A23-B4-C8;
A23-B4-C9;
A23-B4-C10;
A23-B4-C11;
A23-B4-C12;
A23-B4-C13;
A23-B4-C14;
A23-B4-C15;
A23-B4-C16;
A23-B4-C17;
A23-B4-C18;
A23-B4-C19;
A23-B4-C20;
A23-B4-C21;
A23-B4-C22;
A23-B4-C23;
A23-B4-C24;
A23-B4-C25;
A23-B4-C26;
A23-B4-C27;
A23-B4-C28;
A23-B4-C29;
A23-B4-C30;
A23-B4-C31;
A23-B4-C32;
A23-B4-C33;
A23-B4-C34;
A23-B4-C35;
A23-B4-C36;
A23-B4-C37;
A23-B4-C38;
A23-B4-C39;
A23-B4-C40;
A23-B4-C41;
A23-B4-C42;
A23-B4-C43;
A23-B4-C44;
A23-B4-C45;
A23-B4-C46;
A23-B4-C47;
A23-B4-C48;
A23-B4-C49;
A23-B4-C50;
A23-B4-C51;
A23-B4-C52;
A23-B4-C53;
A23-B4-C54;
A23-B4-C55;
A23-B4-C56;
A23-B4-C57;
A23-B4-C58;
A23-B4-C59;
A24-B4-C1;
A24-B4-C2;
A24-B4-C3;
A24-B4-C4;
A24-B4-C5;
A24-B4-C6;
A24-B4-C7;
A24-B4-C8;
A24-B4-C9;
A24-B4-C10;
A24-B4-C11;
A24-B4-C12;
A24-B4-C13;
A24-B4-C14;
A24-B4-C15;
A24-B4-C16;
A24-B4-C17;
A24-B4-C18;
A24-B4-C19;
A24-B4-C20;
A24-B4-C21;
A24-B4-C22;
A24-B4-C23;
A24-B4-C24;
A24-B4-C25;
A24-B4-C26;
A24-B4-C27;
A24-B4-C28;
A24-B4-C29;
A24-B4-C30;
A24-B4-C31;
A24-B4-C32;
A24-B4-C33;
A24-B4-C34;
A24-B4-C35;
A24-B4-C36;
A24-B4-C37;
A24-B4-C38;
A24-B4-C39;
A24-B4-C40;
A24-B4-C41;
A24-B4-C42;
A24-B4-C43;
A24-B4-C44;
A24-B4-C45;
A24-B4-C46;
A24-B4-C47;
A24-B4-C48;
A24-B4-C49;
A24-B4-C50;
A24-B4-C51;
A24-B4-C52;
A24-B4-C53;
A24-B4-C54;
A24-B4-C55;
A24-B4-C56;
A24-B4-C57;
A24-B4-C58;
A24-B4-C59;
A25-B4-C1;
A25-B4-C2;
A25-B4-C3;
A25-B4-C4;
A25-B4-C5;
A25-B4-C6;
A25-B4-C7;
A25-B4-C8;
A25-B4-C9;
A25-B4-C10;
A25-B4-C11;
A25-B4-C12;
A25-B4-C13;
A25-B4-C14;
A25-B4-C15;
A25-B4-C16;
A25-B4-C17;
A25-B4-C18;

-continued

A25-B4-C19;
A25-B4-C20;
A25-B4-C21;
A25-B4-C22;
A25-B4-C23;
A25-B4-C24;
A25-B4-C25;
A25-B4-C26;
A25-B4-C27;
A25-B4-C28;
A25-B4-C29;
A25-B4-C30;
A25-B4-C31;
A25-B4-C32;
A25-B4-C33;
A25-B4-C34;
A25-B4-C35;
A25-B4-C36;
A25-B4-C37;
A25-B4-C38;
A25-B4-C39;
A25-B4-C40;
A25-B4-C41;
A25-B4-C42;
A25-B4-C43;
A25-B4-C44;
A25-B4-C45;
A25-B4-C46;
A25-B4-C47;
A25-B4-C48;
A25-B4-C49;
A25-B4-C50;
A25-B4-C51;
A25-B4-C52;
A25-B4-C53;
A25-B4-C54;
A25-B4-C55;
A25-B4-C56;
A25-B4-C57;
A25-B4-C58;
A25-B4-C59;
A26-B4-C1;
A26-B4-C2;
A26-B4-C3;
A26-B4-C4;
A26-B4-C5;
A26-B4-C6;
A26-B4-C7;
A26-B4-C8;
A26-B4-C9;
A26-B4-C10;
A26-B4-C11;
A26-B4-C12;
A26-B4-C13;
A26-B4-C14;
A26-B4-C15;
A26-B4-C16;
A26-B4-C17;
A26-B4-C18;
A26-B4-C19;
A26-B4-C20;
A26-B4-C21;
A26-B4-C22;
A26-B4-C23;
A26-B4-C24;
A26-B4-C25;
A26-B4-C26;
A26-B4-C27;
A26-B4-C28;
A26-B4-C29;
A26-B4-C30;
A26-B4-C31;
A26-B4-C32;
A26-B4-C33;
A26-B4-C34;
A26-B4-C35;
A26-B4-C36;
A26-B4-C37;
A26-B4-C38;

-continued

A26-B4-C39;
A26-B4-C40;
A26-B4-C41;
A26-B4-C42;
A26-B4-C43;
A26-B4-C44;
A26-B4-C45;
A26-B4-C46;
A26-B4-C47;
A26-B4-C48;
A26-B4-C49;
A26-B4-C50;
A26-B4-C51;
A26-B4-C52;
A26-B4-C53;
A26-B4-C54;
A26-B4-C55;
A26-B4-C56;
A26-B4-C57;
A26-B4-C58;
A26-B4-C59;
A27-B4-C1;
A27-B4-C2;
A27-B4-C3;
A27-B4-C4;
A27-B4-C5;
A27-B4-C6;
A27-B4-C7;
A27-B4-C8;
A27-B4-C9;
A27-B4-C10;
A27-B4-C11;
A27-B4-C12;
A27-B4-C13;
A27-B4-C14;
A27-B4-C15;
A27-B4-C16;
A27-B4-C17;
A27-B4-C18;
A27-B4-C19;
A27-B4-C20;
A27-B4-C21;
A27-B4-C22;
A27-B4-C23;
A27-B4-C24;
A27-B4-C25;
A27-B4-C26;
A27-B4-C27;
A27-B4-C28;
A27-B4-C29;
A27-B4-C30;
A27-B4-C31;
A27-B4-C32;
A27-B4-C33;
A27-B4-C34;
A27-B4-C35;
A27-B4-C36;
A27-B4-C37;
A27-B4-C38;
A27-B4-C39;
A27-B4-C40;
A27-B4-C41;
A27-B4-C42;
A27-B4-C43;
A27-B4-C44;
A27-B4-C45;
A27-B4-C46;
A27-B4-C47;
A27-B4-C48;
A27-B4-C49;
A27-B4-C50;
A27-B4-C51;
A27-B4-C52;
A27-B4-C53;
A27-B4-C54;
A27-B4-C55;
A27-B4-C56;
A27-B4-C57;
A27-B4-C58;

-continued

A27-B4-C59;
A28-B4-C1;
A28-B4-C2;
A28-B4-C3;
A28-B4-C4;
A28-B4-C5;
A28-B4-C6;
A28-B4-C7;
A28-B4-C8;
A28-B4-C9;
A28-B4-C10;
A28-B4-C11;
A28-B4-C12;
A28-B4-C13;
A28-B4-C14;
A28-B4-C15;
A28-B4-C16;
A28-B4-C17;
A28-B4-C18;
A28-B4-C19;
A28-B4-C20;
A28-B4-C21;
A28-B4-C22;
A28-B4-C23;
A28-B4-C24;
A28-B4-C25;
A28-B4-C26;
A28-B4-C27;
A28-B4-C28;
A28-B4-C29;
A28-B4-C30;
A28-B4-C31;
A28-B4-C32;
A28-B4-C33;
A28-B4-C34;
A28-B4-C35;
A28-B4-C36;
A28-B4-C37;
A28-B4-C38;
A28-B4-C39;
A28-B4-C40;
A28-B4-C41;
A28-B4-C42;
A28-B4-C43;
A28-B4-C44;
A28-B4-C45;
A28-B4-C46;
A28-B4-C47;
A28-B4-C48;
A28-B4-C49;
A28-B4-C50;
A28-B4-C51;
A28-B4-C52;
A28-B4-C53;
A28-B4-C54;
A28-B4-C55;
A28-B4-C56;
A28-B4-C57;
A28-B4-C58;
A28-B4-C59;
A29-B4-C1;
A29-B4-C2;
A29-B4-C3;
A29-B4-C4;
A29-B4-C5;
A29-B4-C6;
A29-B4-C7;
A29-B4-C8;
A29-B4-C9;
A29-B4-C10;
A29-B4-C11;
A29-B4-C12;
A29-B4-C13;
A29-B4-C14;
A29-B4-C15;
A29-B4-C16;
A29-B4-C17;
A29-B4-C18;
A29-B4-C19;
A29-B4-C20;
A29-B4-C21;
A29-B4-C22;
A29-B4-C23;
A29-B4-C24;
A29-B4-C25;
A29-B4-C26;
A29-B4-C27;
A29-B4-C28;
A29-B4-C29;
A29-B4-C30;
A29-B4-C31;
A29-B4-C32;
A29-B4-C33;
A29-B4-C34;
A29-B4-C35;
A29-B4-C36;
A29-B4-C37;
A29-B4-C38;
A29-B4-C39;
A29-B4-C40;
A29-B4-C41;
A29-B4-C42;
A29-B4-C43;
A29-B4-C44;
A29-B4-C45;
A29-B4-C46;
A29-B4-C47;
A29-B4-C48;
A29-B4-C49;
A29-B4-C50;
A29-B4-C51;
A29-B4-C52;
A29-B4-C53;
A29-B4-C54;
A29-B4-C55;
A29-B4-C56;
A29-B4-C57;
A29-B4-C58;
A29-B4-C59;
A30-B4-C1;
A30-B4-C2;
A30-B4-C3;
A30-B4-C4;
A30-B4-C5;
A30-B4-C6;
A30-B4-C7;
A30-B4-C8;
A30-B4-C9;
A30-B4-C10;
A30-B4-C11;
A30-B4-C12;
A30-B4-C13;
A30-B4-C14;
A30-B4-C15;
A30-B4-C16;
A30-B4-C17;
A30-B4-C18;
A30-B4-C19;
A30-B4-C20;
A30-B4-C21;
A30-B4-C22;
A30-B4-C23;
A30-B4-C24;
A30-B4-C25;
A30-B4-C26;
A30-B4-C27;
A30-B4-C28;
A30-B4-C29;
A30-B4-C30;
A30-B4-C31;
A30-B4-C32;
A30-B4-C33;
A30-B4-C34;
A30-B4-C35;
A30-B4-C36;
A30-B4-C37;
A30-B4-C38;
A30-B4-C39;

-continued

A30-B4-C40;
A30-B4-C41;
A30-B4-C42;
A30-B4-C43;
A30-B4-C44;
A30-B4-C45;
A30-B4-C46;
A30-B4-C47;
A30-B4-C48;
A30-B4-C49;
A30-B4-C50;
A30-B4-C51;
A30-B4-C52;
A30-B4-C53;
A30-B4-C54;
A30-B4-C55;
A30-B4-C56;
A30-B4-C57;
A30-B4-C58;
A30-B4-C59;
A31-B4-C1;
A31-B4-C2;
A31-B4-C3;
A31-B4-C4;
A31-B4-C5;
A31-B4-C6;
A31-B4-C7;
A31-B4-C8;
A31-B4-C9;
A31-B4-C10;
A31-B4-C11;
A31-B4-C12;
A31-B4-C13;
A31-B4-C14;
A31-B4-C15;
A31-B4-C16;
A31-B4-C17;
A31-B4-C18;
A31-B4-C19;
A31-B4-C20;
A31-B4-C21;
A31-B4-C22;
A31-B4-C23;
A31-B4-C24;
A31-B4-C25;
A31-B4-C26;
A31-B4-C27;
A31-B4-C28;
A31-B4-C29;
A31-B4-C30;
A31-B4-C31;
A31-B4-C32;
A31-B4-C33;
A31-B4-C34;
A31-B4-C35;
A31-B4-C36;
A31-B4-C37;
A31-B4-C38;
A31-B4-C39;
A31-B4-C40;
A31-B4-C41;
A31-B4-C42;
A31-B4-C43;
A31-B4-C44;
A31-B4-C45;
A31-B4-C46;
A31-B4-C47;
A31-B4-C48;
A31-B4-C49;
A31-B4-C50;
A31-B4-C51;
A31-B4-C52;
A31-B4-C53;
A31-B4-C54;
A31-B4-C55;
A31-B4-C56;
A31-B4-C57;
A31-B4-C58;
A31-B4-C59;

-continued

A32-B4-C1;
A32-B4-C2;
A32-B4-C3;
A32-B4-C4;
A32-B4-C5;
A32-B4-C6;
A32-B4-C7;
A32-B4-C8;
A32-B4-C9;
A32-B4-C10;
A32-B4-C11;
A32-B4-C12;
A32-B4-C13;
A32-B4-C14;
A32-B4-C15;
A32-B4-C16;
A32-B4-C17;
A32-B4-C18;
A32-B4-C19;
A32-B4-C20;
A32-B4-C21;
A32-B4-C22;
A32-B4-C23;
A32-B4-C24;
A32-B4-C25;
A32-B4-C26;
A32-B4-C27;
A32-B4-C28;
A32-B4-C29;
A32-B4-C30;
A32-B4-C31;
A32-B4-C32;
A32-B4-C33;
A32-B4-C34;
A32-B4-C35;
A32-B4-C36;
A32-B4-C37;
A32-B4-C38;
A32-B4-C39;
A32-B4-C40;
A32-B4-C41;
A32-B4-C42;
A32-B4-C43;
A32-B4-C44;
A32-B4-C45;
A32-B4-C46;
A32-B4-C47;
A32-B4-C48;
A32-B4-C49;
A32-B4-C50;
A32-B4-C51;
A32-B4-C52;
A32-B4-C53;
A32-B4-C54;
A32-B4-C55;
A32-B4-C56;
A32-B4-C57;
A32-B4-C58;
A32-B4-C59;
A33-B4-C1;
A33-B4-C2;
A33-B4-C3;
A33-B4-C4;
A33-B4-C5;
A33-B4-C6;
A33-B4-C7;
A33-B4-C8;
A33-B4-C9;
A33-B4-C10;
A33-B4-C11;
A33-B4-C12;
A33-B4-C13;
A33-B4-C14;
A33-B4-C15;
A33-B4-C16;
A33-B4-C17;
A33-B4-C18;
A33-B4-C19;
A33-B4-C20;

A33-B4-C21;
A33-B4-C22;
A33-B4-C23;
A33-B4-C24;
A33-B4-C25;
A33-B4-C26;
A33-B4-C27;
A33-B4-C28;
A33-B4-C29;
A33-B4-C30;
A33-B4-C31;
A33-B4-C32;
A33-B4-C33;
A33-B4-C34;
A33-B4-C35;
A33-B4-C36;
A33-B4-C37;
A33-B4-C38;
A33-B4-C39;
A33-B4-C40;
A33-B4-C41;
A33-B4-C42;
A33-B4-C43;
A33-B4-C44;
A33-B4-C45;
A33-B4-C46;
A33-B4-C47;
A33-B4-C48;
A33-B4-C49;
A33-B4-C50;
A33-B4-C51;
A33-B4-C52;
A33-B4-C53;
A33-B4-C54;
A33-B4-C55;
A33-B4-C56;
A33-B4-C57;
A33-B4-C58;
A33-B4-C59;
A34-B4-C1;
A34-B4-C2;
A34-B4-C3;
A34-B4-C4;
A34-B4-C5;
A34-B4-C6;
A34-B4-C7;
A34-B4-C8;
A34-B4-C9;
A34-B4-C10;
A34-B4-C11;
A34-B4-C12;
A34-B4-C13;
A34-B4-C14;
A34-B4-C15;
A34-B4-C16;
A34-B4-C17;
A34-B4-C18;
A34-B4-C19;
A34-B4-C20;
A34-B4-C21;
A34-B4-C22;
A34-B4-C23;
A34-B4-C24;
A34-B4-C25;
A34-B4-C26;
A34-B4-C27;
A34-B4-C28;
A34-B4-C29;
A34-B4-C30;
A34-B4-C31;
A34-B4-C32;
A34-B4-C33;
A34-B4-C34;
A34-B4-C35;
A34-B4-C36;
A34-B4-C37;
A34-B4-C38;
A34-B4-C39;
A34-B4-C40;
A34-B4-C41;
A34-B4-C42;
A34-B4-C43;
A34-B4-C44;
A34-B4-C45;
A34-B4-C46;
A34-B4-C47;
A34-B4-C48;
A34-B4-C49;
A34-B4-C50;
A34-B4-C51;
A34-B4-C52;
A34-B4-C53;
A34-B4-C54;
A34-B4-C55;
A34-B4-C56;
A34-B4-C57;
A34-B4-C58;
A34-B4-C59;
A35-B4-C1;
A35-B4-C2;
A35-B4-C3;
A35-B4-C4;
A35-B4-C5;
A35-B4-C6;
A35-B4-C7;
A35-B4-C8;
A35-B4-C9;
A35-B4-C10;
A35-B4-C11;
A35-B4-C12;
A35-B4-C13;
A35-B4-C14;
A35-B4-C15;
A35-B4-C16;
A35-B4-C17;
A35-B4-C18;
A35-B4-C19;
A35-B4-C20;
A35-B4-C21;
A35-B4-C22;
A35-B4-C23;
A35-B4-C24;
A35-B4-C25;
A35-B4-C26;
A35-B4-C27;
A35-B4-C28;
A35-B4-C29;
A35-B4-C30;
A35-B4-C31;
A35-B4-C32;
A35-B4-C33;
A35-B4-C34;
A35-B4-C35;
A35-B4-C36;
A35-B4-C37;
A35-B4-C38;
A35-B4-C39;
A35-B4-C40;
A35-B4-C41;
A35-B4-C42;
A35-B4-C43;
A35-B4-C44;
A35-B4-C45;
A35-B4-C46;
A35-B4-C47;
A35-B4-C48;
A35-B4-C49;
A35-B4-C50;
A35-B4-C51;
A35-B4-C52;
A35-B4-C53;
A35-B4-C54;
A35-B4-C55;
A35-B4-C56;
A35-B4-C57;
A35-B4-C58;
A35-B4-C59;
A1-B5-C36;

-continued

A1-B5-C37;
A1-B5-C38;
A1-B5-C39;
A1-B5-C40;
A1-B5-C41;
A1-B5-C42;
A1-B5-C43;
A1-B5-C44;
A1-B5-C45;
A1-B5-C46;
A1-B5-C47;
A1-B5-C48;
A1-B5-C49;
A1-B5-C50;
A1-B1-C51;
A1-B5-C52;
A1-B5-C53;
A1-B5-C54;
A1-B5-C55;
A1-B5-C56;
A1-B5-C57;
A1-B5-C58;
A1-B5-C59;
A2-B5-C1;
A2-B5-C2;
A2-B5-C3;
A2-B5-C4;
A2-B5-C5;
A2-B5-C6;
A2-B5-C7;
A2-B5-C8;
A2-B5-C9;
A2-B5-C10;
A2-B5-C11;
A2-B5-C12;
A2-B5-C13;
A2-B5-C14;
A2-B5-C15;
A2-B5-C16;
A2-B5-C17;
A2-B5-C18;
A2-B5-C19;
A2-B5-C20;
A2-B5-C21;
A2-B5-C22;
A2-B5-C23;
A2-B5-C24;
A2-B5-C25;
A2-B5-C26;
A2-B5-C27;
A2-B5-C28;
A2-B5-C29;
A2-B5-C30;
A2-B5-C31;
A2-B5-C32;
A2-B5-C33;
A2-B5-C34;
A2-B5-C35;
A2-B5-C36;
A2-B5-C37;
A2-B5-C38;
A2-B5-C39;
A2-B5-C40;
A2-B5-C41;
A2-B5-C42;
A2-B5-C43;
A2-B5-C44;
A2-B5-C45;
A2-B5-C46;
A2-B5-C47;
A2-B5-C48;
A2-B5-C49;
A2-B5-C50;
A2-B5-C51;
A2-B5-C52;
A2-B5-C53;
A2-B5-C54;
A2-B5-C55;
A2-B5-C56;

-continued

A2-B5-C57;
A2-B5-C58;
A2-B5-C59;
A3-B5-C1;
A3-B5-C2;
A3-B5-C3;
A3-B5-C4;
A3-B5-C5;
A3-B5-C6;
A3-B5-C7;
A3-B5-C8;
A3-B5-C9;
A3-B5-C10;
A3-B5-C11;
A3-B5-C12;
A3-B5-C13;
A3-B5-C14;
A3-B5-C15;
A3-B5-C16;
A3-B5-C17;
A3-B5-C18;
A3-B5-C19;
A3-B5-C20;
A3-B5-C21;
A3-B5-C22;
A3-B5-C23;
A3-B5-C24;
A3-B5-C25;
A3-B5-C26;
A3-B5-C27;
A3-B5-C28;
A3-B5-C29;
A3-B5-C30;
A3-B5-C31;
A3-B5-C32;
A3-B5-C33;
A3-B5-C34;
A3-B5-C35;
A3-B5-C36;
A3-B5-C37;
A3-B5-C38;
A3-B5-C39;
A3-B5-C40;
A3-B5-C41;
A3-B5-C42;
A3-B5-C43;
A3-B5-C44;
A3-B5-C45;
A3-B5-C46;
A3-B5-C47;
A3-B5-C48;
A3-B5-C49;
A3-B5-C50;
A3-B5-C51;
A3-B5-C52;
A3-B5-C53;
A3-B5-C54;
A3-B5-C55;
A3-B5-C56;
A3-B5-C57;
A3-B5-C58;
A3-B5-C59;
A4-B5-C1;
A4-B5-C2;
A4-B5-C3;
A4-B5-C4;
A4-B5-C5;
A4-B5-C6;
A4-B5-C7;
A4-B5-C5;
A4-B5-C9;
A4-B5-C10;
A4-B5-C11;
A4-B5-C12;
A4-B5-C13;
A4-B5-C14;
A4-B5-C15;
A4-B5-C16;
A4-B5-C17;

-continued

A4-B5-C18;
A4-B5-C19;
A4-B5-C20;
A4-B5-C21,
A4-B5-C22;
A4-B5-C23;
A4-B5-C24;
A4-B5-C25;
A4-B5-C26;
A4-B5-C27;
A4-B5-C28;
A4-B5-C29;
A4-B5-C30;
A4-B5-C31;
A4-B5-C32;
A4-B5-C33;
A4-B5-C34;
A4-B5-C35;
A4-B5-C36;
A4-B5-C37;
A4-B5-C38;
A4-B5-C39;
A4-B5-C40;
A4-B5-C41;
A4-B5-C42;
A4-B5-C43;
A4-B5-C44;
A4-B5-C45;
A4-B5-C46;
A4-B5-C47;
A4-B5-C48;
A4-B5-C49;
A4-B5-C50;
A4-B5-C51;
A4-B5-C52;
A4-B5-C53;
A4-B5-C54;
A4-B5-C55;
A4-B5-C56;
A4-B5-C57;
A4-B5-C58;
A4-B5-C59;
A5-B5-C1;
A5-B5-C2;
A5-B5-C3;
A5-B5-C4;
A5-B5-C5;
A5-B5-C6;
A5-B5-C7;
A5-B5-C8;
A5-B5-C9;
A5-B5-C10;
A5-B5-C11;
A5-B5-C12;
A5-B5-C13;
A5-B5-C14;
A5-B5-C15;
A5-B5-C16;
A5-B5-C17;
A5-B5-C18;
A5-B5-C19;
A5-B5-C20;
A5-B5-C21;
A5-B5-C22;
A5-B5-C23;
A5-B5-C24;
A5-B5-C25;
A5-B5-C26;
A5-B5-C27;
A5-B5-C28;
A5-B5-C29;
A5-B5-C30;
A5-B5-C31;
A5-B5-C32;
A5-B5-C33;
A5-B5-C34;
A5-B5-C35;
A5-B5-C36;
A5-B5-C37;

-continued

A5-B5-C38;
A5-B5-C39;
A5-B5-C40;
A5-B5-C41;
A5-B5-C42;
A5-B5-C43;
A5-B5-C44;
A5-B5-C45;
A5-B5-C46;
A5-B5-C47;
A5-B5-C48;
A5-B5-C49;
A5-B5-C50;
A5-B5-C51;
A5-B5-C52;
A5-B5-C53;
A5-B5-C54;
A5-B5-C55;
A5-B5-C56;
A5-B5-C57;
A5-B5-C58;
A5-B5-C59;
A6-B5-C1;
A6-B5-C2;
A6-B5-C3;
A6-B5-C4;
A6-B5-C5;
A6-B5-C6;
A6-B5-C7;
A6-B5-C8;
A6-B5-C9;
A6-B5-C10;
A6-B5-C11;
A6-B5-C12;
A6-B5-C13;
A6-B5-C14;
A6-B5-C15;
A6-B5-C16;
A6-B5-C17;
A6-B5-C18;
A6-B5-C19;
A6-B5-C20;
A6-B5-C21;
A6-B5-C22;
A6-B5-C23;
A6-B5-C24;
A6-B5-C25;
A6-B5-C26;
A6-B5-C27;
A6-B5-C28;
A6-B5-C29;
A6-B5-C30;
A6-B5-C31;
A6-B5-C32;
A6-B5-C33;
A6-B5-C34;
A6-B5-C35;
A6-B5-C36;
A6-B5-C37;
A6-B5-C38;
A6-B5-C39;
A6-B5-C40;
A6-B5-C41;
A6-B5-C42;
A6-B5-C43;
A6-B5-C44;
A6-B5-C45;
A6-B5-C46;
A6-B5-C47;
A6-B5-C48;
A6-B5-C49;
A6-B5-C50;
A6-B5-C5i;
A6-B5-C52;
A6-B5-C53;
A6-B5-C54;
A6-B5-C55;
A6-B5-C56;
A6-B5-C57;

-continued

A6-B5-C58;
A6-B5-C59;
A7-B5-C1;
A7-B5-C2;
A7-B5-C3;
A7-B5-C4;
A7-B5-C5;
A7-B5-C6;
A7-B5-C7;
A7-B5-C8;
A7-B5-C9;
A7-B5-C10;
A7-B5-C11;
A7-B5-C12;
A7-B5-C13;
A7-B5-C14;
A7-B5-C15;
A7-B5-C16;
A7-B5-C17;
A7-B5-C18;
A7-B5-C19;
A7-B5-C20;
A7-B5-C21;
A7-B5-C22;
A7-B5-C23;
A7-B5-C24;
A7-B5-C25;
A7-B5-C26;
A7-B5-C27;
A7-B5-C28;
A7-B5-C29;
A7-B5-C30;
A7-B5-C31;
A7-B5-C32;
A7-B5-C33;
A7-B5-C34;
A7-B5-C35;
A7-B5-C36;
A7-B5-C37;
A7-B5-C38;
A7-B5-C39;
A7-B5-C40;
A7-B5-C41;
A7-B5-C42;
A7-B5-C43;
A7-B5-C44;
A7-B5-C45;
A7-B5-C46;
A7-B5-C47;
A7-B5-C48;
A7-B5-C49;
A7-B5-C50;
A7-B5-C51;
A7-B5-C52;
A7-B5-C53;
A7-B5-C54;
A7-B5-C55;
A7-B5-C56;
A7-B5-C57;
A7-B5-C58;
A7-B5-C59;
A8-B5-C1;
A8-B5-C2;
A8-B5-C3;
A8-B5-C4;
A8-B5-C5;
A8-B5-C6;
A8-B5-C7;
A8-B5-C8;
A8-B5-C9;
A8-B5-C10;
A8-B5-C11;
A8-B5-C12;
A8-B5-C13;
A8-B5-C14;
A8-B5-C15;
A8-B5-C16;
A8-B5-C17;
A8-B5-C18;

-continued

A8-B5-C19;
A8-B5-C20;
A8-B5-C21;
A8-B5-C22;
A8-B5-C23;
A8-B5-C24;
A8-B5-C25;
A8-B5-C26;
A8-B5-C27;
A8-B5-C28;
A8-B5-C29;
A8-B5-C30;
A8-B5-C31;
A8-B5-C32;
A8-B5-C33;
A8-B5-C34;
A8-B5-C35;
A8-B5-C36;
A8-B5-C37;
A8-B5-C38;
A8-B5-C39;
A8-B5-C40;
A8-B5-C41;
A8-B5-C42;
A8-B5-C43;
A8-B5-C44;
A8-B5-C45;
A8-B5-C46;
A8-B5-C47;
A8-B5-C48;
A8-B5-C49;
A8-B5-C50;
A8-B5-C51;
A8-B5-C52;
A8-B5-C53;
A8-B5-C54;
A8-B5-C55;
A8-B5-C56;
A8-B5-C57;
A8-B5-C58;
A8-B5-C59;
A9-B5-C1;
A9-B5-C2;
A9-B5-C3;
A9-B5-C4;
A9-B5-C5;
A9-B5-C6;
A9-B5-C7;
A9-B5-C8;
A9-B5-C9;
A9-B5-C10;
A9-B5-C11;
A9-B5-C12;
A9-B5-C13;
A9-B5-C14;
A9-B5-C15;
A9-B5-C16;
A9-B5-C17;
A9-B5-C18;
A9-B5-C19;
A9-B5-C20;
A9-B5-C21;
A9-B5-C22;
A9-B5-C23;
A9-B5-C24;
A9-B5-C25;
A9-B5-C26;
A9-B5-C27;
A9-B5-C28;
A9-B5-C29;
A9-B5-C30;
A9-B5-C31;
A9-B5-C32;
A9-B5-C33;
A9-B5-C34;
A9-B5-C35;
A9-B5-C36;
A9-B5-C37;
A9-B5-C38;

A9-B5-C39;
A9-B5-C40;
A9-B5-C41;
A9-B5-C42;
A9-B5-C43;
A9-B5-C44;
A9-B5-C45;
A9-B5-C46;
A9-B5-C47;
A9-B5-C48;
A9-B5-C49;
A9-B5-C50;
A9-B5-C51;
A9-B5-C52;
A9-B5-C53;
A9-B5-C54;
A9-B5-C55;
A9-B5-C56;
A9-B5-C57;
A9-B5-C58;
A9-B5-C59;
A10-B5-C1;
A10-B5-C2;
A10-B5-C3;
A10-B5-C4;
A10-B5-C5;
A10-B5-C6;
A10-B5-C7;
A10-B5-C8;
A10-B5-C9;
A10-B5-C10;
A10-B5-C11;
A10-B5-C12;
A10-B5-C13;
A10-B5-C14;
A10-B5-C15;
A10-B5-C16;
A10-B5-C17;
A10-B5-C18;
A10-B5-C19;
A10-B5-C20;
A10-B5-C21;
A10-B5-C22;
A10-B5-C23;
A10-B5-C24;
A10-B5-C25;
A10-B5-C26;
A10-B5-C27;
A10-B5-C28;
A10-B5-C29;
A10-B5-C30;
A10-B5-C31;
A10-B5-C32;
A10-B5-C33;
A10-B5-C34;
A10-B5-C35;
A10-B5-C36;
A10-B5-C37;
A10-B5-C38;
A10-B5-C39;
A10-B5-C40;
A10-B5-C41;
A10-B5-C42;
A10-B5-C43;
A10-B5-C44;
A10-B5-C45;
A10-B5-C46;
A10-B5-C47;
A10-B5-C48;
A10-B5-C49;
A10-B5-C50;
A10-B5-C51;
A10-B5-C52;
A10-B5-C53;
A10-B5-C54;
A10-B5-C55;
A10-B5-C56;
A10-B5-C57;
A10-B5-C58;
A10-B5-C59;
A11-B5-C1;
A11-B5-C2;
A11-B5-C3;
A11-B5-C4;
A11-B5-C5;
A11-B5-C6;
A11-B5-C7;
A11-B5-C8;
A11-B5-C9;
A11-B5-C10;
A11-B5-C11;
A11-B5-C12;
A11-B5-C13;
A11-B5-C14;
A11-B5-C15;
A11-B5-C16;
A11-B5-C17;
A11-B5-C18;
A11-B5-C19;
A11-B5-C20;
A11-B5-C21;
A11-B5-C22;
A11-B5-C23;
A11-B5-C24;
A11-B5-C25;
A11-B5-C26;
A11-B5-C27;
A11-B5-C28;
A11-B5-C29;
A11-B5-C30;
A11-B5-C31;
A11-B5-C32;
A11-B5-C33;
A11-B5-C34;
A11-B5-C35;
A11-B5-C36;
A11-B5-C37;
A11-B5-C38;
A11-B5-C39;
A11-B5-C40;
A11-B5-C41;
A11-B5-C42;
A11-B5-C43;
A11-B5-C44;
A11-B5-C45;
A11-B5-C46;
A11-B5-C47;
A11-B5-C48;
A11-B5-C49;
A11-B5-C50;
A11-B5-C51;
A11-B5-C52;
A11-B5-C53;
A11-B5-C54;
A11-B5-C55;
A11-B5-C56;
A11-B5-C57;
A11-B5-C58;
A11-B5-C59;
A12-B5-C1;
A12-B5-C2;
A12-B5-C3;
A12-B5-C4;
A12-B5-C5;
A12-B5-C6;
A12-B5-C7;
A12-B5-C8;
A12-B5-C9;
A12-B5-C10;
A12-B5-C11;
A12-B5-C12;
A12-B5-C13;
A12-B5-C14;
A12-B5-C15;
A12-B5-C16;
A12-B5-C17;
A12-B5-C18;
A12-B5-C19;

-continued

A12-B5-C20;
A12-B5-C21;
A12-B5-C22;
A12-B5-C23;
A12-B5-C24;
A12-B5-C25;
A12-B5-C26;
A12-B5-C27;
A12-B5-C28;
A12-B5-C29;
A12-B5-C30;
A12-B5-C31;
A12-B5-C32;
A12-B5-C33;
A12-B5-C34;
A12-B5-C35;
A12-B5-C36;
A12-B5-C37;
A12-B5-C38;
A12-B5-C39;
A12-B5-C40;
A12-B5-C41;
A12-B5-C42;
A12-B5-C43;
A12-B5-C44;
A12-B5-C45;
A12-B5-C46;
A12-B5-C47;
A12-B5-C48;
A12-B5-C49;
A12-B5-C50;
A12-B5-C51;
A12-B5-C52;
A12-B5-C53;
A12-B5-C54;
A12-B5-C55;
A12-B5-C56;
A12-B5-C57;
A12-B5-C58;
A12-B5-C59;
A13-B5-C1;
A13-B5-C2;
A13-B5-C3;
A13-B5-C4;
A13-B5-C5;
A13-B5-C6;
A13-B5-C7;
A13-B5-C8;
A13-B5-C9;
A13-B5-C10;
A13-B5-C11;
A13-B5-C12;
A13-B5-C13;
A13-B5-C14;
A13-B5-C15;
A13-B5-C16;
A13-B5-C17;
A13-B5-C18;
A13-B5-C19;
A13-B5-C20;
A13-B5-C21;
A13-B5-C22;
A13-B5-C23;
A13-B5-C24;
A13-B5-C25;
A13-B5-C26;
A13-B5-C27;
A13-B5-C28;
A13-B5-C29;
A13-B5-C30;
A13-B5-C31;
A13-B5-C32;
A13-B5-C33;
A13-B5-C34;
A13-B5-C35;
A13-B5-C36;
A13-B5-C37;
A13-B5-C38;
A13-B5-C39;

-continued

A13-B5-C40;
A13-B5-C41;
A13-B5-C42;
A13-B5-C43;
A13-B5-C44;
A13-B5-C45;
A13-B5-C46;
A13-B5-C47;
A13-B5-C48;
A13-B5-C49;
A13-B5-C50;
A13-B5-C51;
A13-B5-C52;
A13-B5-C53;
A13-B5-C54;
A13-B5-C55;
A13-B5-C56;
A13-B5-C57;
A13-B5-C58;
A13-B5-C59;
A14-B5-C1;
A14-B5-C2;
A14-B5-C3;
A14-B5-C4;
A14-B5-C5;
A14-B5-C6;
A14-B5-C7;
A14-B5-C8;
A14-B5-C9;
A14-B5-C10;
A14-B5-C11;
A14-B5-C12;
A14-B5-C13;
A14-B5-C14;
A14-B5-C15;
A14-B5-C16;
A14-B5-C17;
A14-B5-C18;
A14-B5-C19;
A14-B5-C20;
A14-B5-C21;
A14-B5-C22;
A14-B5-C23;
A14-B5-C24;
A14-B5-C25;
A14-B5-C26;
A14-B5-C27;
A14-B5-C28;
A14-B5-C29;
A14-B5-C30;
A14-B5-C31;
A14-B5-C32;
A14-B5-C33;
A14-B5-C34;
A14-B5-C35;
A14-B5-C36;
A14-B5-C37;
A14-B5-C38;
A14-B5-C39;
A14-B5-C40;
A14-B5-C41;
A14-B5-C42;
A14-B5-C43;
A14-B5-C44;
A14-B5-C45;
A14-B5-C46;
A14-B5-C47;
A14-B5-C48;
A14-B5-C49;
A14-B5-C50;
A14-B5-C51;
A14-B5-C52;
A14-B5-C53;
A14-B5-C54;
A14-B5-C55;
A14-B5-C56;
A14-B5-C57;
A14-B5-C58;
A14-B5-C59;

-continued

A15-B5-C1;
A15-B5-C2;
A15-B5-C3;
A15-B5-C4;
A15-B5-C5;
A15-B5-C6;
A15-B5-C7;
A15-B5-C8;
A15-B5-C9;
A15-B5-C10;
A15-B5-C11;
A15-B5-C12;
A15-B5-C13;
A15-B5-C14;
A15-B5-C15;
A15-B5-C16;
A15-B5-C17;
A15-B5-C18;
A15-B5-C19;
A15-B5-C20;
A15-B5-C21;
A15-B5-C22;
A15-B5-C23;
A15-B5-C24;
A15-B5-C25;
A15-B5-C26;
A15-B5-C27;
A15-B5-C28;
A15-B5-C29;
A15-B5-C30;
A15-B5-C31;
A15-B5-C32;
A15-B5-C33;
A15-B5-C34;
A15-B5-C35;
A15-B5-C36;
A15-B5-C37;
A15-B5-C38;
A15-B5-C39;
A15-B5-C40;
A15-B5-C41;
A15-B5-C42;
A15-B5-C43;
A15-B5-C44;
A15-B5-C45;
A15-B5-C46;
A15-B5-C47;
A15-B5-C48;
A15-B5-C49;
A15-B5-C50;
A15-B5-C51;
A15-B5-C52;
A15-B5-C53;
A15-B5-C54;
A15-B5-C55;
A15-B5-C56;
A15-B5-C57;
A15-B5-C58;
A15-B5-C59;
A16-B5-C1;
A16-B5-C2;
A16-B5-C3;
A16-B5-C4;
A16-B5-C5;
A16-B5-C6;
A16-B5-C7;
A16-B5-C8;
A16-B5-C9;
A16-B5-C10;
A16-B5-C11;
A16-B5-C12;
A16-B5-C13;
A16-B5-C14;
A16-B5-C15;
A16-B5-C16;
A16-B5-C17;
A16-B5-C18;
A16-B5-C19;
A16-B5-C20;

-continued

A16-B5-C21;
A16-B5-C22;
A16-B5-C23;
A16-B5-C24;
A16-B5-C25;
A16-B5-C26;
A16-B5-C27;
A16-B5-C28;
A16-B5-C29;
A16-B5-C30;
A16-B5-C31;
A16-B5-C32;
A16-B5-C33;
A16-B5-C34;
A16-B5-C35;
A16-B5-C36;
A16-B5-C37;
A16-B5-C38;
A16-B5-C39;
A16-B5-C40;
A16-B5-C41;
A16-B5-C42;
A16-B5-C43;
A16-B5-C44;
A16-B5-C45;
A16-B5-C46;
A16-B5-C47;
A16-B5-C48;
A16-B5-C49;
A16-B5-C50;
A16-B5-C51;
A16-B5-C52;
A16-B5-C53;
A16-B5-C54;
A16-B5-C55;
A16-B5-C56;
A16-B5-C57;
A16-B5-C58;
A16-B5-C59;
A17-B5-C1;
A17-B5-C2;
A17-B5-C3;
A17-B5-C4;
A17-B5-C5;
A17-B5-C6;
A17-B5-C7;
A17-B5-C8;
A17-B5-C9;
A17-B5-C10;
A17-B5-C11;
A17-B5-C12;
A17-B5-C13;
A17-B5-C14;
A17-B5-C15;
A17-B5-C16;
A17-B5-C17;
A17-B5-C18;
A17-B5-C19;
A17-B5-C20;
A17-B5-C21;
A17-B5-C22;
A17-B5-C23;
A17-B5-C24;
A17-B5-C25;
A17-B5-C26;
A17-B5-C27;
A17-B5-C28;
A17-B5-C29;
A17-B5-C30;
A17-B5-C31;
A17-B5-C32;
A17-B5-C33;
A17-B5-C34;
A17-B5-C35;
A17-B5-C36;
A17-B5-C37;
A17-B5-C38;
A17-B5-C39;
A17-B5-C40;

A17-B5-C41;
A17-B5-C42;
A17-B5-C43;
A17-B5-C44;
A17-B5-C45;
A17-B5-C46;
A17-B5-C47;
A17-B5-C48;
A17-B5-C49;
A17-B5-C50;
A17-B5-C51;
A17-B5-C52;
A17-B5-C53;
A17-B5-C54;
A17-B5-C55;
A17-B5-C56;
A17-B5-C57;
A17-B5-C58;
A17-B5-C59;
A18-B5-C1;
A18-B5-C2;
A18-B5-C3;
A18-B5-C4;
A18-B5-C5;
A18-B5-C6;
A18-B5-C7;
A18-B5-C8;
A18-B5-C9;
A18-B5-C10;
A18-B5-C11;
A18-B5-C12;
A18-B5-C13;
A18-B5-C14;
A18-B5-C15;
A18-B5-C16;
A18-B5-C17;
A18-B5-C18;
A18-B5-C19;
A18-B5-C20;
A18-B5-C21;
A18-B5-C22;
A18-B5-C23;
A18-B5-C24;
A18-B5-C25;
A18-B5-C26;
A18-B5-C27;
A18-B5-C28;
A18-B5-C29;
A18-B5-C30;
A18-B5-C31;
A18-B5-C32;
A18-B5-C33;
A18-B5-C34;
A18-B5-C35;
A18-B5-C36;
A18-B5-C37;
A18-B5-C38;
A18-B5-C39;
A18-B5-C40;
A18-B5-C41;
A18-B5-C42;
A18-B5-C43;
A18-B5-C44;
A18-B5-C45;
A18-B5-C46;
A18-B5-C47;
A18-B5-C48;
A18-B5-C49;
A18-B5-C50;
A18-B5-C51;
A18-B5-C52;
A18-B5-C53;
A18-B5-C54;
A18-B5-C55;
A18-B5-C56;
A18-B5-C57;
A18-B5-C58;
A18-B5-C59;
A19-B5-C1;
A19-B5-C2;
A19-B5-C3;
A19-B5-C4;
A19-B5-C5;
A19-B5-C6;
A19-B5-C7;
A19-B5-C8;
A19-B5-C9;
A19-B5-C10;
A19-B5-C11;
A19-B5-C12;
A19-B5-C13;
A19-B5-C14;
A19-B5-C15;
A19-B5-C16;
A19-B5-C17;
A19-B5-C18;
A19-B5-C19;
A19-B5-C20;
A19-B5-C21;
A19-B5-C22;
A19-B5-C23;
A19-B5-C24;
A19-B5-C25;
A19-B5-C26;
A19-B5-C27;
A19-B5-C28;
A19-B5-C29;
A19-B5-C30;
A19-B5-C31;
A19-B5-C32;
A19-B5-C33;
A19-B5-C34;
A19-B5-C35;
A19-B5-C36;
A19-B5-C37;
A19-B5-C38;
A19-B5-C39;
A19-B5-C40;
A19-B5-C41;
A19-B5-C42;
A19-B5-C43;
A19-B5-C44;
A19-B5-C45;
A19-B5-C46;
A19-B5-C47;
A19-B5-C48;
A19-B5-C49;
A19-B5-C50;
A19-B5-C51;
A19-B5-C52;
A19-B5-C53;
A19-B5-C54;
A19-B5-C55;
A19-B5-C56;
A19-B5-C57;
A19-B5-C58;
A19-B5-C59;
A20-B5-C1;
A20-B5-C2;
A20-B5-C3;
A20-B5-C4;
A20-B5-C5;
A20-B5-C6;
A20-B5-C7;
A20-B5-C8;
A20-B5-C9;
A20-B5-C10;
A20-B5-C11;
A20-B5-C12;
A20-B5-C13;
A20-B5-C14;
A20-B5-C15;
A20-B5-C16;
A20-B5-C17;
A20-B5-C18;
A20-B5-C19;
A20-B5-C20;
A20-B5-C21;

-continued

A20-B5-C22;
A20-B5-C23;
A20-B5-C24;
A20-B5-C25;
A20-B5-C26;
A20-B5-C27;
A20-B5-C28;
A20-B5-C29;
A20-B5-C30;
A20-B5-C31;
A20-B5-C32;
A20-B5-C33;
A20-B5-C34;
A20-B5-C35;
A20-B5-C36;
A20-B5-C37;
A20-B5-C38;
A20-B5-C39;
A20-B5-C40;
A20-B5-C41;
A20-B5-C42;
A20-B5-C43;
A20-B5-C44;
A20-B5-C45;
A20-B5-C46;
A20-B5-C47;
A20-B5-C48;
A20-B5-C49;
A20-B5-C50;
A20-B5-C51;
A20-B5-C52;
A20-B5-C53;
A20-B5-C54;
A20-B5-C55;
A20-B5-C56;
A20-B5-C57;
A20-B5-C58;
A20-B5-C59;
A21-B5-C1;
A21-B5-C2;
A21-B5-C3;
A21-B5-C4;
A21-B5-C5;
A21-B5-C6;
A21-B5-C7;
A21-B5-C8;
A21-B5-C9;
A21-B5-C10;
A21-B5-C11;
A21-B5-C12;
A21-B5-C13;
A21-B5-C14;
A21-B5-C15;
A21-B5-C16;
A21-B5-C17;
A21-B5-C18;
A21-B5-C19;
A21-B5-C20;
A21-B5-C21;
A21-B5-C22;
A21-B5-C23;
A21-B5-C24;
A21-B5-C25;
A21-B5-C26;
A21-B5-C27;
A21-B5-C28;
A21-B5-C29;
A21-B5-C30;
A21-B5-C31;
A21-B5-C32;
A21-B5-C33;
A21-B5-C34;
A21-B5-C35;
A21-B5-C36;
A21-B5-C37;
A21-B5-C38;
A21-B5-C39;
A21-B5-C40;
A21-B5-C41;

-continued

A21-B5-C42;
A21-B5-C43;
A21-B5-C44;
A21-B5-C45;
A21-B5-C46;
A21-B5-C47;
A21-B5-C48;
A21-B5-C49;
A21-B5-C50;
A21-B5-C51;
A21-B5-C52;
A21-B5-C53;
A21-B5-C54;
A21-B5-C55;
A21-B5-C56;
A21-B5-C57;
A21-B5-C58;
A21-B5-C59;
A22-B5-C1;
A22-B5-C2;
A22-B5-C3;
A22-B5-C4;
A22-B5-C5;
A22-B5-C6;
A22-B5-C7;
A22-B5-C8;
A22-B5-C9;
A22-B5-C10;
A22-B5-C11;
A22-B5-C12;
A22-B5-C13;
A22-B5-C14;
A22-B5-C15;
A22-B5-C16;
A22-B5-C17;
A22-B5-C18;
A22-B5-C19;
A22-B5-C20;
A22-B5-C21;
A22-B5-C22;
A22-B5-C23;
A22-B5-C24;
A22-B5-C25;
A22-B5-C26;
A22-B5-C27;
A22-B5-C28;
A22-B5-C29;
A22-B5-C30;
A22-B5-C31;
A22-B5-C32;
A22-B5-C33;
A22-B5-C34;
A22-B5-C35;
A22-B5-C36;
A22-B5-C37;
A22-B5-C38;
A22-B5-C39;
A22-B5-C40;
A22-B5-C41;
A22-B5-C42;
A22-B5-C43;
A22-B5-C44;
A22-B5-C45;
A22-B5-C46;
A22-B5-C47;
A22-B5-C48;
A22-B5-C49;
A22-B5-C50;
A22-B5-C51;
A22-B5-C52;
A22-B5-C53;
A22-B5-C54;
A22-B5-C55;
A22-B5-C56;
A22-B5-C57;
A22-B5-C58;
A22-B5-C59;
A23-B5-C1;
A23-B5-C2;

-continued

A23-B5-C3;
A23-B5-C4;
A23-B5-C5;
A23-B5-C6;
A23-B5-C7;
A23-B5-C8;
A23-B5-C9;
A23-B5-C10;
A23-B5-C11;
A23-B5-C12;
A23-B5-C13;
A23-B5-C14;
A23-B5-C15;
A23-B5-C16;
A23-B5-C17;
A23-B5-C18;
A23-B5-C19;
A23-B5-C20;
A23-B5-C21;
A23-B5-C22;
A23-B5-C23;
A23-B5-C24;
A23-B5-C25;
A23-B5-C26;
A23-B5-C27;
A23-B5-C28;
A23-B5-C29;
A23-B5-C30;
A23-B5-C31;
A23-B5-C32;
A23-B5-C33;
A23-B5-C34;
A23-B5-C35;
A23-B5-C36;
A23-B5-C37;
A23-B5-C38;
A23-B5-C39;
A23-B5-C40;
A23-B5-C41;
A23-B5-C42;
A23-B5-C43;
A23-B5-C44;
A23-B5-C45;
A23-B5-C46;
A23-B5-C47;
A23-B5-C48;
A23-B5-C49;
A23-B5-C50;
A23-B5-C51;
A23-B5-C52;
A23-B5-C53;
A23-B5-C54;
A23-B5-C55;
A23-B5-C56;
A23-B5-C57;
A23-B5-C58;
A23-B5-C59;
A24-B5-C1;
A24-B5-C2;
A24-B5-C3;
A24-B5-C4;
A24-B5-C5;
A24-B5-C6;
A24-B5-C7;
A24-B5-C8;
A24-B5-C9;
A24-B5-C10;
A24-B5-C11;
A24-B5-C12;
A24-B5-C13;
A24-B5-C14;
A24-B5-C15;
A24-B5-C16;
A24-B5-C17;
A24-B5-C18;
A24-B5-C19;
A24-B5-C20;
A24-B5-C21;
A24-B5-C22;

-continued

A24-B5-C23;
A24-B5-C24;
A24-B5-C25;
A24-B5-C26;
A24-B5-C27;
A24-B5-C28;
A24-B5-C29;
A24-B5-C30;
A24-B5-C31;
A24-B5-C32;
A24-B5-C33;
A24-B5-C34;
A24-B5-C35;
A24-B5-C36;
A24-B5-C37;
A24-B5-C38;
A24-B5-C39;
A24-B5-C40;
A24-B5-C41;
A24-B5-C42;
A24-B5-C43;
A24-B5-C44;
A24-B5-C45;
A24-B5-C46;
A24-B5-C47;
A24-B5-C48;
A24-B5-C49;
A24-B5-C50;
A24-B5-C51;
A24-B5-C52;
A24-B5-C53;
A24-B5-C54;
A24-B5-C55;
A24-B5-C56;
A24-B5-C57;
A24-B5-C58;
A24-B5-C59;
A25-B5-C1;
A25-B5-C2;
A25-B5-C3;
A25-B5-C4;
A25-B5-C5;
A25-B5-C6;
A25-B5-C7;
A25-B5-C8;
A25-B5-C9;
A25-B5-C10;
A25-B5-C11;
A25-B5-C12;
A25-B5-C13;
A25-B5-C14;
A25-B5-C15;
A25-B5-C16;
A25-B5-C17;
A25-B5-C18;
A25-B5-C19;
A25-B5-C20;
A25-B5-C21;
A25-B5-C22;
A25-B5-C23;
A25-B5-C24;
A25-B5-C25;
A25-B5-C26;
A25-B5-C27;
A25-B5-C28;
A25-B5-C29;
A25-B5-C30;
A25-B5-C31;
A25-B5-C32;
A25-B5-C33;
A25-B5-C34;
A25-B5-C35;
A25-B5-C36;
A25-B5-C37;
A25-B5-C38;
A25-B5-C39;
A25-B5-C40;
A25-B5-C41;
A25-B5-C42;

-continued

A25-B5-C43;
A25-B5-C44;
A25-B5-C45;
A25-B5-C46;
A25-B5-C47;
A25-B5-C48;
A25-B5-C49;
A25-B5-C50;
A25-B5-C51;
A25-B5-C52;
A25-B5-C53;
A25-B5-C54;
A25-B5-C55;
A25-B5-C56;
A25-B5-C57;
A25-B5-C58;
A25-B5-C59;
A26-B5-C1;
A26-B5-C2;
A26-B5-C3;
A26-B5-C4;
A26-B5-C5;
A26-B5-C6;
A26-B5-C7;
A26-B5-C8;
A26-B5-C9;
A26-B5-C10;
A26-B5-C11;
A26-B5-C12;
A26-B5-C13;
A26-B5-C14;
A26-B5-C15;
A26-B5-C16;
A26-B5-C17;
A26-B5-C18;
A26-B5-C19;
A26-B5-C20;
A26-B5-C21;
A26-B5-C22;
A26-B5-C23;
A26-B5-C24;
A26-B5-C25;
A26-B5-C26;
A26-B5-C27;
A26-B5-C28;
A26-B5-C29;
A26-B5-C30;
A26-B5-C31;
A26-B5-C32;
A26-B5-C33;
A26-B5-C34;
A26-B5-C35;
A26-B5-C36;
A26-B5-C37;
A26-B5-C38;
A26-B5-C39;
A26-B5-C40;
A26-B5-C41;
A26-B5-C42;
A26-B5-C43;
A26-B5-C44;
A26-B5-C45;
A26-B5-C46;
A26-B5-C47;
A26-B5-C48;
A26-B5-C49;
A26-B5-C50;
A26-B5-C51;
A26-B5-C52;
A26-B5-C53;
A26-B5-C54;
A26-B5-C55;
A26-B5-C56;
A26-B5-C57;
A26-B5-C58;
A26-B5-C59;
A27-B5-C1;
A27-B5-C2;
A27-B5-C3;

-continued

A27-B5-C4;
A27-B5-C5;
A27-B5-C6;
A27-B5-C7;
A27-B5-C8;
A27-B5-C9;
A27-B5-C10;
A27-B5-C11;
A27-B5-C12;
A27-B5-C13;
A27-B5-C14;
A27-B5-C15;
A27-B5-C16;
A27-B5-C17;
A27-B5-C18;
A27-B5-C19;
A27-B5-C20;
A27-B5-C21;
A27-B5-C22;
A27-B5-C23;
A27-B5-C24;
A27-B5-C25;
A27-B5-C26;
A27-B5-C27;
A27-B5-C28;
A27-B5-C29;
A27-B5-C30;
A27-B5-C31;
A27-B5-C32;
A27-B5-C33;
A27-B5-C34;
A27-B5-C35;
A27-B5-C36;
A27-B5-C37;
A27-B5-C38;
A27-B5-C39;
A27-B5-C40;
A27-B5-C41;
A27-B5-C42;
A27-B5-C43;
A27-B5-C44;
A27-B5-C45;
A27-B5-C46;
A27-B5-C47;
A27-B5-C48;
A27-B5-C49;
A27-B5-C50;
A27-B5-C51;
A27-B5-C52;
A27-B5-C53;
A27-B5-C54;
A27-B5-C55;
A27-B5-C56;
A27-B5-C57;
A27-B5-C58;
A27-B5-C59;
A28-B5-C1;
A28-B5-C2;
A28-B5-C3;
A28-B5-C4;
A28-B5-C5;
A28-B5-C6;
A28-B5-C7;
A28-B5-C8;
A28-B5-C9;
A28-B5-C10;
A28-B5-C11;
A28-B5-C12;
A28-B5-C13;
A28-B5-C14;
A28-B5-C15;
A28-B5-C16;
A28-B5-C17;
A28-B5-C18;
A28-B5-C19;
A28-B5-C20;
A28-B5-C21;
A28-B5-C22;
A28-B5-C23;

-continued

A28-B5-C24;
A28-B5-C25;
A28-B5-C26;
A28-B5-C27;
A28-B5-C28;
A28-B5-C29;
A28-B5-C30;
A28-B5-C31;
A28-B5-C32;
A28-B5-C33;
A28-B5-C34;
A28-B5-C35;
A28-B5-C36;
A28-B5-C37;
A28-B5-C38;
A28-B5-C39;
A28-B5-C40;
A28-B5-C41;
A28-B5-C42;
A28-B5-C43;
A28-B5-C44;
A28-B5-C45;
A28-B5-C46;
A28-B5-C47;
A28-B5-C48;
A28-B5-C49;
A28-B5-C50;
A28-B5-C51;
A28-B5-C52;
A28-B5-C53;
A28-B5-C54;
A28-B5-C55;
A28-B5-C56;
A28-B5-C57;
A28-B5-C58;
A28-B5-C59;
A29-B5-C1;
A29-B5-C2;
A29-B5-C3;
A29-B5-C4;
A29-B5-C5;
A29-B5-C6;
A29-B5-C7;
A29-B5-C8;
A29-B5-C9;
A29-B5-C10;
A29-B5-C11;
A29-B5-C12;
A29-B5-C13;
A29-B5-C14;
A29-B5-C15;
A29-B5-C16;
A29-B5-C17;
A29-B5-C18;
A29-B5-C19;
A29-B5-C20;
A29-B5-C21;
A29-B5-C22;
A29-B5-C23;
A29-B5-C24;
A29-B5-C25;
A29-B5-C26;
A29-B5-C27;
A29-B5-C28;
A29-B5-C29;
A29-B5-C30;
A29-B5-C31;
A29-B5-C32;
A29-B5-C33;
A29-B5-C34;
A29-B5-C35;
A29-B5-C36;
A29-B5-C37;
A29-B5-C38;
A29-B5-C39;
A29-B5-C40;
A29-B5-C41;
A29-B5-C42;
A29-B5-C43;

-continued

A29-B5-C44;
A29-B5-C45;
A29-B5-C46;
A29-B5-C47;
A29-B5-C48;
A29-B5-C49;
A29-B5-C50;
A29-B5-C51;
A29-B5-C52;
A29-B5-C53;
A29-B5-C54;
A29-B5-C55;
A29-B5-C56;
A29-B5-C57;
A29-B5-C58;
A29-B5-C59;
A30-B5-C1;
A30-B5-C2;
A30-B5-C3;
A30-B5-C4;
A30-B5-C5;
A30-B5-C6;
A30-B5-C7;
A30-B5-C8;
A30-B5-C9;
A30-B5-C10;
A30-B5-C11;
A30-B5-C12;
A30-B5-C13;
A30-B5-C14;
A30-B5-C15;
A30-B5-C16;
A30-B5-C17;
A30-B5-C18;
A30-B5-C19;
A30-B5-C20;
A30-B5-C21;
A30-B5-C22;
A30-B5-C23;
A30-B5-C24;
A30-B5-C25;
A30-B5-C26;
A30-B5-C27;
A30-B5-C28;
A30-B5-C29;
A30-B5-C30;
A30-B5-C31;
A30-B5-C32;
A30-B5-C33;
A30-B5-C34;
A30-B5-C35;
A30-B5-C36;
A30-B5-C37;
A30-B5-C38;
A30-B5-C39;
A30-B5-C40;
A30-B5-C41;
A30-B5-C42;
A30-B5-C43;
A30-B5-C44;
A30-B5-C45;
A30-B5-C46;
A30-B5-C47;
A30-B5-C48;
A30-B5-C49;
A30-B5-C50;
A30-B5-C51;
A30-B5-C52;
A30-B5-C53;
A30-B5-C54;
A30-B5-C55;
A30-B5-C56;
A30-B5-C57;
A30-B5-C58;
A30-B5-C59;
A31-B5-C1;
A31-B5-C2;
A31-B5-C3;
A31-B5-C4;

-continued

A31-B5-C5;
A31-B5-C6;
A31-B5-C7;
A31-B5-C8;
A31-B5-C9;
A31-B5-C10;
A31-B5-C11;
A31-B5-C12;
A31-B5-C13;
A31-B5-C14;
A31-B5-C15;
A31-B5-C16;
A31-B5-C17;
A31-B5-C18;
A31-B5-C19;
A31-B5-C20;
A31-B5-C21;
A31-B5-C22;
A31-B5-C23;
A31-B5-C24;
A31-B5-C25;
A31-B5-C26;
A31-B5-C27;
A31-B5-C28;
A31-B5-C29;
A31-B5-C30;
A31-B5-C31;
A31-B5-C32;
A31-B5-C33;
A31-B5-C34;
A31-B5-C35;
A31-B5-C36;
A31-B5-C37;
A31-B5-C38;
A31-B5-C39;
A31-B5-C40;
A31-B5-C41;
A31-B5-C42;
A31-B5-C43;
A31-B5-C44;
A31-B5-C45;
A31-B5-C46;
A31-B5-C47;
A31-B5-C48;
A31-B5-C49;
A31-B5-C50;
A31-B5-C51;
A31-B5-C52;
A31-B5-C53;
A31-B5-C54;
A31-B5-C55;
A31-B5-C56;
A31-B5-C57;
A31-B5-C58;
A31-B5-C59;
A32-B5-C1;
A32-B5-C2;
A32-B5-C3;
A32-B5-C4;
A32-B5-C5;
A32-B5-C6;
A32-B5-C7;
A32-B5-C8;
A32-B5-C9;
A32-B5-C10;
A32-B5-C11;
A32-B5-C12;
A32-B5-C13;
A32-B5-C14;
A32-B5-C15;
A32-B5-C16;
A32-B5-C17;
A32-B5-C18;
A32-B5-C19;
A32-B5-C20;
A32-B5-C21;
A32-B5-C22;
A32-B5-C23;
A32-B5-C24;

-continued

A32-B5-C25;
A32-B5-C26;
A32-B5-C27;
A32-B5-C28;
A32-B5-C29;
A32-B5-C30;
A32-B5-C31;
A32-B5-C32;
A32-B5-C33;
A32-B5-C34;
A32-B5-C35;
A32-B5-C36;
A32-B5-C37;
A32-B5-C38;
A32-B5-C39;
A32-B5-C40;
A32-B5-C41;
A32-B5-C42;
A32-B5-C43;
A32-B5-C44;
A32-B5-C45;
A32-B5-C46;
A32-B5-C47;
A32-B5-C48;
A32-B5-C49;
A32-B5-C50;
A32-B5-C51;
A32-B5-C52;
A32-B5-C53;
A32-B5-C54;
A32-B5-C55;
A32-B5-C56;
A32-B5-C57;
A32-B5-C58;
A32-B5-C59;
A33-B5-C1;
A33-B5-C2;
A33-B5-C3;
A33-B5-C4;
A33-B5-C5;
A33-B5-C6;
A33-B5-C7;
A33-B5-C8;
A33-B5-C9;
A33-B5-C10;
A33-B5-C11;
A33-B5-C12;
A33-B5-C13;
A33-B5-C14;
A33-B5-C15;
A33-B5-C16;
A33-B5-C17;
A33-B5-C18;
A33-B5-C19;
A33-B5-C20;
A33-B5-C21;
A33-B5-C22;
A33-B5-C23;
A33-B5-C24;
A33-B5-C25;
A33-B5-C26;
A33-B5-C27;
A33-B5-C28;
A33-B5-C29;
A33-B5-C30;
A33-B5-C31;
A33-B5-C32;
A33-B5-C33;
A33-B5-C34;
A33-B5-C35;
A33-B5-C36;
A33-B5-C37;
A33-B5-C38;
A33-B5-C39;
A33-B5-C40;
A33-B5-C41;
A33-B5-C42;
A33-B5-C43;
A33-B5-C44;

A33-B5-C45;
A33-B5-C46;
A33-B5-C47;
A33-B5-C48;
A33-B5-C49;
A33-B5-C50;
A33-B5-C51;
A33-B5-C52;
A33-B5-C53;
A33-B5-C54;
A33-B5-C55;
A33-B5-C56;
A33-B5-C57;
A33-B5-C58;
A33-B5-C59;
A34-B5-C1;
A34-B5-C2;
A34-B5-C3;
A34-B5-C4;
A34-B5-C5;
A34-B5-C6;
A34-B5-C7;
A34-B5-C8;
A34-B5-C9;
A34-B5-C10;
A34-B5-C11;
A34-B5-C12;
A34-B5-C13;
A34-B5-C14;
A34-B5-C15;
A34-B5-C16;
A34-B5-C17;
A34-B5-C18;
A34-B5-C19;
A34-B5-C20;
A34-B5-C21;
A34-B5-C22;
A34-B5-C23;
A34-B5-C24;
A34-B5-C25;
A34-B5-C26;
A34-B5-C27;
A34-B5-C28;
A34-B5-C29;
A34-B5-C30;
A34-B5-C31;
A34-B5-C32;
A34-B5-C33;
A34-B5-C34;
A34-B5-C35;
A34-B5-C36;
A34-B5-C37;
A34-B5-C38;
A34-B5-C39;
A34-B5-C40;
A34-B5-C41;
A34-B5-C42;
A34-B5-C43;
A34-B5-C44;
A34-B5-C45;
A34-B5-C46;
A34-B5-C47;
A34-B5-C48;
A34-B5-C49;
A34-B5-C50;
A34-B5-C51;
A34-B5-C52;
A34-B5-C53;
A34-B5-C54;
A34-B5-C55;
A34-B5-C56;
A34-B5-C57;
A34-B5-C58;
A34-B5-C59;
A35-B5-C1;
A35-B5-C2;
A35-B5-C3;
A35-B5-C4;
A35-B5-C5;
A35-B5-C6;
A35-B5-C7;
A35-B5-C8;
A35-B5-C9;
A35-B5-C10;
A35-B5-C11;
A35-B5-C12;
A35-B5-C13;
A35-B5-C14;
A35-B5-C15;
A35-B5-C16;
A35-B5-C17;
A35-B5-C18;
A35-B5-C19;
A35-B5-C20;
A35-B5-C21;
A35-B5-C22;
A35-B5-C23;
A35-B5-C24;
A35-B5-C25;
A35-B5-C26;
A35-B5-C27;
A35-B5-C28;
A35-B5-C29;
A35-B5-C30;
A35-B5-C31;
A35-B5-C32;
A35-B5-C33;
A35-B5-C34;
A35-B5-C35;
A35-B5-C36;
A35-B5-C37;
A35-B5-C38;
A35-B5-C39;
A35-B5-C40;
A35-B5-C41;
A35-B5-C42;
A35-B5-C43;
A35-B5-C44;
A35-B5-C45;
A35-B5-C46;
A35-B5-C47;
A35-B5-C48;
A35-B5-C49;
A35-B5-C50;
A35-B5-C51;
A35-B5-C52;
A35-B5-C53;
A35-B5-C54;
A35-B5-C55;
A35-B5-C56;
A35-B5-C57;
A35-B5-C58;
A35-B5-C59;
A1-B6-C36;
A1-B6-C37;
A1-B6-C38;
A1-B6-C39;
A1-B6-C40;
A1-B6-C41;
A1-B6-C42;
A1-B6-C43;
A1-B6-C44;
A1-B6-C45;
A1-B6-C46;
A1-B6-C47;
A1-B6-C48;
A1-B6-C49;
A1-B6-C50;
A1-B1-C51;
A1-B6-C52;
A1-B6-C53;
A1-B6-C54;
A1-B6-C55;
A1-B6-C56;
A1-B6-C57;
A1-B6-C58;
A1-B6-C59;
A2-B6-C1;

A2-B6-C2;
A2-B6-C3;
A2-B6-C4;
A2-B6-C5;
A2-B6-C6;
A2-B6-C7;
A2-B6-C8;
A2-B6-C9;
A2-B6-C10;
A2-B6-C11;
A2-B6-C12;
A2-B6-C13;
A2-B6-C14;
A2-B6-C15;
A2-B6-C16;
A2-B6-C17;
A2-B6-C18;
A2-B6-C19;
A2-B6-C20;
A2-B6-C21;
A2-B6-C22;
A2-B6-C23;
A2-B6-C24;
A2-B6-C25;
A2-B6-C26;
A2-B6-C27;
A2-B6-C28;
A2-B6-C29;
A2-B6-C30;
A2-B6-C31;
A2-B6-C32;
A2-B6-C33;
A2-B6-C34;
A2-B6-C35;
A2-B6-C36;
A2-B6-C37;
A2-B6-C38;
A2-B6-C39;
A2-B6-C40;
A2-B6-C41;
A2-B6-C42;
A2-B6-C43;
A2-B6-C44;
A2-B6-C45;
A2-B6-C46;
A2-B6-C47;
A2-B6-C48;
A2-B6-C49;
A2-B6-C50;
A2-B6-C51;
A2-B6-C52;
A2-B6-C53;
A2-B6-C54;
A2-B6-C55;
A2-B6-C56;
A2-B6-C57;
A2-B6-C58;
A2-B6-C59;
A3-B6-C1;
A3-B6-C2;
A3-B6-C3;
A3-B6-C4;
A3-B6-C5;
A3-B6-C6;
A3-B6-C7;
A3-B6-C8;
A3-B6-C9;
A3-B6-C10;
A3-B6-C11;
A3-B6-C12;
A3-B6-C13;
A3-B6-C14;
A3-B6-C15;
A3-B6-C16;
A3-B6-C17;
A3-B6-C18;
A3-B6-C19;
A3-B6-C20;
A3-B6-C21;
A3-B6-C22;
A3-B6-C23;
A3-B6-C24;
A3-B6-C25;
A3-B6-C26;
A3-B6-C27;
A3-B6-C28;
A3-B6-C29;
A3-B6-C30;
A3-B6-C31;
A3-B6-C32;
A3-B6-C33;
A3-B6-C34;
A3-B6-C35;
A3-B6-C36;
A3-B6-C37;
A3-B6-C38;
A3-B6-C39;
A3-B6-C40;
A3-B6-C41;
A3-B6-C42;
A3-B6-C43;
A3-B6-C44;
A3-B6-C45;
A3-B6-C46;
A3-B6-C47;
A3-B6-C48;
A3-B6-C49;
A3-B6-C50;
A3-B6-C51;
A3-B6-C52;
A3-B6-C53;
A3-B6-C54;
A3-B6-C55;
A3-B6-C56;
A3-B6-C57;
A3-B6-C58;
A3-B6-C59;
A4-B6-C1;
A4-B6-C2;
A4-B6-C3;
A4-B6-C4;
A4-B6-C5;
A4-B6-C6;
A4-B6-C7;
A4-B6-C5;
A4-B6-C9;
A4-B6-C10;
A4-B6-C11;
A4-B6-C12;
A4-B6-C13;
A4-B6-C14;
A4-B6-C15;
A4-B6-C16;
A4-B6-C17;
A4-B6-C18;
A4-B6-C19;
A4-B6-C20;
A4-B6-C21,
A4-B6-C22;
A4-B6-C23;
A4-B6-C24;
A4-B6-C25;
A4-B6-C26;
A4-B6-C27;
A4-B6-C28;
A4-B6-C29;
A4-B6-C30;
A4-B6-C31;
A4-B6-C32;
A4-B6-C33;
A4-B6-C34;
A4-B6-C35;
A4-B6-C36;
A4-B6-C37;
A4-B6-C38;
A4-B6-C39;
A4-B6-C40;
A4-B6-C41;

A4-B6-C42;
A4-B6-C43;
A4-B6-C44;
A4-B6-C45;
A4-B6-C46;
A4-B6-C47;
A4-B6-C48;
A4-B6-C49;
A4-B6-C50;
A4-B6-C51;
A4-B6-C52;
A4-B6-C53;
A4-B6-C54;
A4-B6-C55;
A4-B6-C56;
A4-B6-C57;
A4-B6-C58;
A4-B6-C59;
A5-B6-C1;
A5-B6-C2;
A5-B6-C3;
A5-B6-C4;
A5-B6-C5;
A5-B6-C6;
A5-B6-C7;
A5-B6-C8;
A5-B6-C9;
A5-B6-C10;
A5-B6-C11;
A5-B6-C12;
A5-B6-C13;
A5-B6-C14;
A5-B6-C15;
A5-B6-C16;
A5-B6-C17;
A5-B6-C18;
A5-B6-C19;
A5-B6-C20;
A5-B6-C21;
A5-B6-C22;
A5-B6-C23;
A5-B6-C24;
A5-B6-C25;
A5-B6-C26;
A5-B6-C27;
A5-B6-C28;
A5-B6-C29;
A5-B6-C30;
A5-B6-C31;
A5-B6-C32;
A5-B6-C33;
A5-B6-C34;
A5-B6-C35;
A5-B6-C36;
A5-B6-C37;
A5-B6-C38;
A5-B6-C39;
A5-B6-C40;
A5-B6-C41;
A5-B6-C42;
A5-B6-C43;
A5-B6-C44;
A5-B6-C45;
A5-B6-C46;
A5-B6-C47;
A5-B6-C48;
A5-B6-C49;
A5-B6-C50;
A5-B6-C51;
A5-B6-C52;
A5-B6-C53;
A5-B6-C54;
A5-B6-C55;
A5-B6-C56;
A5-B6-C57;
A5-B6-C58;
A5-B6-C59;
A6-B6-C1;
A6-B6-C2;
A6-B6-C3;
A6-B6-C4;
A6-B6-C5;
A6-B6-C6;
A6-B6-C7;
A6-B6-C8;
A6-B6-C9;
A6-B6-C10;
A6-B6-C11;
A6-B6-C12;
A6-B6-C13;
A6-B6-C14;
A6-B6-C15;
A6-B6-C16;
A6-B6-C17;
A6-B6-C18;
A6-B6-C19;
A6-B6-C20;
A6-B6-C21;
A6-B6-C22;
A6-B6-C23;
A6-B6-C24;
A6-B6-C25;
A6-B6-C26;
A6-B6-C27;
A6-B6-C28;
A6-B6-C29;
A6-B6-C30;
A6-B6-C31;
A6-B6-C32;
A6-B6-C33;
A6-B6-C34;
A6-B6-C35;
A6-B6-C36;
A6-B6-C37;
A6-B6-C38;
A6-B6-C39;
A6-B6-C40;
A6-B6-C41;
A6-B6-C42;
A6-B6-C43;
A6-B6-C44;
A6-B6-C45;
A6-B6-C46;
A6-B6-C47;
A6-B6-C48;
A6-B6-C49;
A6-B6-C50;
A6-B6-C5i;
A6-B6-C52;
A6-B6-C53;
A6-B6-C54;
A6-B6-C55;
A6-B6-C56;
A6-B6-C57;
A6-B6-C58;
A6-B6-C59;
A7-B6-C1;
A7-B6-C2;
A7-B6-C3;
A7-B6-C4;
A7-B6-C5;
A7-B6-C6;
A7-B6-C7;
A7-B6-C8;
A7-B6-C9;
A7-B6-C10;
A7-B6-C11;
A7-B6-C12;
A7-B6-C13;
A7-B6-C14;
A7-B6-C15;
A7-B6-C16;
A7-B6-C17;
A7-B6-C18;
A7-B6-C19;
A7-B6-C20;
A7-B6-C21;
A7-B6-C22;

-continued

A7-B6-C23;
A7-B6-C24;
A7-B6-C25;
A7-B6-C26;
A7-B6-C27;
A7-B6-C28;
A7-B6-C29;
A7-B6-C30;
A7-B6-C31;
A7-B6-C32;
A7-B6-C33;
A7-B6-C34;
A7-B6-C35;
A7-B6-C36;
A7-B6-C37;
A7-B6-C38;
A7-B6-C39;
A7-B6-C40;
A7-B6-C41;
A7-B6-C42;
A7-B6-C43;
A7-B6-C44;
A7-B6-C45;
A7-B6-C46;
A7-B6-C47;
A7-B6-C48;
A7-B6-C49;
A7-B6-C50;
A7-B6-C51;
A7-B6-C52;
A7-B6-C53;
A7-B6-C54;
A7-B6-C55;
A7-B6-C56;
A7-B6-C57;
A7-B6-C58;
A7-B6-C59;
A8-B6-C1;
A8-B6-C2;
A8-B6-C3;
A8-B6-C4;
A8-B6-C5;
A8-B6-C6;
A8-B6-C7;
A8-B6-C8;
A8-B6-C9;
A8-B6-C10;
A8-B6-C11;
A8-B6-C12;
A8-B6-C13;
A8-B6-C14;
A8-B6-C15;
A8-B6-C16;
A8-B6-C17;
A8-B6-C18;
A8-B6-C19;
A8-B6-C20;
A8-B6-C21;
A8-B6-C22;
A8-B6-C23;
A8-B6-C24;
A8-B6-C25;
A8-B6-C26;
A8-B6-C27;
A8-B6-C28;
A8-B6-C29;
A8-B6-C30;
A8-B6-C31;
A8-B6-C32;
A8-B6-C33;
A8-B6-C34;
A8-B6-C35;
A8-B6-C36;
A8-B6-C37;
A8-B6-C38;
A8-B6-C39;
A8-B6-C40;
A8-B6-C41;
A8-B6-C42;

-continued

A8-B6-C43;
A8-B6-C44;
A8-B6-C45;
A8-B6-C46;
A8-B6-C47;
A8-B6-C48;
A8-B6-C49;
A8-B6-C50;
A8-B6-C51;
A8-B6-C52;
A8-B6-C53;
A8-B6-C54;
A8-B6-C55;
A8-B6-C56;
A8-B6-C57;
A8-B6-C58;
A8-B6-C59;
A9-B6-C1;
A9-B6-C2;
A9-B6-C3;
A9-B6-C4;
A9-B6-C5;
A9-B6-C6;
A9-B6-C7;
A9-B6-C8;
A9-B6-C9;
A9-B6-C10;
A9-B6-C11;
A9-B6-C12;
A9-B6-C13;
A9-B6-C14;
A9-B6-C15;
A9-B6-C16;
A9-B6-C17;
A9-B6-C18;
A9-B6-C19;
A9-B6-C20;
A9-B6-C21;
A9-B6-C22;
A9-B6-C23;
A9-B6-C24;
A9-B6-C25;
A9-B6-C26;
A9-B6-C27;
A9-B6-C28;
A9-B6-C29;
A9-B6-C30;
A9-B6-C31;
A9-B6-C32;
A9-B6-C33;
A9-B6-C34;
A9-B6-C35;
A9-B6-C36;
A9-B6-C37;
A9-B6-C38;
A9-B6-C39;
A9-B6-C40;
A9-B6-C41;
A9-B6-C42;
A9-B6-C43;
A9-B6-C44;
A9-B6-C45;
A9-B6-C46;
A9-B6-C47;
A9-B6-C48;
A9-B6-C49;
A9-B6-C50;
A9-B6-C51;
A9-B6-C52;
A9-B6-C53;
A9-B6-C54;
A9-B6-C55;
A9-B6-C56;
A9-B6-C57;
A9-B6-C58;
A9-B6-C59;
A10-B6-C1;
A10-B6-C2;
A10-B6-C3;

A10-B6-C4;
A10-B6-C5;
A10-B6-C6;
A10-B6-C7;
A10-B6-C8;
A10-B6-C9;
A10-B6-C10;
A10-B6-C11;
A10-B6-C12;
A10-B6-C13;
A10-B6-C14;
A10-B6-C15;
A10-B6-C16;
A10-B6-C17;
A10-B6-C18;
A10-B6-C19;
A10-B6-C20;
A10-B6-C21;
A10-B6-C22;
A10-B6-C23;
A10-B6-C24;
A10-B6-C25;
A10-B6-C26;
A10-B6-C27;
A10-B6-C28;
A10-B6-C29;
A10-B6-C30;
A10-B6-C31;
A10-B6-C32;
A10-B6-C33;
A10-B6-C34;
A10-B6-C35;
A10-B6-C36;
A10-B6-C37;
A10-B6-C38;
A10-B6-C39;
A10-B6-C40;
A10-B6-C41;
A10-B6-C42;
A10-B6-C43;
A10-B6-C44;
A10-B6-C45;
A10-B6-C46;
A10-B6-C47;
A10-B6-C48;
A10-B6-C49;
A10-B6-C50;
A10-B6-C51;
A10-B6-C52;
A10-B6-C53;
A10-B6-C54;
A10-B6-C55;
A10-B6-C56;
A10-B6-C57;
A10-B6-C58;
A10-B6-C59;
A11-B6-C1;
A11-B6-C2;
A11-B6-C3;
A11-B6-C4;
A11-B6-C5;
A11-B6-C6;
A11-B6-C7;
A11-B6-C8;
A11-B6-C9;
A11-B6-C10;
A11-B6-C11;
A11-B6-C12;
A11-B6-C13;
A11-B6-C14;
A11-B6-C15;
A11-B6-C16;
A11-B6-C17;
A11-B6-C18;
A11-B6-C19;
A11-B6-C20;
A11-B6-C21;
A11-B6-C22;
A11-B6-C23;
A11-B6-C24;
A11-B6-C25;
A11-B6-C26;
A11-B6-C27;
A11-B6-C28;
A11-B6-C29;
A11-B6-C30;
A11-B6-C31;
A11-B6-C32;
A11-B6-C33;
A11-B6-C34;
A11-B6-C35;
A11-B6-C36;
A11-B6-C37;
A11-B6-C38;
A11-B6-C39;
A11-B6-C40;
A11-B6-C41;
A11-B6-C42;
A11-B6-C43;
A11-B6-C44;
A11-B6-C45;
A11-B6-C46;
A11-B6-C47;
A11-B6-C48;
A11-B6-C49;
A11-B6-C50;
A11-B6-C51;
A11-B6-C52;
A11-B6-C53;
A11-B6-C54;
A11-B6-C55;
A11-B6-C56;
A11-B6-C57;
A11-B6-C58;
A11-B6-C59;
A12-B6-C1;
A12-B6-C2;
A12-B6-C3;
A12-B6-C4;
A12-B6-C5;
A12-B6-C6;
A12-B6-C7;
A12-B6-C8;
A12-B6-C9;
A12-B6-C10;
A12-B6-C11;
A12-B6-C12;
A12-B6-C13;
A12-B6-C14;
A12-B6-C15;
A12-B6-C16;
A12-B6-C17;
A12-B6-C18;
A12-B6-C19;
A12-B6-C20;
A12-B6-C21;
A12-B6-C22;
A12-B6-C23;
A12-B6-C24;
A12-B6-C25;
A12-B6-C26;
A12-B6-C27;
A12-B6-C28;
A12-B6-C29;
A12-B6-C30;
A12-B6-C31;
A12-B6-C32;
A12-B6-C33;
A12-B6-C34;
A12-B6-C35;
A12-B6-C36;
A12-B6-C37;
A12-B6-C38;
A12-B6-C39;
A12-B6-C40;
A12-B6-C41;
A12-B6-C42;
A12-B6-C43;

A12-B6-C44;
A12-B6-C45;
A12-B6-C46;
A12-B6-C47;
A12-B6-C48;
A12-B6-C49;
A12-B6-C50;
A12-B6-C51;
A12-B6-C52;
A12-B6-C53;
A12-B6-C54;
A12-B6-C55;
A12-B6-C56;
A12-B6-C57;
A12-B6-C58;
A12-B6-C59;
A13-B6-C1;
A13-B6-C2;
A13-B6-C3;
A13-B6-C4;
A13-B6-C5;
A13-B6-C6;
A13-B6-C7;
A13-B6-C8;
A13-B6-C9;
A13-B6-C10;
A13-B6-C11;
A13-B6-C12;
A13-B6-C13;
A13-B6-C14;
A13-B6-C15;
A13-B6-C16;
A13-B6-C17;
A13-B6-C18;
A13-B6-C19;
A13-B6-C20;
A13-B6-C21;
A13-B6-C22;
A13-B6-C23;
A13-B6-C24;
A13-B6-C25;
A13-B6-C26;
A13-B6-C27;
A13-B6-C28;
A13-B6-C29;
A13-B6-C30;
A13-B6-C31;
A13-B6-C32;
A13-B6-C33;
A13-B6-C34;
A13-B6-C35;
A13-B6-C36;
A13-B6-C37;
A13-B6-C38;
A13-B6-C39;
A13-B6-C40;
A13-B6-C41;
A13-B6-C42;
A13-B6-C43;
A13-B6-C44;
A13-B6-C45;
A13-B6-C46;
A13-B6-C47;
A13-B6-C48;
A13-B6-C49;
A13-B6-C50;
A13-B6-C51;
A13-B6-C52;
A13-B6-C53;
A13-B6-C54;
A13-B6-C55;
A13-B6-C56;
A13-B6-C57;
A13-B6-C58;
A13-B6-C59;
A14-B6-C1;
A14-B6-C2;
A14-B6-C3;
A14-B6-C4;
A14-B6-C5;
A14-B6-C6;
A14-B6-C7;
A14-B6-C8;
A14-B6-C9;
A14-B6-C10;
A14-B6-C11;
A14-B6-C12;
A14-B6-C13;
A14-B6-C14;
A14-B6-C15;
A14-B6-C16;
A14-B6-C17;
A14-B6-C18;
A14-B6-C19;
A14-B6-C20;
A14-B6-C21;
A14-B6-C22;
A14-B6-C23;
A14-B6-C24;
A14-B6-C25;
A14-B6-C26;
A14-B6-C27;
A14-B6-C28;
A14-B6-C29;
A14-B6-C30;
A14-B6-C31;
A14-B6-C32;
A14-B6-C33;
A14-B6-C34;
A14-B6-C35;
A14-B6-C36;
A14-B6-C37;
A14-B6-C38;
A14-B6-C39;
A14-B6-C40;
A14-B6-C41;
A14-B6-C42;
A14-B6-C43;
A14-B6-C44;
A14-B6-C45;
A14-B6-C46;
A14-B6-C47;
A14-B6-C48;
A14-B6-C49;
A14-B6-C50;
A14-B6-C51;
A14-B6-C52;
A14-B6-C53;
A14-B6-C54;
A14-B6-C55;
A14-B6-C56;
A14-B6-C57;
A14-B6-C58;
A14-B6-C59;
A15-B6-C1;
A15-B6-C2;
A15-B6-C3;
A15-B6-C4;
A15-B6-C5;
A15-B6-C6;
A15-B6-C7;
A15-B6-C8;
A15-B6-C9;
A15-B6-C10;
A15-B6-C11;
A15-B6-C12;
A15-B6-C13;
A15-B6-C14;
A15-B6-C15;
A15-B6-C16;
A15-B6-C17;
A15-B6-C18;
A15-B6-C19;
A15-B6-C20;
A15-B6-C21;
A15-B6-C22;
A15-B6-C23;
A15-B6-C24;

A15-B6-C25;
A15-B6-C26;
A15-B6-C27;
A15-B6-C28;
A15-B6-C29;
A15-B6-C30;
A15-B6-C31;
A15-B6-C32;
A15-B6-C33;
A15-B6-C34;
A15-B6-C35;
A15-B6-C36;
A15-B6-C37;
A15-B6-C38;
A15-B6-C39;
A15-B6-C40;
A15-B6-C41;
A15-B6-C42;
A15-B6-C43;
A15-B6-C44;
A15-B6-C45;
A15-B6-C46;
A15-B6-C47;
A15-B6-C48;
A15-B6-C49;
A15-B6-C50;
A15-B6-C51;
A15-B6-C52;
A15-B6-C53;
A15-B6-C54;
A15-B6-C55;
A15-B6-C56;
A15-B6-C57;
A15-B6-C58;
A15-B6-C59;
A16-B6-C1;
A16-B6-C2;
A16-B6-C3;
A16-B6-C4;
A16-B6-C5;
A16-B6-C6;
A16-B6-C7;
A16-B6-C8;
A16-B6-C9;
A16-B6-C10;
A16-B6-C11;
A16-B6-C12;
A16-B6-C13;
A16-B6-C14;
A16-B6-C15;
A16-B6-C16;
A16-B6-C17;
A16-B6-C18;
A16-B6-C19;
A16-B6-C20;
A16-B6-C21;
A16-B6-C22;
A16-B6-C23;
A16-B6-C24;
A16-B6-C25;
A16-B6-C26;
A16-B6-C27;
A16-B6-C28;
A16-B6-C29;
A16-B6-C30;
A16-B6-C31;
A16-B6-C32;
A16-B6-C33;
A16-B6-C34;
A16-B6-C35;
A16-B6-C36;
A16-B6-C37;
A16-B6-C38;
A16-B6-C39;
A16-B6-C40;
A16-B6-C41;
A16-B6-C42;
A16-B6-C43;
A16-B6-C44;
A16-B6-C45;
A16-B6-C46;
A16-B6-C47;
A16-B6-C48;
A16-B6-C49;
A16-B6-C50;
A16-B6-C51;
A16-B6-C52;
A16-B6-C53;
A16-B6-C54;
A16-B6-C55;
A16-B6-C56;
A16-B6-C57;
A16-B6-C58;
A16-B6-C59;
A17-B6-C1;
A17-B6-C2;
A17-B6-C3;
A17-B6-C4;
A17-B6-C5;
A17-B6-C6;
A17-B6-C7;
A17-B6-C8;
A17-B6-C9;
A17-B6-C10;
A17-B6-C11;
A17-B6-C12;
A17-B6-C13;
A17-B6-C14;
A17-B6-C15;
A17-B6-C16;
A17-B6-C17;
A17-B6-C18;
A17-B6-C19;
A17-B6-C20;
A17-B6-C21;
A17-B6-C22;
A17-B6-C23;
A17-B6-C24;
A17-B6-C25;
A17-B6-C26;
A17-B6-C27;
A17-B6-C28;
A17-B6-C29;
A17-B6-C30;
A17-B6-C31;
A17-B6-C32;
A17-B6-C33;
A17-B6-C34;
A17-B6-C35;
A17-B6-C36;
A17-B6-C37;
A17-B6-C38;
A17-B6-C39;
A17-B6-C40;
A17-B6-C41;
A17-B6-C42;
A17-B6-C43;
A17-B6-C44;
A17-B6-C45;
A17-B6-C46;
A17-B6-C47;
A17-B6-C48;
A17-B6-C49;
A17-B6-C50;
A17-B6-C51;
A17-B6-C52;
A17-B6-C53;
A17-B6-C54;
A17-B6-C55;
A17-B6-C56;
A17-B6-C57;
A17-B6-C58;
A17-B6-C59;
A18-B6-C1;
A18-B6-C2;
A18-B6-C3;
A18-B6-C4;
A18-B6-C5;

A18-B6-C6;
A18-B6-C7;
A18-B6-C8;
A18-B6-C9;
A18-B6-C10;
A18-B6-C11;
A18-B6-C12;
A18-B6-C13;
A18-B6-C14;
A18-B6-C15;
A18-B6-C16;
A18-B6-C17;
A18-B6-C18;
A18-B6-C19;
A18-B6-C20;
A18-B6-C21;
A18-B6-C22;
A18-B6-C23;
A18-B6-C24;
A18-B6-C25;
A18-B6-C26;
A18-B6-C27;
A18-B6-C28;
A18-B6-C29;
A18-B6-C30;
A18-B6-C31;
A18-B6-C32;
A18-B6-C33;
A18-B6-C34;
A18-B6-C35;
A18-B6-C36;
A18-B6-C37;
A18-B6-C38;
A18-B6-C39;
A18-B6-C40;
A18-B6-C41;
A18-B6-C42;
A18-B6-C43;
A18-B6-C44;
A18-B6-C45;
A18-B6-C46;
A18-B6-C47;
A18-B6-C48;
A18-B6-C49;
A18-B6-C50;
A18-B6-C51;
A18-B6-C52;
A18-B6-C53;
A18-B6-C54;
A18-B6-C55;
A18-B6-C56;
A18-B6-C57;
A18-B6-C58;
A18-B6-C59;
A19-B6-C1;
A19-B6-C2;
A19-B6-C3;
A19-B6-C4;
A19-B6-C5;
A19-B6-C6;
A19-B6-C7;
A19-B6-C8;
A19-B6-C9;
A19-B6-C10;
A19-B6-C11;
A19-B6-C12;
A19-B6-C13;
A19-B6-C14;
A19-B6-C15;
A19-B6-C16;
A19-B6-C17;
A19-B6-C18;
A19-B6-C19;
A19-B6-C20;
A19-B6-C21;
A19-B6-C22;
A19-B6-C23;
A19-B6-C24;
A19-B6-C25;
A19-B6-C26;
A19-B6-C27;
A19-B6-C28;
A19-B6-C29;
A19-B6-C30;
A19-B6-C31;
A19-B6-C32;
A19-B6-C33;
A19-B6-C34;
A19-B6-C35;
A19-B6-C36;
A19-B6-C37;
A19-B6-C38;
A19-B6-C39;
A19-B6-C40;
A19-B6-C41;
A19-B6-C42;
A19-B6-C43;
A19-B6-C44;
A19-B6-C45;
A19-B6-C46;
A19-B6-C47;
A19-B6-C48;
A19-B6-C49;
A19-B6-C50;
A19-B6-C51;
A19-B6-C52;
A19-B6-C53;
A19-B6-C54;
A19-B6-C55;
A19-B6-C56;
A19-B6-C57;
A19-B6-C58;
A19-B6-C59;
A20-B6-C1;
A20-B6-C2;
A20-B6-C3;
A20-B6-C4;
A20-B6-C5;
A20-B6-C6;
A20-B6-C7;
A20-B6-C8;
A20-B6-C9;
A20-B6-C10;
A20-B6-C11;
A20-B6-C12;
A20-B6-C13;
A20-B6-C14;
A20-B6-C15;
A20-B6-C16;
A20-B6-C17;
A20-B6-C18;
A20-B6-C19;
A20-B6-C20;
A20-B6-C21;
A20-B6-C22;
A20-B6-C23;
A20-B6-C24;
A20-B6-C25;
A20-B6-C26;
A20-B6-C27;
A20-B6-C28;
A20-B6-C29;
A20-B6-C30;
A20-B6-C31;
A20-B6-C32;
A20-B6-C33;
A20-B6-C34;
A20-B6-C35;
A20-B6-C36;
A20-B6-C37;
A20-B6-C38;
A20-B6-C39;
A20-B6-C40;
A20-B6-C41;
A20-B6-C42;
A20-B6-C43;
A20-B6-C44;
A20-B6-C45;

-continued

A20-B6-C46;
A20-B6-C47;
A20-B6-C48;
A20-B6-C49;
A20-B6-C50;
A20-B6-C51;
A20-B6-C52;
A20-B6-C53;
A20-B6-C54;
A20-B6-C55;
A20-B6-C56;
A20-B6-C57;
A20-B6-C58;
A20-B6-C59;
A21-B6-C1;
A21-B6-C2;
A21-B6-C3;
A21-B6-C4;
A21-B6-C5;
A21-B6-C6;
A21-B6-C7;
A21-B6-C8;
A21-B6-C9;
A21-B6-C10;
A21-B6-C11;
A21-B6-C12;
A21-B6-C13;
A21-B6-C14;
A21-B6-C15;
A21-B6-C16;
A21-B6-C17;
A21-B6-C18;
A21-B6-C19;
A21-B6-C20;
A21-B6-C21;
A21-B6-C22;
A21-B6-C23;
A21-B6-C24;
A21-B6-C25;
A21-B6-C26;
A21-B6-C27;
A21-B6-C28;
A21-B6-C29;
A21-B6-C30;
A21-B6-C31;
A21-B6-C32;
A21-B6-C33;
A21-B6-C34;
A21-B6-C35;
A21-B6-C36;
A21-B6-C37;
A21-B6-C38;
A21-B6-C39;
A21-B6-C40;
A21-B6-C41;
A21-B6-C42;
A21-B6-C43;
A21-B6-C44;
A21-B6-C45;
A21-B6-C46;
A21-B6-C47;
A21-B6-C48;
A21-B6-C49;
A21-B6-C50;
A21-B6-C51;
A21-B6-C52;
A21-B6-C53;
A21-B6-C54;
A21-B6-C55;
A21-B6-C56;
A21-B6-C57;
A21-B6-C58;
A21-B6-C59;
A22-B6-C1;
A22-B6-C2;
A22-B6-C3;
A22-B6-C4;
A22-B6-C5;
A22-B6-C6;

-continued

A22-B6-C7;
A22-B6-C8;
A22-B6-C9;
A22-B6-C10;
A22-B6-C11;
A22-B6-C12;
A22-B6-C13;
A22-B6-C14;
A22-B6-C15;
A22-B6-C16;
A22-B6-C17;
A22-B6-C18;
A22-B6-C19;
A22-B6-C20;
A22-B6-C21;
A22-B6-C22;
A22-B6-C23;
A22-B6-C24;
A22-B6-C25;
A22-B6-C26;
A22-B6-C27;
A22-B6-C28;
A22-B6-C29;
A22-B6-C30;
A22-B6-C31;
A22-B6-C32;
A22-B6-C33;
A22-B6-C34;
A22-B6-C35;
A22-B6-C36;
A22-B6-C37;
A22-B6-C38;
A22-B6-C39;
A22-B6-C40;
A22-B6-C41;
A22-B6-C42;
A22-B6-C43;
A22-B6-C44;
A22-B6-C45;
A22-B6-C46;
A22-B6-C47;
A22-B6-C48;
A22-B6-C49;
A22-B6-C50;
A22-B6-C51;
A22-B6-C52;
A22-B6-C53;
A22-B6-C54;
A22-B6-C55;
A22-B6-C56;
A22-B6-C57;
A22-B6-C58;
A22-B6-C59;
A23-B6-C1;
A23-B6-C2;
A23-B6-C3;
A23-B6-C4;
A23-B6-C5;
A23-B6-C6;
A23-B6-C7;
A23-B6-C8;
A23-B6-C9;
A23-B6-C10;
A23-B6-C11;
A23-B6-C12;
A23-B6-C13;
A23-B6-C14;
A23-B6-C15;
A23-B6-C16;
A23-B6-C17;
A23-B6-C18;
A23-B6-C19;
A23-B6-C20;
A23-B6-C21;
A23-B6-C22;
A23-B6-C23;
A23-B6-C24;
A23-B6-C25;
A23-B6-C26;

-continued

A23-B6-C27;
A23-B6-C28;
A23-B6-C29;
A23-B6-C30;
A23-B6-C31;
A23-B6-C32;
A23-B6-C33;
A23-B6-C34;
A23-B6-C35;
A23-B6-C36;
A23-B6-C37;
A23-B6-C38;
A23-B6-C39;
A23-B6-C40;
A23-B6-C41;
A23-B6-C42;
A23-B6-C43;
A23-B6-C44;
A23-B6-C45;
A23-B6-C46;
A23-B6-C47;
A23-B6-C48;
A23-B6-C49;
A23-B6-C50;
A23-B6-C51;
A23-B6-C52;
A23-B6-C53;
A23-B6-C54;
A23-B6-C55;
A23-B6-C56;
A23-B6-C57;
A23-B6-C58;
A23-B6-C59;
A24-B6-C1;
A24-B6-C2;
A24-B6-C3;
A24-B6-C4;
A24-B6-C5;
A24-B6-C6;
A24-B6-C7;
A24-B6-C8;
A24-B6-C9;
A24-B6-C10;
A24-B6-C11;
A24-B6-C12;
A24-B6-C13;
A24-B6-C14;
A24-B6-C15;
A24-B6-C16;
A24-B6-C17;
A24-B6-C18;
A24-B6-C19;
A24-B6-C20;
A24-B6-C21;
A24-B6-C22;
A24-B6-C23;
A24-B6-C24;
A24-B6-C25;
A24-B6-C26;
A24-B6-C27;
A24-B6-C28;
A24-B6-C29;
A24-B6-C30;
A24-B6-C31;
A24-B6-C32;
A24-B6-C33;
A24-B6-C34;
A24-B6-C35;
A24-B6-C36;
A24-B6-C37;
A24-B6-C38;
A24-B6-C39;
A24-B6-C40;
A24-B6-C41;
A24-B6-C42;
A24-B6-C43;
A24-B6-C44;
A24-B6-C45;
A24-B6-C46;

-continued

A24-B6-C47;
A24-B6-C48;
A24-B6-C49;
A24-B6-C50;
A24-B6-C51;
A24-B6-C52;
A24-B6-C53;
A24-B6-C54;
A24-B6-C55;
A24-B6-C56;
A24-B6-C57;
A24-B6-C58;
A24-B6-C59;
A25-B6-C1;
A25-B6-C2;
A25-B6-C3;
A25-B6-C4;
A25-B6-C5;
A25-B6-C6;
A25-B6-C7;
A25-B6-C8;
A25-B6-C9;
A25-B6-C10;
A25-B6-C11;
A25-B6-C12;
A25-B6-C13;
A25-B6-C14;
A25-B6-C15;
A25-B6-C16;
A25-B6-C17;
A25-B6-C18;
A25-B6-C19;
A25-B6-C20;
A25-B6-C21;
A25-B6-C22;
A25-B6-C23;
A25-B6-C24;
A25-B6-C25;
A25-B6-C26;
A25-B6-C27;
A25-B6-C28;
A25-B6-C29;
A25-B6-C30;
A25-B6-C31;
A25-B6-C32;
A25-B6-C33;
A25-B6-C34;
A25-B6-C35;
A25-B6-C36;
A25-B6-C37;
A25-B6-C38;
A25-B6-C39;
A25-B6-C40;
A25-B6-C41;
A25-B6-C42;
A25-B6-C43;
A25-B6-C44;
A25-B6-C45;
A25-B6-C46;
A25-B6-C47;
A25-B6-C48;
A25-B6-C49;
A25-B6-C50;
A25-B6-C51;
A25-B6-C52;
A25-B6-C53;
A25-B6-C54;
A25-B6-C55;
A25-B6-C56;
A25-B6-C57;
A25-B6-C58;
A25-B6-C59;
A26-B6-C1;
A26-B6-C2;
A26-B6-C3;
A26-B6-C4;
A26-B6-C5;
A26-B6-C6;
A26-B6-C7;

-continued

A26-B6-C8;
A26-B6-C9;
A26-B6-C10;
A26-B6-C11;
A26-B6-C12;
A26-B6-C13;
A26-B6-C14;
A26-B6-C15;
A26-B6-C16;
A26-B6-C17;
A26-B6-C18;
A26-B6-C19;
A26-B6-C20;
A26-B6-C21;
A26-B6-C22;
A26-B6-C23;
A26-B6-C24;
A26-B6-C25;
A26-B6-C26;
A26-B6-C27;
A26-B6-C28;
A26-B6-C29;
A26-B6-C30;
A26-B6-C31;
A26-B6-C32;
A26-B6-C33;
A26-B6-C34;
A26-B6-C35;
A26-B6-C36;
A26-B6-C37;
A26-B6-C38;
A26-B6-C39;
A26-B6-C40;
A26-B6-C41;
A26-B6-C42;
A26-B6-C43;
A26-B6-C44;
A26-B6-C45;
A26-B6-C46;
A26-B6-C47;
A26-B6-C48;
A26-B6-C49;
A26-B6-C50;
A26-B6-C51;
A26-B6-C52;
A26-B6-C53;
A26-B6-C54;
A26-B6-C55;
A26-B6-C56;
A26-B6-C57;
A26-B6-C58;
A26-B6-C59;
A27-B6-C1;
A27-B6-C2;
A27-B6-C3;
A27-B6-C4;
A27-B6-C5;
A27-B6-C6;
A27-B6-C7;
A27-B6-C8;
A27-B6-C9;
A27-B6-C10;
A27-B6-C11;
A27-B6-C12;
A27-B6-C13;
A27-B6-C14;
A27-B6-C15;
A27-B6-C16;
A27-B6-C17;
A27-B6-C18;
A27-B6-C19;
A27-B6-C20;
A27-B6-C21;
A27-B6-C22;
A27-B6-C23;
A27-B6-C24;
A27-B6-C25;
A27-B6-C26;
A27-B6-C27;

-continued

A27-B6-C28;
A27-B6-C29;
A27-B6-C30;
A27-B6-C31;
A27-B6-C32;
A27-B6-C33;
A27-B6-C34;
A27-B6-C35;
A27-B6-C36;
A27-B6-C37;
A27-B6-C38;
A27-B6-C39;
A27-B6-C40;
A27-B6-C41;
A27-B6-C42;
A27-B6-C43;
A27-B6-C44;
A27-B6-C45;
A27-B6-C46;
A27-B6-C47;
A27-B6-C48;
A27-B6-C49;
A27-B6-C50;
A27-B6-C51;
A27-B6-C52;
A27-B6-C53;
A27-B6-C54;
A27-B6-C55;
A27-B6-C56;
A27-B6-C57;
A27-B6-C58;
A27-B6-C59;
A28-B6-C1;
A28-B6-C2;
A28-B6-C3;
A28-B6-C4;
A28-B6-C5;
A28-B6-C6;
A28-B6-C7;
A28-B6-C8;
A28-B6-C9;
A28-B6-C10;
A28-B6-C11;
A28-B6-C12;
A28-B6-C13;
A28-B6-C14;
A28-B6-C15;
A28-B6-C16;
A28-B6-C17;
A28-B6-C18;
A28-B6-C19;
A28-B6-C20;
A28-B6-C21;
A28-B6-C22;
A28-B6-C23;
A28-B6-C24;
A28-B6-C25;
A28-B6-C26;
A28-B6-C27;
A28-B6-C28;
A28-B6-C29;
A28-B6-C30;
A28-B6-C31;
A28-B6-C32;
A28-B6-C33;
A28-B6-C34;
A28-B6-C35;
A28-B6-C36;
A28-B6-C37;
A28-B6-C38;
A28-B6-C39;
A28-B6-C40;
A28-B6-C41;
A28-B6-C42;
A28-B6-C43;
A28-B6-C44;
A28-B6-C45;
A28-B6-C46;
A28-B6-C47;

-continued

A28-B6-C48;
A28-B6-C49;
A28-B6-C50;
A28-B6-C51;
A28-B6-C52;
A28-B6-C53;
A28-B6-C54;
A28-B6-C55;
A28-B6-C56;
A28-B6-C57;
A28-B6-C58;
A28-B6-C59;
A29-B6-C1;
A29-B6-C2;
A29-B6-C3;
A29-B6-C4;
A29-B6-C5;
A29-B6-C6;
A29-B6-C7;
A29-B6-C8;
A29-B6-C9;
A29-B6-C10;
A29-B6-C11;
A29-B6-C12;
A29-B6-C13;
A29-B6-C14;
A29-B6-C15;
A29-B6-C16;
A29-B6-C17;
A29-B6-C18;
A29-B6-C19;
A29-B6-C20;
A29-B6-C21;
A29-B6-C22;
A29-B6-C23;
A29-B6-C24;
A29-B6-C25;
A29-B6-C26;
A29-B6-C27;
A29-B6-C28;
A29-B6-C29;
A29-B6-C30;
A29-B6-C31;
A29-B6-C32;
A29-B6-C33;
A29-B6-C34;
A29-B6-C35;
A29-B6-C36;
A29-B6-C37;
A29-B6-C38;
A29-B6-C39;
A29-B6-C40;
A29-B6-C41;
A29-B6-C42;
A29-B6-C43;
A29-B6-C44;
A29-B6-C45;
A29-B6-C46;
A29-B6-C47;
A29-B6-C48;
A29-B6-C49;
A29-B6-C50;
A29-B6-C51;
A29-B6-C52;
A29-B6-C53;
A29-B6-C54;
A29-B6-C55;
A29-B6-C56;
A29-B6-C57;
A29-B6-C58;
A29-B6-C59;
A30-B6-C1;
A30-B6-C2;
A30-B6-C3;
A30-B6-C4;
A30-B6-C5;
A30-B6-C6;
A30-B6-C7;
A30-B6-C8;
A30-B6-C9;
A30-B6-C10;
A30-B6-C11;
A30-B6-C12;
A30-B6-C13;
A30-B6-C14;
A30-B6-C15;
A30-B6-C16;
A30-B6-C17;
A30-B6-C18;
A30-B6-C19;
A30-B6-C20;
A30-B6-C21;
A30-B6-C22;
A30-B6-C23;
A30-B6-C24;
A30-B6-C25;
A30-B6-C26;
A30-B6-C27;
A30-B6-C28;
A30-B6-C29;
A30-B6-C30;
A30-B6-C31;
A30-B6-C32;
A30-B6-C33;
A30-B6-C34;
A30-B6-C35;
A30-B6-C36;
A30-B6-C37;
A30-B6-C38;
A30-B6-C39;
A30-B6-C40;
A30-B6-C41;
A30-B6-C42;
A30-B6-C43;
A30-B6-C44;
A30-B6-C45;
A30-B6-C46;
A30-B6-C47;
A30-B6-C48;
A30-B6-C49;
A30-B6-C50;
A30-B6-C51;
A30-B6-C52;
A30-B6-C53;
A30-B6-C54;
A30-B6-C55;
A30-B6-C56;
A30-B6-C57;
A30-B6-C58;
A30-B6-C59;
A31-B6-C1;
A31-B6-C2;
A31-B6-C3;
A31-B6-C4;
A31-B6-C5;
A31-B6-C6;
A31-B6-C7;
A31-B6-C8;
A31-B6-C9;
A31-B6-C10;
A31-B6-C11;
A31-B6-C12;
A31-B6-C13;
A31-B6-C14;
A31-B6-C15;
A31-B6-C16;
A31-B6-C17;
A31-B6-C18;
A31-B6-C19;
A31-B6-C20;
A31-B6-C21;
A31-B6-C22;
A31-B6-C23;
A31-B6-C24;
A31-B6-C25;
A31-B6-C26;
A31-B6-C27;
A31-B6-C28;

-continued

A31-B6-C29;
A31-B6-C30;
A31-B6-C31;
A31-B6-C32;
A31-B6-C33;
A31-B6-C34;
A31-B6-C35;
A31-B6-C36;
A31-B6-C37;
A31-B6-C38;
A31-B6-C39;
A31-B6-C40;
A31-B6-C41;
A31-B6-C42;
A31-B6-C43;
A31-B6-C44;
A31-B6-C45;
A31-B6-C46;
A31-B6-C47;
A31-B6-C48;
A31-B6-C49;
A31-B6-C50;
A31-B6-C51;
A31-B6-C52;
A31-B6-C53;
A31-B6-C54;
A31-B6-C55;
A31-B6-C56;
A31-B6-C57;
A31-B6-C58;
A31-B6-C59;
A32-B6-C1;
A32-B6-C2;
A32-B6-C3;
A32-B6-C4;
A32-B6-C5;
A32-B6-C6;
A32-B6-C7;
A32-B6-C8;
A32-B6-C9;
A32-B6-C10;
A32-B6-C11;
A32-B6-C12;
A32-B6-C13;
A32-B6-C14;
A32-B6-C15;
A32-B6-C16;
A32-B6-C17;
A32-B6-C18;
A32-B6-C19;
A32-B6-C20;
A32-B6-C21;
A32-B6-C22;
A32-B6-C23;
A32-B6-C24;
A32-B6-C25;
A32-B6-C26;
A32-B6-C27;
A32-B6-C28;
A32-B6-C29;
A32-B6-C30;
A32-B6-C31;
A32-B6-C32;
A32-B6-C33;
A32-B6-C34;
A32-B6-C35;
A32-B6-C36;
A32-B6-C37;
A32-B6-C38;
A32-B6-C39;
A32-B6-C40;
A32-B6-C41;
A32-B6-C42;
A32-B6-C43;
A32-B6-C44;
A32-B6-C45;
A32-B6-C46;
A32-B6-C47;
A32-B6-C48;

-continued

A32-B6-C49;
A32-B6-C50;
A32-B6-C51;
A32-B6-C52;
A32-B6-C53;
A32-B6-C54;
A32-B6-C55;
A32-B6-C56;
A32-B6-C57;
A32-B6-C58;
A32-B6-C59;
A33-B6-C1;
A33-B6-C2;
A33-B6-C3;
A33-B6-C4;
A33-B6-C5;
A33-B6-C6;
A33-B6-C7;
A33-B6-C8;
A33-B6-C9;
A33-B6-C10;
A33-B6-C11;
A33-B6-C12;
A33-B6-C13;
A33-B6-C14;
A33-B6-C15;
A33-B6-C16;
A33-B6-C17;
A33-B6-C18;
A33-B6-C19;
A33-B6-C20;
A33-B6-C21;
A33-B6-C22;
A33-B6-C23;
A33-B6-C24;
A33-B6-C25;
A33-B6-C26;
A33-B6-C27;
A33-B6-C28;
A33-B6-C29;
A33-B6-C30;
A33-B6-C31;
A33-B6-C32;
A33-B6-C33;
A33-B6-C34;
A33-B6-C35;
A33-B6-C36;
A33-B6-C37;
A33-B6-C38;
A33-B6-C39;
A33-B6-C40;
A33-B6-C41;
A33-B6-C42;
A33-B6-C43;
A33-B6-C44;
A33-B6-C45;
A33-B6-C46;
A33-B6-C47;
A33-B6-C48;
A33-B6-C49;
A33-B6-C50;
A33-B6-C51;
A33-B6-C52;
A33-B6-C53;
A33-B6-C54;
A33-B6-C55;
A33-B6-C56;
A33-B6-C57;
A33-B6-C58;
A33-B6-C59;
A34-B6-C1;
A34-B6-C2;
A34-B6-C3;
A34-B6-C4;
A34-B6-C5;
A34-B6-C6;
A34-B6-C7;
A34-B6-C8;
A34-B6-C9;

-continued

A34-B6-C10;
A34-B6-C11;
A34-B6-C12;
A34-B6-C13;
A34-B6-C14;
A34-B6-C15;
A34-B6-C16;
A34-B6-C17;
A34-B6-C18;
A34-B6-C19;
A34-B6-C20;
A34-B6-C21;
A34-B6-C22;
A34-B6-C23;
A34-B6-C24;
A34-B6-C25;
A34-B6-C26;
A34-B6-C27;
A34-B6-C28;
A34-B6-C29;
A34-B6-C30;
A34-B6-C31;
A34-B6-C32;
A34-B6-C33;
A34-B6-C34;
A34-B6-C35;
A34-B6-C36;
A34-B6-C37;
A34-B6-C38;
A34-B6-C39;
A34-B6-C40;
A34-B6-C41;
A34-B6-C42;
A34-B6-C43;
A34-B6-C44;
A34-B6-C45;
A34-B6-C46;
A34-B6-C47;
A34-B6-C48;
A34-B6-C49;
A34-B6-C50;
A34-B6-C51;
A34-B6-C52;
A34-B6-C53;
A34-B6-C54;
A34-B6-C55;
A34-B6-C56;
A34-B6-C57;
A34-B6-C58;
A34-B6-C59;
A35-B6-C1;
A35-B6-C2;
A35-B6-C3;
A35-B6-C4;
A35-B6-C5;
A35-B6-C6;
A35-B6-C7;
A35-B6-C8;
A35-B6-C9;
A35-B6-C10;
A35-B6-C11;
A35-B6-C12;
A35-B6-C13;
A35-B6-C14;
A35-B6-C15;
A35-B6-C16;
A35-B6-C17;
A35-B6-C18;
A35-B6-C19;
A35-B6-C20;
A35-B6-C21;
A35-B6-C22;
A35-B6-C23;
A35-B6-C24;
A35-B6-C25;
A35-B6-C26;
A35-B6-C27;
A35-B6-C28;
A35-B6-C29;

-continued

A35-B6-C30;
A35-B6-C31;
A35-B6-C32;
A35-B6-C33;
A35-B6-C34;
A35-B6-C35;
A35-B6-C36;
A35-B6-C37;
A35-B6-C38;
A35-B6-C39;
A35-B6-C40;
A35-B6-C41;
A35-B6-C42;
A35-B6-C43;
A35-B6-C44;
A35-B6-C45;
A35-B6-C46;
A35-B6-C47;
A35-B6-C48;
A35-B6-C49;
A35-B6-C50;
A35-B6-C51;
A35-B6-C52;
A35-B6-C53;
A35-B6-C54;
A35-B6-C55;
A35-B6-C56;
A35-B6-C57;
A35-B6-C58;
A35-B6-C59;

and the corresponding N-oxides, and their prodrugs; and pharmaceutically acceptable salts and solvates (e.g. hydrates) of such compounds and their N-oxides and prodrugs.

Thus, for example, in the above list the compound denoted as A1-B1-C1 is the product of the combination of group $A^1$ in Table 1 and B1 in Table 2 and C1 in Table 3, namely

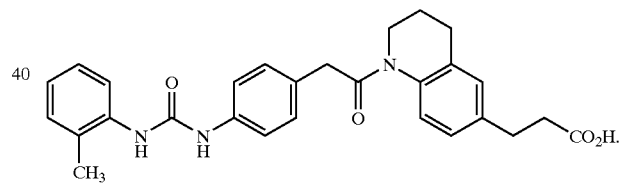

Preferred compounds of the invention are:

3-(1-{[3-methoxy-4-(3-[2-methylphenyl]-ureido)-phenyl]-acetyl}-1,2,3,4-tetrahydro-quinolin-6-yl)-propionic acid;

3-(1-{[3-methoxy-4-(3-o-tolyl-ureido)-phenyl]-acetyl}-2,3-dihydro-1H-indol-5-yl)-butyric acid;

3-(1-{[3-methoxy-4-(3-o-tolyl-ureido)-phenyl]-acetyl}-1,2,3,4-tetrahydro-quinolinyl)-butyric acid;

3-(1-{[3-methoxy-4-(3-o-tolyl-ureido)-phenyl]-acetyl}-2,3-dihydro-1H-indol-5-yl)-pentanedioic acid;

3-(1-{[3-methoxy-4-(3-o-tolyl-ureido)-phenyl]-acetyl}-1,2,3,4-tetrahydro-quinolin-6-yl)-pentanedioic acid;

4-[2-carboxy-1-(1-{[3-methoxy-4-(3-o-tolyl-ureido)-phenyl]-acetyl}-1,2,3,4-tetrahydro-quinolin-6-yl)-ethylcarbamoyl]-butyric acid;

N-[2-carboxy-1-(1-{[3-methoxy-4-(3-o-tolyl-ureido)-phenyl]-acetyl}-1,2,3,4-tetrahydro-quinolin-6-yl)-ethyl]-succinamic acid;

3-(1-{[3-methoxy-4-(3-o-tolyl-ureido)-phenyl]-acetyl}-1,2,3,4-tetrahydro-quinolin-6-yl)-3-[(5-methyl-isoxazole-3-carbonyl)-amino]-propionic acid;

3-(1-{[3-methoxy-4-(3-o-tolyl-ureido)-phenyl]-acetyl}-2,3-dihydro-1H-indol-5-yl)-3-phenyl-propionic acid;

3-(1-{[3-methoxy-4-(3-o-tolyl-ureido)-phenyl]-acetyl}-2,3-dihydro-1H-indol-5-yl)-pentanoic acid;

and the corresponding N-oxide, and its prodrugs; and pharmaceutically acceptable salts and solvates (e.g. hydrates) of such compounds and their N-oxides and prodrugs.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention block the interaction of the ligand VCAM-1 to its integrin receptor VLA-4 ($\alpha 4 \beta 1$) according to tests described in the literature and described in vitro and in vivo procedures hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of an inhibitor of $\alpha a 4 \beta 1$ mediated cell adhesion. For example, compounds of the present invention are useful in the treatment of inflammatory diseases, for example joint inflammation, including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds may be useful in the treatment of acute synovitis, autoimmune diabetes, autoimmune encephalomyelitis, collitis, atherosclerosis, peripheral vascular disease, cardiovascular disease, multiple sclerosis, asthma, psoriasis restenosis, myocarditis, inflammatory bowel disease and melanoma cell division in metastasis.

A special embodiment of the therapeutic methods of the present invention is the treating of asthma.

Another special embodiment of the therapeutic methods of the present invention is the treating of joint inflammation.

Another special embodiment of the therapeutic methods of the present invention is the treating of inflammatory bowel disease.

According to a further feature of the invention there is provided a method for the treatment of a human or animal patient suffering from, or subject to, conditions which can be ameliorated by the administration of an inhibitor of the interaction of the ligand VCAM-1 to its integrin receptor VLA-4 ($\alpha 4 \beta 1$), for example conditions as hereinbefore described, which comprises the administration to the patient of an effective amount of compound of the invention or a composition containing a compound of the invention. "Effective amount" is meant to describe an amount of compound of the present invention effective in inhibiting the interaction of the ligand VCAM-1 to its integrin receptor VLA-4 ($\alpha 4 \beta 1$), and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of formula (I), wherein $R^1$, $R^2$, $A^1$, $L^1$ and $Z^1$ are as hereinbefore defined, and where Y is carboxy, may be prepared by hydrolysis of esters of formula (I), wherein $R^1$, $R^2$, $A^1$, $L^1$ and $Z^1$ are as hereinbefore defined and Y is a —$CO_2R^{16}$ group (in which $R^{16}$ is alkyl, alkenyl or arylalkyl). The hydrolysis may conveniently be carried out by alkaline hydrolysis using a base, such as an alkali metal hydroxide, e.g. sodium hydroxide or lithium hydroxide, or an alkali metal carbonate, e.g. potassium carbonate, in the presence of an aqueous/organic solvent mixture, using organic solvents such as dioxan, tetrahydrofuran or methanol, at a temperature from about ambient temperature to about reflux temperature. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds of formula (I), wherein $R^1$, $R^2$, $A^1$, $L^1$ and $Z^1$ are as hereinbefore defined, and where Y is carboxy, may be prepared by acid catalysed removal of the tert-butyl group of tert-butyl esters of formula (I), wherein $R^1$, $R^2$, $A^1$, $L^1$ and $Z^1$ are as hereinbefore defined and Y is a —$CO_2R^{16}$ group (in which $R^{16}$ is tert-butyl), using standard reaction conditions, for example reaction with trifluoroacetic acid at a temperature at about room temperature.

As another example compounds of formula (I), wherein $R^1$, $R^2$, $A^1$, $L^1$ and $Z^1$ are as hereinbefore defined, and where Y is carboxy, may be prepared by hydrogenation of compounds of formula (I) wherein $R^1$, $R^2$, $A^1$, $L^1$ and $Z^1$ are as hereinbefore defined and Y is a —$CO_2R^{16}$ group (in which $R^{16}$ is arylmethyl, e.g. benzyl). The reaction may be carried out in the presence of ammonium formate and a suitable metal catalyst, e.g. palladium, supported on an inert carrier such as carbon, preferably in a solvent such as methanol or ethanol and at a temperature at about reflux temperature. The reaction may alternatively be carried out in the presence of a suitable metal catalyst, e.g. platinum or palladium optionally supported on an inert carrier such as carbon, preferably in a solvent such as methanol or ethanol. This reaction is most suitable for compounds of formula (I) where $L^1$ does not contain carbon-carbon multiple bonds.

In a process A compounds of formula (I), containing an amide bond may be prepared by coupling of an acid (or an acid halide) with an amine to give an amide bond using standard peptide coupling procedures as described hereinafter.

As an example of process A, compounds of formula (I) wherein $R^2$, $A^1$, $L^1$, Y and $Z^1$ are as hereinbefore defined and $R^1$ is a group selected from $R^3$—$Z^3$—, $R^3$—$L^2$—$R^4$—$Z^3$, $R^3$—$L^3$—$Ar^1$—$L^4$—$Z^3$— or $R^3$—$L^3$—$Ar^1$—$L^2$—$R^4$—$Z^3$—[in which $R^3$, $R^4$, $L^2$, $L^3$, $L^4$ and $Ar^1$ are as hereinbefore defined and $Z^3$ is C(=O)] may be prepared by:

(i) treating bromo-Wang resin (4-bromomethylphenoxylated styrene/divinylbenzene copolymer) with an acid of formula (II) wherein $A^1$, $Z^1$, $R^2$, and $L^1$ are as hereinbefore defined and $R^{17}$ is a suitable imino-protecting group, such as 9H-fluoren-9-ylmethoxylcarbonyl, in the presence of a tertiary amine, such as diisopropylethylamine, and cesium iodide, in an inert solvent, such as dimethylformamide, at a temperature at about room temperature, to give Resin A:

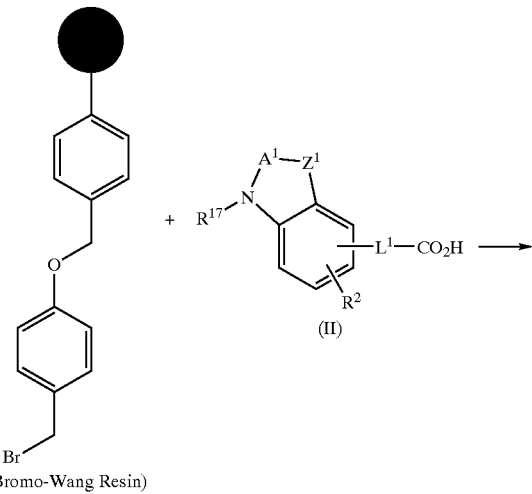

(Bromo-Wang Resin)

-continued

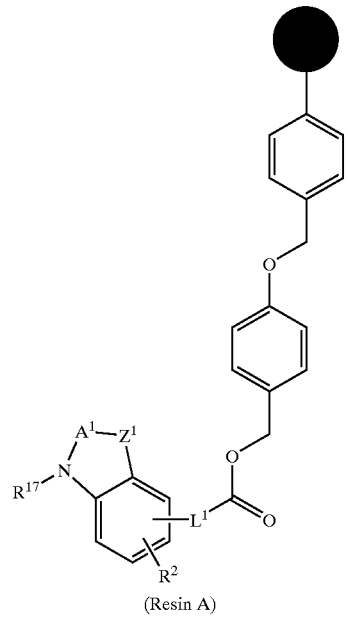

(Resin A)

where

represents the polymeric core comprising polystyrene crosslinked with 1% to 2% divinylbenzene;

(ii) treatment of Resin A with piperidine in an inert solvent, such as dimethyl formamide, and at a temperature at about room temperature to give Resin B:

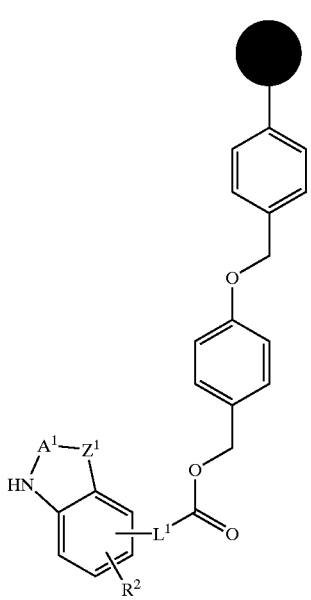

(Resin B)

wherein $A^1$, $Z^1$, $R^2$, $L^1$ and

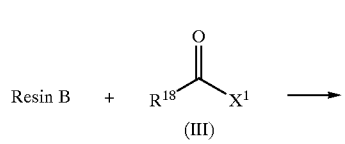

are as hereinbefore defined;

(iii) Reaction of Resin B with compounds of formula (III) wherein $R^{18}$ is $R^3$—, $R^3$—$L^2$—$R^4$—, $R^3$—$L^3$—$Ar^1$—$L^4$— or $R^3$—$L^3$—$Ar^1$—$L^2$—$R^4$— (in which $R^3$, $R^4$, $L^2$, $L^3$, $Ar^1$ and $L^4$ are as hereinbefore defined) and $X^1$ is a hydroxy group or a halogen, preferably chlorine, atom to give Resin C wherein $R^2$, $R^{18}$, $A^1$, $Z^1$, $L^1$ and

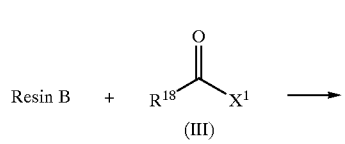

are as hereinbefore defined [When $X^1$ is a hydroxy group the reaction may be carried out using standard peptide coupling procedures for example coupling in the presence of O-(7-azabenzotriazol-1-yl)-1,1,3,3-tetramethyluronium hexafluorophosphate and triethylamine (or diisopropylethylamine) in tetrahydrofuran (or dimethylformamide), at room temperature. When $X^1$ is a halogen atom the acylation reaction may be carried out with the aid of a base, such pyridine, preferably in a solvent such as tetrahydrofuran and at a temperature at about room temperature];

Resin B + R^{18}—C(=O)—X^1 ⟶

(III)

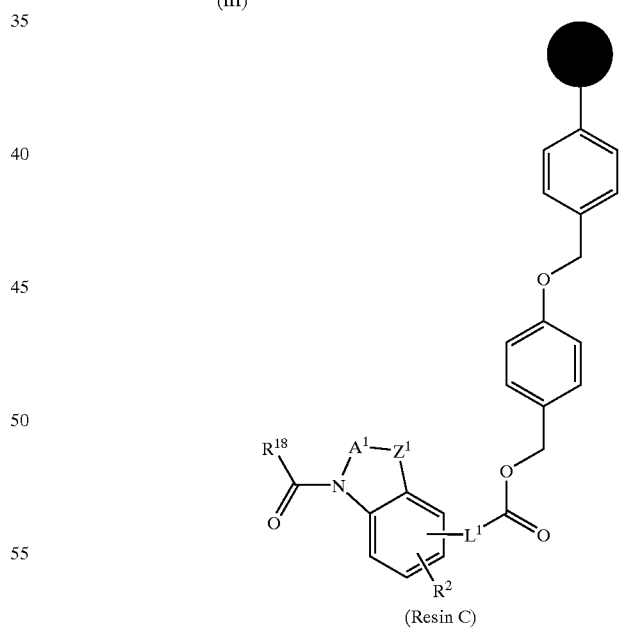

(Resin C)

(iv) treatment of Resin C with trifluoroacetic acid in an inert solvent, such as dichloromethane, and at a temperature at about room temperature.

As another example of process A, compounds of formula (I) wherein $R^1$, $R^2$, $A^1$, $Y$ and $Z^1$ are as hereinbefore defined and $L^1$ contains a —N($R^8$)—C(=O)—$R^9$ group (in which $R^8$ and $R^9$ are as hereinbefore defined) may be prepared by reaction of the corresponding compounds of formula (I)

wherein $R^1$, $R^2$, $A^1$, Y and $Z^1$ are as hereinbefore defined and $L^1$ contains a —NH($R^8$) group (in which $R^8$ is as hereinbefore defined) with acids (or acid chlorides) of formula $R^9$—C(=O)—$X^1$ wherein $R^9$ and $X^1$ are as hereinbefore defined, using standard coupling conditions, for example those described hereinbefore.

Esters of formula (I), wherein $R^1$, $R^2$, $A^1$ and $Z^1$ are as hereinbefore defined, Y is a —$CO_2R^{16}$ group (in which $R^{16}$ is as hereinbefore defined) and $L^1$ contains a —N($R^8$)—C(=O)—$R^9$ group (in which $R^8$ and $R^9$ are as herein before defined) may be similarly prepared from the corresponding esters of formula (I) where $L^1$ contains a —$NHR^8$ group (in which $R^8$ is as hereinbefore defined) by reaction with a compound of formula $R^9$—C(=O)—$X^1$ wherein $R^9$ and $X^1$ are as hereinbefore defined.

Esters of formula (I), wherein $R^2$, $A^1$, $L^1$ and $Z^1$ are as hereinbefore defined, $R^1$ is a group selected from $R^3$—$Z^3$—, $R^3$—$L^2$—$R^4$—$Z^3$—, $R^3$—$L^3$—$Ar^1$—$L^4$—$Z^3$— or $R^3$—$L^3$—$Ar^1$—$L^2$—$R^4$—$Z^3$— [in which $R^3$, $R^4$, $L^2$, $L^3$, $L^4$ and $Ar^1$ are as hereinbefore defined and $Z^3$ is C(=O)] and Y is a —$CO_2R^{16}$ group (in which $R^{16}$ is as hereinbefore defined), may be prepared by reacting a compound of formula (III) wherein $R^{18}$ is $R^3$—, $R^3$—$L^2$—$R^4$—, $R^3$—$L^3$—$Ar^1$—$L^4$— or $R^3$—$L^3$—$Ar^1$—$L^2$—$R^4$— (in which $R^3$, $R^4$, $L^2$, $L^3$, $Ar^1$ and $L^4$ are as hereinbefore defined) and $X^1$ is a hydroxy group, a halogen, preferably chlorine, atom with an amine of formula (IV):

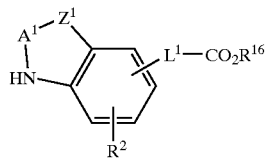

(IV)

wherein $R^2$, $A^1$, $L^1$, $Z^1$ and $R^{16}$ are as hereinbefore defined, using standard coupling conditions, for example those described hereinbefore.

Esters of formula (I), wherein $R^2$, $A^1$, $L^1$ and $Z^1$ are as hereinbefore defined, $R^1$ is a group selected from $R^3$—$Z^3$—, $R^3$—$L^2$—$R^4$—$Z^3$—, $R^3$—$L^3$—$Ar^1$—$L^4$—$Z^3$— or $R^3$—$L^3$—$Ar^1$—$L^2$—$R^4$—$Z^3$— (in which $R^3$, $R^4$, $L^2$, $L^3$, $L^4$ and $Ar^1$ are as hereinbefore defined and $Z^3$ is $SO_2$) and Y is a —$CO_2R^{16}$ group (in which $R^{16}$ is as hereinbefore defined), may be prepared by sulphonylation of a compound of formula (IV), wherein $R^2$, $A^1$, $L^1$, $Z^1$ and $R^{16}$ are as hereinbefore defined, using a sulphonyl chloride of formula (V):

$R^{18}$—$SO_2$—Cl  (V)

wherein $R^{18}$ is as defined hereinabove. The reaction is preferably carried out with the aid of a base, such as a tertiary amine, for example triethylamine, preferably in a solvent such as tetrahydrofuran and at a temperature from about 0° C. to about room temperature.

Esters of formula (I), wherein $R^1$, $R^2$, $A^1$ and $Z^1$ are as hereinbefore defined, Y is a —$CO_2R^{16}$ group (in which $R^{16}$ is as hereinbefore defined) and $L^1$ contains a —N($R^8$)—$SO_2$—$R^9$ group (in which $R^8$ and $R^9$ are as hereinbefore defined), may be similarly prepared from the corresponding esters of formula (I) where $L^1$ contains a —$NHR^8$ group (in which $R^8$ is as hereinbefore defined) by reaction with sulphonyl chlorides of formula $R^9$—$SO_2Cl$ wherein $R^9$ is as hereinbefore defined.

Esters of formula (I), wherein $R^2$, $A^1$, $L^1$ and $Z^1$ are as hereinbefore defined, $R^1$ is $R^3$—$L^3$—$Ar^1$—$L^4$—$Z^3$— (in which $R^3$, $L^3$, $L^4$ and $Ar^1$ are as hereinbefore defined, $Z^3$ is NHC(=O) and Y is a —$CO_2R^{16}$ group (in which $R^{16}$ is as hereinbefore defined), may be prepared by reacting a compound of formula (IV), wherein $R^2$, $A^1$, $L^1$, $Z^1$ and $R^{16}$ are as hereinbefore defined, with an isocyanate of formula (VI):

$R^3$—$L^3$—$Ar^1$—$L^4$—NCO  (VI)

wherein $R^3$, $L^3$, $L^4$ and $Ar^1$ are as hereinbefore defined. The reaction is preferably carried out with the aid of a base, such as a tertiary amine, for example triethylamine, preferably in a solvent such as dichloromethane, and at a temperature at about room temperature.

Esters of formula (I), wherein $R^2$, $A^1$, $L^1$ and $Z^1$ are as hereinbefore defined, $R^1$ is $R^3$—$Z^3$— [in which $R^3$ is as hereinbefore defined and $Z^3$ is NHC(=O)] may be similarly prepared by reacting a compound of formula (IV), wherein $R^2$, $A^1$, $L^1$, $Z^1$ and $R^{16}$ are as hereinbefore defined, with an isocyanate of formula $R^3$—NCO wherein $R^3$ is as hereinbefore defined.

Esters of formula (I), wherein $R^2$, $A^1$, $L^1$ and $Z^1$ are as hereinbefore defined, $R^1$ is a group selected from $R^3$—$Z^3$— (in which $R^3$ is as hereinbefore defined [except aryl and heteroaryl] and $Z^3$ is a direct bond), $R^3$—$L^2$—$R^4$—$Z^3$—, $R^3$—$L^3$—$Ar^1$—$L^4$—$Z^3$—, or $R^3$—$L^3$—$Ar^1$—$L^2$—$R^4$—$Z^3$— (in which $R^3$, $L^2$, $L^3$, $L^4$ and $Ar^1$ are as hereinbefore defined, and $Z^3$ is a direct bond) and Y is a —$CO_2R^{16}$ group (in which $R^{16}$ is as hereinbefore defined), may be prepared by alkylation of a compound of formula (IV), wherein $R^2$, $A^1$, $L^1$, $Z^1$ and $R^{16}$ are as hereinbefore defined, with a compound of formula (VII):

$R^3$—$X^2$  (VII)

wherein $R^3$ is as immediately hereinbefore defined and $X^2$ is a halogen, preferably bromine, atom. The alkylation may for example be carried out in the presence of a base, such as an alkali metal hydride, e.g. sodium hydride, in dimethylformamide, or dimethyl sulphoxide, at a temperature from about 0° C. to about 100° C.

Esters of formula (I), wherein $R^1$, $R^2$, $A^1$ and $Z^1$ are as hereinbefore defined, Y is a —$CO_2R^{16}$ group (in which $R^{16}$ is as hereinbefore defined) and $L^1$ contains a —$NHR^8$ group (in which $R^8$ is alkyl, arylalkyl, cycloalkylalkyl, heteroarylalkyl or heterocycloalkylalkyl), may be similarly prepared by alkylation of the corresponding derivatives of formula (I) where $L^1$ contains a —$NH_2$ group, with the appropriate alkyl (or arylalkyl, cycloalkylalkyl, heteroarylalkyl or heterocycloalkylalkyl) halide.

Esters of formula (I), wherein $R^2$, $A^1$, $L^1$ and $Z^1$ are as hereinbefore defined, $R^1$ is a group selected from $R^3$—$Z^3$— [in which $R^3$ is as herein defined and $Z^3$ is OC(=O)] may be prepared by reaction of a compound of formula (IV), wherein $R^2$, $A^1$, $L^1$, $Z^1$ and $R^{16}$ are as hereinbefore defined, with a compound of formula (VIII):

$R^3$—O—C(=O)—$X^3$  (VIII)

wherein $R^3$ is as hereinbefore defined and $X^3$ is a halogen, preferably chlorine atom, in the presence of a suitable base, such as triethylamine or pyridine, and at a temperature from about 0° C. to about room temperature.

Esters of formula (I), wherein $R^1$, $R^2$, $A^1$ and $Z^1$ are as hereinbefore defined, Y is a $CO_2R^{16}$ group (in which $R^{16}$ is as hereinbefore defined) and $L^1$ contains a —N($R^8$)—C(=O)—$OR^9$ group (in which $R^8$ and $R^9$ are as herein before defined), may be similarly prepared from the corresponding derivatives of formula (I) where $L^1$ contains a —$NHR^8$ group (in which $R^8$ is as hereinbefore defined) by reaction with compounds of formula R⁹O—C(=O)—X³ wherein R⁹ and X³ are as hereinbefore defined.

Esters of formula (I), wherein R¹, R², A¹ and Z¹ are as hereinbefore defined, Y is a —CO₂R¹⁶ group (in which R¹⁶ is as hereinbefore defined) and L¹ is

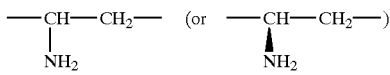

may be prepared by hydrogenation of the corresponding derivatives of formula (I), where L¹ is

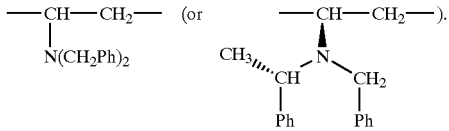

The reaction may be carried out in the presence of formic acid and a suitable metal catalyst, e.g. palladium, supported on an inert carrier such as carbon, at a temperature at about 60° C. The reaction may conveniently be carried out in the presence of a suitable metal catalyst, e.g. platinum or palladium optionally supported on an inert carrier such as carbon, preferably in a solvent such as methanol or ethanol.

Esters of formula (I), wherein R¹, R², A¹ and Z¹ are as herein before defined, Y is a —CO₂R¹⁶ group (in which R¹⁶ is as hereinbefore defined) and L¹ is a

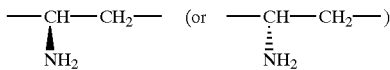

linkage, may also be obtained from the racemic mixture following standard recrystallisation of a suitable salt (for example recrystallisation of the tartrate salt), or by the application of standard enzymatic resolution procedures (for example those described by Soloshonok, V. A., et. al., Tetrahedron: Asymmetry 6 (1995) 7, 1601–1610).

Esters of formula (I), wherein R¹, R², A¹ and Z¹ are as hereinbefore defined, Y is a —CO₂R¹⁶ group (in which R¹⁶ is as hereinbefore defined) and L¹ is a

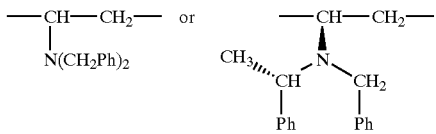

linkage, may be prepared by reacting an ester of formula (I), wherein R¹, R², A¹ and Z¹ are as hereinbefore defined, Y is a —CO₂R¹⁶ group (in which R¹⁶ is as hereinbefore defined) and L¹ is a —CH=CH— linkage, with an alkali metal hydride, such as sodium hydride in an inert solvent, e.g. tetrahydrofuran, and at a temperature at about room temperature, and subsequent reaction with the anion derived from treating dibenzylamine, or (S)-N-benzyl-α-methylbenzylamine, with butyllithium, at a temperature at about −78° C.

Esters of formula (I), wherein R¹, R², A¹ and Z¹ are as hereinbefore defined, Y is a —CO₂R¹⁶ group (in which R¹⁶ is as hereinbefore defined) and L¹ contains an alkenylene, alkynylene or cycloalkenylene in which the aliphatic carbon-carbon multiple bond is attached directly to the phenyl moiety in formula (X), may be prepared by coupling of compounds of formula (IX):

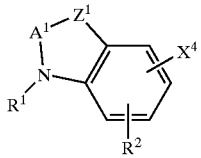

wherein R¹, R², A¹ and Z¹ are as hereinbefore defined and X⁴ is a halogen, preferably bromine or iodine, atom with a compound of formula (X):

wherein R¹⁶ is as hereinbefore defined and R¹⁹ is alkenyl, alkynyl or cycloalkenyl. When X⁴ is a bromine or iodine atom the reaction may be conveniently carried out in the presence of palladium acetate, a triarylphosphine, such as tri-o-tolylphosphine, and a tertiary amine, such as tributylamine, at a temperature up to about 110° C. This reaction is particularly suitable for the preparation of esters of formula (I) in which L¹ is vinylene. When X⁴ is a chlorine atom the reaction may be conveniently carried out in the presence of sodium iodide, nickel bromide, palladium(0) bis(dibenzylideneacetone), a triarylphosphine, such as tri-o-tolylphosphine, and a tertiary amine, such as tributylamine, at a temperature up to about 110° C.

According to a further feature of the present invention, compounds of the invention may be prepared by interconversion of other compounds of the invention.

For example compounds of formula (I), wherein R¹, R², A¹, L¹ and Z¹ are as hereinbefore defined and Y is a group —C(=O)—NHOH, may be prepared by reacting compounds of formula (I), wherein R¹, R², A¹, L¹ and Z¹ are as hereinbefore defined and Y is carboxy, with hydroxylamine using standard peptide coupling procedures such as treatment with a carbodiimide, for example dicyclohexylcarbodiimide, in the presence of triethylamine, in an inert solvent such as dichloromethane or tetrahydrofuran and at a temperature at about room temperature. The coupling may also be carried out using 1-hydroxybenzotriazole and 1-(3-dimethylaminopropyl)-3-ethylcarbodiimide in dichloromethane at room temperature. The preparation may also be carried out using an O-protected hydroxylamine such as O-(trimethylsilyl)hydroxylamine, O-(t-butyldimethylsilyl)-hydroxylamine, or O-(tetrahydropyranyl)hydroxylamine followed by treatment with acid.

As another example of the interconversion process, compounds of formula (I) containing sulphoxide linkages may be prepared by the oxidation of corresponding compounds containing —S— linkages. For example, the oxidation may conveniently be carried out by means of reaction with a peroxyacid, e.g. 3-chloroperbenzoic acid, preferably in an inert solvent, e.g. dichloromethane, preferably at or near room temperature, or alternatively by means of potassium hydrogen peroxomonosulphate in a medium such as aqueous methanol, buffered to about pH5, at temperatures between about 0° C. and room temperature. This latter method is preferred for compounds containing an acid-labile group.

As another example of the interconversion process, compounds of formula (I) containing sulphone linkages may be prepared by the oxidation of corresponding compounds containing —S— or sulphoxide linkages. For example, the oxidation may conveniently be carried out by means of reaction with a peroxyacid, e.g. 3-chloroperbenzoic acid, preferably in an inert solvent, e.g. dichloromethane, preferably at or near room temperature.

As another example of the interconversion process, compounds of formula (I), wherein $R^1$, $R^2$, $A^1$, $Z^1$ and Y are as hereinbefore defined, and $L^1$ is optionally substituted alkylene, may be prepared by hydrogenation of the corresponding compounds of formula (I) in which $L^1$ is the corresponding optionally substituted alkenylene. The hydrogenation may be carried out using hydrogen (optionally under pressure) in the presence of a suitable metal catalyst, e.g. platinum or palladium optionally supported on an inert carrier such as carbon, preferably in a solvent such as methanol or ethanol, and at a temperature at about room temperature.

As another example of the interconversion process, compounds of formula (I), wherein $R^1$, $R^2$, $A^1$, $L^1$ and $Z^1$ are as hereinbefore defined, $L^1$ is an alkylene linkage substituted by —$CONY^4Y^5$ and Y is carboxy, may be prepared by reacting compounds of formula (I), wherein $R^1$, $R^2$, $A^1$, $L^1$ and $Z^1$ are as hereinbefore defined, $L^1$ is an alkylene linkage substituted by —$CO_2H$ and Y is carboxy, with an anhydride, such as trifluoroacetic anhydride, in an inert solvent e.g. tetrahydrofuran, followed by treatment with an amine $HNY^4Y^5$.

As another example of the interconversion process, compounds of formula (I), wherein $R^1$, $R^2$, $A^1$, $L^1$ and Y are as hereinbefore defined, and $Z^1$ is C(=O) may be prepared by oxidation of compounds of formula (I), wherein $R^1$, $R^2$, $A^1$, $L^1$ and Y are as hereinbefore defined, and $Z^1$ is $CH_2$. For example the oxidation may conveniently be carried out by reaction with potassium permanganate.

As another example of the interconversion process, compounds of formula (I), wherein $R^1$, $R^2$, $A^1$, $L^1$ and Y are as hereinbefore defined, and $Z^1$ is CH(OH) may be prepared by reduction of compounds of formula (X), wherein $R^1$, $R^2$, $A^1$, $L^1$ and Y are as hereinbefore defined, and $Z^1$ is C(=O). For example the reduction may conveniently be carried out by reaction with sodium borohydride in aqueous ethanol at a temperature at about room temperature.

As another example of the interconversion process, compounds of the invention containing a heterocyclic group wherein the hetero atom is a nitrogen atom may be oxidised to their corresponding N-oxides. The oxidation may conveniently be carried out by means of reaction with a mixture of hydrogen peroxide and an organic acid, e.g. acetic acid, preferably at or above room temperature, for example at a temperature of about 60–90° C. Alternatively, the oxidation may be carried out by reaction with a peracid, for example peracetic acid or m-chloroperoxybenzoic acid, in an inert solvent such as chloroform or dichloromethane, at a temperature from about room temperature to reflux, preferably at elevated temperature. The oxidation may alternatively be carried out by reaction with hydrogen peroxide in the presence of sodium tungstate at temperatures between room temperature and about 60° C.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Reference Examples or their obvious chemical equivalents.

Compounds of formula (III) wherein $R^{18}$ is $R^3$—$L^3$—$Ar^1$—$L^4$— group (in which $R^3$, $R^4$, $L^2$, $L^3$, $L^4$ and $Ar^1$ are as hereinbefore defined) may be prepared by the application or adaptation of methods described in the specification of International Patent Application Publication No. WO 96/22966.

Acids of formula (III) wherein $R^{18}$ is $R^3$—$L^3$—$Ar^1$—$L^4$— (in which $R^3$ and $L^4$ are as defined above, $L^3$ is NH, $Ar^1$ is

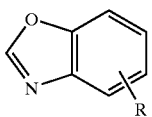

(in which R is as hereinbefore defined) and $X^1$ is a hydroxy group may be prepared by reaction of compounds of formula (1):

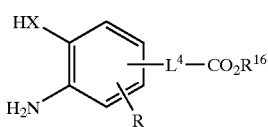     (1)

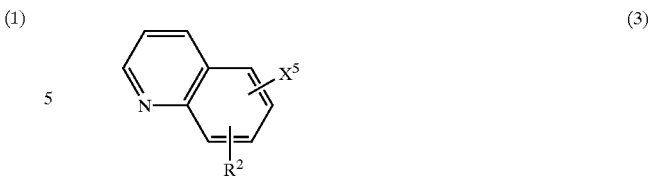     (3)

wherein R and $L^4$ are as hereinbefore defined, $R^{16}$ is lower alkyl and X is O, with isocyanates of formula $R^3$—N=C=O (in which $R^3$ is as hereinbefore defined) in ethanol and at room temperature, followed by reaction with a carbodiimide, such as dicyclohexylcarbodiimide or diisopropylcarbodiimide in ethanol and at a temperature from about room temperature to about reflux temperature, and subsequent hydrolysis using standard conditions, for example those described hereinbefore.

Acids of formula (III) wherein $R^{18}$ is $R^3$—$L^3$—$Ar^1$—$L^4$— (in which $R^3$ and $L^4$ are as hereinbefore defined, $Ar^1$ is

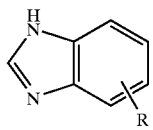

(in which R is as hereinbefore defined), $L^3$ is NH and $X^1$ is hydroxy may be similarly prepared from compounds of formula (1) wherein R, $L^4$ and $R^{16}$ are as hereinbefore defined and X is NH.

Acid chlorides of formula (III) wherein $R^{18}$ is as hereinbefore defined and $X^1$ is a chlorine atom may be prepared from the corresponding acids of formula (II) wherein $R^{18}$ is as hereinbefore defined and $X^1$ is hydroxy, by the application of standard procedures for the conversion of acids to acid chlorides for example by reaction with oxalyl chloride.

Compounds of formula (IV) wherein $R^2$ and $R^{16}$ are as hereinbefore defined, $Z^1$ is $CH_2$, $L^1$ is as defined hereinbefore (except where $L^1$ contains a non-aromatic carbon-carbon multiple bond) and $A^1$ is an ethylene linkage, may be prepared by hydrogenation of the corresponding quinoline analogues of formula (2):

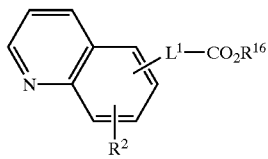     (2)

wherein $R^2$ and $R^{16}$ are as hereinbefore defined and $L^1$ is as defined immediately hereinbefore, in the presence of a suitable metal catalyst The reduction may conveniently be carried out at a pressure of 50 bars of hydrogen, in the presence of 5% rhodium in carbon powder as catalyst, in hydrochloric acid, and at a temperature at about room temperature.

Compounds of formula (2), wherein $R^2$ and $R^{16}$ are as hereinbefore defined and $L^1$ is alkylene may be prepared by an electrochemical coupling reaction between a compound of formula (3):

wherein $R^2$ is as hereinbefore defined and $X^5$ is iodo, or preferably bromo, and an alkenoic ester of formula (X) wherein $R^{16}$ is as hereinbefore defined and $R^{20}$ is alkenyl. The reaction may conveniently be carried out in the presence of nickel salt catalyst, such as nickel bromide trihydrate, tetrabutylammonium bromide, tetrabutylammonium iodide and 1,2-dibromoethane, in an inert solvent, or a mixture of inert solvents, such as dimethylformamide and pyridine, and at a temperature at about 60° C. This reaction is particularly suitable for the preparation of compounds of formula (1) in which $L^1$ is ethylene.

Compounds of formula (2), wherein $R^2$ and $R^{16}$ are as defined hereinbefore and $L^1$ is an alkylene linkage substituted by —$CH_2OR^3$ (for example —$CH_2OCH_3$) may be prepared from compounds of formula (2), wherein $R^2$ and $R^{16}$ are as defined hereinbefore and $L^1$ is an alkenylene linkage where the carbon-carbon double bond is substituted by a methyl group, using the following standard reaction procedures: (i) allylic bromination with N-bromosuccinimide; (ii) displacement of the allylic bromo with $OR^3$ by reaction with an alkali metal salt of formula $R^3O^-M^+$ (for example sodium methoxide); (iii) hydrogenation.

Compounds of formula (2), wherein $R^2$ and $R^{16}$ are as defined hereinbefore and $L^1$ is alkenylene, alkynylene or cycloalkenylene in which the carbon-carbon multiple bond is attached directly to the phenyl moiety in formula (I), may be prepared by reacting a compound of formula (3) wherein $R^2$ is as hereinbefore defined and $X^5$ is an iodine, or preferably a bromine, atom with a compound of formula (X) wherein $R^{16}$ and $R^{19}$ are as hereinbefore defined using standard Heck coupling reaction conditions, for example reaction in the presence of palladium acetate, triphenylphosphine and tributylamine at a temperature up to about 120° C.

Compounds of formula (2), wherein $R^2$ and $R^{16}$ are as defined hereinbefore and $L^1$ is an optionally substituted arylene or an optionally substituted heteroaryldiyl linkage, may be prepared by reacting a compound of formula (3) wherein $R^2$ is as hereinbefore defined and $X^5$ is iodo or bromo with a compound of formula (4):

     (4)

wherein $R^{16}$ are as defined hereinbefore and $L^1$ is an optionally substituted arylene or an optionally substituted heteroaryldiyl linkage in the presence of a complex metal catalyst such as tetrakis(triphenylphosphine)palladium(0), using standard reaction conditions, for example those described by Trecourt et al, Tetrahedron, 51(1995) 43, pages 11743–11750.

Compounds of formula (IV) or (2) wherein $R^2$ and $R^{16}$ are as defined hereinbefore and $L^1$ is

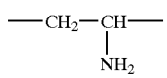

may be prepared by standard methodology for the preparation of α-amino-acids for example those described in Organic Syntheses Based On Name Reactions and Unnamed Reactions, A. Hassner and C. Stumer, Pergamon, pages 275 and 374.

Compounds of formula (2) wherein $R^2$ and $R^{16}$ are as defined hereinbefore and $L^1$ is

may be prepared by reaction of compounds of formula (5):

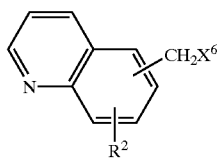
(5)

wherein $R^2$ is as hereinbefore defined and $X^6$ is a bromine or chlorine atom with the anion derived from reaction of (2R)-(−)-2,5-dihydro-3,6-dimethoxy-2-isopropylpyrazine with butyllithium according to the method described by D. L. Boger and D. Yohannes, J. Org. Chem. [JOCEAH], 1990, 55, for the preparation of compound 31 on page 6010.

Compounds of formula (IV) wherein $R^2$, $R^{16}$, $A^1$ and $Z^1$ are as hereinbefore defined and $L^1$ is

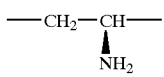

may be similarly prepared from compounds of formula (6):

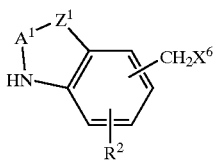
(6)

wherein $R^2$, $A^1$, $X^6$ and $Z^1$ are as hereinbefore defined.

Compounds of formula (6) wherein $R^2$, $A^1$, $X^6$ are as hereinbefore defined and $Z^1$ is $CH_2$ may be prepared by the application or adaptation of methodologies described in U.S. Pat. No. 4,156,734, for example the preparation of the N-protected dihydroindole, 1-benzoyl-5-chloromethyl-2,3-dihydro-1H-indole from 1-benzoyl-2,3-dihydro-1H-indole (Beilstein, 20, 257) is described as Example 23A.

Compounds of formula (IV) wherein $R^2$, $R^{16}$ and $L^1$ are as hereinbefore defined, $Z^1$ is $CH_2$, $A^1$ is a straight chain $C_{1-3}$alkylene linkage and $L^1$ contains an alkenylene, alkynylene or cycloalkenylene group in which the aliphatic carbon-carbon multiple bond is attached directly to the phenyl moiety in formula (IV), may be prepared by coupling of compounds of formula (7):

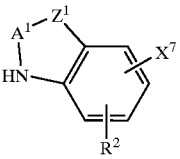
(7)

wherein $R^2$ is as hereinbefore defined, $A^1$ is a straight chain $C_{1-3}$alkylene linkage, $X^7$ is a halogen, preferably bromine or iodine, atom and $Z^1$ is $CH_2$ with a compound of formula (X) wherein $R^{16}$ is as hereinbefore defined and $R^{19}$ is alkenyl, alkynyl or cycloalkenyl. The cross-coupling reaction may conveniently be carried out in the presence of palladium acetate and tris(o-tolyl)phosphine using standard coupling conditions such as those described hereinbefore. In this reaction a suitable protecting group for the NH group is for example a tertiary-butyloxycarbonyl group.

Compounds of formula (IV) wherein $R^2$, $R^{16}$ and $L^1$ are as hereinbefore defined, $Z^1$ is $CH_2$, $A^1$ is a straight chain $C_{1-3}$alkylene linkage and $L^1$ contains an alkylene or cycloalkylene group may be prepared by hydrogenation of the corresponding compounds of formula (IV) in which $L^1$ contains an alkenylene, alkynylene or cycloalkenylene group using standard hydrogenation procedures for example those described hereinbefore.

Compounds of formula (7) wherein $R^2$ is hydrogen, $A^1$ is ethylene, $Z^1$ is $CH_2$ and $X^6$ is an iodine atom attached to the 6 position of the tetrahydroquinoline ring may be prepared by iodination of 1,2,3,4-tetrahydroquinoline with iodine monochloride in acetic acid at a temperature at about room temperature.

2,3-Dihydro-4(1H)-quinolones of formula (7) wherein $R^2$ is hydrogen, $A^1$ is ethylene, $Z^1$ is C(=O) and $X^6$ is a halogen atom attached to the 6 position of the tetrahydroquinoline ring may be prepared by the application or adaptation of the Fries-type acid catalysed rearrangement of 1-arylazetidin-2-ones described by S. Kano et. at. J. Chem. Soc., Perkin Trans. 1 1098, 10 pages 2105–2111.

Compounds of formula (IV) wherein $R^2$, $R^{16}$, $L^1$ and $A^1$ are as hereinbefore defined and $Z^1$ is $CH_2$, and $L^1$ is a

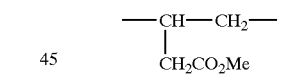

linkage, may be prepared by reacting an ester of formula (I), wherein $R^1$, $R^2$ and $A^1$ are as hereinbefore defined, Y is a —$CO_2R^{16}$ group (in which $R^{16}$ is as hereinbefore defined), $Z^1$ is $CH_2$, and $L^1$ is a —CH=CH— linkage, with dimethyl malonate, in the presence of an alkali metal alkoxide, such as sodium methoxide, in methanol and at a temperature at about reflux temperature.

Compounds of formula (IV) wherein $R^2$, $R^{16}$ and $A^1$ are as hereinbefore defined and $Z^1$ is $CH_2$, and the moiety —$L^2$—Y is

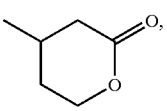

may be prepared coupling of compounds of formula (8) wherein $R^2$ and $A^1$ are as hereinbefore defined, and $X^6$ is a halogen, preferably bromine or iodine, atom with 5,6-dihydropyran-2-one in the presence of tetrakis (triphenylphosphine)palladium(0) and triethylamine in an inert solvent, such as dimethylformamide, at a temperature at about 95° C. and in a sealed vessel.

Compounds of formula (IV) wherein $R^2$, $R^{16}$, $L^1$ and $A^1$ are as hereinbefore defined and $Z^1$ is $CH_2$, and $L^1$ contains a —N($R^8$)—C(=O)—$R^9$ group (in which $R^8$ and $R^9$ are as hereinbefore defined) may be prepared from the corresponding compounds of formula (IV) where $L^1$ contains a —NH$R^8$ group (in which $R^8$ is as hereinbefore defined) by reaction with a compound of formula $R^9$—C(=O)—$X^1$ wherein $R^9$ and $X^1$ are as hereinbefore defined, using standard peptide coupling procedures for example those described hereinbefore.

Compounds of formula (IV) wherein $R^1$, $R^2$, $A^1$ and $Z^1$ are as hereinbefore defined, Y is a —CO$_2$$R^{16}$ group (in which $R^{16}$ is as hereinbefore defined) and $L^1$ is

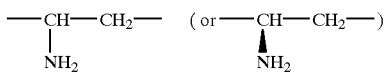

may be prepared by hydrogenation of the corresponding derivatives of formula (IV), where $L^1$ is

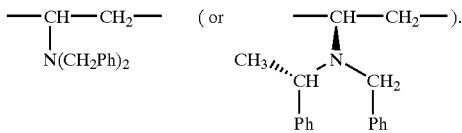

The reaction may be carried out in the presence of formic acid and a suitable metal catalyst, e.g. palladium, supported on an inert carrier such as carbon, at a temperature at about 60° C. The reaction may conveniently be carried out in the presence of a suitable metal catalyst, e.g. platinum or palladium optionally supported on an inert carrier such as carbon, preferably in a solvent such as methanol or ethanol.

Compounds of formula (IV) wherein $R^1$, $R^2$, $A^1$ and $Z^1$ are as hereinbefore defined, Y is a —CO$_2$$R^{16}$ group (in which $R^{16}$ is as hereinbefore defined) and $L^1$ is a

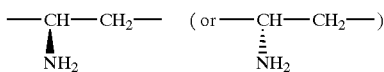

linkage, may also be obtained from the racemic mixture following standard recrystallisation of a suitable salt (for example recrystallisation of the tartrate salt), or by the application of standard enzymatic resolution procedures (for example those described by Soloshonok, V. A., et. al., Tetrahedron: Asymmetry 6 (1995) 7, 1601–1610).

Compounds of formula (IV) wherein $R^1$, $R^2$, $A^1$ and $Z^1$ are as hereinbefore defined, Y is a —CO$_2$$R^{16}$ group (in which $R^{16}$ is as hereinbefore defined) and $L^1$ is a

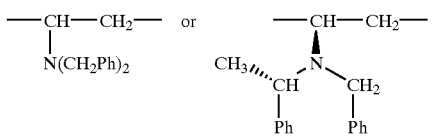

linkage, may be prepared by reacting compounds of formula (IV) wherein $R^1$, $R^2$, $A^1$ and $Z^1$ are as hereinbefore defined, Y is a —CO$_2$$R^{16}$ group (in which $R^{16}$ is as hereinbefore defined) and $L^1$ is a —CH=CH— linkage, with an alkali metal hydride, such as sodium hydride, in an inert solvent, e.g. tetrahydrofuran, and at a temperature at about room temperature, and subsequent reaction with the anion derived from treating dibenzylamine, or (S)-N-benzyl-α-methylbenzylamine, with butyllithium, at a temperature at about −78° C.

Compounds of formula (IX) wherein $R^1$, $R^2$ and $X^4$ are as described hereinbefore, $A^1$ is methylene and $Z^1$ is C(=O) may be prepared by the application or adaptation of methods described by Bourlot, A. S. et. al., Synthesis, 1994, 4, 411–416.

Compounds of formula (IX) wherein $R^1$, $R^2$ and $X^4$ are as described hereinbefore, $A^1$ is ethylene and $Z^1$ is C(=O) may be prepared by the application or adaptation of methods described in U.S. Pat. No. 4,421,918.

Intermediates of formulae (IV), (IX) and (2) are novel compounds and, as such, they and processes described herein for their preparation constitute further features of the present invention.

The present invention is further Exemplified but not limited by the following illustrative Examples and Reference Examples.

In the nuclear magnetic resonance spectra (NMR) the chemical shifts are expressed in ppm relative to tetramethylsilane. Abbreviations have the following significances: s=singlet; d=doublet; t=triplet; m=multiplet.

Mass spectra (MS) for Example 4(b) and for the Reference Examples (unless otherwise indicated) were recorded on a Micromass Platform II mass spectrometer fitted with an Electrospray source and an HP1100 liquid chromatograph; using a mixture of acetonitrile and water (1:1, v/v) as the mobile phase, a flow rate of 0.3 ml/minute, an injection volume of 200 µl, a run time of 2.0 minutes, a scan range of 150–850 Daltons Positive/Negative, a scan time of 2.0 seconds, an ESI voltage of 3.5 Kv, an ESI pressure of 20 n/m2 Nitrogen.

Mass spectra [MS (ES$^+$)] for the Examples 1–12 were recorded on a Micromass LCT Mass Spectrometer (Orthogonal Acceleration Time of Flight Mass Spectrometer), with the Z-Flow Atmospheric pressure ionisation source operating in positive ion electrospray mode (ES$^+$), connected to an HP1100 liquid chromatograph. The conditions used were as follows: 3 micron Luna C18 HPLC column (30 mm×4.6 mm) operated under gradient elution conditions with a mixture of acetonitrile and water as the mobile phase gradient: 0.00 minutes, 95% water:5% acetonitrile; 0.50 minutes, 95% water:5% acetonitrile; 4.50 minutes, 5% water:95% acetonitrile; 5.00 minutes, 5%water:95% acetonitrile; 5.50 minutes, 95%water:5% acetonitrile; flow rate 2 ml/minute with approximately 200 ml/minute split to the Mass Spectrometer; injection volume 10–40 ml; in line Diode Array detection (220–450 nm), in line Evaporative light scattering (ELS) detection ELS—temperature 50° C., Gain 8—1.8 ml/minute; Source temperature 150° C.

EXAMPLE 1

3-(1-{[3-Methoxy-4-(3-[2-methylphenyl]-ureido)-phenyl]-acetyl}-1,2,3,4-tetrahydro-quinolin-6-yl)-propionic Acid A solution of ethyl 3-(1-{[3-methoxy-4-[(2-toluidinocarbonyl)amino]phenyl}acetyl)-1,2,3,4-tetrahydroquinolin-6-yl)-propanoate (0.24 g, Reference Example 1) in anhydrous ethanol (4 ml), at 20° C., was treated dropwise with a solution of lithium hydroxide monohydrate (33 mg) in distilled water (1 ml). After stirring for 3 hours at 20° C. the reaction mixture was evaporated under reduced pressure (2.7 kPa) at 40° C. The residue was treated with distilled water (35 ml) and the resulting solution was washed twice with diethyl ether (20 ml), then acidified to pH 3 by addition of hydrochloric acid (0.8 ml, 1N) and then extracted twice with ethyl acetate (25 ml). The combined organic extracts were washed twice with water (5 ml), then dried over magnesium sulfate and then evaporated under reduced pressure (2.7 kPa) at 40° C. The resulting white foamy solid (191 mg) was subjected to chromatography on silica gel plates (4 plates, 20×20 cm, thickness=0.5 mm), eluting with a mixture of dichloromethane and methanol (9:1, v/v) to give the title compound (148 mg) as a white foamy solid. $^1$H NMR (300 MHz, $(CD_3)_2SO$): δ 1.81 (m, 2H); 2.27 (s, 3H); from 2.45–2.70 (m, 4H), 2.82 (t, J=7.5 Hz, 2H); 3.72 (t, J=6.5 Hz, 2H); 3.82 (s, 2H); 3.87 (s, 3H); 6.60–7.50 (m, 8H); 7.82 (d, J=8 Hz, 1H); 8.05 (d, J=8 Hz, 1H); 8.50 (s, 1H); 8.60 (s, 1H). MS (Electron Impact recorded on a Finnigan SSQ 7000 spectrometer at 70 eV) 501 ($M^+$).

EXAMPLE 2

(a) (R/S) 3-(1-{[3-Methoxy-4-(3-o-tolyl-ureido)-phenyl]-acetyl}-2,3-dihydro-1H-indol-5-yl)-butyric Acid A solution of ethyl (R/S) 3-(1-{[3-methoxy-4-(3-o-tolyl-ureido)-phenyl]-acetyl}-2,3-dihydro-1H-indol-5-yl)-butyrate [2.8 g, Reference Example 4(a)] in methanol (about 150 ml) was treated with aqueous sodium hydroxide solution (15 ml, 1M). The mixture was warmed at about 50° C. for 3 hours, then treated with a further aliquot of aqueous sodium hydroxide solution (7.5 ml). After a further 2–3 hours at 50° C. TLC analysis indicated complete reaction. The bulk of the methanol was removed by evaporation and the residue was diluted with hydrochloric acid (about 200 ml, 1M). The resulting mixture was stirred for about 30 minutes, then the solid was collected by filtration, washed with water, and dried to give the title compound (2.3 g) as a very light orange powder. LC-MS: $R_T$=3.84 minutes (100% total area by ELS); MS ($ES^+$) 502 ($MH^+$), 524 ($MNa^+$).

(b) By proceeding in a similar manner to Example 2(a) but using ethyl (R/S) 3-{1-[(2-o-tolylamino-3H-benzimidazol-5-yl)-acetyl]-1,2,3,4-tetrahydro-quinolin-6-yl}-butyrate (Reference Example 4(k)] and carrying out the hydrolysis at room temperature there was prepared (R/S) 3-{1-[(2-o-tolylamino-3H-benzimidazol-5-yl)-acetyl]-1,2,3,4-tetrahydro-quinolin-6-yl}-butyric acid as a white solid. [Elemental analysis: C, 71.11; H, 6.55; N, 8.66%. Calculated for $C_{30}H_{31}N_3O_4.0.5H_2O$: C, 71.15; H, 6.32; N, 8.30%]. MS ($ES^+$) 498 ($MH^+$).

(c) By proceeding in a similar manner to Example 2(a) but using a suspension of ethyl (R/S) 3-(1-{[3-methoxy-4-(3-o-tolyl-ureido)-phenyl]-acetyl}-2,3-dihydro-1H-indol-5-yl)-hetanoate [Reference Example 4(p)] in industrial methylated spirits and carrying out the reaction at 80° C. for 45 minutes there was prepared (R/S) 3-(1-{[3-methoxy-4-(3-o-tolyl-ureido)-phenyl]-acetyl}-2,3-dihydro-1H-indol-5-yl)-heptanoic acid as a white solid. LC-MS (using 0.1 v/v formic acid in acetonitrile to replace acetonitrile for the gradient elution): $R_T$=4.31 minutes (100% total area by ELS); MS ($ES^+$) 544 ($MH^+$), 566 ($MNa^+$).

(d) By proceeding in a similar manner to Example 2(a) but using ethyl (R/S) 3-[-({4-[(2,3-dihydro-indole-1-carbonyl)-amino]-3-methoxy-phenyl}-acetyl)-2,3-dihydro-1H-indol-5-yl]-heptanoate [Reference Example 4(q)] in industrial methylated spirits and carrying out the reaction at 80° C. for 45 minutes there was prepared (R/S) 3-[-({4-[(2,3-dihydro-indole-1-carbonyl)-amino]-3-methoxy-phenyl}-acetyl)-2,3-dihydro-1H-indol-5-yl]-heptanoic acid as a white powder. LC-MS (using 0.1 v/v formic acid in acetonitrile to replace acetonitrile for the gradient elution): $R_T$=4.47 minutes (100% total area by ELS); MS ($ES^+$) 556 ($MH^+$), 578 ($MNa^+$).

(e) By proceeding in a similar manner to Example 2(a) but using ethyl (R/S) 3-(1-{[3-methoxy-4-(3-o-tolyl-ureido)-phenyl]-acetyl}-2,3-dihydro-1H-indol-5-yl)-pentanoate [Reference Example 4(r)] and carrying out the reaction at reflux temperature for 1 hour there was prepared (R/S) 3-(1-{[3-methoxy-4-(3-o-tolyl-ureido)-phenyl]-acetyl}-2,3-dihydro-1H-indol-5-yl)-pentanoic acid as a pale fawn solid. LC-MS: $R_T$=3.01 minutes; MS ($ES^+$) 538 ($MNa^+$).

(f) By proceeding in a similar manner to Example 2(a) but using ethyl (R/S) 3-[-({4-[(2,3-dihydro-indole-1-carbonyl)-amino]-3-methoxy-phenyl}-acetyl)-2,3-dihydro-1H-indol-5-yl]-pentanoate [Reference Example 4(s)] in industrial methylated spirits and carrying out the reaction at 80° C. for 45 minutes there was prepared (R/S) 3-[-({4-[(2,3-dihydro-indole-1-carbonyl)-amino]-3-methoxy-phenyl}-acetyl)-2,3-dihydro-1H-indol-5-yl]-pentanoic acid as a white powder. LC-MS (using 0.1 v/v formic acid in acetonitrile to replace acetonitrile for the gradient elution): $R_T$=4.17 minutes (100% total area by ELS); MS ($ES^+$) 528 ($MH^+$), 550 ($MNa^+$).

(g) By proceeding in a similar manner to Example 2(a) but using ethyl (R/S) 3-(1-{[3-methoxy-4-(3-o-tolyl-ureido)-phenyl]-acetyl}-2,3-dihydro-1H-indol-5-yl)-3-phenyl-propionate [Reference Example 4(s)] and carrying out the reaction at reflux temperature for 1 hour there was prepared (R/S) 3-(1-{[3-methoxy-4-(3-o-tolyl-ureido)-phenyl]-acetyl}-2,3-dihydro-1H-indol-5-yl)-3-phenyl-prop)ionic acid as an off-white solid. LC-MS: $R_T$=3.17 minutes; MS ($ES^+$) 564 ($MH^+$), 586 ($MNa^+$).

(h) By proceeding in a similar manner to Example 2(a) but using R/S ethyl 3-[-({4-[(2,3-dihydro-indole-1-carbonyl)-amino]-3-methoxy-phenyl}-acetyl)-2,3-dihydro-1H-indol-5-yl]-3-phenyl-propionate [Reference Example 4(u)] in industrial methylated spirits and carrying out the reaction at 80° C. for 90 minutes there was prepared (R/S) 3-[-({4-[(2,3-dihydro-indole-1-carbonyl)-amino]-3-methoxy-phenyl}-acetyl)-2,3-dihydro-1H-indol-5-yl]-3-phenyl-propionic acid as an off-white powder. LC-MS (using 0.1 v/v formic acid in acetonitrile to replace acetonitrile for the gradient elution): $R_T$=4.27 minutes (100% total area by ELS); MS ($ES^+$) 576 ($MH^+$), 598 ($MNa^+$).

EXAMPLE 3

(a) (R/S) 3-(1-{[4-(3-o-Tolyl-ureido)-phenyl]-acetyl}-2,3-dihydro-1H-indol-5-yl)-butyric Acid A mixture of ethyl (R/S) 3-(1-{[4-(3-o-tolyl-ureido)-phenyl]-acetyl}-2,3-dihydro-1H-indol-5-yl)-butyrate [0.55 g, Reference Example 4(b)], aqueous sodium hydroxide solution (5.5 ml, 1M), methanol (5.5 ml) and tetrahydrofuran (11 ml) was stirred at room temperature overnight then evaporated to low bulk. The residue was diluted with water and the mixture was acidified by the addition of hydrochloric acid. The precipitate was collected by filtration, washed with water and then dried to give the title compound (0.41 g) as a white powder. LC-MS: $R_T$=3.77 minutes (100% total area by ELS); MS ($ES^+$) 472 ($MH^+$), 494 ($MNa^+$).

(b) By proceeding in a similar manner to Example 3(a) but using ethyl (R/S) 3-(1-{[3-methoxy-4-(3-o-tolyl-ureido)- phenyl]-acetyl}-1,2,3,4-tetrahydro-quinolin-6-yl)-butyrate [Reference Example 4(e)] there was prepared (R/S) 3-(1-{[3-methoxy-4-(3-o-tolyl-ureido)-phenyl]-acetyl}-1,2,3,4-tetrahydro-quinolin-6-yl)-butyric acid as a white powder. LC-MS: $R_T$=3.89 minutes (100% total area by ELS); MS (ES$^+$) 516 (MH$^+$), 538 (MNa$^+$).

(c) By proceeding in a similar manner to Example 3(a) but using ethyl (R/S) 3-(1-{[4-(3-o-tolyl-ureido)-phenyl]-acetyl}-1,2,3,4-tetrahydro-quinolin-6-yl)-butyrate [Reference Example 4(f)] there was prepared (R/S) 3-(1-{[4-(3-o-tolyl-ureido)-phenyl]-acetyl}-1,2,3,4-tetrahydro-quinolin-6-yl)-butyric acid as a white solid. LC-MS: $R_T$=2.92 minutes (100% total area by ELS); MS (ES$^+$) 508 (MNa$^+$).

(d) By proceeding in a similar manner to Example 3(a) but using ethyl (R/S) 3-{1-[(2-o-tolylamino-benzoxazol-6-yl)-acetyl]-1,2,3,4-tetrahydro-quinolin-6-yl}-butrate [Reference Example 4(g)] there was prepared (R/S) 3-{1-[(2-o-tolylamino-benzoxazol-6-yl)-acetyl]-1,2,3,4-tetrahydro-quinolin-6-yl}-butyric acid as a colourless foam. LC-MS: $R_T$=3.01 minutes (100% total area by ELS); MS (ES$^+$) 484 (MH$^+$), 506 (MNa$^+$).

EXAMPLE 4

(a) 3-(1-{[3-Methoxy-4-(3-o-tolyl-ureido)-phenyl]-acetyl}-2,3-dihydro-1H-indol-5-yl)-pentanedioic Acid A stirred suspension of dimethyl 3-(1-{[3-methoxy-4-(3-o-tolyl-ureido)-phenyl]-acetyl}-2,3-dihydro-1H-indol-5-yl)-pentanedioate [270 mg, Reference Example 4(c)] in ethanol (10 ml) was treated with a solution of sodium hydroxide (190 mg) in water (2 ml) and the mixture stirred at reflux for 3 hours. After cooling to room temperature the mixture was treated with water (10 ml) and then carefully acidified to pH1 by the addition of hydrochloric acid (3M) with ice cooling. the resultant precipitate was collected by filtration, then dried and then recrystallised from ethyl acetate to give the title compound (60 mg) as a white crystalline solid. LC-MS: $R_T$=2.44 minutes (100% total area by ELS); MS (ES$^+$) 568 (MNa$^+$).

(b) By proceeding in a similar manner to Example 4(a) but using dimethyl 3-(1-{[4-(3-o-tolyl-ureido)-phenyl]-acetyl}-2,3-dihydro-1H-indol-5-yl)-pentanedioate [Reference Example 4(d)] there was prepared 3-(1-{[4-(3-o-tolyl-ureido)-phenyl]-acetyl}-2,3-dihydro-1H-indol-5-yl)-pentanedioic acid as a white solid. MS (ES$^-$) 514 (M$^-$).

(c) By proceeding in a similar manner to Example 4(a) but using dimethyl 3-(1-{[3-methoxy-4-(3-o-tolyl-ureido)-phenyl]-acetyl}-1,2,3,4-tetrahydro-quinolin-6-yl)-pentanedioate [Reference Example 4(h)] and subjecting the product to flash chromatography on silica eluting with a mixture of methanol and dichloromethane (1:9, v/v) there was prepared 3-(1-{[3-methoxy-4-(3-o-tolyl-ureido)-phenyl]-acetyl}-1,2,3,4-tetrahydro-quinolin-6-yl)-pentanedioic acid as a white foam. LC-MS: $R_T$=2.40 minutes (100% total area by ELS); MS (ES$^+$) 582 (MNa$^+$).

(d) By proceeding in a similar manner to Example 4(a) but using methyl (R) 4-[2-methoxycarbonyl-1-(1-{[3-methoxy-4-(3-o-tolyl-ureido)-phenyl]-acetyl)-1,2,3,4-tetrahydro-quinolin-6-yl)-ethylcarbamoyl]-butyrate [Reference Example 4(i)] and subjecting the product to flash chromatography on silica eluting with a mixture of methanol and dichloromethane (1:9, v/v) there was prepared (R) 4-[2-carboxy-1-(1-{[3-methoxy-4-(3-o-tolyl-ureido)-phenyl]-acetyl}-1,2,3,4-tetrahydro-quinolin-6-yl)-ethylcarbamoyl]-butyric acid as a white powder. LC-MS: $R_T$=2.43 minutes (100% total area by ELS); MS (ES$^+$) 653 (MNa$^+$).

(e) By proceeding in a similar manner to Example 4(a) but using methyl (R) N-[2-methoxycarbonyl-1-(1-{[3-methoxy-4-(3-o-tolyl-ureido)-phenyl]-acetyl}-1,2,3,4-tetrahydro-quinolin-6-yl)-ethyl]-succinamate [Reference Example 40)] and subjecting the product to flash chromatography on silica eluting with a mixture of methanol and dichloromethane (1:9, v/v) there was prepared (R) N-[2-carboxy-1-(1-{[3-methoxy-4-(3-o-tolyl-ureido)-phenyl]-acetyl}-1,2,3,4-tetrahydro-quinolin-6-yl)-ethyl]-succinamic acid as a colourless gum. LC-MS: $R_T$=2.44 minutes (100% total area by ELS); MS (ES$^+$) 639 (MNa$^+$).

EXAMPLE 5

(R/S) 1-(4-{2-oxo-2-[-(2-oxo-Tetrahydro-pyran-4-yl)-3,4-dihydro-2H-quinolin-1-yl]-ethyl}-phenyl)-3-o-tolyl-urea A solution of [4-(3-o-tolyl-ureido)-phenyl}-acetic acid (310 mg) and diisopropylethylamine (310 mg) dimethylformamide (5 ml) was treated successively with O-(7-azabenzotriazol-1-yl)-N,N,N',N'-tetramethyluronium hexafluorophosphate (450 mg), then (R/S) 4-(1,2,3,4-tetrahydro-quinolin-6-yl)-tetrahydro-pyran-2-one [250 mg, Reference Example 5(c)]. After standing at room temperature for 2 hours the mixture was partitioned between ethyl acetate (100 ml) and dilute hydrochloric acid (100 ml). The layers were separated and the organic layer was washed with water, dried and evaporated. The residue was subjected to flash chromatography on silica eluting with ethyl acetate to give a yellow gum. This was dissolved in the minimum volume of ethanol and the solution was then treated with ether to yield a yellow solid, which was collected by filtration and dried to give the title compound (80 mg) as a yellow solid. LC-MS: $R_T$=3.74 minutes (100% total area by ELS); MS (ES$^+$) 520 (MNa$^+$).

EXAMPLE 6

(R) 3-(1-{[3-Methoxy-4-(3-o-tolyl-ureido)-phenyl]-acetyl}-1,2,3,4-tetrahydro-quinolin-6-yl)-3-[(5-methyl-isoxazole-3-carbonyl)-amino]-propionic Acid Methyl (R) 3-(1-boc-1,2,3,4-tetrahydro-quinolin-6-yl)-3-[(5-methyl-isoxazole-3-carbonyl)-amino]-propionate [310 mg, Reference Example 17] was dissolved in a mixture of trifluoroacetic acid and dichloromethane (1:3, v/v) and the clear solution allowed to stand at room temperature for 2 hours. The residue obtained on evaporation of this solution was added to a mixture of [3-methoxy-4-(3-o-tolyl-ureido)-phenyl]-acetic acid (280 mg), O-(7-azabenzotriazol-1-yl)-N,N,N',N'-tetramethyluronium hexafluorophosphate (340 mg) and diisopropylethylamine (1 ml) in dimethylformamide (30 ml). The resultant mixture was stirred at room temperature for 3 hours and then allowed to stand overnight. The mixture was evaporated to low bulk and the residue was partitioned between ethyl acetate and dilute hydrochloric acid. The layers were separated and the organic layer was washed with sodium carbonate solution, dried and evaporated to give 580 mg of an orange oil. Purification by flash chromatography eluting with 1:1 ethyl acetate and dichloromethane gave an orange foam. This product was dissolved in methanol (20 ml) and the solution treated with 1.0 M sodium hydroxide solution. After refluxing for 2 hours the mixture was evaporated to low bulk and the residue diluted with water. Acidification with dilute hydrochloric acid gave a gummy product which was extracted into ethyl acetate solution. This solution was dried and evaporated to give the title compound (110 mg) as a light yellow foam. LC-MS: $R_T$=2.94 minutes (100% total area by ELS); MS (ES$^+$) 648 (MNa$^+$).

EXAMPLE 7

(a) (S) 2-(2-Chloro-6-methyl-benzoylamino)-3-[1-(2,6-dichloro-benzoyl)-1,2,3,4-tetrahydro-quinolin-6-yl]-propionic Acid A mixture of methyl (S) 2-amino-3-[1-(2,6-dichloro-benzoyl)-1,2,3,4-tetrahydro-quinolin-6-yl]-propionate (200 mg, Reference Example 18), O-(7-azabenzotriazol-1-yl)-N,N,N',N'-tetramethyluronium hexafluorophosphate (200 mg) and 2-chloro-6-methylbenzoic acid (90 mg) in dimethylformamide was treated with diisopropylethylamine (150 mg) and the clear solution allowed to stand at room temperature overnight. The reaction mixture was partitioned between ethyl acetate (50 ml) and dilute hydrochloric acid (50 ml). The organic phase was washed with sodium bicarbonate solution, then dried and then evaporated. The residue was examined by Thin Layer Chromatography on silica using a mixture of ethyl acetate and dichloromethane (1:9, v/v) and showed two very close spots, of approximately equal intensity. The product was subjected to flash chromatography on silica eluting with a mixture of ethyl acetate and dichloromethane (1:9, v/v): the bulk of the fractions contained mixed spots, but separate fractions containing each of the pure components was obtained. On standing in solution for more than about one hour, each pure component reverted to an identical mixture of the two components, suggesting that the two spots represented stable rotamers. Accordingly, all fractions containing either or both spots were combined and evaporated to give a colourless oil (160 mg). This material was dissolved in methanol (10 ml) and treated with lithium hydroxide solution (4 ml, 1M). After standing at room temperature for 30 minutes the mixture was evaporated to low bulk and the residue dissolved in water (10 ml). Acidification with dilute hydrochloric acid afforded a white precipitate, which was collected by filtration, washed with water and then dried to give the title compound (105 mg) as a white solid. LC-MS: (indicated a mixture of two stable rotamers): rotamer 1, $R_T$=2.79 minutes (57% total area by ELS), MS (ES$^+$) 567, 569 (MNa$^+$); rotamer 2, $R_T$=3.96 minutes (43% total area by ELS), MS (ES$^+$) 567, 569 (MNa$^+$).

(b) By proceeding in a similar manner to Example 7(a) but using tetrahydro-pyran-4-carboxylic acid there was prepared (S) 3-[1-(2,6-dichloro-benzoyl)-1,2,3,4-tetrahydro-quinolin-6-yl]-2-[tetrahydro-pyran-4-carbonyl)-amino]-propionic acid as a white powder. LC-MS: (indicated a mixture of two stable rotamers): rotamer 1, $R_T$=2.47 minutes (52% total area by ELSD), MS (ES$^+$) 527 and 529 (MNa$^+$); rotamer 2, $R_T$=2.66 minutes (48% total area by ELS), MS (ES$^+$) 527 and 529 (MNa$^+$).

EXAMPLE 8

(S) 2-(2,6-Dichloro-benzoylamino)-3-[1-(2,6-dichloro-benzoyl)-1,2,3,4-tetrahydro-quinolin-6-yl]-propionic Acid A solution of methyl (S) 2-amino-3-[1-(2,6-dichloro-benzoyl)-1,2,3,4-tetrahydro-quinolin-6-yl]-propionate (180 mg, reference Example 18) in dichloromethane (10 ml) was treated with diisopropylethylamine (150 mg) then with 2,6-dichlorobenzoyl chloride (130 mg). After standing at room temperature overnight the mixture was partitioned between ethyl acetate (50 ml) and dilute hydrochloric acid (50 ml). The organic phase was washed with sodium bicarbonate solution, then dried and then evaporated. The residue was subjected to flash chromatography on silica eluting with a mixture of ethyl acetate and dichloromethane (1:9, v/v) to give a colourless oil (160 mg). This material was treated with methanol (10 ml) and then with lithium hydroxide solution (4 ml, 1M). After standing at room temperature for one hour the mixture was evaporated to low bulk and the residue was dissolved in water (10 ml). The solution was acidification by addition of dilute hydrochloric. The resulting white precipitate was filtered then washed with water and then dried to give the title compound (120 mg) as a white solid. LC-MS (indicated a mixture of stable rotamers): rotamer 1, $R_T$=2.79 minutes (48% total area by ELS), MS (ES$^+$) 587, 599 (MNa$^+$); rotamer 2, $R_T$=3.74 minutes (10 total area by ELS), MS (ES$^+$) 587, 589 (MNa$^+$); rotamer 3, $R_T$=3.96 minutes (46% total area by ELS), MS (ES$^+$) 587, 599 (MNa$^+$).

EXAMPLE 9

(R/S) 3-[1-({4-[(2,3-Dihydro-indole-1-carbonyl)-amino]-3-methoxy-phenyl}-acetyl)-1,2,3,4-tetrahydro-quinolin-6-yl]-butyric Acid Step 1. Bromo-Wang resin (1 g, nominal loading of 1 mmol/g, Novabiochem) was suspended in dimethylformamide (15 ml) and treated successively with a solution of (R/S) 6-(2-carboxy-1-methyl-ethyl)-3,4-dihydro-2H-quinoline-1-carboxylic acid 9H-fluoren-9-ylmethyl ester (880 mg, Reference Example 28) in dimethylformamide (5 ml), diisopropylethylamine (0.35 ml) and cesium iodide (270 mg). The mixture was allowed to stand at room temperature with occasional shaking overnight. The resin was drained then washed (i) five times with dimethylformamide, (ii) three times with water, (iii) three times with dimethylformamide, (iv) three times with methanol, (v) four times with dichloromethane, and (vi) twice with ether, and then dried.

Step 2. The resin from Step 1 was then suspended in a mixture of piperidine and dimethylformamide (20 ml, 1:4, v/v) and the mixture was kept at room temperature with occasional shaking for about 2 hours. The resin was drained then washed (i) five times with dimethylformamide, (ii) three times with methanol, (iii) four times with dimethylformamide, and (vi) twice with ether, and then dried.

Step 3. The resin from Step 2 was then suspended in dimethylformamide (15 ml) and treated successively with O-(7-azabenzotriazol-1-yl)-N,N,N',N'-tetramethyluronium hexafluorophosphate (570 mg), {4-[(2,3-dihydro-indole-1-carbonyl)-amino]-3-methoxy-phenyl}-acetic acid (490 mg) and diisopropylethylamine (0.52 ml) and the mixture allowed to stand at room temperature with occasional shaking overnight. The resin was drained washed then washed (i) five times with dimethylformamide, (ii) three times with methanol, (iii) four times with dimethylformamide, and (vi) twice with ether, and then dried.

Step 4. The resin from Step 3 was treated with a mixture of trifluoroacetic acid and dichloromethane (about 10 ml, 1:1, v/v) and the mixture kept at room temperature with occasional shaking for about 1 hour. The resin was drained and then washed with a mixture of trifluoroacetic acid and dichloromethane (about 1 ml, 1:1, v/v). The combined filtrates were evaporated and the residual brown oil was treated with dilute sodium hydroxide solution. The resulting aqueous solution was washed with ether, then with dichloromethane, and then acidified by addition of hydrochloric acid. The precipitated product was extracted four times with dichloromethane. The combined extracts were dried and then evaporated. The residue was triturated with ether to give the title compound (120 mg) as a cream solid. LC-MS: $R_T$=3.16 minutes (100% total area by ELS); MS (ES$^+$) 550 (MNa$^+$).

EXAMPLE 10

(S) 2-Acetylamino-3-(1-{[3-methoxy-4-(3-o-tolyl-ureido)-phenyl]-acetyl}-1,2,3,4-tetrahydro-quinolin-6-yl)-propionic Acid A solution of methyl (S) 2-acetylamino-3-(1-{[3-methoxy-4-(3-o-tolyl-ureido)-phenyl]-acetyl}-1,2,3,4-tetrahydro-quinolin-6-yl)-propionate [220 mg, Reference Example 4(1)] in dioxane (3 ml) was treated with a solution of lithium hydroxide hydrate (50 mg) in water (1 ml). The mixture was stirred at room temperature for 3 hours, then treated with water (5 ml), then acidified to pH 1–2 by the addition of dilute hydrochloric acid (with ice cooling). The resulting precipitate was extracted three times with ethyl acetate and the combined extracts were washed with brine, then with brine, then dried and then evaporated. The residue was recrystallised from ethyl acetate to give the title compound (21 mg)as a white powder. LC-MS: $R_T$=2.77 minutes (100% total area by ELS); MS (ES$^+$) 581 (MNa$^+$).

EXAMPLE 11

(R/S) 3-(1-{[3-Methoxy-4-(3-o-tolyl-ureido)-phenyl]-acetyl}-2,3-dihydro-1H-indol-5-yl)-butyric Acid, Sodium Salt A solution of (R/S) 3-(1-{[3-methoxy-4-(3-o-tolyl-ureido)-phenyl]-acetyl}-2,3-dihydro-1H-indol-5-yl)-butyric acid (2.1 g) in methanol (about 150 ml) was treated with exactly one equivalent of 0.1M sodium hydroxide solution. The methanol was evaporated off and the residue diluted with water (about 120 ml) and lyophilised. The lyophilate was triturated with ether and the insoluble material was then washed with ether, then with pentane and then dried to give the title compound (1.9 g) as an off-white, free-flowing powder. MS (ES$^+$) 525 (MH$^+$). [Elemental analysis: Found: C, 60.01; H, 6.13; N, 7.28; H$_2$O, 8.25%. Calculated for C$_{29}$H$_{30}$N$_3$NaO$_5$.0.3H$_2$O: C, 60.25; H, 6.20; N, 7.27; H$_2$O, 9.3%].

EXAMPLE 12

(a) (S) 2-(2,6-Dichloro-benzoylamino)-3-{1-[(2-o-tolylamino-benzoxazol-6-yl)-acetyl]-1,2,3,4-tetrahydro-quinolin-6-yl}-propionic Acid Methyl (S) 2-(N-boc-amino)-3-{1-[(2-o-tolylamino-benzoxazol-6-yl)-acetyl]-1,2,3,4-tetrahydro-quinolin-6-yl}-propionate [200 mg, Reference Example 4(m)] was treated with trifluoroacetic acid (3 ml) and the resulting solution was left at room temperature for 15 minutes then evaporated. The residue was dissolved in dichloromethane (20 ml) and treated with diisopropylethylamine (260 mg) and then with 2,6-dichlorobenzoyl chloride (140 mg). After standing at room temperature overnight the mixture was evaporated to low bulk and the residue partitioned between ethyl acetate (50 ml) and dilute hydrochloric acid. The organic phase was washed with sodium bicarbonate solution, then dried and then evaporated. The residue was subjected to flash chromatography on silica eluting with a mixture of ethyl acetate and dichloromethane (15:85. v/v). The resulting colourless gum was treated with methanol (10 ml) and then with lithium hydroxide solution (2 ml, 1M). After standing at room temperature for 2 hours the mixture was evaporated to low bulk, the residue was treated with water (10 ml) and the mixture acidified by addition of dilute hydrochloric acid. The resulting white precipitate was filtered, then washed with water, and then dried to give the title compound (90 mg) as a white powder. LC-MS: $R_T$=2.97 minutes (100% total area by ELS); MS (ES$^+$) 657 and 659 (MH$^+$), 679 and 681 (MNa$^+$).

(b) By proceeding in a similar manner to Example 12(a) but using methyl (S) 3-[1-(2-chloro-benzoyl)-1,2,3,4-tetrahydro-quinolin-6-yl]-2-(N-boc-amino)-propionate [Reference Example 4(n)] and 2-chloro-6-methylbenzoyl chloride there was prepared (S) 3-[1-(2-chloro-benzoyl)-1,2,3,4-tetrahydro-quinolin-6-yl]-2-(2-chloro-6-methyl-benzoylamino)-propionic acid as a white powder. LC-MS: $R_T$=2.76 minutes (100% total area by ELS); MS (ES$^+$) 533 and 535 (MNa$^+$).

(c) By proceeding in a similar manner to Example 12(a) but using methyl (S) 3-{1-[(4-acetoxy-3-chloro-phenyl)-acetyl]-1,2,3,4-tetrahydro-quinolin-6-yl}-2-(N-boc-amino)-propionate [Reference Example 4(o)] and 2-chloro-6-methylbenzoyl chloride there was prepared (S) 3-{1-[(3-chloro-4-hydroxy-phenyl)-acetyl]-1,2,3,4-tetrahydro-quinolin-6-yl}-2-(2-chloro-6-methyl-benzoylamino)-propionic acid. LC-MS: $R_T$=2.67 minutes (100% total area by ELS); MS (ES$^+$) 563 and 565 (MNa$^+$).

REFERENCE EXAMPLE 1

Ethyl 3-[1-(2-{3-Methoxy-4-[(2-toluidinocarbonyl)amino]phenyl}acetyl)-1,2,3,4-tetrahydro-6-quinolinyl]propanoate A stirred solution of 3-methoxy-4-[3-(2-methylphenyl)ureido]phenylacetic acid (0.232 g, prepared as described in Example 52B of International Patent Application Publication No. WO 96/22966) in anhydrous tetrahydrofuran (5 ml), under an atmosphere of argon and at 20° C., was treated with powdered molecular sieves 4 Å (2 g), ethyl 3-(1,2,3,4-tetrahydro-6-quinolinyl)propanoate (0.115 g, Reference Example 2), triethylamine (0.275 ml), O-(7-azabenzotriazol-1-yl)-N,N,N',N'-tetramethyluronium hexafluorophosphate (0.223 g) and 4-dimethylaminopyridine (6 mg). After stirring at 20° C. for 1 hour the reaction mixture was filtered through a pad of celite. The filtrate was evaporated under reduced pressure (2.7 kPa) at 40° C. and the residue was treated with ethyl acetate (25 ml). The solution obtained was washed twice with saturated aqueous ammonium chloride solution (5 ml), then with water (5 ml), then dried over magnesium sulfate, and then evaporated under reduced pressure (2.7 kPa) at 40° C. The resulting white foamy solid (0.457 g) was subjected to flash chromatography on silica (0,040–0,063 mm) eluting with a mixture of cyclohexane and ethyl acetate (250 ml, 9:1, then 500 ml, 7:3, then 1000 ml, 4:6; v/v) to give the title compound (0.244 g) as a white foamy solid.

REFERENCE EXAMPLE 2

Ethyl 3-(1,2,3,4-Tetrahydro-6-quinolinyl)propanoate

A stirred mixture of ethyl 3-(6-quinolinyl)propanoate (0.3 g, Reference Example 3) in hydrochloric acid (3 ml, 0.1N)

and 5% rhodium in carbon powder (33 mg) was hydrogenated in a 22 cm³ stainless steel pressure reactor at a pressure of 50 bars of hydrogen. After stirring for 4 hours at 25° C. a further portion of 30 mg of 5% rhodium in carbon powder (33 mg) was added and the hydrogenation was continued under a pressure of 50 bars at 25° C. for 1 hour. The reaction mixture was filtered through a pad of celite and the filter pad was washed with hydrochloric acid (3 ml, 0.1N) then with ethyl acetate (25 ml). The combined filtrate and washings were combined and the aqueous phase was decanted from the organic phase. The aqueous phase was extracted twice with ethyl acetate (25 ml) and combined with the aforementioned organic phase. The combined solutions were dried over magnesium sulfate then evaporated under reduced pressure (2.0 kPa) at 40° C. to give the title compound (0.121 g) as a brown oil.

REFERENCE EXAMPLE 3

Ethyl 3-(6-Quinolinyl)propanoate

Into the electrochemical apparatus described below were introduced successively, dimethylformamide (45 ml), pyridine (5 ml), tetrabutylammonium bromide (250 mg), tetrabutylammonium iodide (18.8 mg) and 1,2-dibromoethane (0.15 ml). The solution was deoxygenated by bubbling argon through the solution for about 10 minutes. After carrying out a pre-electrolysis, constant current of 125 mA during 30 minutes, the stirred mixture was treated with nickel bromide trihydrate (341 mg), 6-bromoquinoline (2.6 g), and ethyl acrylate (3.12 g). Stirring was continued until complete dissolution. The reaction medium was heated to 60° C. and then electrolysis was carried out using a constant current of 250 mA whilst maintaining the temperature at 60° C. After 3 hours and the passage of 2810 coulombs (i.e. 2.33 Faradays per mole of 6-bromoquinoline) the electrolysis was stopped. The electrolysed solution plus dimethylformamide washings (20 ml) from the electrochemical apparatus and the electrodes was treated with water (250 ml) and then extracted three times with heptane (70 ml), ethyl acetate (50 ml) and diethyl ether (50 ml). The combined extracts, were evaporated under reduced pressure (2.7 kPa) at 40° C. The residual yellow oil (2.78 g) was subjected to Pressure Column Chromatography on silica [40 mm diameter column containing 100 g of silica 60 Merck (0,040–0,063 mm)] eluting with a mixture of cyclohexane, ethyl acetate and 2-propanol (90:8:2 then 85/12/3; v/v/v) under a slight pressure of argon (approximately 30 Kpa) to give the title compound (1.92 g) as a yellowish oil.

The electrochemical apparatus is made up of: a cylindrical body (50 ml volume) which contains the reaction medium and into which is plunged a 10 mm diameter soft iron bar (the consumable anode) and a cylindrical nickel foam grid (diameter 30 mm, height 42.5 mm, surfaces connect approximately 40 ml) concentrically laid out around the anode; a glass lid provided with 5 threaded outputs; a central output for the electrical contact of the anode; four peripheral outputs for the electrical contact of the cathode, thermometer, tubing for argon arrival and a cooling agent with water. The two parts of the electrolyser are associated by the intermediate of a 60 mm interior diameter flat grinding, ensuring the scaling. The reaction medium is maintained under an inert atmosphere by continuously bubbling argon through the electrolysed solution. The electrodes are connected to a stabilized power supply or an intentiostat. Moreover, in the circuit of the anode, a current integrator is connected in series. The reaction medium is stirred by a Teflon® covered magnet bar. The body of the electrochemical apparatus can be plunged in an oil bath at the required temperature for the reaction.

REFERENCE EXAMPLE 4

(a) Ethyl (R/S) 3-(1-{[3-Methoxy-4-(3-o-tolyl-ureido)-phenyl]-acetyl}-2,3-dihydro-1H-indol-5-yl)-butyrate A solution of [3-methoxy-4-(3-o-tolyl-ureido)-phenyl]-acetic acid (2.9 g) and O-(7-azabenzotriazol-1-yl)-N,N,N',N'-tetramethyluronium hexafluorophosphate (3.7 g) in dimethylformamide (about 40 ml) was treated with diisopropylethylamine (10 ml), followed after about 30 seconds by a solution of (R/S) ethyl 3-(2,3-dihydro-1H-indol-5-yl)butyrate [about 2.5 g, Reference Example 5(a)] in dimethylformamide (about 10 ml). The resulting clear, dark brown solution was kept at room temperature for about one hour then evaporated to low bulk. The residue was partitioned between water and ethyl acetate and the organic layer was washed with dilute hydrochloric acid, then with aqueous sodium bicarbonate solution, then with brine, then dried and then evaporated. The residual brown gum was subjected to flash chromatography on silica eluting with a mixture of ethyl acetate and petrol (3:2 to 3:1, v/v) to give the title compound (2.8 g) as a light yellow, amorphous foam. MS (ES$^+$) 552 (M–Na$^+$).

(b) By proceeding in a similar manner to Reference Example 4(a) but coupling [4-(3-o-tolyl-ureido)-phenyl]-acetic acid with (R/S) ethyl 3-(2,3-dihydro-1H-indol-5-yl)butyrate there was prepared ethyl (R/S) 3-(1-{[4-(3-o-tolyl-ureido)-phenyl]-acetyl}-2,3-dihydro-1H-indol-5-yl)-butyrate as an off-white solid. MS (ES$^+$) 500 (MH$^+$), 522 (MNa$^+$). MS (ES$^-$) 498 (M$^-$).

(c) By proceeding in a similar manner to Reference Example 4(a) but coupling [3-methoxy-4-(3-o-tolyl-ureido)-phenyl]-acetic acid with dimethyl 2-(2,3-dihydro-1H-indol-5-ylmethyl)-pentanedioate (Reference Example 9) there was prepared dimethyl 3-(1-{[3-methoxy-4-(3-o-tolyl-ureido)-phenyl]-acetyl}-2,3-dihydro-1H-indol-5-yl)-pentanedioate as an off-white foam. MS (ES$^+$) 574 (MH$^+$), 596 (MNa$^+$).

(d) By proceeding in a similar manner to Reference Example 4(a) but coupling [4-(3-o-tolyl-ureido)-phenyl]-acetic acid with dimethyl 2-(2,3-dihydro-1H-indol-5-ylmethyl)-pentanedioate (Reference Example 9) there was prepared dimethyl 3-(1-{[4-(3-o-tolyl-ureido)phenyl]-acetyl}-2,3-dihydro-1H-indol-5-yl)-pentanedioate as a white foam. MS (ES$^+$) 566 (MNa$^+$). MS (ES$^-$) 542 (M$^-$).

(e) By proceeding in a similar manner to Reference Example 4(a) but coupling [3-methoxy-4-(3-o-tolyl-ureido)-phenyl]-acetic acid with ethyl (R/S) 3-(1,2,3,4-tetrahydro-quinolin-6-yl)butyrate [Reference Example 5(b)] there was prepared ethyl (R/S) 3-(1-{[3-methoxy-4-(3-o-tolyl-ureido)-phenyl]-acetyl}-1,2,3,4-tetrahydro-quinolin-6-yl)-butyrate as a yellow gum. MS (ES$^+$) 544 (MH$^+$), 566 (MNa$^+$). MS (ES$^-$) 542 (M$^-$).

(f) By proceeding in a similar manner to Reference Example 4(a) but coupling [4-(3-o-tolyl-ureido)-phenyl]-acetic acid with ethyl (R/S) 3-(1,2,3,4-tetrahydro-quinolin-6-yl)butyrate [Reference Example 5(b)] there was prepared ethyl (R/S) 3-(1-{[4-(3-o-tolyl-ureido)-phenyl]-acetyl}-1,2,3,4-tetrahydro-quinolin-6-yl)-butyrate.

(g) By proceeding in a similar manner to Reference Example 4(a) but coupling (2-o-tolylamino-benzoxazol-6-yl)-acetic acid with ethyl (R/S) 3-(1,2,3,4-tetrahydro-quinolin-6-yl)butyrate [Reference Example 5(b)] there was prepared ethyl (R/S) 3-{1-[(2-o-tolylamino-benzoxazol-6-yl)-acetyl]-1,2,3,4-tetrahydro-quinolin-6-yl}-butyrate.

(h) By proceeding in a similar manner to Reference Example 4(a) but coupling [3-methoxy-4-(3-o-tolyl-ureido)- phenyl]-acetic acid with dimethyl 3-(1,2,3,4-tetrahydro-quinolin-6-yl)-pentanedioate [Reference Example 9(b)] and subjecting the product to flash chromatography on silica eluting with a mixture of ethyl acetate and petrol (3:1, v/v) there was prepared dimethyl 3-(1-{[3-methoxy-4-(3-o-tolyl-ureido)-phenyl-acetyl)-1,2,3,4-tetrahydro-quinolin-6-yl)-pentanedioate as an off-white foam. MS (ES$^+$) 588 (MH$^+$), 610 (MNa$^+$). MS (ES$^-$) 586 (M$^-$).

(i) By proceeding in a similar manner to Reference Example 4(a) but coupling [3-methoxy-4-(3-o-tolyl-ureido)-phenyl]-acetic acid with methyl (R) 4-[1-(1,2,3,4-tetrahydro-quinolin-6yl)-2-methoxycarbonyl-ethylcarbamoyl)-butyrate [Reference Example 13(a)] and subjecting the product to flash chromatography on silica eluting with a mixture of methanol and dichloromethane (1:19, v/v) there was prepared methyl (R) 4-[2-methoxycarbonyl-1-(1-={[3-methoxy-4-(3-o-tolyl-ureido)-phenyl]-acetyl}-1,2,3,4-tetrahydro-quinolin-6-yl)-ethylcarbamoyl]-butyrate as a pale orange foam. MS (ES$^+$) 659 (MH$^+$), 681 (MNa$^+$). MS (ES$^-$) 658 (M$^-$).

(j) By proceeding in a similar manner to Reference Example 4(a) but coupling [3-methoxy-4-(3-o-tolyl-ureido)-phenyl]-acetic acid with (R) N-[2-methoxycarbonyl-1-(1,2,3,4-tetrahydro-quinolin-6-yl)-ethyl]-succinamate [Reference Example 13(b)] and subjecting the product to flash chromatography on silica eluting with a mixture of methanol and dichloromethane (1:19, v/v) there was prepared methyl (R) N-[2-methoxycarbonyl-1-(1-{[3-methoxy-4-(3-o-tolyl-ureido)-phenyl]-acetyl}-1,2,3,4-tetrahydro-quinolin-6-yl)-ethyl]-succinamate as a light orange foam. MS (ES$^+$) 667 (MNa$^+$).

(k) By proceeding in a similar manner to Reference Example 4(a) but coupling ethyl (R/S) 3-(1,2,3,4-tetrahydro-quinolin-6-yl)butyrate [Reference Example 5(b)] with (1-boc-2-o-tolylamino-1H-benzimidazol-5-yl)-acetic acid (Reference Example 22) and subjecting the product to flash chromatography on silica eluting with a mixture of ethyl acetate and cyclohexane (3:7, v/v), there was prepared ethyl (R/S) 3-{1-[(2-o-tolylamino-3H-benzimidazol-5-yl)-acetyl]-1,2,3,4-tetrahydro-quinolin-6-yl}-butyric acid.

(l) By proceeding in a similar manner to Reference Example 4(a) but coupling [3-methoxy-4-(3-o-tolyl-ureido)-phenyl]-acetic acid with (S) methyl 2-acetylamino-3-(1,2,3,4-tetrahydro-quinolin-6-yl)-propionate [Reference Example 19(b)] and subjecting the product to flash chromatography on silica eluting with a mixture of methanol and dichloromethane (1:19, v/v) there was prepared methyl (S) 2-acetylamino-3-(1-{[3-methoxy-4-(3-o-tolyl-ureido)-phenyl]-acetyl}-1,2,3,4-tetrahydro-quinolin-6-yl)-propionate as an off-white foam. MS (ES$^+$) 573 (MH$^+$), MS (ES$^-$) 572 (M$^-$).

(m) By proceeding in a similar manner to Reference Example 4(a) but coupling (2-o-tolylamino-benzoxazol-6-yl)-acetic acid with (S) Methyl 2-(N-boc-amino)-3-(1,2,3,4-tetrahydro-quinolin-6-yl)-propionate (Reference Example 19) and subjecting the product to flash chromatography on silica eluting with a mixture of ethyl acetate and dichloromethane (1:9, v/v) there was prepared (S) methyl 2-(N-boc-amino)-3-{1-[(2-o-tolylamino-benzoxazol-6-yl)-acetyl]-1,2,3,4-tetrahydro-quinolin-6-yl}-propionate as a colourless gum.

(n) By proceeding in a similar manner to Reference Example 4(a) but coupling 2-chlorobenzoic acid with methyl (S) 2-(N-boc-amino)-3-(1,2,3,4-tetrahydro-quinolin-6-yl)-propionate (Reference Example 19) and subjecting the product to flash chromatography on silica eluting with a mixture of ethyl acetate and dichloromethane (15:85, v/v) there was prepared methyl (S) 3-[1-(2-chloro-benzoyl)-1,2,3,4-tetrahydro-quinolin-6-yl]-2-(N-boc-amino)-propionate as a colourless oil.

(o) By proceeding in a similar manner to Reference Example 4(a) but coupling (4-acetoxy-3-chloro-phenyl)-acetic acid with methyl (S) 2-(N-boc-amino)-3-(1,2,3,4-tetrahydro-quinolin-6-yl)-propionate (Reference Example 19) and subjecting the product to flash chromatography on silica eluting with a mixture of ethyl acetate and dichloromethane (15:85, v/v) there was prepared (S) methyl 3-{1-[(4-acetoxy-3-chloro-phenyl)-acetyl]-1,2,3,4-tetrahydro-quinolin-6-yl}-2-(N-boc-amino)-propionate as a colourless oil.

(p) By proceeding in a similar manner to Reference Example 4(a) but coupling 3-methoxy-4-(3-o-tolyl-ureido)-phenylacetic acid with ethyl (R/S) 3-(2,3-dihydro-1H-indol-5-yl)-heptanoate [Reference Example 24(a)] and subjecting the product to flash chromatography on silica eluting with a mixture of ethyl acetate and pentane (11:9, v/v) there was prepared ethyl (R/S) 3-(1-{[3-methoxy-4-(3-o-tolyl-ureido)-phenyl]-acetyl}-2,3-dihydro-1H-indol-5-yl)-heptanoate as a foam.

(q) By proceeding in a similar manner to Reference Example 4(a) but coupling 4-[(2,3-dihydro-indole-1-carbonyl)-amino]-3-methoxy-phenylacetic acid with ethyl (R/S) 3-(2,3-dihydro-1H-indol-5-yl)-heptanoate [Reference Example 24(a)] there was prepared ethyl (R/S) 3-[-({4-[(2,3-dihydro-indole-1-carbonyl)-amino]-3-methoxy-phenyl}-acetyl)-2,3-dihydro-1H-indol-5-yl]-heptanoate as a white solid. MS (ES$^+$) 606 (MNa$^+$).

(r) By proceeding in a similar manner to Reference Example 4(a) but coupling 3-methoxy-4-(3-o-tolyl-ureido)-phenylacetic acid with ethyl (R/S) 3-(2,3-dihydro-1H-indol-5-yl)-pentanoate [Reference Example 24(b)] and subjecting the product to flash chromatography on silica eluting with a mixture of dichloromethane and methanol (99:1, v/v) there was prepared ethyl (R/S) 3-(1-{[3-methoxy-4-(3-o-tolyl-ureido)-phenyl]-acetyl}-2,3-dihydro-1H-indol-5-yl)-pentanoate as a glass.

(s) By proceeding in a similar manner to Reference Example 4(a) but coupling 4-[(2,3-dihydro-indole-1-carbonyl)-amino]-3-methoxy-phenylacetic acid with ethyl (R/S) 3-(2,3-dihydro-1H-indol-5-yl)-pentanoate (Reference Example 24(b)] there was prepared ethyl (R/S) 3-[-({4-[(2,3-dihydro-indole-1-carbonyl)-amino]-3-methoxy-phenyl}-acetyl)-2,3-dihydro-1H-indol-5-yl]-pentanoate as a white solid. MS (ES$^+$) 578 (MNa$^+$).

(t) By proceeding in a similar manner to Reference Example 4(a) but coupling 3-methoxy-4-(3-o-tolyl-ureido)-phenylacetic acid with ethyl (R/S) 3-(2,3-dihydro-1H-indol-5-yl)-3-phenyl-propionate [Reference Example 24(c)] and subjecting the product to flash chromatography on silica eluting with a mixture of pentane and ethyl acetate (1:1, v/v) there was prepared ethyl (R/S) 3-(1-{[3-methoxy-4-(3-o-tolyl-ureido)-phenyl]-acetyl}-2,3-dihydro 1H-indol-5-yl)-3-phenyl-propionate as a foam.

(u) By proceeding in a similar manner to Reference Example 4(a) but coupling 4-[(2,3-dihydro-indole-1-carbonyl)-amino]-3-methoxy-phenylacetic acid with ethyl (R/S) 3-(2,3-dihydro-1H-indol-5-yl)-3-phenyl-propionate [Reference Example 24(c)] there was prepared ethyl (R/S) 3-[-({4-[(2,3-dihydro-indole-1-carbonyl)-amino]-3-methoxy-phenyl}-acetyl)-2,3-dihydro-1H-indol-5-yl]-3-phenyl-propionate as an off-white solid. MS (ES$^+$) 626 (MNa$^+$).

REFERENCE EXAMPLE 5

(a) Ethyl (R/S) 3-(2,3-Dihydro-1H-indol-5-yl)butyrate

A solution of (R/S) ethyl 3-(1-boc-2,3-dihydro-1H-indol-5-yl)butyrate (3.1 g, Reference Example 6) in dichloromethane (30 ml), cooled in an ice bath, was treated with trifluoroacetic acid (30 ml). After about 30 minutes the reaction mixture was evaporated and traces of trifluoroacetic acid were removed by chasing off with toluene (twice), to give the title compound as a dark viscous gum, which was used immediately without further purification.

(b) By proceeding in a similar manner as in reference Example 4(a) but using ethyl (R/S) 3-(1-boc-1,2,3,4-tetrahydro-quinolin-6-yl)butyrate (Reference Example 11) there was prepared ethyl (R/S) 3-(1,2,3,4-tetrahydro-quinolin-6-yl)butyrate.

(c) By proceeding in a similar manner as in reference Example 4(a) but using (R/S) 4-(1-boc-1,2,3,4-tetrahydro-quinolin-6-yl)-tetrahydro-pyran-2-one (Reference Example 16) and carrying out the reaction at room temperature there was prepared (R/S) 4-(1,2,3,4-tetrahydro-quinolin-6-yl)-tetrahydro-pyran-2-one as a brown solid.

REFERENCE EXAMPLE 6

(R/S) Ethyl 3-(1-boc-2,3-Dihydro-1H-indol-5-yl)butyrate

A mixture of ethyl 3-(1-boc-2,3-dihydro-1H-indol-5-yl)crotonate (11.4 g, Reference Example 7) and ammonium formate (about 30 g) in ethanol (about 200 ml) was warmed in an oil-bath to 60° C. Palladium on charcoal (10%, about 1 g) was added in one portion under a blanket of nitrogen—effervescence began almost immediately. The mixture was stirred at about 60° C. for about one hour, then cooled to room temperature and filtered through Celite. The filtrate was evaporated and the residue was partitioned between water and ethyl acetate. The organic layer was washed with water, then dried and then evaporated to give the title compound (11.1 g) as a colourless, mobile oil.

REFERENCE EXAMPLE 7

(a) Ethyl 3-(1-boc-2,3-Dihydro-1H-indol-5-yl)crotonate

A mixture of 1-boc-5-bromoindoline (15.0 g, Reference Example 8), ethyl crotonate (8.6 g), palladium acetate (480 mg), tris(o-tolyl)phosphine (1.6 g) and triethylamine (10 ml) in dimethylformamide (60 ml) was stirred in a sealed vessel under an atmosphere of argon at about 100° C. for about 4 hours. After cooling to room temperature the dark mass was poured onto hydrochloric acid (about 1 L, 1M) and the product extracted into ethyl acetate. The combined extracts were washed with aqueous sodium bicarbonate solution, then with brine, then dried and then evaporated. The residual light yellow oil was subjected to flash chromatography on silica eluting initially with a mixture of ethyl acetate and petrol (5:95, v/v) to remove high running impurities, then eluting with a mixture of ethyl acetate and petrol (1:9, v/v) to give the title compound (11.4 g) as a colourless, mobile oil.

(b) By proceeding in a similar manner to Reference Example 7(a) but using methyl acrylate and carrying out the reaction at 80° C. there was prepared methyl 3-(1-boc-2,3-dihydro-1H-indol-5-yl)acrylate as a light yellow solid. MS (ES$^+$) 629 (2MNa$^+$).

(c) By proceeding in a similar manner to Reference Example 7(a) but using 1-boc-6-iodo-1,2,3,4-tetrahydroquinoline (Reference Example 12) there was prepared ethyl 3-(1-boc-1,2,3,4-tetrahydro-quinolin-6-yl)crotonate as a light yellow solid.

(d) By proceeding in a similar manner to Reference Example 7(a) but using 1-boc-6-iodo-1,2,3,4-tetrahydroquinoline (Reference Example 12) and methyl acrylate and carrying out the reaction at 80° C. there was prepared methyl 3-(1-boc-1,2,3,4-tetrahydro-quinolin-6-yl)acrylate as a light yellow powder.

REFERENCE EXAMPLE 8

1-boc-5-Bromoindoline 5-bromoindoline (10 g) was added in one portion to molten Boc-anhydride (11.6 g) at 30–40° C. Immediate effervescence was followed by the formation of a solid cake which was triturated with pentane to give the title compound (15 g) as a white powder.

REFERENCE EXAMPLE 9

(a) Dimethyl 2-(2,3-Dihydro-1H-indol-5-ylmethyl)-pentanedioate

A mixture of dimethyl 3-(1-boc-2,3-dihydro-1H-indol-5-yl)-2-methoxycarbonyl-pentanedioate [530 mg, Reference Example 10(a)] and concentrated hydrochloric acid (20 ml) was stirred at reflux overnight then evaporated. The residual clear foam (370 mg) was treated with methanol (20 ml), then with concentrated sulphuric acid (10 drops). The resulting solution was stirred at reflux for 2 hours then evaporated. The residue was partitioned between ethyl acetate and aqueous sodium bicarbonate solution. The layers were separated and the aqueous layer was extracted with ethyl acetate. The combined organic layer and extracts were washed with brine, then dried and then evaporated. The residue was subjected to flash chromatography on silica eluting with a mixture of ethyl acetate and petrol (1:1, v/v) to give the title compound (150 mg) as a clear oil. MS (ES$^+$) 278 (MH$^+$).

(b) By proceeding in a similar manner to Reference Example 9(a) but using ethyl 3-(1-boc-1,2,3,4-tetrahydro-quinolin-6-yl)-2-ethoxycarbonyl-pentanedioate [Reference Example 10(b)] there was prepared dimethyl 3-(1,2,3,4-tetrahydro-quinolin-6-yl)-pentanedioate as a colourless oil. MS (ES$^+$) 292 (MH$^+$), 314 (MNa$^+$).

REFERENCE EXAMPLE 10

(a) Dimethyl 3-(1-boc-2,3-Dihydro-1H-indol-5-yl)-2-methoxycarbonyl-pentanedioate A stirred solution of sodium (156 mg) in methanol (15 ml) was treated with dimethyl malonate (0.8 ml) and after stirring for 15 minutes the mixture was then treated with a solution of methyl 3-(1-boc-2,3-dihydro-1H-indol-5-yl)acrylate [1.0 g, reference Example 7(b)] in tetrahydrofuran (15 ml). The mixture was stirred at reflux for 3 hours, then cooled to room temperature, then treated with water (2 ml) and then evaporated. The residue was partitioned between ethyl acetate and water. The layers were separated and the aqueous layer was extracted with fresh ethyl acetate. The combined organic layer and extracts were washed with brine, then dried and then evaporated. The residue was subjected to flash chromatography on silica eluting with a mixture of ethyl acetate and petrol (15:85, v/v) to give the title compound (530 mg) as a clear oil. MS (ES$^+$) 458 (MNa$^+$). MS (ES$^-$) 434 (M$^-$).

(b) By proceeding in a similar manner to Reference Example 10(a) but using methyl 3-(1-boc-1,2,3,4-tetrahydro-quinolin-6-yl)acrylate [Reference Example 7(d)]

there was prepared ethyl 3-(1-boc-1,2,3,4-tetrahydro-quinolin-6-yl)-2-ethoxycarbonyl-pentanedioate. MS (ES$^+$) 514 (MNa$^+$). MS (ES$^-$) 490 (M$^-$).

REFERENCE EXAMPLE 11

(a) Ethyl (R/S) 3-(1-boc-1,2,3,4-Tetrahydro-quinolin-6-yl)butyrate

A mixture of ethyl 3-(1-boc-1,2,3,4-tetrahydro-quinolin-6-yl)crotonate [9 g, Reference Example 7(c)] and 5% palladium on charcoal (2.5 g) in ethanol (250 ml) was hydrogenated at room temperature and pressure overnight. The spent catalyst was removed by filtration through Celite and the filtrate was evaporated to give the title compound (9.1 g) as a colourless oil.

(b) By proceeding in a similar manner to Reference Example 11(a) but using E and Z ethyl 3-(1-acetyl-2,3-dihydro-1H-indol-5-yl)-hept-2-enoate [Reference Example 26(a)] and carrying out the hydrogenation at 2 bar pressure of hydrogen gas for 4.5 hours there was prepared ethyl (R/S) 3-(1-acetyl-2,3-dihydro-1H-indol-5-yl)-heptanoate as a white solid.

(c) By proceeding in a similar manner to Reference Example 11(a) but using E and Z ethyl 3-(1-acetyl-2,3-dihydro-1H-indol-5-yl)pent-2-enoate [Reference Example 26(b)] and carrying out the hydrogenation at 2 bar pressure of hydrogen gas for 100 minutes there was prepared ethyl (R/S) 3-(1-acetyl-2,3-dihydro-1H-indol-5-yl)-pentanoate as a white solid.

(d) By proceeding in a similar manner to Reference Example 11(a) but using E and Z ethyl 3-(1-acetyl-2,3-dihydro-111-indol-5-yl)-cinnamate [Reference Example 26(c)] and carrying out the hydrogenation at 2 bar pressure of hydrogen gas for 120 minutes there was ethyl (R/S) 3-(1-acetyl-2,3-dihydro-1H-indol-5-yl)-3-phenyl-propionate as a white solid.

REFERENCE EXAMPLE 12

1-Boc-6-Iodo-1,2,3,4-tetrahydroquinoline

A solution of iodine monochloride (16.2 g) in acetic acid (30 ml) was added to a stirred solution of 1,2,3,4-tetrahydroquinoline (12.6 ml) in acetic acid (125 ml) at room temperature under nitrogen. After stirring at room temperature for a further hour the dark mixture was poured onto water (about 500 ml) and the mixture was basified by the cautious addition of solid potassium carbonate. The aqueous layer was extracted with tert-butyl methyl ether, and this extract was washed successively with aqueous sodium thiosulphate solution, then with brine, then dried and then evaporated. The residual brown gum (22 g) was treated with boc anhydride (44 g) in tetrahydrofuran (250 ml). The mixture was stirred at reflux overnight then evaporated and the residue was partitioned between ethyl acetate and dilute hydrochloric acid. The organic layer was washed with brine, then dried and then evaporated. Crystallisation of the residue from heptane gave the title compound (15 g) as a light yellow powder.

REFERENCE EXAMPLE 13

(a) Methyl (R) 4-[1-(1,2,3,4-Tetrahydro-quinolin-6-yl)-2-methoxycarbonyl-ethylcarbamoyl]-butyrate A stirred solution of methyl (R) 3-amino-3-(1-boc-1,2,3,4-tetrahydro-quinolin-6-yl)-propionate (1.7 g, Reference Example 14) in tetrahydrofuran (50 ml) was treated with glutaric anhydride. After stirring for 4 hours the mixture was evaporated to dryness the residue was dissolved in methanol (40 ml) and treated with conc. sulphuric acid (20 drops). This solution was stirred at reflux for 3 hours and then allowed to stand at room temperature overnight. After the addition of solid sodium bicarbonate (10 g) the mixture was evaporated to dryness and the residue was partitioned between ethyl acetate and aqueous sodium bicarbonate solution. The aqueous layer was extracted with fresh ethyl acetate. The combined organic layer and extracts were washed with brine, then dried and then evaporated. The residue was subjected to flash chromatography on silica eluting with ethyl acetate to give the title compound (1.6 g) as a yellow oil. MS (ES$^+$) 363 (MH$^+$), 385 (MNa$^+$) MS (ES$^-$) 361 (MH$^-$).

(b) By proceeding in a similar manner to Reference Example 13(a) but using succinic anhydride there was prepared (R) N-[2-methoxycarbonyl-1-(1,2,3,4-tetrahydro-quinolin-6-yl)-ethyl]-succinamate as a colourless oil. MS (ES$^+$) 371 (MNa$^+$).

REFERENCE EXAMPLE 14

(R) Methyl 3-Amino-3-(1-boc-1,2,3,4-tetrahydro-quinolin-6-yl)-propionate

A solution of methyl 3-{R}-[benzyl-({S}-1-phenyl-ethyl)-amino]-3-(1-boc-1,2,3,4-tetrahydro-quinolin-6-yl)-propionate (6.5 g, Reference Example 15) in ethanol (100 ml) was treated with 20% palladium hydroxide on charcoal (1.0 g), acetic acid (3.6 ml) and water (10 ml) and the mixture was hydrogenated at room temperature overnight. The spent catalyst was removed by filtration through Celite and the filtrate was evaporated to low bulk. The residue was taken up in ether and this solution was washed with aqueous sodium bicarbonate solution, and the layers separated. The aqueous layer was extracted twice with fresh ether and the combined ether extracts were washed with brine, then dried and then evaporated. The residue was subjected to flash chromatography on silica eluting with a mixture of methanol and dichloromethane (1:9, v/v) to give the title compound (1.7 g) as a clear oil which slowly crystallised on standing. MS (ES$^+$) 335 (MH$^+$), 357 (MNa$^+$), 669 (2MH$^+$).

REFERENCE EXAMPLE 15

Methyl 3-{R}-[Benzyl-({S}-1-phenyl-ethyl)-amino]-3-(1-boc-1,2,3,4-tetrahydro-quinolin-6-yl)-propionate A solution of (S)-N-benzyl-α-methylbenzylamine (2.6 ml) in anhydrous tetrahydrofuran (50 ml), cooled to −70° C. and under nitrogen, was treated dropwise with a solution of butyllithium in hexanes (5 ml, 2.5M) over about 5 minutes to give a red solution. After stirring at −70° C. for a further 40 minutes the mixture was treated dropwise with a solution of methyl 3-(1-boc-1,2,3,4-tetrahydro-quinolin-6-yl) acrylate [2.0 g, Reference Example 7(d)] in tetrahydrofuran (20 ml) over about 10 minutes. Stirring was continued at low temperature for a further 20 minutes and then the reaction mixture was allowed to warm to room temperature. The mixture was partitioned between ether and water, the layers separated, and the organic layer washed with water then with brine, then dried and then evaporated. The residue was subjected to flash chromatography on silica eluting with a mixture of ethyl acetate and petrol (initially 1:9 and then 15:85, v/v) to give the title compound as a viscous, colourless oil, 1.5 g.

REFERENCE EXAMPLE 16

(R/S) 4-(1-boc-1,2,3,4-Tetrahydro-quinolin-6-yl)-tetrahydro-pyran-2-one

A mixture of 1-boc-6-iodo-1,2,3,4-tetrahydroquinoline (2.0 g, Reference Example 12), 5,6-dihydro-pyran-2-one (1.1 g), tetrakis(triphenylphosphine)palladium(0) and triethylamine (2.2 g) in dimethylformamide (5 ml) was stirred at about 95° C. in a sealed vessel under an atmosphere of nitrogen overnight. The reaction mixture was partitioned between ethyl acetate and dilute hydrochloric acid, the layers separated, and the organic layer washed with sodium bicarbonate solution, then dried, and then evaporated. The residue was subjected to flash chromatography on silica eluting with a mixture of ethyl acetate and cyclohexane (2:3,v/v) to give the title compound as a brown oil, 1.2 g.

REFERENCE EXAMPLE 17

Methyl (R) 3-(1-boc-1,2,3,4-Tetrahydro-quinolin-6-yl)-3-[(5-methyl-isoxazole-3-carbonyl)-amino]-propionate A solution of 5-methyl-isoxazole-3-carboxylic acid (65 mg) in dimethylformamide (30 ml) was treated successively with O-(7-azabenzotriazol-1-yl)-N,N,N',N'-tetramethyluronium hexafluorophosphate (190 mg), diisopropylethylamine (1 ml) and methyl (R) 3-amino-3-(1-boc-1,2,3,4-tetrahydro-quinolin-6-yl)-propionate (200 mg, Reference Example 14). After standing at room temperature overnight the mixture was evaporated to low bulk and the residue partitioned between ethyl acetate and dilute hydrochloric acid. The layers were separated and the organic layer was washed with sodium carbonate solution, dried, and evaporated. The residue was purified by flash chromatography to give the title compound as an orange gum, 310 mg.

REFERENCE EXAMPLE 18

Methyl (S) 2-Amino-3-[1-(2,6-dichloro-benzoyl)-1,2,3,4-tetrahydro-quinolin-6-yl]-propionate A solution of methyl (S) 2-(N-boc-amino)-3-(1,2,3,4-tetrahydro-quinolin-6-yl)-propionate [500 mg, Reference Example 19(a)] in tetrahydrofuran (20 ml) was treated successively with triethylamine (360 mg) and 2,6-dichlorobenzoyl chloride (380 mg). The mixture was stirred at 40° C. for 2 hours and then partitioned between ethyl acetate (100 ml) and dilute hydrochloric acid (100 ml). The organic phase was washed with sodium bicarbonate solution, then dried and then evaporated. The residue was dissolved in trifluoroacetic acid (2 ml) and the clear solution was left at room temperature for 30 minutes then evaporated. The residue was partitioned between ethyl acetate and dilute hydrochloric acid. The organic phase was washed with sodium bicarbonate solution, then dried and then evaporated to give the title compound (200 mg) as a colourless oil.

REFERENCE EXAMPLE 19

(a) (S) Methyl 2-(N-boc-Amino)-3-(1,2,3,4-tetrahydro-quinolin-6-yl)-propionate

A solution of methyl (S) 2-(N-boc-amino)-3-quinolin-6-yl-propionate [3.8 g, Reference Example 20(a)] in ethanol (100 ml) at 60° C. was treated with ammonium formate (10 g) and 10% palladium on charcoal (500 mg). After stirring at 60° C. further ammonium formate (about 5 g) and palladium on charcoal (about 250 mg) were added, and this was repeated at 30 minute intervals for a further 2 hours, at which time TLC analysis indicated the reaction was complete. After cooling to room temperature the mixture was filtered through Celite to remove spent catalyst, and the filtrate was evaporated. The residue was partitioned between ethyl acetate (200 ml) and sodium bicarbonate solution (200 ml). The organic phase was dried and evaporated to give the title compound (3.8 g) as a colourless oil which slowly crystallised on standing.

(b) By proceeding in a similar manner to Reference Example 19(a) but using methyl (S) 2-(acetylamino)-3-quinolin-6-yl-propionate [Reference Example 20(b)] and carrying out the reaction at reflux temperature for 2 hours there was prepared methyl (S) 2-acetylamino-3-(1,2,3,4-tetrahydro-quinolin-6-yl)-propionate as a colourless oil MS (ES$^+$) 277 (MH$^+$), 299 (MNa$^+$).

REFERENCE EXAMPLE 20

(a) Methyl (S) 2-(N-boc-Amino)-3-quinolin-6-yl-propionate

A mixture of methyl (S) 2-amino-3-quinolin-6-yl-propionate (3.0 g, Reference Example 21) and boc-anhydride (3.2 g) in tetrahydrofuran (30 ml) was stirred at reflux for 30 minutes. The reaction mixture was evaporated and the residue was triturated with pentane to give the title compound (3.8 g) as a white powder.

(b) By proceeding in a similar manner to Reference Example 20(a) but using acetic anhydride there was prepared methyl (S) 2-(acetyl-amino)-3-quinolin-6-yl-propionate as a colourless oil which crystallised slowly on standing. MS (ES$^+$) 273 (MH$^+$), MS (ES$^-$) 271 (M$^-$).

REFERENCE EXAMPLE 21

Methyl (S) 2-Amino-3-quinolin-6-yl-propionate

A solution of butyllithium in hexanes (13.4 ml, 2.5M) was added dropwise to a stirred solution of (R) 2,5-dihydro-3,6-dimethoxy-2-isopropylpyrazine (5.2 g) in anhydrous tetrahydrofuran (80 ml) at −78° C. under an atmosphere of nitrogen. After stirring at −78° C. for 10 minutes this solution was treated with a solution of 6-(chloromethyl) quinoline [5.0 g, prepared according to the procedure described by Mahiou, Belaid; Gleicher, Gerald Jay. J. Org. Chem. (1990), 55(14), 4466–9] in tetrahydrofuran (20 ml). The resultant dark orange mixture was stirred at −78° C. for 2 hours. The cold reaction mixture was poured onto a mixture of ethyl acetate (200 ml) and brine (200 ml). The organic phase was dried and then evaporated. The residue was subjected to flash chromatography on silica eluting with a mixture of ethyl acetate and dichloromethane (1:1, v/v) to give a colourless oil (6 g). This material was treated with hydrochloric acid (250 ml, 0.25M) and the resulting solution was allowed to stand at room temperature for one hour then evaporated. The residue was treated with water (30 ml) and the solution basified by addition of concentrated ammonia (50 ml). This mixture was extracted three times with dichloromethane (100 ml). The combined extracts were dried and then evaporated. The residue was subjected to flash chromatography on silica eluting with a mixture of ethyl acetate to remove high running impurities and then with a mixture of methanol and ethyl acetate (1:1, v/v) to give the title compound (3.0 g) as a colourless gum.

REFERENCE EXAMPLE 22

(1-boc-2-o-Tolylamino-1H-benzimidazol-5-yl)-acetic Acid

Ethyl (R/S) (2-o-tolylamino-1H-benzimidazol-5-yl)-acetate (1.6 g, Reference Example 23) was suspended in ethanol (30 ml) and treated with sodium hydroxide solution (5 ml, 1M). After stirring at 40° C. for 2 hours the mixture was evaporated. The residue was partitioned between dilute acetic acid (50 ml) and dichloromethane (50 ml) and the resulting white precipitate (650 mg) was dissolved in acetonitrile (30 ml) and the solution was then treated with boc-anhydride (580 mg) and dimethylaminopyridine (10 mg). After standing at room temperature overnight the mixture was evaporated and the residue was partitioned between ethyl acetate and dilute acetic acid. The organic layer was dried and then evaporated. The residue was dissolved in methanol (2 ml) and the solution was treated with ether. The resulting precipitate was collected by filtration to the title compound (500 mg) as a white powder.

REFERENCE EXAMPLE 23

Ethyl (R/S) (2-o-Tolylamino-1H-benzimidazol-5-yl)-acetate

A solution of ethyl (3,4-diaminophenyl)acetate (4.1 g) in ethanol (50 ml) and treated with o-tolylisothiocyanate (3.1 g). After standing at room temperature overnight the clear solution was evaporated to give a yellow gum which was treated with ethanol (70 ml). The resulting solution was treated with diisopropylcarbodiimide (5.3 g), and the mixture stirred at 55° C. for 4 hours then evaporated. The residue was subjected to by flash chromatography on silica eluting initially with ether and then with a mixture of methanol and ether (1:9, v/v), to give the title compound (4.1 g) as a light yellow gum.

REFERENCE EXAMPLE 24

(a) Ethyl (R/S) 3-(2,3-Dihydro-1H-indol-5-yl)-heptanoate

A solution of R/S 3-(2,3-dihydro-1H-indol-5-yl)-heptanoic acid hydrochloride [4.13 g, Reference Example 25(a)] in absolute ethanol (100 mL) containing concentrated sulphuric acid (1.4 mL) was stirred for 6 hours then allowed to stand overnight at room temperature. The mixture was concentrated to a low volume and the residue was partitioned between ethyl acetate (200 mL) and saturated aqueous sodium bicarbonate (200 mL). The organic phase was washed with saturated aqueous sodium bicarbonate (50 mL). The aqueous phases were further extracted with ethyl acetate and the combined organic phases were dried over magnesium sulphate then evaporated. The residue was subjected to flash chromatography on silica eluting with a mixture of pentane and ethyl acetate (2:1, v/v) to give the title compound (2.88 g) as a pale yellow oil.

(b) By proceeding in a similar manner to Reference Example 24(a) but using R/S 3-(2,3-dihydro-1H-indol-5-yl)-pentanoic acid hydrochloride [Reference Example 25(b)] there was prepared ethyl (R/S) 3-(2,3-dihydro-1H-indol-5-yl)-pentanoate as a light yellow oil.

(c) By proceeding in a similar manner to Reference Example 24(a) but using R/S 3-(2,3-dihydro-1H-indol-5-yl)-3-phenyl-propionic acid hydrochloride [Reference Example 25(c)] there was prepared ethyl (R/S) 3-(2,3-dihydro-1H-indol-5-yl)-3-phenyl-propionate as a light orange oil.

REFERENCE EXAMPLE 25

(a) (R/S) 3-(2,3-Dihydro-1H-indol-5-yl)-heptanoic Acid Hydrochloride

A suspension of ethyl (R/S) 3-(1-acetyl-2,3-dihydro-1H-indol-5-yl)-heptanoate [3.95 g, Reference Example 11(b)] in aqueous hydrochloric acid (120 mL, 6M) was heated at 85° C. for 7 hours. After cooling to room temperature the mixture was evaporated. The residue was treated with toluene and the solvent evaporated under reduced pressure (repeated twice more). Final drying in a dessicator afforded the title compound (4.13 g) as an orange-brown oil. LC-MS: $R_T$=3.36 minutes; M (ES$^+$) 248 (MH$^+$).

(b) By proceeding in a similar manner to Reference Example 25(a) but using ethyl (R/S) 3-(1-acetyl-2,3-dihydro-1H-indol-5-yl)-pentanoate [Reference Example 11(c)] there was prepared (R/S) 3-(2,3-dihydro-1H-indol-5-yl)-pentanoic acid hydrochloride as a brown oil.

(c) By proceeding in a similar manner to Reference Example 25(a) but using ethyl (R/S) 3-(1-acetyl-2,3-dihydro-1H-indol-5-yl)-3-phenyl-propionate [Reference Example 11(d)] there was prepared R/S 3-(2,3-dihydro-1H-indol-5-yl)-3-phenyl-propionic acid hydrochloride as a brown solid.

REFERENCE EXAMPLE 26

(a) E and Z Ethyl 3-(1-Acetyl-2,3-dihydro-1H-indol-5-yl)-hept-2-enoate

Sodium hydride (1.09 g, 60% dispersion in mineral oil) was suspended in tetrahydrofuran (156 mL). The mixture was cooled in an ice-bath under a nitrogen atmosphere and triethyl phosphonoacetate (4.75 mL) was added during 3 minutes. After 45 minutes a solution of 1-acetyl-5-pentanoyl-2,3-dihydro-1H-indole [5.33 g, Reference Example 27(a)] in tetrahydrofuran (50 mL) was added dropwise over 50 minutes. After stirring for 15 minutes the reaction mixture was allowed to warm to room temperature, then heated on a steam bath for 20 hours under a nitrogen atmosphere. In a separate flask, sodium hydride (1.09 g, 60% dispersion in mineral oil) was suspended in tetrahydrofuran (150 mL). The mixture was cooled in an ice-bath under a nitrogen atmosphere, triethyl phosphonoacetate (4.75 mL) was added during 3 minutes and the mixture was stirred for 70 minutes. This mixture was added by canula to the main reaction mixture with ice-bath cooling. The reaction mixture was then refluxed for 43 hours, then cooled, then concentrated to half volume and then partitioned between ethyl acetate and 0.33M aqueous hydrochloric acid. The organic phase was separated and the aqueous phase re-extracted with ethyl acetate. The combined organics were dried over magnesium sulphate then evaporated to give an orange-brown oil which was subjected to flash chromatography on silica eluting with a mixture of ethyl acetate and pentane (1:1, v/v) to give the title compound (4.3 g).

(b) By proceeding in a similar manner to Reference Example 26(a) but using 1-acetyl-5-propanoyl-2,3-dihydro-1H-indole [Reference Example 27(b)] there was prepared E and Z ethyl 3-(1-acetyl-2,3-dihydro-1H-indol-5-yl)-pent-2-enoate as a cream solid.

(c) By proceeding in a similar manner to Reference Example 26(a) but using 1-acetyl-5-benzoyl-2,3-dihydro-1H-in dole (Reference Example 27(c)] there was prepared E and Z ethyl 3-(1-acetyl-2,3-dihydro-1H-indol-5-yl)-cinnamate as a yellow solid.

REFERENCE EXAMPLE 27

(a) 1-Acetyl-5-pentanoyl-2,3-dihydro-1H-indole

Pentanoyl chloride (10.8 g) was added dropwise to a mixture of anhydrous aluminium chloride (28.2 g) and 1-acetyl-2,3-dihydro-1H-indole (10 g) in 1,2-dichloroethane (100 mL) with mechanical stirring. The mixture was stirred at reflux for 16 hours, then cooled, then poured into ice-water. The mixture was extracted with dichloromethane. The extracts were washed with 1M aqueous sodium hydroxide, then dried over magnesium sulphate, then evaporated to give the title compound (10.3 g) as a dark gum.

(b) By proceeding in a similar manner to Reference Example 27(a) but using propionyl chloride and subjecting the product to flash chromatography on silica eluting with a mixture of ethyl acetate and pentane (3:2, v/v) there was prepared 1-acetyl-5-propanoyl-2,3-dihydro-1H-indole as a cream-orange solid.

(c) By proceeding in a similar manner to Reference Example 27(a) but using benzoyl chloride and subjecting the product to flash chromatography on silica eluting with a mixture of ethyl acetate and pentane (3:2, v/v) there was prepared 1-acetyl-5-benzoyl-2,3-dihydro-1H-indole as a cream solid.

REFERENCE EXAMPLE 28

(R/S) 6-(2-Carboxy-1-methyl-ethyl)-3,4-dihydro-2H-quinoline-1-carboxylic Acid 9H-Fluoren-9-ylmethyl Ester A suspension of (R/S) 3-(1,2,3,4-tetrahydro-quinolin-6-yl)-butyric acid (2.6 g) and sodium bicarbonate (2.2 g) in acetone (40 ml) and water (40 ml) was treated with 2,5-dioxo-pyrrolidine-1-carboxylic acid 9H-fluoren-9-ylmethyl ester (4.0 g) and the resulting mixture was stirred at room temperature overnight. The mixture was filtered and the filtrate evaporated to low bulk. The residue was treated with dilute hydrochloric acid and the resulting gummy precipitate was extracted into a mixture of tetrahydrofuran, ethyl acetate and dichloromethane. This solution was washed with brine, then dried and then evaporated to give the title compound (5.8 g) as a light brown oil, which solidified on standing. MS (ES$^+$) 464 (MNa$^+$), MS (ES$^-$) 440 (M$^-$).

IN VITRO AND IN VIVO TEST PROCEDURES

1. Inhibitory Effects of Compounds on VLA4 Dependent Cell Adhesion to Fibronectin and VCAM 1.1 Metabolic Labelling of RAMOS Cells.

RAMOS cells (a pre-B cell line from ECACC, Porton Down, UK) are cultured in RPMI culture medium (Gibco, UK) supplemented with 5% foetal calf serum (FCS, Gibco, UK). Prior to assay the cells are suspended at a concentration of 0.5×10$^6$ cells/ml RPMI and labelled with 400 µCi/100 mls of [$^3$H]-methionine (Amersham, UK) for 18 hours at 37° C.

1.2 96 Well Plate Preparation for Adhesion Assay.

Cytostar plates (Amersham, UK) were coated with 50 µl/well of either 3 µg/ml human soluble VCAM-1 (R&D Systems Ltd, UK) or 28.8 µg/ml human tissue Fibronectin (Sigma, UK). In control non-specific binding wells 50 µl phosphate buffered saline was added. The plates were then left to dry in an incubator at 25° C., overnight. The next day the plates were blocked with 200 µl/well of Pucks buffer (Gibco, UK) supplemented with 1% BSA (Sigma, UK). The plates were left at room temperature in the dark for 2 hours. The blocking buffer was then disposed of and the plates dried by inverting the plate and gently tapping it on a paper tissue. 50 µl/well of 3.6% dimethyl sulphoxide in Pucks buffer supplemented with 5 mM manganese chloride (to activate the integrin receptor Sigma, UK) and 0.2% BSA (Sigma, UK), was added to the appropriate control test binding and non-specific binding assay wells in the plate. 50 µl/well of the test compounds at the appropriate concentrations diluted in 3.6% dimethyl sulphoxide in Pucks buffer supplemented with 5 mM manganese chloride and 0.2% BSA, was added to the test wells.

Metabolically labelled cells were suspended at 4×10$^6$ cells/ml in Pucks buffer that was supplemented with manganese chloride and BSA as above. 50 µl/well of cells in 3.6% dimethyl sulphoxide in Pucks buffer and supplements was added to all plate wells.

The same procedure exists for plates coated with either VCAM-1 or fibronectin and data is determined for compound inhibition of cell binding to both substrates.

1.3 Performance of Assay and Data Analysis.

The plates containing cells in control or compound test wells are incubated in the dark at room temperature for 1 hour.

The plates are then counted on a Wallac Microbeta scintillation counter (Wallac, UK) and the captured data processed in Microsoft Excel (Microsoft, US). The data was expressed as an IC50, namely the concentration of inhibitor at which 50% of control binding occurs. The percentage binding is determined from the equation:

$$\{[(C_{TB}-C_{NS})-(C_I-C_{NS})]/(C_{TB}-C_{NS})\}\times 100 = \% \text{ binding}$$

where $C_{TB}$ are the counts bound to fibronectin (or VCAM-1) coated wells without inhibitor present, $C_{NS}$ are the counts present in wells without substrate, and $C_I$ are the counts present in wells containing a cell adhesion inhibitor.

Compound data of this invention is expressed for IC$_{50}$s for inhibition of cell adhesion to both fibronectin and VCAM-1. Particular compounds of the invention inhibit cell adhesion to fibronectin and VCAM-1 with IC50s in the range 100 micromolar to 0.1 nanomolar. Preferred compounds of the invention inhibit cell adhesion to fibronectin and VCAM-1 with IC50s in the range 10 nanomolar to 0.1 nanomolar.

2. Inhibition of Antigen-induced Airway Inflammation in the Mouse and Rat 2.1 Sensitization of the Animals.

Rats (Brown Norway, Harland Olac, UK) are sensitized on days 0, 12 and 21 with ovalbumin (100 µg, intraperitoneally [i.p], Sigma, UK) administered with aluminium hydroxide adjuvant (100 mg, i.p., Sigma, UK) in saline (1 ml, i.p.).

In addition mice (C57) are sensitized on days 0 and 12 with ovalbumin (10 µg, i.p.) administered with aluminium hydroxide adjuvant (20 mg, i.p.) in saline (0.2 ml, i.p.).

2.2 Antigen Challenge.

Rats are challenged on any one day between days 28–38, while mice are challenged on any one day between days 20–30.

The animals are challenged by exposure for 30 minutes (rats) or 1 hour (mice) to an aerosol of ovalbumin (10 g/l) generated by an ultrasonic nebulizer (deVilbiss Ultraneb, US) and passed into an exposure chamber.

2.3 Treatment Protocols.

Animals are treated as required before or after antigen challenge. The aqueous-soluble compounds of this invention can be prepared in water (for oral, p.o. dosing) or saline (for intratracheal, i.t. dosing). Non-soluble compounds are prepared as suspensions by grinding and sonicating the solid in 0.5% methyl cellulose/0.2% polysorbate 80 in water (for p.o. dosing, both Merck UK Ltd., UK) or saline (for i.t. dosing). Dose volumes are: for rats 1 ml/kg, p.o. or 0.5 mg/kg, i.t.; for mice 10 ml/kg, p.o. or 1 ml/kg,i.t.

2.4 Assessment of Airway Inflammation.

The cell accumulation in the lung is assessed 24 hours after challenge (rats) or 48–72 hours after challenge (mice). The animals are euthanized with sodium pentobarbitone (200 mg/kg, i.p., Pasteur Merieux, France) and the trachea is immediately cannulated. Cells are recovered from the airway lumen by bronchoalveolar lavage (BAL) and from the lung tissue by enzymatic (collagenase, Sigma, UK) disaggregation as follows.

BAL is performed by flushing the airways with 2 aliquots (each 10 ml/kg) RPMI 1640 medium (Gibco, UK) containing 10% fetal calf serum (FCS, Serotec Ltd., UK). The recovered BAL aliquots are pooled and cell counts made as described below.

Immediately after BAL, the lung vasculature is flushed with RPMI 1640/FCS to remove the blood pool of cells. The lung lobes are removed and cut into 0.5 mm pieces. Samples (rats: 400 mg; mice: 150 mg) of homogenous lung tissue are incubated in RPMI 1640 FCS with collagenase (20 U/ml for 2 hours, then 60 U/ml for 1 hour, 37° C.) to disaggregate cells from the tissue. Recovered cells are washed in RPMI 1640/FCS.

Counts of total leukocytes recovered from the airway lumen and the lung tissue are made with an automated cell counter (Cobas Argos, US). Differential counts of eosinophils, neutrophils and mononuclear cells are made by light microscopy of cytocentrifuge preparations stained with Wright-Giemza stain (Sigma, UK). T cells are counted by flow cytometry (EPICS XL, Coulter Electronics, US) using fluophore-labelled antibodies against CD2 (a pan-T cell marker used to quantify total T cells), CD4, CD8 and CD25 (a marker of activated T cells). All antibodies were supplied by Serotec Ltd., UK).

2.5 Data Analysis.

The cell data was expressed as mean cell numbers in unchallenged, challenged and vehicle treated, and challenged and compound treated groups, including the standard error of the means. Statistical analysis of the difference among treatment groups was evaluated using one-way analysis of variance via the Mann-Whitney test. Where $p<0.05$ no statistical significance existed.

What is claimed is:

1. A compound of general formula (I):

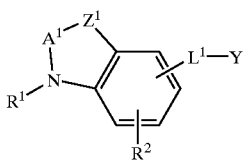

wherein:

$R^1$ represents $R^3$—$L^3$—$Ar^1$—$L^4$—$Z^3$—;

$R^2$ represents hydrogen, halogen, $C_{1-4}$alkyl or $C_{1-4}$alkoxy;

$R^3$ represents alkyl, alkenyl allynyl, aryl, arylalkyl, arylalkenyl, arylalkynyl, cycloalkyl, cycloalkylalkyl, cycloalkylalkenyl, cycloalkylalkynyl, cycloalkenyl, cycloalkenylalkyl, heteroaryl, heteroarylalkyl, heteroarylalkenyl, heteroarylalkynyl, heterocycloalkyl or heterocycloalylalkyl;

$R^5$ represents hydrogen or $C_{1-4}$alkyl;

$R^7$ and $R^{7a}$ are each independently hydrogen or $C_{1-4}$alkyl;

$R^8$ represents hydrogen, alkyl, aryl, arylalkyl, cycloalkyl, cycloalkylalkyl, heteroaryl, heteroarylalkyl, heterocycloalkyl or heterocycloalkylalkyl;

$R^9$ represents alkyl, aryl, cycloalkyl, heteroaryl or heterocycloalkyl, or alkyl substituted by aryl, carboxy, cycloalkyl, heteroaryl, heterocycloallyl, —$S(O)_m R^3$, —$C(=O)$—$NY^4Y^5$ or —$NY^4Y^5$;

$R^{10}$ represents hydrogen, $R^3$ or alkyl substituted with alkoxy, cycloalkyl, hydroxy, mercapto, alkylthio or —$NY^4Y^5$;

$R^{14}$ represents alkyl, aryl, arylalkyl, cycloalkyl, cycloalkylalkyl, heteroaryl, hetetoarylalkyl, heterocycloalkyl or heterocycloalkylalkyl;

$A^1$ represents a methylene or ethylene linkage;

$Ar^1$ represents arylene;

$L^1$ represents:

an allylene linkage optionally substituted by (a) carboxy, hydroxy, mercapto, $R^3$, —$N(R^8)$—$C(=O)$—$R^9$, —$N(R^8)$—$C(=O)$—$OR^9$, —$N(R^8)$—$SO_2$—$R^9$ or —$NY^4Y^5$, or by (b) alkyl substituted by carboxy, hydroxy, mercapto, $S(O)_m R^9$, —$C(=O)$—$NY^4Y^5$ or —$NY^4Y^5$;

$L^3$ represents an —$NR^5$—$C(=Z)$—$NR^5$— linkage;

$L^4$ represents an alkylene chain;

$Y^1$ and $Y^2$ are independently hydrogen, alkenyl, alkyl, aryl, arylalkyl, cycloalkyl, heteroaryl or heteroarylalkyl; or the group —$NY^1Y^2$ may form a cyclic amine;

$Y^4$ and $Y^5$ are independently hydrogen, alkenyl, alkyl, alkynyl, aryl, cycloalkenyl, cycloalkyl, heteroaryl, heterocycloalkyl, or alkyl substituted by alkoxy, aryl, cyano, cycloalkyl, heteroaryl, heterocycloalkyl, hydroxy, oxo, —$NY^1Y^2$, or one or more —$CO^2 R^8$ or —$C(=O)$—$NY^1Y^2$ groups; or the group —$NY^4Y^5$ may form a 5- to 7-membered cyclic amine which (i) may be optionally substituted with one or more substituents selected from alkoxy, carboxamido, carboxy, hydroxy, oxo, or a 5-, 6- or 7-membered cyclic acetal derivative thereof, or $R^{10}$; (ii) may also contain a after heteroatom selected from O, S, $SO_2$, or $NY^6$; and (iii) may also be fused to additional aryl, heteroaryl, heterocycloalkyl or cycloalkyl rings to form a bicyclic or tricyclic ring system;

$Y^6$ represents hydrogen, alkyl, aryl, arylalkyl, —$C(=O)$—$R^{14}$, —$C(=O)OR^{14}$ or $SO_2R^{14}$;

Z is an oxygen or sulphur atom;

$Z^1$ is $C(R^7)(R^{7a})$;

$Z^3$ is $C(=O)$ or $OC(=O)$;

m is an integer 1 or 2; and

Y is carboxy;

and their ester prodrugs; and phamaceutically acceptable salts and solvates of such compounds and their ester prodrugs.

2. A compound according to claim 1 in which $R^1$ represents a group $R^3$—$L^3$—$Ar^1$—$L^4$—$Z^3$— in which $Z^3$ is $C(=O)$, $L^4$ is a straight or branched $C_{1-6}$alkylene chain, $Ar^1$ is optionally substituted phenylene, $L^3$ is an —NH—$C(=O)$—NH— linkage and $R^3$ is optionally substituted aryl.

3. A compound according to claim 2 in which $L^4$ is methylene, $Ar^1$ is optionally substituted p-phenylene and $R^3$ is optionally substituted phenyl.

4. A compound according to claim 3 in which $Ar^1$ is p-phenylene or p-phenylene substituted in the 3-position by halo, $C_{1-4}$alkyl, $C_{1-4}$alkoxy, $C_{1-4}$alkylthio, $C_{1-4}$alkylsulphinyl or $C_{1-4}$alkylsulphonyl and $R^3$ is phenyl substituted in the 2-position by $C_{1-4}$alkyl.

5. A compound according to claim 1 in which $R^2$ is hydrogen.

6. A compound according to claim 1 in which $A^1$ is methylene.

7. A compound according to claim 1 in which $A^1$ is ethylene.

8. A compound according to claim 1 in which $Z^1$ is $CH_2$.

9. A compound according to claim 1 in which $L^1$ is ethylene or propylene, each optionally substituted by $C_{1-4}$alkyl, aryl, heteroaryl, —$N(R^8)$—$C(=O)$—$R^9$, —N(R$^8$)—C(=O)—OR$^9$, —N(R$^8$)—SO$_2$—R$^9$ or —NY$^4$Y$^5$; or alkyl substituted by carboxy, —ZH, —ZR$^3$, —C(=O)—NY$^4$Y$^5$ or —NY$^4$Y$^5$, wherein R$^3$, R$^8$, R$^9$, Y$^4$, Y$^5$ and Z are as defined in claim 1.

10. A compound according to claim 1 in which L$^1$ is a group

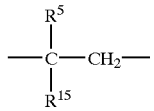

where R$^5$ is hydrogen or C$_{1-4}$alkyl and R$^{15}$ is hydrogen or C$_{1-4}$alkyl, or where R$^5$ is hydrogen and R$^{15}$ is aryl, heteroaryl, —N(R$^8$)—C(=O)—R$^9$, —N(R$^8$)—C(=O)—OR$^9$, —N(R$^8$)—SO$_2$—R$^9$ or —NY$^4$Y$^5$; or alkyl substituted by carboxy, —ZH, —ZR$^3$, —C(=O)—NY$^4$Y$^5$ or —NY$^4$Y$^5$, wherein R$^3$, R$^8$, R$^9$, Y$^4$, Y$^5$ and Z are as defined in claim 1.

11. A compound according to claim 10 in which L$^1$ is a group

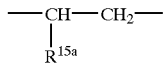

where R$^{15}$ represents hydrogen, C$_{1-4}$alkyl, aryl, heteroaryl, —N(R$^8$)—C(=O)—R$^9$, —N(R$^8$)—C(=O)—OR$^9$, —N(R$^8$)—SO$_2$—R$^9$ or —NY$^4$Y$^5$, or alkyl substituted by carboxy, —OH, —OR$^3$ or —C(=O)—NY$^4$Y$^5$, wherein R$^3$, R$^8$, R$^9$, Y$^4$ and Y$^5$ are as defined in claim 1.

12. A compound according to claim 10 in which L$^1$ is a group

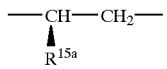

where R$^{15}$ represents hydrogen, C$_{1-4}$alkyl, aryl, heteroaryl, —N(R$^8$)—C(=O)—R$^9$, —N(R$^8$)—C(=O)—OR$^9$, —N(R$^8$)—SO$_2$—R$^9$ or —NY$^4$Y$^5$, or alkyl substituted by carboxy, —OH, —OR$^3$ or —C(=O)—NY$^4$Y$^5$, wherein R$^3$, R$^8$, R$^9$, Y$^4$ and Y$^5$ are as defined in claim 1.

13. A compound according to claim 1 in which L$^1$ is a group

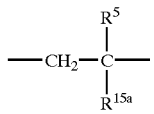

where R$^5$ is hydrogen or C$_{1-4}$alkyl and R$^{15a}$ represents C$_{1-4}$alkyl, or where R$^5$ is hydrogen and R$^{15a}$ represents aryl, heteroaryl, —N(R$^8$)—C(=O)—R$^9$, —N(R$^8$)—C(=O)—OR$^9$, —N(R$^8$)—SO$_2$—R$^9$ or —NY$^4$Y$^5$, or alkyl substituted by carboxy, —ZH, —ZR$^3$, —C(=O)—NY$^4$Y$^5$ or —NY$^4$Y$^5$, wherein R$^3$, R$^5$, R$^8$, R$^9$, Y$^4$, Y$^5$ and Z are as defined in claim 1.

14. A compound according to claim 13 in which L$^1$ is a group

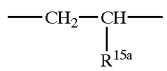

where R$^{15a}$ represents, —N(R$^8$)—C(=O)—R$^9$ or —N(R$^8$)—SO$_2$—R$^9$, wherein R$^8$ and R$^9$ are as defined in claim 1.

15. A compound according to claim 13 which L$^1$ is a group

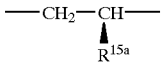

where R$^{15a}$ represents —N(R$^8$)—C(=O)—R$^9$ or —N(R$^8$)—SO$_2$—R$^9$, wherein R$^8$ and R$^9$ are as defined in claim 1.

16. A compound according to claim 1 having the formula (Ia):

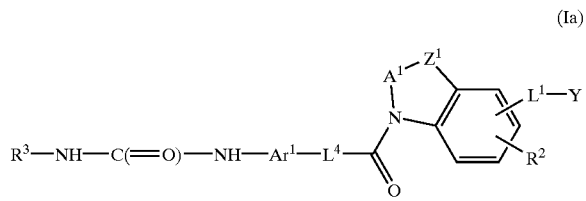

(Ia)

in which R$^2$, R$^3$, A$^1$, Ar$^1$, L$^1$, L$^4$, Y and Z$^1$ are as defined in claim 1, and their ester prodrugs; and pharmaceutically acceptable salts and solvates of such compounds and their ester prodrugs.

17. A compound according to claim 16 in which R$^3$ is phenyl substituted in the 2-position by C$_{1-4}$alkyl.

18. A compound according to claim 16 in which Ar$^1$ is p-phenylene or p-phenylene substituted in the 3-position by halo, C$_{1-4}$alkyl, C$_{1-4}$alkoxy, C$_{1-4}$alkylthio, C$_{1-4}$alkylsulphinyl or C$_{1-4}$alkylsulphonyl.

19. A compound according to claim 16 in which L$^4$ is a straight or branched C$_{1-4}$alkylene chain.

20. A compound according to claim 19 in which L$^4$ is methylene.

21. A compound according to claim 16 in which A$^1$ is methylene.

22. A compound according to claim 16 in which A$^1$ is ethylene.

23. A compound according to claim 16 in which Z$^1$ is CH$_2$.

24. A compound according to claim 16 which R$^2$ is hydrogen.

25. A compound of formula (Ia) according to claim 16 in which R$^2$ is hydrogen, R$^3$ is a 2-substituted phenyl, A$^1$ is methylene or ethylene, Ar$^1$ is optionally substituted m- or p-phenylene or optionally substituted p-pyridinediyl L$^1$ is a

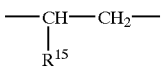

where R$^{15}$ represents hydrogen, C$_{1-4}$alkyl, aryl, heteroaryl, —N(R$^8$)—C(=O)—R$^9$, —N(R$^8$)—C(=O)—OR$^9$, —N(R$^8$)—SO$_2$—R$^9$ or —NY$^4$Y$^5$, or alkyl substituted by carboxy, —OH, —OR$^3$, —C(=O)—NY$^4$Y$^5$, L$^4$ represents a straight or branched C$_{1-6}$alkylene chain and Z$^1$ represents CH$_2$; and their ester prodrugs; and pharmaceutically acceptable salts and solvates of such compounds and their ester prodrugs.

26. A compound of formula (Ia) according to claim 16 in which R$^2$ is hydrogen, R$^3$ is a 2-substituted phenyl, A$^1$ is methylene or ethylene, Ar$^1$ is optionally substituted m- or p-phenylene, L$^1$ is a

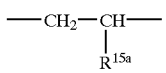

group where $R^{15a}$ represents —N($R^8$)—C(=O)—$R^9$ or —N($R^8$)—$SO_2$—$R^9$, $L^4$ represents a straight or branched $C_{1-6}$alkylene chain and $Z^1$ represents $CH_2$; and their ester prodrugs; and pharmaceutically acceptable salts and solvates of such compounds and their ester prodrugs.

27. A compound according to claim 26 in which $L^1$ is a group

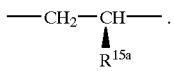

28. A compound according to claim 27 in which $R^{15a}$ represents —N($R^8$)—C(=O)—$R^9$ where $R^8$ is hydrogen or $C_{1-4}$alkyl and $R^9$ is $C_{1-4}$alkyl, aryl, heteroaryl, alkyl substituted by alkoxy, alkyl substituted by carboxy or alkyl substituted by —N$Y^4Y^5$.

29. A compound according to claim 27 in which $R^{15a}$ represents —N($R^8$)—C(=O)—$R^9$ where $R^8$ is hydrogen or $C_{1-4}$alkyl and $R^9$ is selected from 2-chlorophenyl, 5-chloro-2-cyanophenyl, 2-chloro-6-methylphenyl, 2,6-dichlorophenyl, 2,6-difluorophenyl, 4-fluoro-2-trifluoromethyl, 2-methyl-4-nitrophenyl, 2-methyl-5-nitrophenyl, 2-nitrophenyl, 3-nitrophenyl and 2-phenoxyphenyl.

30. A compound according to claim 27 in which $R^{15a}$ represents —N($R^8$)—C(=O)—$R^9$ where $R^8$ is hydrogen or $C_{1-4}$alkyl and $R^9$ is selected from quinolin-4-yl, isoquinolin-2-yl, 2,4-pyridin-3-yl, 2,6-dimethyl-4-trifluoromethylpyridin-3-yl, 4-trifluoromethylpyridin3-yl, 2-phenyl-4-methyl-1,2,3-triazol-5-yl, 3,5-dimethylisoxazol4-yl, 2,7-dimethylpyrazolo-[1,5-a]pyrimidin-6-yl, 2-isopropyl-4-methylthiazol-5-yl and 4-trifluoromethylpyrimidin-5-yl.

31. A compound according to claim 1 selected from:
- 3-(1-{[3-methoxy-4-(3-[2-methylphenyl]-ureido)-phenyl]-acetyl}-1,2,3,4-tetrahydro-quinolin-6-yl)-propionic acid;
- 3-(1-{[3-methoxy-4-(3-o-tolyl-ureido)-phenyl]-acetyl}-2,3-dihydro-1H-indol-5-yl)-butyric acid;
- 3-(1-{[3-methoxy-4-(3-o-tolyl-ureido)-phenyl]-acetyl}-1,2,3,4-tetrahydro-quinolinyl-6-yl)-butyric acid;
- 3-(1-{[3-methoxy-4-(3-o-tolyl-ureido)-phenyl]-acetyl}-2,3-dihydro-1H-indol-5-yl)-pentanedioic acid;
- 3-(1-{[3-methoxy-4-(3-o-tolyl-ureido)-phenyl]-acetyl}-1,2,3,4-tetrahydro-quinolin-6-yl)-pentanedioic acid;
- 4-[2-carboxy-1-(1-{[3-methoxy-4-(3-o-tolyl-ureido)-phenyl]-acetyl}-1,2,3,4-tetrahydro-quinolin-6-yl)-ethylcarbamoyl]-butyric acid;
- N-[2-carboxy-1-(1-{[3-methoxy-4-(3-o-tolyl-ureido)-phenyl]-acetyl}-1,2,3,4-tetrahydro-quinolin-6-yl)-ethyl]-succinamic acid;
- 3-(1-{[3-methoxy-4-(3-o-tolyl-ureido)-phenyl]-acetyl}-1,2,3,4-tetrahydro-quinolin-6-yl)-3-[(5-methylisoxazole-3-carbonyl)-amino]-propionic acid;
- 3-(1-{[3-methoxy-4-(3-o-tolyl-ureido)-phenyl]-acetyl}-2,3-dihydro-1H-indol-5-yl)-3-phenyl-propionic acid;
- 3-(1-{[3-methoxy-4-(3-o-tolyl-ureido)-phenyl]-acetyl}-2,3-dihydro-1H-indol-5-yl)-pentanoic acid;

and their ester prodrugs; and pharmaceutically acceptable salts and solvates of such compounds and their ester prodrugs.

32. A pharmaceutical composition comprising an effective amount of a compound according to claim 1, or an ester prodrug thereof; or a pharmaceutically acceptable salt or solvate of such a compound or an ester prodrug thereof, in association with a pharmaceutically acceptable carrier or excipient.

33. A method for the treatment of a human or non-human animal patient suffering from, or subject to, a condition which can be ameliorated by the administration of an inhibitor of α4β1 mediated cell adhesion comprising administering to said patient an effective amount of a compound according to claim 1, or an ester prodrug thereof, or a pharmaceutically acceptable salt or solvate of such a compound or an ester prodrug thereof.

34. A method according to claim 33 wherein said condition is an inflammatory disease.

35. A method according to claim 33 wherein said condition is asthma.

36. A method for the treatment of a human or non-human animal patient suffering from, or subject to, a condition which can be ameliorated by the administration of an inhibitor of α4β1 mediated cell adhesion comprising administering to said patient an effective amount of a composition according to claim 32.

37. A method according to claim 36 wherein said condition is an inflammatory disease.

38. A method according to claim 36 wherein said condition is asthma.

* * * * *